United States Patent
Stoltz et al.

(10) Patent No.: US 11,214,568 B2
(45) Date of Patent: Jan. 4, 2022

(54) GEM-DISUBSTITUTED PYRROLIDINES, PIPERAZINES, AND DIAZEPANES, AND COMPOSITIONS AND METHODS OF MAKING THE SAME

(71) Applicant: California Institute of Technology, Pasadena, CA (US)

(72) Inventors: Brian M. Stoltz, San Marino, CA (US); Alexander W. Sun, Irvine, CA (US); Stephan N. Hess, Pasadena, CA (US); Carina I. Jette, Pasadena, CA (US); Irina Geibel, Bad Zwischenahn (DE); Shoshana Bachman, Las Vegas, NV (US); Masaki Hayashi, Kanagawa (JP); Hideki Shimizu, Hyogo (JP); Jeremy B. Morgan, Wilmington, NC (US); Shunya Sakurai, Kyoto (JP); Zachary P. Sercel, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 16/657,672

(22) Filed: Oct. 18, 2019

(65) Prior Publication Data

US 2020/0199114 A1 Jun. 25, 2020

Related U.S. Application Data

(60) Provisional application No. 62/792,811, filed on Jan. 15, 2019, provisional application No. 62/749,591, filed on Oct. 23, 2018, provisional application No. 62/747,511, filed on Oct. 18, 2018.

(51) Int. Cl.
| | |
|---|---|
| C07D 243/08 | (2006.01) |
| C07D 413/14 | (2006.01) |
| C07D 207/26 | (2006.01) |
| C07D 239/06 | (2006.01) |
| C07D 507/00 | (2006.01) |
| C07D 241/08 | (2006.01) |

(52) U.S. Cl.
CPC ......... *C07D 413/14* (2013.01); *C07D 207/26* (2013.01); *C07D 239/06* (2013.01); *C07D 241/08* (2013.01); *C07D 243/08* (2013.01); *C07D 507/00* (2013.01)

(58) Field of Classification Search
CPC .................................................. C07D 243/08
See application file for complete search history.

(56) References Cited

U.S. PATENT DOCUMENTS

| | | | |
|---|---|---|---|
| 2,886,487 A | 5/1959 | Kupferberg et al. | |
| 4,639,462 A | 1/1987 | Kramer et al. | |
| 5,591,769 A | 1/1997 | Himmelsbach et al. | |
| 6,774,132 B1 | 8/2004 | Claesson et al. | |
| 7,235,698 B2 | 6/2007 | Behenna et al. | |
| 8,822,679 B2 | 9/2014 | Stoltz et al. | |
| 9,518,034 B2 | 12/2016 | Stoltz et al. | |
| 10,035,769 B2 | 7/2018 | Stoltz et al. | |
| 10,040,784 B2 | 8/2018 | Stoltz et al. | |
| 10,106,479 B2 | 10/2018 | Stoltz et al. | |
| 10,343,996 B2 | 7/2019 | Stoltz et al. | |
| 10,358,422 B2 | 7/2019 | Stoltz et al. | |
| 10,421,696 B2 | 9/2019 | Stoltz et al. | |
| 10,745,354 B2 | 2/2020 | Stoltz et al. | |
| 10,906,875 B2 | 2/2021 | Stoltz et al. | |
| 2006/0041004 A1 | 2/2006 | Gutman et al. | |
| 2006/0084820 A1 | 4/2006 | Behenna et al. | |
| 2010/0298293 A1 | 11/2010 | Allerheiligen et al. | |
| 2013/0267699 A1 | 10/2013 | Stoltz et al. | |
| 2015/0105552 A1 | 4/2015 | Stoltz et al. | |
| 2016/0096810 A1 | 4/2016 | Stoltz et al. | |
| 2016/0176773 A1 | 6/2016 | Stoltz et al. | |
| 2016/0280623 A1 | 9/2016 | Stoltz et al. | |
| 2020/0048201 A1 | 2/2020 | Stoltz et al. | |
| 2020/0157020 A1 | 5/2020 | Stoltz et al. | |
| 2020/0157049 A1 | 5/2020 | Stoltz et al. | |
| 2021/0155592 A1 | 5/2021 | Stoltz et al. | |

FOREIGN PATENT DOCUMENTS

| | | |
|---|---|---|
| DE | 668489 C | 12/1938 |
| WO | WO-9525088 A1 | 9/1995 |
| WO | WO-2003/062265 | 7/2003 |
| WO | WO-2005/012320 A2 | 2/2005 |
| WO | WO-2005/037823 A1 | 4/2005 |
| WO | WO-2009/013390 A1 | 1/2009 |
| WO | WO-2009/153178 A2 | 12/2009 |
| WO | WO-2011/153509 A1 | 12/2011 |
| WO | WO-2011/154374 A1 | 12/2011 |

(Continued)

OTHER PUBLICATIONS

Amat, et al., "Enantioselective Synthesis of 3,3-Disubstituted Piperidine Derivatives by Enolate Dialkylation of Phenylglycinol-derived oxazolopiperidone Lactams," J Org Chem, 72(12): 4431-4439 (2007).
Appeal Brief for U.S. Appl. No. 16/166,893 dated Feb. 11, 2020.
Bach, et al., "Regioselective Reducing Ring Opening of 2-(2-Hydroxyphenyl)-3-[(trimethylsily)oxy]oxetanes at the More Substituted C-2-Position," Liebigs Annalen, 7:1529-1536 (1997).
Badillo, et al., "Enantioselective synthesis of substituted oxindoles and spirooxindoles with applications in drug discovery," Curr Opin Drug Discov Devel, 13(6): 758-776 (2010).
Baussanne, et al., "Diastereoselective Bis-Alkylation of Chiral Non-Racemic α,β-Unsaturated γ-Lactams," Tetrahedron Lett, 35(23): 3931-3934 (1994).
Behenna, et al., "Enantioselective construction of quaternary N-heterocycles by palladium-catalysed decarboxylative allylic alkylation of lactams," Nat Chem, 4(2): 130-133 (2012).

(Continued)

*Primary Examiner* — Brenda L Coleman
(74) *Attorney, Agent, or Firm* — Foley Hoag LLP; Janine S. Ladislaw

(57) ABSTRACT

Described here are transition metal-catalyzed enantioselective arylation and vinylation reactions of α-substituted lactams, such as γ-lactams. The use of various electrophiles and ligands are described, and result in the construction of α-quaternary centers in good yields (up to 91% yield) and high enantioselectivities (up to 97% ee).

14 Claims, 14 Drawing Sheets

(56) References Cited

FOREIGN PATENT DOCUMENTS

| WO | WO-2012/178129 A2 | 12/2012 |
|---|---|---|
| WO | WO-2017/156239 A1 | 9/2017 |

OTHER PUBLICATIONS

Behenna, et al., "Enantioselective Decarboxylative Alkylation Reactions: Catalyst Developement, Substrate Scope, and Mechanistic Studies," Chem Eur J, 17(50): 14199-14223 (2011).

Behenna, et al., "The Enantioselective Tsuji Allylation," J Am Chem Soc, 126(46): 15044-15045 (2004).

Bell, et al., "Organocatalytic asymmetric deconjugative Michael additions," J Org Chem, 71(14): 5407-5410 (2006).

Bennett, et al., "A Unified Approach to the Daucane and Sphenolobane Bicyclo[5.3.0]decane Core: Enantioselective Total Synthesis of Daucene, Daucenal, Epoxydaucenal B, and 14-para-Anisoyloxydauc-4,8-diene", Chem Eur J, 19(52): 17745-17750 (2013).

Bennett, et al., "Expanding Insight into Asymmetric Palladium-Catalyzed Allylic Alkylation of N-Heterocyclic Molecules and Cyclic Ketones," Chem Eur J, 19(14): 4414-4418 (2013).

Bennett, et al., "Synthesis of enantioenriched γ-quaternary cycloheptenones using a combined allylic alkylation/Stork-Danheiser approach: preparation of mono-, bi-, and tricyclic systems", Org Biomol Chem, 10(1): 56-59 (2012).

Bobranski, et al., "Hydration of Phenyldiallylacetamide," Bulletin de l'Academie Polonaise de Sciences, Serie des Sciences, Chimiques, Geologiques et Geographiques, 7: 399-401 (1959).

Bulman Page, et al., "Short and Versatile Route to a Key Intermediate for Lactacystin Synthesis," Org Lett, 5(3): 353-355 (2003).

CAS Registry No. 1823805-71-5, (Entered STN: Dec. 6, 2015).

Chattopadhyay et al., "Mechanistic Origin of the Stereodivergence in Decarboxylative Allylation," Org Lett, 12(13): 3042-3045 (2010).

Coates, et al., "Efficient synthesis of 3-substituted lactams using Meerwein Eschenmoser Claisen [3,3] sigmatropic rearrangements," Tetrahedron Lett, 32(33): 4199-4202 (1991).

Dashkina et al., "Palladium-catalyzed allylation of salts of unsubstituted and substituted 5-nitro-1,3-dioxanes," Zhurnal Organicheskoi Khimii 30(11):1656-1659 (1994).

Day, et al., "The Catalytic Enantioselective Total Synthesis of (+)—Liphagal," Angew Chem Int Ed, 50(30): 6814-6818 (2011).

Desmaele, et al., "Stereocontrolled Elaboration of Quaternary Carbon Centers through the Asymmetric Michael-Type Alkylation of Chiral Imines/Secondary Enamines: Enantioselective Synthesis of (+)—Vincamine," J Org Chem, 62(12): 3890-3901 (1997).

Elz et al., "Synthesis, Biological in vitro evaluation and stereoselectivity of ondansetron analogues: novel 5-HT2A receptor antagonists," Bioorg Med Chem Letts 5(7):667-672 (1995).

Enders, et al., "Asymmetric Electrophilic Substitutions at the α-Position of γ- and δ-Lactams," Eur J Org Chem, 2001(23): 4463-4477 (2001).

Enquist, et al., "The total synthesis of (-)—cyanthiwigin F by means of double catalytic enantioselective alkylation," Nature, 453(7199): 1228-1231 (2008).

Enquist, et al., "Total Syntheses of Cyanthiwigins B, F, and G," Chem Eur J, 17(36): 9957-9969 (2011).

Extended European Search Report for EP Application No. 18203943.8 dated Mar. 21, 2019.

Extended European Search Report for EP Application No. EP 17764072 dated Jul. 29, 2019.

Extended European Search Report for EP application No. EP12802759.6 dated Mar. 14, 2016.

Extended European Search Report received for EP Patent Application No. 16773845.9, dated Oct. 9, 2018.

Ezquerra, et al., "Stereoselective Double Alkylation of Ethyl N-Boc-pyroglutamate," J Org Chem, 59(15): 4327-4331 (1994).

Fuji, et al., "Addition-elimination strategy for asymmetric induction: a chiral sulfoxide as a leaving group," Tetrahedron Lett, 31(17): 2419-2422 (1990). (CAS abstract).

Gartshore, et al., "Enantioselective Palladium-Catalyzed Decarboxylative Allylation of Carbazolones and Indolones: Formal Synthesis of (+)—Kopsihainanine A," Angew Chem Int Ed, 52(15): 4113-4116 (2013).

Groaning, et al., "Chiral Non-Racemic Bicyclic Lactams. Auxiliary-Based Asymmetric Reactions," Tetrahedron, 56(51): 9843-9873 (2000).

Ha et al., "Enantioselective Phase-Transfer Catalytic [α]—Benzylation and [α]—Allylation of [α]—tert—Butoxycarbonyl-lactones," Advanced Synthesis & Catalysis, 355(4): 637-642 (2013).

Hayashi et al., "Ni-Catalyzed Enantioselective C-Acylation of α-Substituted Lactams," J Am Chem Soc, 138(29):8997-9000 (2016).

Heathcock et al., "Daphniphyllum alkaloids. 15. Total syntheses of (±)—methyl homodaphniphyllate and (±)—daphnilactone A," J Org Chem, 57(9):2585-2594 (1992).

Helmchen, et al., "Phosphinooxazolines—A New Class of Versatile, Modular P,N-Ligands for Asymmetric Catalysis," Acc Chem Res, 33(6): 336-345 (2000).

Hong, et al., "Biosynthesis and Chemical Synthesis of Presilphiperfolanol Natural Products," Angew Chem Int Ed, 53(21): 5248-5260 (2014).

Hong, et al., "Enantioselective Total Synthesis of the Reported Structures of (-)—9-epi-Presilphiperfolan-1-ol and (-)—Presilphiperfolan-1-ol: Structural Confirmation and Reassignment and Biosynthetic Insights," Angew Chem Int Ed, 51(38): 9674-9678 (2012).

Hong, et al., "Palladium-catalyzed asymmetric alkylation in the synthesis of cyclopentanoid and cycloheptanoid core structures bearing all-carbon quaternary stereocenters," Tetrahedron, 67(52): 10234-10248 (2011).

Hong, et al., "The Construction of All-Carbon Quaternary Stereocenters by Use of Pd-Catalyzed Asymmetric Allylic Alkylation Reactions in Total Synthesis," Eur J Org Chem, 14: 2745-2759 (2013).

Imao, et al., "Easy Access to Esters with a Benzylic Quaternary Carbon Center from Diallyl Malonates by Palladium-Catalyzed Decarboxylative Allylation," J Org Chem, 72(5): 1652-1658 (2007).

International Search Report and Written Opinion for International Application No. PCT/US2012/043904 dated Feb. 1, 2013.

International Search Report and Written Opinion for International Application No. PCT/US2016/024238 dated Jul. 11, 2016.

International Search Report and Written Opinion for International Application No. PCT/US2017/021528 dated May 25, 2017.

Jakubec, et al., "Enantio- and diastereoselective Michael additions of C-succinimidyl esters to nitro olefins using cinchonine-derived bifunctional organocatalysts," Tetrahedron: Asymmetry, 22(11): 1147-1155 (2011).

Jing, et al., "Total Synthesis of (±)—Kopsihainanine A," Chem Eur J, 18(22): 6729-6732 (2012).

Johnson, et al., "Asymmetric carbon-carbon bond formations in conjugate additions of lithiated N-Boc allylic and benzylic amines to nitroalkenes: Enantioselective synthesis of substituted piperidines, pyrrolidines, and pyrimidinones," J Am Chem Soc, 124(39): 11689-11698 (2002).

Juaristi, et al., "Enantioselective synthesis of β-amino acids. Part 9: Preparation of enantiopure α,α-disubstituted β-amino acids from 1-benzoyl-2(S)-tert-butyl-3-methylperhydropyrimidin-4-one," Tetrahedron: Asymmetry, 9(21): 3881-3888 (1998).

Keith, et al., "The Reaction Mechanism of the Enantioselective Tsuji Allylation: Inner-Sphere and Outer-Sphere Pathways, Internal Rearrangements, and Asymmetric C—C Bond Formation," J Am Chem Soc, 134(46): 19050-19060 (2012).

Kim, et al., "An Asymmetric Synthesis of (+)—Isonitramine by 'Triple Allylic Strain-Controlled' Intramolecular SN2" Alkylation," Tetrahedron Lett, 37(9): 1433-1434 (1996).

Kita et al., "Asymmetric Allylic Alkylation of β-ketoesters with allylic alcohols by a nickel/diphosphine catalyst," Angewandte Chemie International Edition, 55:1098-1101 (2016).

Korch et al., "Enantioselective synthesis of α-secondary and α-tertiary piperazin-2-ones and piperazines by catalytic asymmetric allylic alkylation," Angew Chem Int Edit, 54(1): 179-183 (2015).

Lee et al., "Asymmetric synthesis and evaluation of [α]-quaternary chiral lactam derivatives as novel anticancer agents," Arch of Pharm Res, 37(10):1264-1270 (2014).

(56) References Cited

OTHER PUBLICATIONS

Li et al., "Synthesis of Mannich Bases of Meldrum's Acid and Its 5-Substituted Derivatives," Synthetic Commun, 30(13):2317-2323 (2000).
Li, et al., "Enantioselective Palladium-Catalyzed Decarboxylative Allylation of Carbazolones: Total Synthesis of (-)—Aspidospermidine and (+)—Kopsihainanine A," Angew Chem Int Ed, 52(15):4117-4121 (2013).
Liu, et al., "Construction of Vicinal Tertiary and All-Carbon Quaternary Stereocenters via Ir-Catalyzed Regio-, Diastereo-, and Enantioselective Allylic Alkylation and Applications in Sequential Pd Catalysis," J Am Chem Soc, 135(29): 10626-10629 (2013).
Lu et al., "Metal-Catalyzed Enantioselective Allylation in Asymmetric Synthesis," Angew Chem Int Ed, 47(2): 258-297 (2008).
Ma, et al., "Palladium-catalyzed decarboxylative allylic alkylation of diastereomeric β-ketoesters," Tetrahedron, 70(27): 4208-4212 (2014).
Marziale et al., "An Efficient Protocol for the Palladium-Catalyzed Asymmetric Decarboxylative Allylic Alkylation Using Low Palladium Concentrations and a Palladium(II) Precatalyst," Adv Synth Catal, 357: 2238-2245 (2015).
McDougal, et al., "High-Throughput Screening of the Asymmetric Decarboxylative Alkylation Reaction of Enolate-Stabilized Enol Carbonates," Synlett 11:1712-1716 (2010).
McDougal, et al., "Rapid synthesis of an electron-deficient t-BuPHOX ligand: cross-coupling of aryl bromides with secondary phosphine oxides," Tetrahedron Lett, 51(42): 5550-5554 (2010).
McFadden, et al., "The Catalytic Enantioselective, Protecting Group-Free Total Synthesis of (+)—Dichroanone," J Am Chem Soc, 128 (24): 7738-7739 (2006).
Melhado et al., "Gold(I)—Catalyzed Diastereo- and Enantioselective 1,3-Dipolar Cycloaddition and Mannich Reactions of Azlactones," J Am Chem Soc, 133(10):3517-3527 (2011).
Mertes, et al., "Glutarimides V: Synthesis of 2-Allyl-2-Phenylglutarimide," J Am Pharm Assoc, 67: 882-885 (1958). (CAS Abstract).
Meyers, et al., "Stereoselective Alkylations in Rigid Systems. Effect of Remote Substituents on pi-Facial Additions to Lactam Enolates. Stereoelectronic and Steric Effects," J Am Chem Soc, 120(30): 7429-7438 (1998).
Mohr, et al., "Deracemization of Quaternary Stereocenters by Pd-Catalyzed Enantioconvergent Decarboxylative Allylation of Racemic β-Ketoesters," Angew Chem Int Ed, 44 (42): 6924-6927 (2005).
Mohr, et al., "Enantioselective Tsuji Allylations," Chem Asian J, 2(12): 1476-1491 (2007).
Moss, et al., "Catalytic Enantio- and Diastereoselective Alkylations with Cyclic Sulfamidates," Angew Chem Int Ed, 49(3): 568-571 (2010).
Ngamnithiporn et al., "Nickel-catalyzed enantioselective allylic alkylation of lactones and lactams with unactivated allylic alcohols," Chemical Science, 9:2547-2551 (2018).
Numajiri, et al., "Enantioselective synthesis of α-quaternary Mannich adducts by palladium-catalyzed allylic alkylation: Total synthesis of (+)—sibirinine," J Am Chem Soc, 137(3): 1040-1043 (2015).
Numajiri, et al., "Enantioselective Synthesis of Dialkylated N-Heterocycles by Palladium-Catalyzed Allylic Alkylation," Organic Letters, 17(5):1082-1085 (2015).
Ojima, et al., "Asymmetric Synthesis with Chiral β-Lactams. Highly Stereoselective Alkylation and Aldol Reaction of a Chiral 3-Amino-4-Styryl-β-Lactam," Tetrahedrom Lett, 31(7): 977-980 (1990).
Padwa, et al., "A Novel Cycloaddition Reaction of α-Diazo-γ-amido Ketones Catalyzed by Rhodium (II) Acetate. Scope and Mechanistic Details of the Process," J Org Chem, 61(7): 2283-2292 (1996). (CAS Abstract).
Park et al., "Highly Enantioselective Total Synthesis of (+)—Isonitramine," Organic Letters, 14(3):852-854 (2012).
Park, et al., "Highly Enantioselective Phase-Transfer Catalytic α-Alkylation of α-tert-Butoxycarbonyllactams: Construction of β-Quaternary Chiral Pyrrolidine and Piperidine Systems," Adv Synth Catal, 353(18): 3313-3318 (2011).
Pre-Appeal Brief Conference Request for Review for U.S. Appl. No. 16/166,893 dated Jul. 11, 2019.
Quirante et al., "Synthesis of Diazatricyclic Core of Madangamines from cis-Perhydroisoquinolines," J Org Chem, 73(2): 768-771 (2008).
Reeves, et al., "Development of (Trimethylsilyl)ethyl Ester Protected Enolates and Applications in Palladium-Catalyzed Enantioselective Allylic Alkylation: Intermolecular Cross-Coupling of Functionalized Electrophiles," Org Lett, 16(9): 2314-2317 (2014).
Reeves, et al., "Enantioselective Construction of α-Quaternary Cyclobutanones by Catalytic Asymmetric Allylic Alkylation," Angew Chem Int Ed, 52(26): 6718-6721 (2013).
Rodriguez, et al., ""Carba" Peptide Bond Surrogates/Different Approaches to Gly-ψ(CH₂—CH₂)-D,L-Xaa Pseudodipeptide Units," Int J Peptide Protein Res, 39(3): 273-277 (1992).
Ruggeri et al., "Synthesis of polycyclic lactam and lactone ethers by intramolecular Reformatskii reactions. A model for construction of the daphnilactone A ring system," J Org Chem, 52(26):5745-5746 (1987).
Sato et al., "N-Heterocyclic carbenes as ligands in palladium-catalyzed Tsuji-Trost allylic substitution," Journal of Organometallic Chemistry, 690(24-25): 5753-5758 (2005).
Schelwies et al., "Gold-Catalyzed Intermolecular Addition of Carbonyl Compounds to 1,6-Enynes: Reactivity, Scope, and Mechanistic Aspects," Chem Eur J 15(41):10888-10900 (2009).
Schwarz, et al., "Tandem α-Cyano Enamine/Enolate Alkylations on Bicyclic Lactams: Asymmetric Carbocycle and Heterocycle Synthesis," J Org Chem, 63(5): 1619-1629 (1998).
Seidel, et al., "Aldol and Claisen condensations with 1-(3,4-dichlorophenyl)—2-pyrrolidinone," J of Heterocyclic Chem, 3(3):311-314 (1966).
Seto, et al., "Catalytic Enantioselective Alkylation of Substituted Dioxanone Enol Ethers: Ready Access to C(α)—Tetrasubstituted Hydroxyketones, Acids, and Esters," Angew Chem Int Ed, 47(36): 6873-6876 (2008).
Sherden, "Mechanistic investigations into the palladium-catalyzed decarboxylative allylic alkylation of ketone enolates using the PHOX ligand architecture," Chapter 1, Dissertation, California Institute of Technology (2011).
Shibuya, et al., "Enantioselective Synthesis of 5-6-7 Carbocyclic Core of the Gagunin Diterpenoids," Org Lett, 15(13): 3480-3483 (2013).
Sternativo, et al., "Synthesis of γ-lactams via a domino Michael addition/cyclization reaction of vinyl selenone with substituted amides." Tetrahedron Letters, 54(49):6755-6757 (2013).
Streuff, et al., "A palladium-catalysed enolate alkylation cascade for the formation of adjacent quaternary and tertiary stereocentres," Nat Chem, 2(3): 192-196 (2010).
Sun et al., "Enantioselective synthesis of gem-disubstituted N-Boc diazaheterocycles via decarboxylative asymmetric allylic alkylation," Chem Sci 10:788-792 (2019).
Supplemental European Search Report for EP application No. EP12802759 dated Oct. 28, 2014.
Takahashi, et al., "Atropisomeric lactam chemistry: catalytic enantioselective synthesis, application to asymmetric enolate chemistry and synthesis of key intermediates for NET inhibitors," Tetrahedron, 66(1): 288-296 (2010).
Tani, et al., "A Facile and Modular Synthesis of Phosphinooxazoline Ligands," Org Lett, 9(13): 2529-2531 (2007).
Tari, et al., "Recoverable Cinchona ammonium salts as organocatalysts in the enantioselective Michael addition of β-Keto esters," Tetrahedron: Asymmetry, 21(23): 2872-2878 (2010).
Tasker et al., "Recent advances in homogeneous nickel catalysis," Nature, 509:299-309 (2014).
Trost, "Asymmetric Allylic Alkylation, an Enabling Methodology," J Org Chem, 69(18): 5813-5837 (2004).
Trost, et al., "Asymmetric Synthesis of Oxindole and Indole Spirocyclic Alkaloid Natural Products," Synthesis, 18:3003-3025 (2009).
Trost, et al., "Enantioselective Synthesis of [α]—Tertiary Hydroxyaldehydes by Palladium-Catalyzed Asymmetric Allylic Alkylation of Enolates," J Am Chem Soc, 129(2): 282-283 (2007).

(56) References Cited

OTHER PUBLICATIONS

Tsuji et al., "Catalytic asymmetric synthesis of pentacyclic core of (-)—nakadomarin A via oxazolidine as an iminium cation equivalent," Org Biomol Chem, 12(40):7919-7922 (2014).
Varea, et al., "Asymmetric Synthesis. XXXV Synthesis of 2-Methyl 5-Substituted Piperidines from Chiral Non-racemic Lactams," Tetrahedron Lett, 36(7): 1035-1038 (1995).
Vijn, et al., "Highly Enantioselective Synthesis of a 2,3-Dihydroindole Mediated by N-Methylephedrine," Angew Chem Int Ed, 23(2): 165-166 (1984).
Weaver, et al., "Transition Metal-Catalyzed Decarboxylative Allylation and Benzylation Reactions," Chem Rev, 111(3): 1846-1913 (2011).
White, et al., "The Catalytic Asymmetric Total Synthesis of Elatol," J Am Chem Soc, 130(3): 810-811 (2008).
Williams, et al., "Asymmetric synthesis of monosubstituted and α,α-disubstituted α-amino acids via diastereoselective glycine enolate alkylations," J Am Chem Soc, 113(24): 9276-9286 (1991).
Yamamoto et al., "Palladium-catalyzed asymmetric cyclization of methyl (E)—oxo-9-phenoxy-7-nonenoate and its analogs," Tetrahedron Letters, 23(30): 3089-3092 (1982).
Yang et al., "A new synthetic method for preparing Mannich bases of Meldrum's acid," Chinese J Org Chem, 22(7):525-527 (2002).
Yendapally, et al., "Design, synthesis, and evaluation of novel ethambutol analogues," Bioorg Med Chem Lett, 18(5):1607-1611 (2008).
Zawisza, et al., "An unexpected palladium-catalyzed cyclization of bis-hydroxy allylic alcohols to dioxabicyclo[2.2.2]octanes," Tetrahedron Lett, 47(19): 3271-3274 (2006).
Zawisza, et al., "Palladium-catalyzed formation of cyclic ethers-regio-, stereo- and enantioselectivity of the reaction," Eur J Org Chem, 2007(14): 2296-2309 (2007).
Zhang et al., "Asymmetric induction in Mn(III)—based oxidative free-radical cyclizations of phenylmethyl acetoacetates and 2,5-Dimethylpyrrolidine Acetoacetamides," J Org Chem 58:7640-7651 (1993).
Zhang et al., "Direct N-Acylation of Lactams, Oxazolidinones, and Imidazolidinones with Aldehydes by Shvo's Catalyst," Org Lett, 14(17): 4646-4649 (2012).
Zhou, et al., "Catalytic Asymmetric Synthesis of Oxindoles Bearing a Tetrasubstituted Stereocenter at the C-3 Position," Adv Synth Catal, 352(9): 1381-1407 (2010).
Extended European Search Report for EP Application No. 20155322.9 dated Aug. 17, 2020.
Notice of Allowance for U.S. Appl. No. 16/427,629 dated Sep. 30, 2020.
Patent Board Decision issued under Appeal No. 2020-005067 for U.S. Appl. No. 16/166,893 dated Oct. 20, 2020 (14 pages).
Altman et al., "Orthogonal Pd- and Cu-based catalyst systems for C- and N-arylation of oxindoles," Journal of the American Chemical Society, 130(29):9613-9620 (2008).
Extended European Search Report for EP Application No. 19204164.8 dated Jul. 23, 2020.
Jette et al., "Palladium-catalyzed construction of quaternary stereocenters by enantioselective arylation of [gamma]—lactams with aryl chlorides and bromides," Angewandte Chemie, 58(13):4297-4301 (2019).
Kavitha et al., "Chemistry of cyclic imides: An overview on the past, present and future," Current Organic Chemistry, 20(19):1955-2001 (2016).
Lu et al., "Palladium-catalyzed enantioselective Csp3-Csp3 cross-coupling for the synthesis of (poly)fluorinated chiral building blocks," Organic Letters, 20(18):5657-5660 (2018).
Mai et al., "Alpha-arylation of 3-aryloxindoles," Organic Letters, 12(10):2306-2309 (2010).
Mangunuru et al., "Enantioselective arylation of oxindoles using modified bi-dime ligands," Synthesis, 50(22):4435-4443 (2018).
Notice of Allowance for U.S. Appl. No. 16/219,214 dated Jul. 1, 2020.
Notice of Allowance for U.S. Appl. No. 16/511,138 dated Apr. 8, 2020.
Taylor et al., "Palladium-catalyzed enantioselective alpha-arylation and alpha-vinylation of oxindoles facilitated by an axially chiral p-stereogenic ligand," Journal of the American Chemical Society, 131(29):9900-9901 (2009).
Appeal Brief for U.S. Appl. No. 16/055,559, filed Aug. 10, 2020.
Examiner's Answer to Appeal Brief for U.S. Appl. No. 16/055,559 dated Sep. 28, 2020.
Examiner's Answer to Appeal Brief for U.S. Appl. No. 16/166,893 dated Apr. 28, 2020.
Lakshmaiah et al., "Total Synthesis of (-)—Horsfiline via Asymmetric Nitroolefination," J. Org. Chem., 64: 1699-1704 (1999).
Liu et al. "Formal total syntheses of classic natural product target molecules via palladium-catalyzed enantioselective alkylation." Beilstein J. Org. Chem. 2014, 10, 2501-2512.
Notice of Allowance for U.S. Appl. No. 16/427,629 dated Nov. 24, 2020.
Reply Brief for U.S. Appl. No. 16/166,893, filed Jun. 26, 2020.
U.S. Appl. No. 17/164,204, Pending.
Amendment and Response to Non-Final Office Action, filed Jun. 7, 2021, U.S. Appl. No. 16/055,559.
Amendment Filed with Request for Continued Examination Under 37 C.F.R. § 1.114, filed Dec. 18, 2020, U.S. Appl. No. 16/166,893.
Amendment in Response to Non-Final Office Action Under 37 C.F.R. § 1.111, filed Jun. 15, 2021, U.S. Appl. No. 16/579,382.
Response to Non-Final Office Action, filed Mar. 11, 2021, U.S. Appl. No. 16/219,214.

Figure 1 (cont'd)

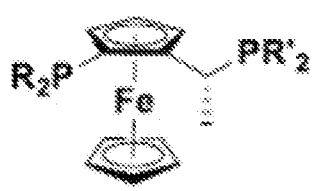

Josiphos
SL-J001-1 (R,R'=Ph, Cy)
SL-J002-1 (R,R'=Ph, tBu)
SL-J003-1 (R,R'=Cy, Cy)
SL-J004-1 (R,R'=Cy, Ph)
SL-J005-1 (R,R'=Ph, Xyl)
SL-J006-1 (R,R'=XylF, Ph)
SL-J007-1 (R,R'=MeOMe2Ph, Cy)
SL-J008-1 (R,R'=XylF, Xyl)
SL-J009-1 (R,R'=Cy, tBu)
SL-J013-1 (R,R'=MeOMe2Ph, tBu)
SL-J015-1 (R,R'=2-furyl, Xyl)
SL-J212-1 (R,R'=2-furyl, tBu)
SL-J216-1 (R,R'=αNp, tBu)
SL-J404-1 (R,R'=αNp, Xyl)
SL-J418-1 (R,R'=MeOMe2Ph, Xyl)
SL-J502-1 (R,R'=tBu, Ph)
SL-J505-1 (R,R'=tBu, 2-tol)

Walphos
SL-W001-1 (R,R'=Ph, XylF)
SL-W002-1 (R,R'=Ph, Ph)
SL-W003-1 (R,R'=Ph, Cy)
SL-W005-1 (R,R'=MeOMe2Ph, XylF)
SL-W006-1 (R,R'=Ph, Xyl)
SL-W008-1 (R,R'=Cy, XylF)
SL-W009-1 (R,R'=Xyl, Xyl)
SL-W022-1 (R,R'=Ph, Norbonyl)

Mandyphos
SL-M001-2 (R=Ph)
SL-M002-2 (R=Cy)
SL-M003-2 (R=Xyl^F)
SL-M004-2 (R=MeOMe$_2$Ph)
SL-M009-2 (R=Xyl)
SL-M012-2 (R=2-tol)

Taniaphos
SL-T001-1 (R=Ph)
SL-T002-1 (R=Cy)

Chenphos
(SL-F356-2)

(2S,5S)-Me-Ferrocelane (R=Me)
(2S,5S)-Et-Ferrocelane (R=Et)
(2S,5S)-iPr-Ferrocelane (R=iPr)

(S)-Me-f-KetalPhos

| entry | ligand | Conv. (%) | ee (%) | biphenyl (%) |
|---|---|---|---|---|
| 1 | L1 | <5 | - | 14 |
| 2 | L2 | <5 | - | 25 |
| 3 | L3 | 16 | 66 | 9 |
| 4 | L4 | <5 | - | 9 |
| 5 | L5 | 11 | 96 | 9 |

| entry | base | temp. | arylation |
|---|---|---|---|
| 1 | LDA | 23 °C | 86% |
| 2 | LiHMDS | 23 °C | not observed |
| 3 | LiHMDS | 60 °C | not observed |
| 4 | NaHMDS | 23 °C | not observed |
| 5 | NaHMDS | 60 °C | observed |
| 6 | KHMDS | 23 °C | observed |
| 7 | KHMDS | 60 °C | observed |

| entry | X | Conv. (%) | ee (%) | biphenyl (%) |
|---|---|---|---|---|
| 1 | Cl | 50 | 94 | 5 |
| 2 | Br | 27 | 55 | <5 |
| 3 | I | 29 | 5 | <5 |
| 4 | OTf | <5 | - | <5 |
| 5 | OTs | <5 | - | <5 |

| entry | additive | mol % | % conv | % Yield (16) |
|---|---|---|---|---|
| 1 | none | 100 | 58 | 31 |
| 2 | LiCl | 100 | 40 | 16 |
| 3 | LiCl | 10 | 68 | 21 |
| 4 | LiBr | 100 | 33 | 7 |
| 5 | NaCl | 100 | 55 | 25 |
| 6 | NaBr | 100 | 60 | 22 |
| 7 | NaI | 100 | 45 | 15 |
| 8 | KCl | 100 | nd | 24 |
| 9 | KBr | 100 | 26 | 20 |
| 10 | CsCl | 100 | 32 | 21 |
| 11 | $ZnCl_2$ | 100 | 27 | 5 |
| 12 | $ZnCl_2$ | 10 | 56 | 17 |
| 13 | CuI | 100 | 10 | <5 |
| 14 | CuI | 10 | 57 | 21 |
| 15 | $AlCl_3$ | 100 | 16 | <5 |
| 16 | $AlCl_3$ | 10 | 50 | 13 |
| 17 | HMDS | 100 | 63 | 17 |
| 18 | COD | 100 | 69 | 20 |

| Entry | Ligand | Conv. (%) | % Yield (*16*) | % anisole (*18*) | ee (%) |
|---|---|---|---|---|---|
| 1 | *L5* | 61 | 27 | 5 | 45 |
| 2 | *L6* | 37 | <5 | 28 | - |
| 3 | *L8* | 88 | 8 | 40 | - |
| 4 | *L4* | 62 | 16 | 6 | 18 |
| 5 | *L15* | 41 | <5 | 25 | - |
| 6 | *L13* | 24 | 20 | 5 | -10 |
| 7 | *L16* | 66 | 24 | 19 | -8 |
| 8 | *L17* | 65 | 47 | 12 | -34 |
| 9 | *L18* | 59 | 43 | 12 | -48 |
| 10 | *L19* | 14 | 8 | 19 | -55 |
| 11 | *L20* | 59 | <5 | 35 | - |
| 12 | *L21* | 35 | 13 | 13 | 54 |
| 13 | *L22* | 4 | <5 | 4 | - |
| 14 | *L23* | 45 | 18 | 13 | 2 |
| 15 | *L24* | 7 | <5 | 4 | - |
| 16 | *L25* | 46 | 21 | 19 | 16 |
| 17 | *L26* | 75 | 38 | 9 | -12 |
| 18 | *L1* | 8 | <5 | 3 | - |
| 19 | *L3* | <5 | <5 | 5 | - |
| 20 | *L27* | <5 | <5 | <5 | - |
| 21 | *L28* | 8 | 7 | <5 | - |
| 22 | *L29* | 58 | 6 | 10 | - |

*L5*: Alkyl = Cy
*L6*: Alkyl = *t*-Bu

*L4*: Alkyl = Cy
*L8*: Alkyl = *t*-Bu

*L15*

*L13*: Ar¹ = 2-furyl, Ar² = 3,5-xylyl
*L16*: Ar¹ = 3,5-xylyl, Ar² = 1-naphthyl

| Entry | Ligand | Base | Conv. (%) | % Yield (XX) | % anisole (XX) | ee (%) |
|---|---|---|---|---|---|---|
| 1 | L18 | LiHMDS | 60 | 19 | 22 | −80 |
| 2 | L18 | NaHMDS | 57 | 7 | 13 | nd |
| 3 | L18 | KHMDS | 81 | 13 | 9 | 4 |
| 4 | L17 | LiHMDS | 73 | 20 | 18 | −76 |
| 5 | L17 | NaHMDS | 67 | 9 | 15 | nd |
| 6 | L17 | KHMDS | 79 | 13 | 11 | 17 |
| 7 | L5 | LiHMDS | 59 | 8 | 9 | nd |
| 8 | L5 | NaHMDS | 70 | 23 | 12 | 59 |
| 9 | L5 | KHMDS | 87 | 27 | 14 | 28 |

| Entry | L | Solvent | Yield (%)[b] | ee (%)[c] |
|---|---|---|---|---|
| 1 | L1 | Tol | 75 | 78 |
| 2 | L2 | Tol | 70 | 1 |
| 3 | L3 | Tol | 83 | 52 |
| 4 | L1 | THF | — | 13 |
| 5 | L1 | MTBE | — | 80 |
| 6 | L1 | 2:1 Hex/Tol | 93 | 93 |

GEM-DISUBSTITUTED PYRROLIDINES, PIPERAZINES, AND DIAZEPANES, AND COMPOSITIONS AND METHODS OF MAKING THE SAME

CROSS-REFERENCE TO RELATED APPLICATIONS

This application claims the benefit of priority to U.S. Patent Application No. 62/792,811 filed Jan. 15, 2019, U.S. Patent Application No. 62/749,591 filed Oct. 23, 2018, and U.S. Patent Application No. 62/747,511 filed Oct. 18, 2018. Each of these applications is incorporated by reference herein in its entirety.

GOVERNMENT SUPPORT

This invention was made with government support under Grant No. GM080269 awarded by the National Institutes of Health. The government has certain rights in the invention.

BACKGROUND

Nitrogen-containing heterocycles are ubiquitous structural motifs that can be found across all areas and applications of organic chemistry. For example, piperazine, a representative diazaheterocycle, is the third most prevalent heterocycle in small molecule pharmaceuticals. As another example, pyrrolidines and pyrrolidinones occur widely in nature, possess a wide range of biological and pharmacological properties, and occur readily in materials and catalysis. As a further example, diazepane heterocycles are common structural motifs found in a variety of pharmaceuticals, including the benzodiazepine anxiolytics, the antipsychotic clozapine, and the anti-insomnia drug suvorexant. For these reasons, the development of stereoselective approaches to functionalized five-, six-, and seven-membered nitrogen-containing heterocycles is a topic of great interest in the synthesis of small molecules and natural products. Chiral gem-disubstituted nitrogen-containing heterocycles are targets of particular interest in pharmaceuticals, because of their increased molecular complexity and correspondingly enhanced binding affinity and specificity for a target, as receptor-ligand binding is often defined by three-dimensional contacts. However, installation of fully substituted chiral centers into azaheterocycles, especially diazaheterocycles, remains a challenge.

Incorporation of a carbonyl group in the heterocycle has been shown to be a useful means of introducing chirality. The oxo group, when introduced on a carbon atom also bearing the nitrogen atom, may be used to selectively introduce chirality at the α position and later removed to produce the functionalized heterocycle or other downstream products. In pyrrolidinones, progress has been made toward enantioselective allylic alkylation and enantioselective α-acylation of γ-butyrolactams; and in piperazines, Stoltz et al. reported in 2015 a palladium-catalyzed decarboxylative asymmetric allylic alkylation reaction to synthesize chiral α,α-disubstituted N4-benzylated piperazin-2-ones. However, α-arylation of γ-butyrolactams has remained elusive, as the use of monocyclic lactams in transition metal-catalyzed α-arylation risks the generation of unwanted aryne intermediates and catalyst decomposition. Likewise, the 2015 Stoltz chiral α,α-disubstituted N4-benzylated piperazin-2-one chemistry is plagued by low product yields owing to side reactions of the benzyl-protected N4, and other protecting groups such as PMB proved recalcitrant to deprotection.

Accordingly, improved methods are needed for generation of gem-disubstituted pyrrolidines, piperazines, and diazepanes.

SUMMARY

In certain embodiments, the invention relates to a method for the preparation of a compound of formula (I):

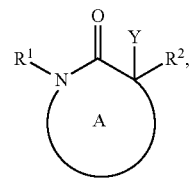

comprising treating a compound of formula (II):

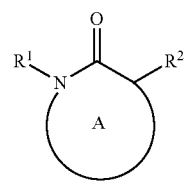

or a salt thereof;
with a Pd or Ni catalyst comprising a chiral ligand;
an optionally substituted aryl halide, optionally substituted aryl pseudohalide, optionally substituted heteroaryl halide, an optionally substituted heteroaryl pseudohalide, or

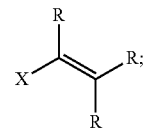

and
a base;
wherein, as valence and stability permit,
ring A represents an optionally substituted heterocycloalkyl, or heterocycloalkenyl group;
R in each occurrence independently represents optionally substituted alkyl, cycloalkyl, (cycloalkyl)alkyl, aryl, aralkyl, heteroaryl, heteroaralkyl, —OR$^{10}$, —SR$^{10}$, or —NR$^{10}$R$^{11}$;
R$^1$ represents hydrogen or optionally substituted alkyl, cycloalkyl, (cycloalkyl)alkyl, aryl, aralkyl, heteroaryl, heteroaralkyl, alkenyl, alkynyl, —C(O)alkyl, —C(O)aryl, —C(O)aralkyl, —C(O)heteroaryl, —C(O)heteroaralkyl, —C(O)O(alkyl), —C(O)O(aryl), —C(O)O(aralkyl), —C(O)O(heteroaryl), —C(O)O(heteroaralkyl), —S(O)$_2$(aryl), —S(O)$_2$(alkyl), —S(O)$_2$(haloalkyl), —OR$^{10}$, —SR$^{10}$, or —NR$^{10}$R$^{11}$;
or R$^1$ taken together with a substituent on ring A and the intervening atoms, form an optionally substituted aryl, heteroaryl, cycloalkyl, cycloalkenyl, heterocycloalkyl, or heterocycloalkenyl group;

or a substituent on ring A taken together with another substituent on ring A and the intervening atoms, form an optionally substituted aryl, heteroaryl, cycloalkyl, cycloalkenyl, heterocycloalkyl, or heterocycloalkenyl group;

$R^2$ represents substituted or unsubstituted alkyl, alkenyl, alkynyl, aralkyl, aralkenyl, aryl, heteroaralkyl, heteroaralkenyl, heteroaryl, (cycloalkyl)alkyl, cycloalkyl, (heterocycloalkyl)alkyl, heterocycloalkyl, alkoxy, amino, or halo;

$R^{10}$ and $R^{11}$ are independently selected for each occurrence from hydrogen or substituted or unsubstituted alkyl, aralkyl, aryl, heteroaralkyl, heteroaryl, (cycloalkyl)alkyl, cycloalkyl, (heterocycloalkyl)alkyl, heterocycloalkyl, alkenyl, and alkynyl;

X is a halogen or pseudohalide; and

Y represents optionally substituted aryl, optionally substituted heteroaryl, or

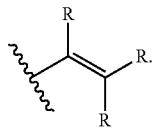

In certain embodiments, the invention relates to a compound of formula (I) made by any of the methods described herein.

In certain embodiments, the invention relates to a method comprising preparing a compound of formula (I) according to any of the methods described herein; and synthesizing a medicinal product from the compound of formula (I).

In certain aspects, the invention relates to a compound of formula (III) or formula (IV):

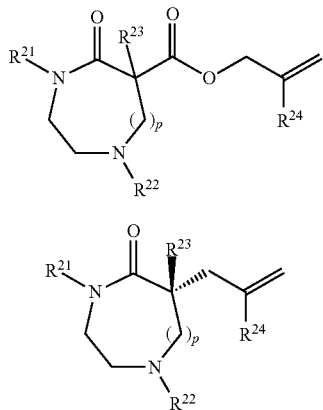

wherein, as valence and stability permit, $R^{21}$ is —C(O)aryl or —C(O)heteroaryl, each optionally substituted with alkoxy, alkyl, or haloalkyl;

$R^{22}$ is —C(O)OR$^{22a}$, —C(O)aryl, or —C(O)heteroaryl, wherein each of aryl and heteroaryl are optionally substituted with alkoxy, alkyl, or haloalkyl;

$R^{22a}$ is $C_{1-6}$ alkyl, $C_{6-10}$ aryl, or $C_{5-9}$ heteroaryl, wherein each of aryl and heteroaryl are optionally substituted with alkoxy, alkyl, or haloalkyl;

$R^{23}$ is H, halogen, alkynyl, alkenyl, or $C_{1-6}$ alkyl, each optionally substituted with OH, cyano, alkoxy, aryloxy, acyl, alkoxycarbonyl, halogen, aryl, or —NHC(O)OR$^{23a}$;

$R^{23a}$ is $C_{1-6}$ alkyl, ($C_{6-10}$ aryl)alkyl, or ($C_{5-9}$ heteroaryl)alkyl;

$R^{24}$ is H or halogen; and p is 0 or 1.

In certain embodiments, p is 0; the compound of formula (III) is a compound of formula (IIIa):

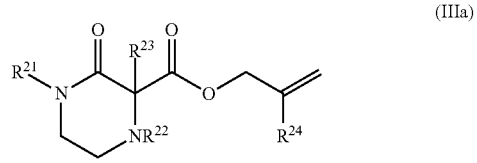

and the compound of formula (IV) is a compound of formula (IVa):

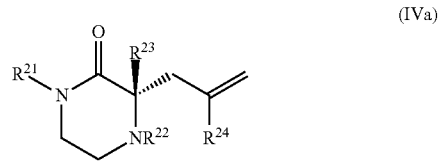

wherein, as valence and stability permit, $R^{21}$ is —C(O)aryl or —C(O)heteroaryl, each optionally substituted with alkoxy, alkyl, or haloalkyl;

$R^{22}$ is —C(O)OR$^{22a}$, —C(O)aryl, or —C(O)heteroaryl, wherein each of aryl and heteroaryl are optionally substituted with alkoxy, alkyl, or haloalkyl;

$R^{22a}$ is $C_{1-6}$ alkyl, $C_{6-10}$ aryl, or $C_{5-9}$ heteroaryl, wherein each of aryl and heteroaryl are optionally substituted with alkoxy, alkyl, or haloalkyl;

$R^{23}$ is H, or $C_{1-6}$ alkyl optionally substituted with OH, cyano, alkoxy, aryloxy, acyl, or —NHC(O)OR$^{23a}$;

$R^{23a}$ is $C_{1-6}$ alkyl, ($C_{6-10}$ aryl)alkyl, or ($C_{5-9}$ heteroaryl)alkyl; and $R^{24}$ is H or halogen.

In certain embodiments, p is 1; the compound of formula (III) is a compound of formula (IIIb):

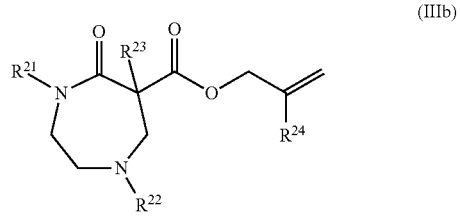

the compound of formula (IV) is a compound of formula (IVb):

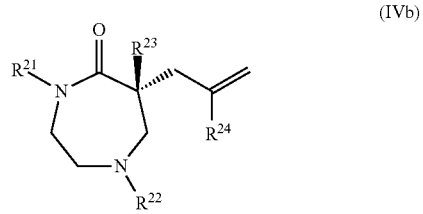

wherein, as valence and stability permit:
R$^{21}$ is —C(O)aryl or —C(O)heteroaryl, each optionally substituted with alkoxy, alkyl, or haloalkyl;
R$^{22}$ is —C(O)OR$^{22a}$;
R$^{22a}$ is C$_{1-6}$ alkyl;
R$^{23}$ is halogen, alkynyl, alkenyl, or C$_{1-6}$ alkyl, each optionally substituted with OH, halogen, cyano, alkoxy, aryloxy, alkoxycarbonyl, or —NHC(O)OR$^{23a}$;
R$^{23a}$ is C$_{1-6}$ alkyl; and
R$^{24}$ is H.

In certain aspects, the invention relates to a compound of formula (V), (VI), or (VII):

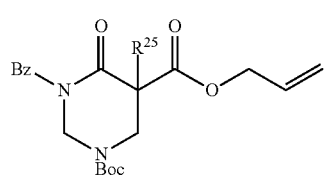
(V)

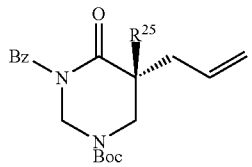
(VI)

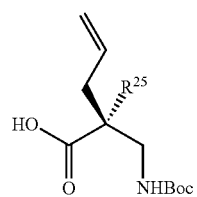
(VII)

wherein, as valence and stability permit,
R$^{25}$ is C$_{1-6}$ alkyl, optionally substituted with halogen, OH, CN, aryl, heteroaryl, aryloxy, alkynyl, or —NHC(O)OR$^{25b}$; halogen; or allyl, optionally substituted with halogen;
R$^{25b}$ is C$_{1-6}$ alkyl, (C$_{6-10}$ aryl)alkyl, or (C$_{5-9}$ heteroaryl)alkyl.

In certain aspects, the invention relates to a compound selected from:

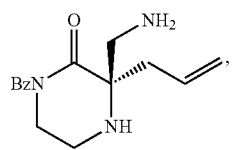
(8)

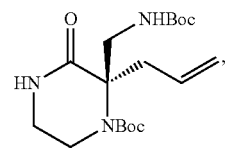
(9)

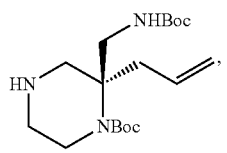
(10)

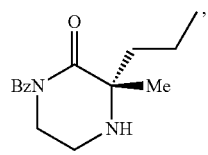
(11)

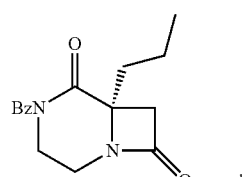
(12)

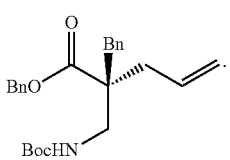
(13)

In certain aspects, the invention relates to a compound of Formula (VIII):

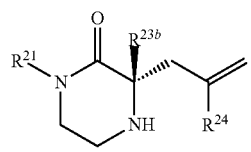
(VIII)

wherein, as valence and stability permit,
R$^{21}$ is —C(O)aryl or —C(O)heteroaryl, each optionally substituted with alkoxy, alkyl, or haloalkyl;
R$^{23b}$ is H, or C$_{1-6}$ alkyl optionally substituted with OH, CN, alkoxy, aryloxy, amino, acyl, or —NHC(O)R$^{23c}$;
R$^{23c}$ is C$_{1-6}$ alkyl, (C$_{6-10}$ aryl)alkyl or (C$_{5-9}$ heteroaryl)alkyl; and
R$^{24}$ is H or halogen.

In certain aspects, the invention relates to a compound of Formula (IX) or (X):

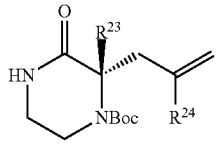
(IX)

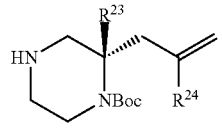
(X)

wherein, as valence and stability permit,
R$^{23d}$ is H, or is C$_{1-6}$ alkyl optionally substituted with cyano, OH, alkoxy, aryloxy, acyl, —NHC(O)OR$^{23a}$;
R$^{23c}$ is C$_{1-6}$ alkyl, (C$_{6-10}$ aryl)alkyl, or (C$_{5-9}$ heteroaryl)alkyl; and
R$^{24}$ is H or halogen.

In certain aspects, the invention relates to a compound of formula (XI):

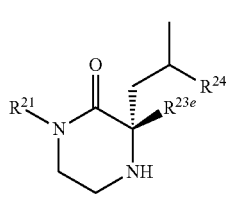
(XI)

wherein, as valence and stability permit,
$R^{21}$ is —C(O)aryl or —C(O)heteroaryl, each optionally substituted with alkoxy, alkyl, or haloalkyl;
$R^{24}$ is H or halogen; and
$R^{23e}$ is H, or is $C_{1-6}$ alkyl optionally substituted with halogen, OH, aryl, aryloxy, CN, acyl, or amino.

In certain aspects, the invention relates to a compound of formula (XII):

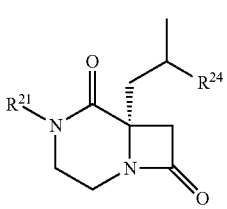
(XII)

wherein, as valence and stability permit,
$R^{21}$ is —C(O)aryl or —C(O)heteroaryl, each optionally substituted with alkoxy, alkyl, or haloalkyl; and
$R^{24}$ is H or halogen.

In certain aspects, the invention relates to a compound of formula (XIII):

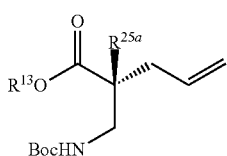
(XIII)

wherein, as valence and stability permit,
$R^{25a}$ is $C_{1-6}$ alkyl, optionally substituted with CN, OH, aryl, heteroaryl, aryloxy, or alkynyl; halogen; or allyl, optionally substituted with halogen; and
$R^{13}$ is aralkyl or hetaralkyl.

In certain aspects, the invention relates to a method for preparation of a compound of formula (IV):

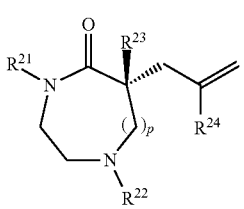
(IV)

the method comprising:
treating a compound of formula (III)

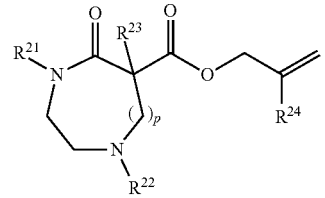
(III)

or a salt thereof,
with a Pd(0) catalyst and a ligand L under alkylation conditions,
wherein, as valence and stability permit,
$R^{21}$ is —C(O)aryl or —C(O)heteroaryl, optionally substituted with alkoxy, alkyl, or haloalkyl;
$R^{22}$ is —C(O)O$R^{22a}$, —C(O)aryl, or —C(O)heteroaryl, wherein each of aryl and heteroaryl is optionally substituted with alkoxy, alkyl, or haloalkyl;
$R^{22a}$ is $C_{1-6}$ alkyl, $C_{6-10}$ aryl, or $C_{5-9}$ heteroaryl;
$R^{23}$ is H, halogen, alkynyl, alkenyl, or $C_{1-6}$ alkyl, each optionally substituted with OH, cyano, alkoxy, aryloxy, acyl, alkoxycarbonyl, halogen, aryl, or —NHC(O)O$R^{23a}$;
$R^{23a}$ is $C_{1-6}$ alkyl, ($C_{6-10}$ aryl)alkyl, or ($C_{5-9}$ heteroaryl)alkyl;
$R^{24}$ is H or halogen; and
p is 0 or 1.

In certain embodiments, p is 0, the compound of formula (IV) is a compound of formula (IVa):

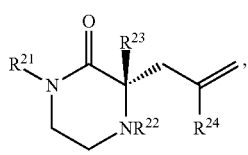
(IVa)

the compound of formula (III) is a compound of formula (IIIc):

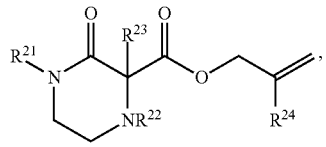
(IIIa)

or a salt thereof,
with a Pd(0) catalyst and a ligand L under alkylation conditions,
wherein, as valence and stability permit,
$R^{21}$ is —C(O)aryl or —C(O)heteroaryl, optionally substituted with alkoxy, alkyl, or haloalkyl;
$R^{22}$ is —C(O)O$R^{22a}$, —C(O)aryl, or —C(O)heteroaryl, wherein each of aryl and heteroaryl is optionally substituted with alkoxy, alkyl, or haloalkyl;
$R^{22a}$ is $C_{1-6}$ alkyl, $C_{6-10}$ aryl, or $C_{5-9}$ heteroaryl;
$R^{23}$ is H, or $C_{1-6}$ alkyl optionally substituted with OH, cyano, alkoxy, aryloxy, acyl, or —NHC(O)O$R^{23a}$;
$R^{23a}$ is $C_{1-6}$ alkyl, ($C_{6-10}$ aryl)alkyl, or ($C_{5-9}$ heteroaryl)alkyl;
and $R^{24}$ is H or halogen.

In certain embodiments, the invention relates to a compound of formula (IVa) made by any of the methods described herein.

In certain embodiments, the invention relates to a method comprising preparing a compound of formula (IVa) according to any of the methods described herein; and synthesizing a medicinal product from the compound of formula (IVa).

In certain embodiments, p is 1; the compound of formula (IV) is a compound of formula (IVb)

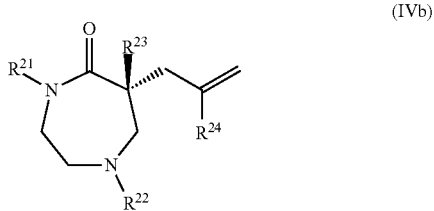

(IVb)

the compound of formula (III) is a compound of formula (IIIb)

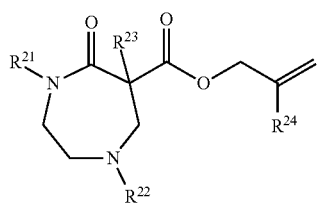

(IIIb)

or a salt thereof,
wherein, as valence and stability permit,
$R^{22}$ is —C(O)OR$^{22a}$;
$R^{22a}$ is C$_{1-6}$ alkyl;
$R^{23}$ is halogen, alkynyl, alkenyl, or C$_{1-6}$ alkyl, each optionally substituted with halogen, OH, cyano, alkoxy, aryloxy, alkoxycarbonyl, or —NHC(O)OR$^{23a}$;
$R^{23a}$ is C$_{1-6}$ alkyl; and
$R^{24}$ is H.

In certain aspects, the invention relates to a compound of formula (E):

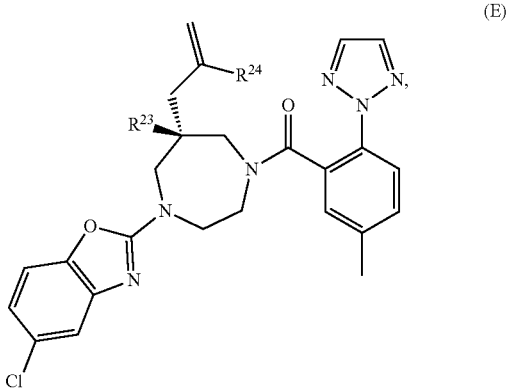

(E)

or a salt thereof,
wherein, as valence and stability permit,
$R^{23}$ is halogen, alkynyl, alkenyl, or C$_{1-6}$ alkyl, each optionally substituted with halogen, OH, cyano, alkoxy, aryloxy, alkoxycarbonyl, or —NHC(O)OR$^{23a}$;

$R^{23a}$ is C$_{1-6}$ alkyl; and
$R^{24}$ is H.

In certain embodiments, the invention relates to a compound of formula (IVb) made by any of the methods described herein.

In certain embodiments, the invention relates to a method comprising preparing a compound of formula (IVb) according to any of the methods described herein; and synthesizing a medicinal product from the compound of formula (IVb).

In certain embodiments, the invention relates to a method of preparation of a compound of formula (VI):

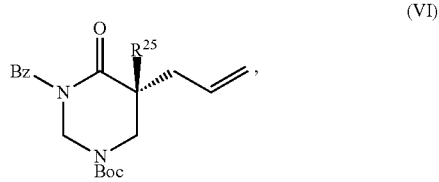

(VI)

the method comprising:
treating a compound of formula (V):

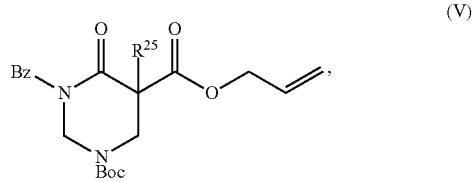

(V)

or a salt thereof,
with a Pd(0) catalyst and a ligand L, under alkylation conditions,
wherein, as valence and stability permit,
$R^{25}$ is C$_{1-6}$ alkyl, optionally substituted with halogen, OH, CN, aryl, heteroaryl, aryloxy, or alkynyl; halogen; or allyl, optionally substituted with halogen.

In certain embodiments, the invention relates to a compound of formula (VI) made by any of the methods described herein.

In certain embodiments, the invention relates to a method comprising preparing a compound of formula (VI) according to any of the methods described herein; and synthesizing a medicinal product from the compound of formula (VI).

In certain embodiments, the invention is directed to a method for preparation of a compound of formula (VIII):

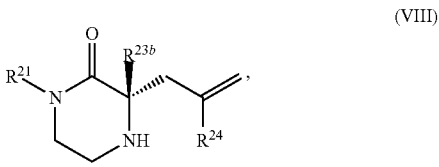

(VIII)

the method comprising:
treating a compound of formula (IVa):

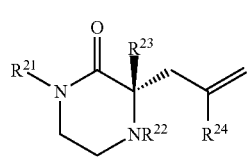

(IVa)

with TFA in a solvent;
wherein, as valence and stability permit,
$R^{21}$ is —C(O)aryl or —C(O)heteroaryl, optionally substituted with alkoxy, alkyl, or haloalkyl;
$R^{22}$ is Boc;
$R^{23}$ is H, or is $C_{1-6}$ alkyl optionally substituted with CN, OH, alkoxy, aryloxy, acyl, or —NHC(O)OR$^{23a}$;
$R^{23a}$ is $C_{1-6}$ alkyl, ($C_{6-10}$ aryl)alkyl, or ($C_{5-9}$ heteroaryl)alkyl;
$R^{24}$ is H or halogen;
$R^{23b}$ is H; or is $C_{1-6}$ alkyl optionally substituted with halogen, OH, CN, alkoxy, aryloxy, amino, acyl, or —NHC(O)OR$^{23}$; and
$R^{23c}$ is ($C_{6-10}$ aryl)alkyl or ($C_{5-9}$ heteroaryl)alkyl.

In certain embodiments, the invention relates to a compound of formula (VIII) made by any of the methods described herein.

In certain embodiments, the invention relates to a method for the preparation of a compound of formula (IX):

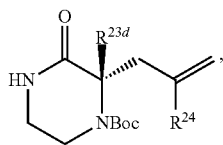

(IX)

the method comprising:
treating a compound of formula (IVa):

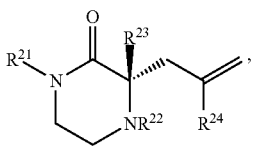

(IVa)

or a salt thereof,
with LiOH in a first solvent,
wherein, as valence and stability permit,
$R^{21}$ is —C(O)aryl or —C(O)heteroaryl, optionally substituted with alkoxy, alkyl, or haloalkyl;
$R^{22}$ is Boc;
$R^{23}$ is H, or $C_{1-6}$ alkyl optionally substituted with halogen, OH, cyano, alkoxy, aryloxy, acyl, or —NHC(O)OR$^{23a}$;
$R^{23a}$ is $C_{1-6}$ alkyl, ($C_{6-10}$ aryl)alkyl, or ($C_{5-9}$ heteroaryl)alkyl;
$R^{23d}$ is H, or is $C_{1-6}$ alkyl optionally substituted with halogen, OH, alkoxy, aryloxy, acyl, or —NHC(O)OR$^{23a}$; and
$R^{24}$ is H or halogen.

In certain embodiments, the invention relates to a compound of formula (IX) made by any of the methods described herein.

In certain embodiments, the invention relates to a method of preparation of a compound of formula (XI):

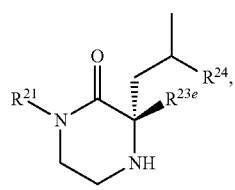

(XI)

the method comprising:
treating a compound of formula (IVa):

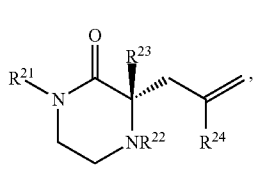

(IVa)

or a salt thereof,
with hydrogen gas in the presence of a Pd/C catalyst in a first solvent, to form a first product mixture;
filtering the first product mixture, to form a crude first product; and
treating the crude first product with TFA in a second solvent;
wherein, as valence and stability permit,
$R^{21}$ is —C(O)aryl or —C(O)heteroaryl, optionally substituted with alkoxy, alkyl, or haloalkyl;
$R^{22}$ is Boc;
$R^{23}$ is H, or is $C_{1-6}$ alkyl optionally substituted with halogen, OH, alkoxy, aryloxy, CN, aryl, or —NHC(O)OR$^{23a}$;
$R^{23a}$ is $C_{1-6}$ alkyl, ($C_{6-10}$ aryl)alkyl, or ($C_{5-9}$ heteroaryl)alkyl;
$R^{23e}$ is H, or is $C_{1-6}$ alkyl optionally substituted with halogen, OH, aryl, aryloxy, CN, acyl, or amino; and
$R^{24}$ is H or halogen.

In certain embodiments, the invention relates to a compound of formula (XI) made by any of the methods described herein.

In certain embodiments, the invention relates to method of preparation of a compound of formula (XIII):

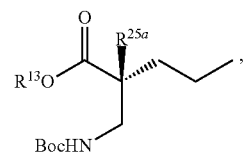

(XIII)

the method comprising:
treating a compound of formula (VI):

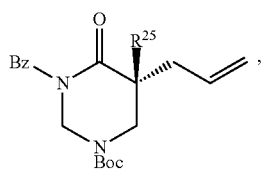

(VI)

or a salt thereof,
with TFA in a first solvent, to form a first product;
treating the first product with lithium hydroxide in a second solvent, to form a second product;
treating the second product with $Boc_2O$ in the presence of a base, to form a third product;
treating the third product with $K_2CO_3$ and $R^{13}—X^{21}$ in a third solvent, to form a compound of formula (XIII);
wherein, as valence and stability permit,
$R^{25}$ is $C_{1-6}$ alkyl, optionally substituted with halogen, OH, CN, aryl, heteroaryl, aryloxy, or alkynyl; halogen; or allyl, optionally substituted with halogen;
$R^{25a}$ is $C_{1-6}$ alkyl, optionally substituted with halogen, OH, CN, aryl, heteroaryl, aryloxy, or alkynyl; halogen; or allyl, optionally substituted with halogen;
$R^{13}$ is aralkyl or hetaralkyl; and
$X^{21}$ is halogen.

In certain embodiments, the invention relates to a compound of formula (XIII) made by any of the methods described herein.

In certain embodiments, the invention relates to any one of the compounds described in the Examples.

DETAILED DESCRIPTION

I. Definitions

Figure 1:
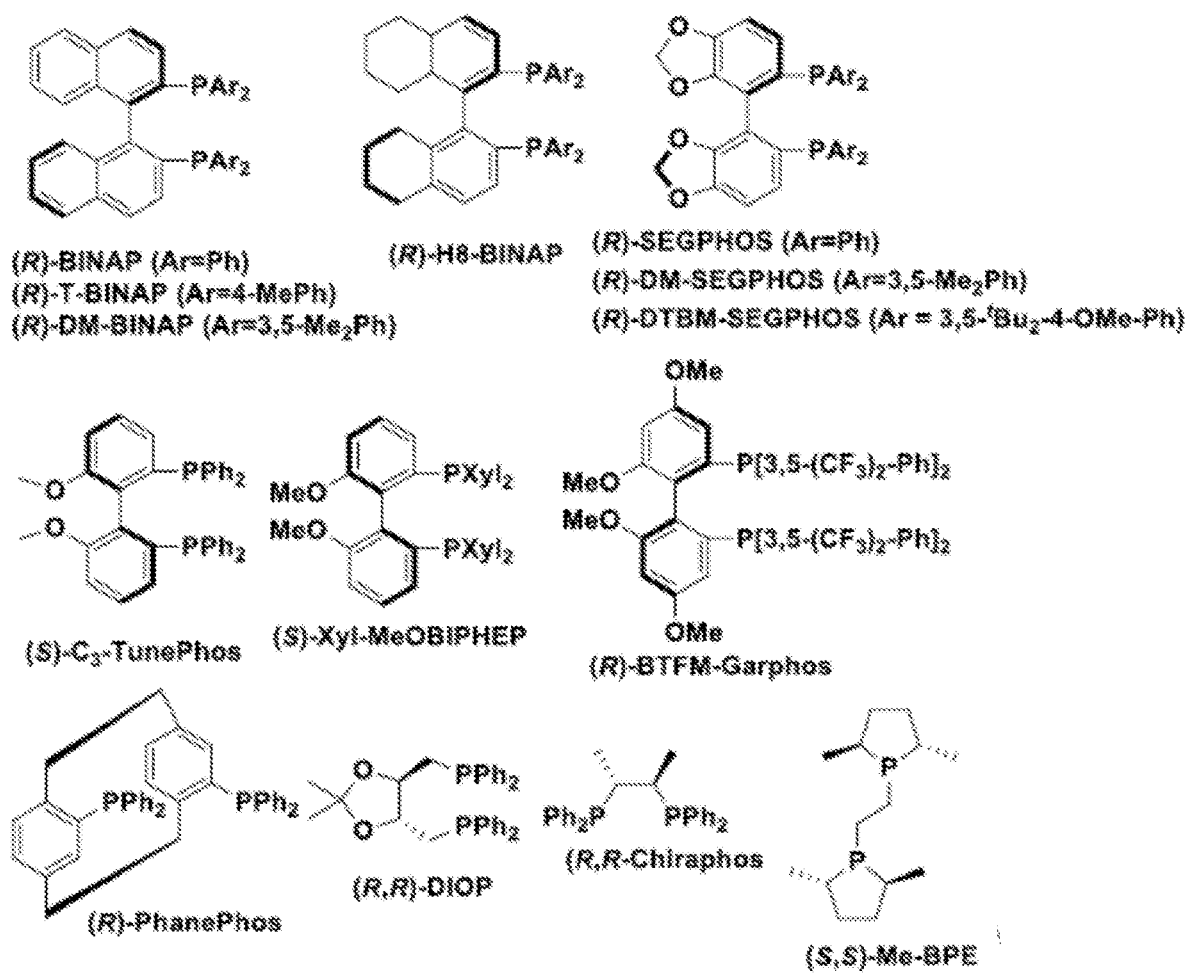
FIG. 1 shows the structures of examples of enantioenriched phosphine ligands.
Figure 1:
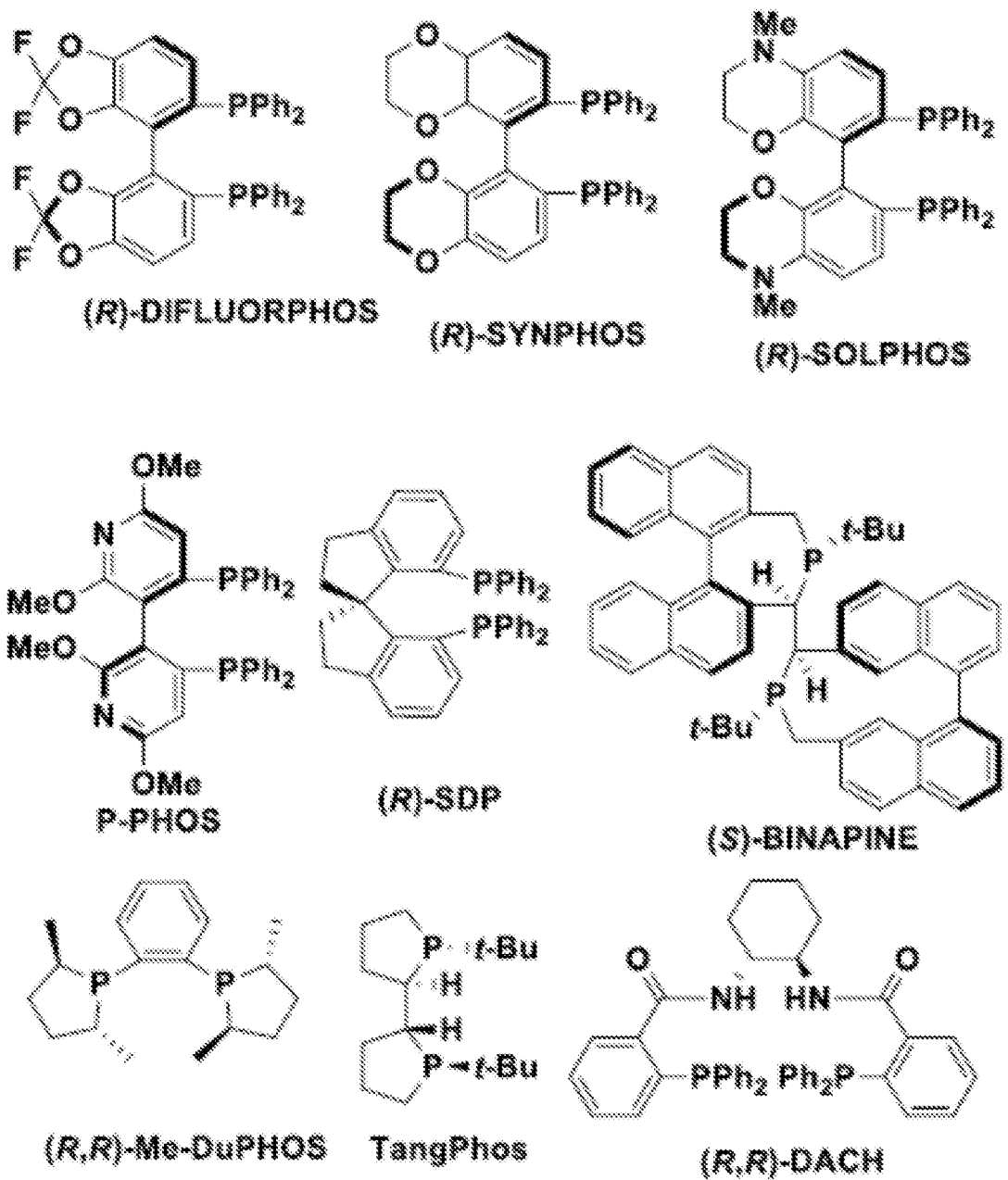
Figure 1:
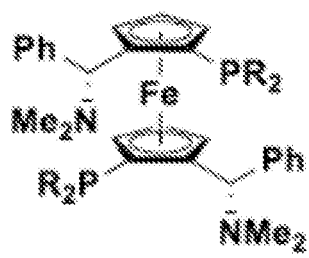
Figure 1:
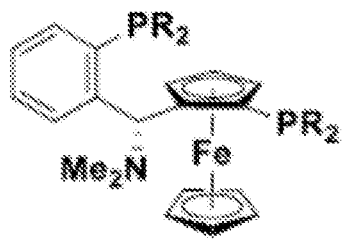
Figure 1:
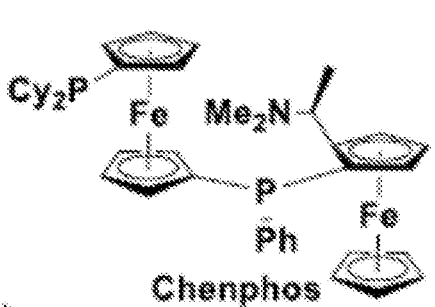
Figure 1:
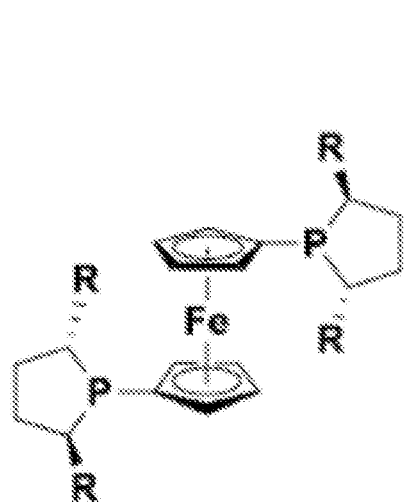
Figure 1:
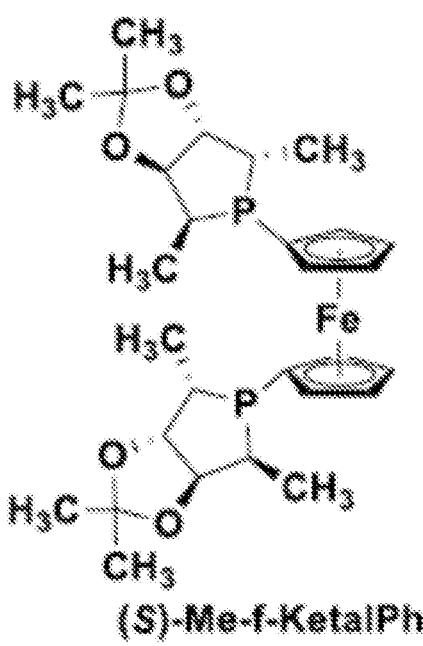
Figure 1:
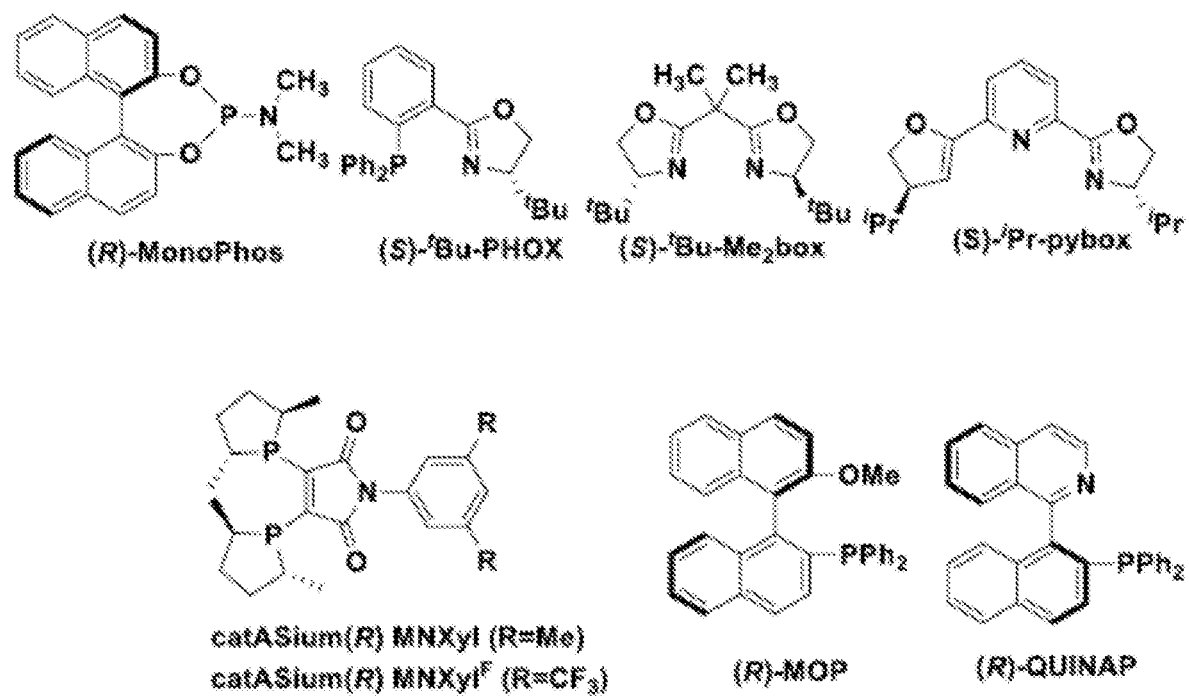

Unless otherwise defined herein, scientific and technical terms used in this application shall have the meanings that are commonly understood by those of ordinary skill in the art. Generally, nomenclature used in connection with, and techniques of, chemistry, cell and tissue culture, molecular biology, cell and cancer biology, neurobiology, neurochemistry, virology, immunology, microbiology, pharmacology, genetics and protein and nucleic acid chemistry, described herein, are those well-known and commonly used in the art.

The methods and techniques of the present disclosure are generally performed, unless otherwise indicated, according to conventional methods well known in the art and as described in various general and more specific references that are cited and discussed throughout this specification. See, e.g., "Principles of Neural Science", McGraw-Hill Medical, New York, N.Y. (2000); Motulsky, "Intuitive Biostatistics", Oxford University Press, Inc. (1995); Lodish et al., "Molecular Cell Biology, 4th ed.", W. H. Freeman & Co., New York (2000); Griffiths et al., "Introduction to Genetic Analysis, 7th ed.", W. H. Freeman & Co., N.Y. (1999); and Gilbert et al., "Developmental Biology, 6th ed.", Sinauer Associates, Inc., Sunderland, Mass. (2000).

Chemistry terms used herein, unless otherwise defined herein, are used according to conventional usage in the art, as exemplified by "The McGraw-Hill Dictionary of Chemical Terms", Parker S., Ed., McGraw-Hill, San Francisco, Calfi. (1985).

All of the above, and any other publications, patents and published patent applications referred to in this application are specifically incorporated by reference herein. In case of conflict, the present specification, including its specific definitions, will control.

The definitions for the terms described below are applicable to the use of the term by itself or in combination with another term.

The term "acyl" is art-recognized and refers to a group represented by the general formula hydrocarbyl-C(O)—, preferably alkyl-C(O)—.

The term "acylamino" is art-recognized and refers to an amino group substituted with an acyl group and may be represented, for example, by the formula hydrocarbyl-C(O)NH—.

The term "acyloxy" is art-recognized and refers to a group represented by the general formula hydrocarbyl-C(O)O—, preferably alkyl-C(O)O—.

The term "alkoxy" refers to an alkyl group, preferably a lower alkyl group, having an oxygen attached thereto. Representative alkoxy groups include methoxy, trifluoromethoxy, ethoxy, propoxy, tert-butoxy and the like.

The term "alkoxyalkyl" refers to an alkyl group substituted with an alkoxy group and may be represented by the general formula alkyl-O-alkyl.

The term "alkenyl", as used herein, refers to an aliphatic group containing at least one double bond and from 1 to about 20 carbon atoms, preferably from 1 to about 10 carbon atoms unless otherwise defined, and is intended to include both "unsubstituted alkenyls" and "substituted alkenyls", the latter of which refers to alkenyl moieties having substituents replacing a hydrogen on one or more carbons of the alkenyl group. Such substituents may occur on one or more carbons that are included or not included in one or more double bonds. Moreover, such substituents include all those contemplated for alkyl groups, as discussed below, except where stability is prohibitive. For example, substitution of alkenyl groups by one or more alkyl, carbocyclyl, aryl, heterocyclyl, or heteroaryl groups is contemplated. A $C_2$-$C_6$ alkenyl group is also referred to as a "lower alkenyl" group.

An "alkyl" group or "alkane" is a straight chained or branched non-aromatic hydrocarbon which is completely saturated. Typically, a straight chained or branched alkyl group has from 1 to about 20 carbon atoms, preferably from 1 to about 10 unless otherwise defined. Examples of straight chained and branched alkyl groups include, but are not limited to, methyl, ethyl, n-propyl, iso-propyl, n-butyl, sec-butyl, tert-butyl, pentyl, hexyl, pentyl and octyl. A $C_1$-$C_6$ straight chained or branched alkyl group is also referred to as a "lower alkyl" group.

Moreover, the term "alkyl" (or "lower alkyl") as used throughout the specification, examples, and claims is intended to include both "unsubstituted alkyls" and "substituted alkyls", the latter of which refers to alkyl moieties having substituents replacing a hydrogen on one or more carbons of the hydrocarbon backbone. Such substituents, if not otherwise specified, can include, for example, a halogen (e.g., fluoro), a hydroxyl, an oxo, a carbonyl (such as a carboxyl, an alkoxycarbonyl, a formyl, or an acyl), a thiocarbonyl (such as a thioester, a thioacetate, or a thioformate), an alkoxy, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. In preferred embodiments, the substituent on substituted alkyls are selected from $C_1$-$C_6$ alkyl, $C_3$-$C_6$ cycloalkyl, halogen, carbonyl, cyano, or hydroxyl. In more preferred embodiments, the substituents on the substituted alkyls are selected from fluoro, carbonyl, cyano, or hydroxyl. It will be understood by those skilled in the art that the moieties substituted on the hydrocarbon chain can themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —$CF_3$, —CN and the like. Exemplary substituted alkyls are described below. Cycloalkyls can be further substituted with alkyls, alkenyls, alkoxys, alkylthios, aminoalkyls, carbonyl-substituted alkyls, —$CF_3$, —CN, and the like.

The term "$C_x$-$C_y$", when used in conjunction with a chemical moiety, such as, acyl, acyloxy, alkyl, alkenyl, alkynyl, or alkoxy is meant to include groups that contain from x to y carbons in the chain. For example, the term "$C_x$-$C_y$ alkyl" refers to substituted or unsubstituted saturated hydrocarbon groups, including straight-chain alkyl and branched-chain alkyl groups that contain from x to y carbons in the chain, including haloalkyl groups. Preferred haloalkyl groups include trifluoromethyl, difluoromethyl, 2,2,2-trifluoroethyl, and pentafluoroethyl. $C_0$ alkyl indicates a hydrogen where the group is in a terminal position, a bond if internal. The terms "$C_2$-$C_y$alkenyl" and "$C_2$-$C_y$alkynyl" refer to substituted or unsubstituted unsaturated aliphatic groups analogous in length and possible substitution to the alkyls described above, but that contain at least one double or triple bond respectively.

The term "alkylamino", as used herein, refers to an amino group substituted with at least one alkyl group.

The term "alkylthio", as used herein, refers to a thiol group substituted with an alkyl group and may be represented by the general formula alkyl-S—.

The term "alkynyl", as used herein, refers to an aliphatic group containing at least one triple bond and is intended to include both "unsubstituted alkynyls" and "substituted alkynyls", the latter of which refers to alkynyl moieties having substituents replacing a hydrogen on one or more carbons of the alkynyl group. Such substituents may occur on one or more carbons that are included or not included in one or more triple bonds. Moreover, such substituents include all those contemplated for alkyl groups, as discussed above, except where stability is prohibitive. For example, substitution of alkynyl groups by one or more alkyl, carbocyclyl, aryl, heterocyclyl, or heteroaryl groups is contemplated.

The term "amide", as used herein, refers to a group

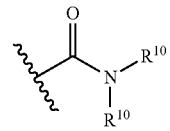

wherein each $R^{10}$ independently represent a hydrogen or hydrocarbyl group, aryl, heteroaryl, acyl, or alkoxy, or two $R^{10}$ are taken together with the N atom to which they are attached complete a heterocycle having from 3 to 8 atoms in the ring structure.

The terms "amine" and "amino" are art-recognized and refer to both unsubstituted and substituted amines and salts thereof, e.g., a moiety that can be represented by

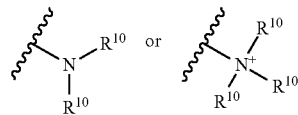

wherein each $R^{10}$ independently represents a hydrogen or a hydrocarbyl group, or two $R^{10}$ are taken together with the N atom to which they are attached complete a heterocycle having from 4 to 8 atoms in the ring structure.

The term "aminoalkyl", as used herein, refers to an alkyl group substituted with an amino group.

The term "aralkyl", as used herein, refers to an alkyl group substituted with an aryl group.

The term "aryl" as used herein include substituted or unsubstituted single-ring aromatic groups in which each atom of the ring is carbon. Preferably the ring is a 6- to 10-membered ring, more preferably a 6-membered ring. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Aryl groups include benzene, naphthalene, phenanthrene, aniline, and the like. Example substitutions on an aryl group include a halogen, a haloalkyl such as trifluoromethyl, a hydroxyl, a carbonyl (such as a carboxyl, an alkoxycarbonyl, a formyl, or an acyl such as an alkylC (O)), a thiocarbonyl (such as a thioester, a thioacetate, or a thioformate), an alkoxy, a phosphoryl, a phosphate, a phosphonate, a phosphinate, an amino, an amido, an amidine, an imine, a cyano, a nitro, an azido, a silyl ether, a sulfhydryl, an alkylthio, a sulfate, a sulfonate, a sulfamoyl, a sulfonamide, a sulfonyl, a heterocyclyl, an aralkyl, or an aromatic or heteroaromatic moiety.

The term "carbamate" is art-recognized and refers to a group

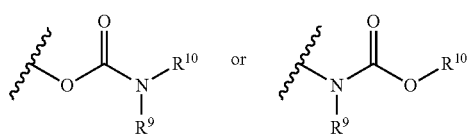

wherein $R^9$ and $R^{10}$ independently represent hydrogen or a hydrocarbyl group, such as an alkyl group, or $R^9$ and $R^{10}$ taken together with the intervening atom(s) complete a heterocycle having from 4 to 8 atoms in the ring structure.

The term "carbocycle" refers to a saturated or unsaturated ring in which each atom of the ring is carbon. The term carbocycle includes both aromatic carbocycles and non-aromatic carbocycles. Non-aromatic carbocycles include both cycloalkyl and cycloalkenyl rings. "Carbocycle" includes 5-7 membered monocyclic and 8-12 membered bicyclic rings. Each ring of a bicyclic carbocycle may be selected from saturated, unsaturated and aromatic rings. Carbocycle includes bicyclic molecules in which one, two or three or more atoms are shared between the two rings. The term "fused carbocycle" refers to a bicyclic carbocycle in which each of the rings shares two adjacent atoms with the other ring. Each ring of a fused carbocycle may be selected from saturated, unsaturated and aromatic rings. In an exemplary embodiment, an aromatic ring, e.g., phenyl, may be fused to a saturated or unsaturated ring, e.g., cyclohexane, cyclopentane, or cyclohexene. Any combination of saturated, unsaturated and aromatic bicyclic rings, as valence permits, is included in the definition of carbocyclic. Exemplary "carbocycles" include cyclopentane, cyclohexane, bicyclo[2.2.1]heptane, 1,5-cyclooctadiene, 1,2,3,4-tetrahydronaphthalene, bicyclo[4.2.0]oct-3-ene, naphthalene and adamantane. Exemplary fused carbocycles include decalin, naphthalene, 1,2,3,4-tetrahydronaphthalene, bicyclo[4.2.0]octane, 4,5,6,7-tetrahydro-1H-indene and bicyclo[4.1.0]hept-3-ene. "Carbocycles" may be substituted at any one or more positions capable of bearing a hydrogen atom.

The term "carbocyclylalkyl", as used herein, refers to an alkyl group substituted with an carbocycle group.

The term "carbonate" is art-recognized and refers to a group $-OCO_2-R^4$, wherein $R^4$ represents a hydrocarbyl group.

The term "carboxy", as used herein, refers to a group represented by the formula $CO_2H$.

A "cycloalkyl" group is a cyclic hydrocarbon, which is completely saturated. "Cycloalkyl" includes monocyclic and bicyclic rings. Typically, a monocyclic cycloalkyl group has from 3 to about 10 carbon atoms, from 3 to 8 carbon atoms, or more typically from 3 to 6 carbon atoms, unless otherwise defined. The second ring of a bicyclic cycloalkyl may be selected from saturated, unsaturated and aromatic rings. Cycloalkyl includes bicyclic substituents in which one, two or three or more atoms are shared between the two rings (e.g., fused bicyclic substituents, bridged bicyclic substituents, and spirocyclic substituents).

The term "fused bicyclic substituent" refers to a bicyclic substituent in which two rings share two adjacent atoms. In other words, the rings share one covalent bond, i.e., the so-called bridgehead atoms are directly connected. For example, in a fused cycloalkyl, each of the rings shares two adjacent atoms with the other ring, and the second ring of a fused bicyclic cycloalkyl may be selected from saturated, unsaturated and aromatic rings.

A "cycloalkenyl" group is a cyclic hydrocarbon containing one or more double bonds.

The term "bridged bicyclic substituent" refers to a bicyclic substituent in which the two rings share three or more atoms, separating the two bridgehead atoms by a bridge containing at least one atom. For example, norbornanyl, also known as bicyclo[2.2.1]heptanyl, can be thought of as a pair of cyclopentane rings each sharing three of their five carbon atoms. The term "spirocyclic substituent" refers to a bicyclic substituent in which the two rings have only one single atom, the Spiro atom, in common.

The term "diazo", as used herein, refers to a group represented by the formula $=N=N$.

The term "disulfide" is art-recognized and refers to a group $-S-S-R^4$, wherein $R^4$ represents a hydrocarbyl group.

The term "enol ester", as used herein, refers to a group $-C(O)O-C(R^4)=C(R^4)_2$ wherein $R^4$ represents a hydrocarbyl group.

The term "ester", as used herein, refers to a group $-C(O)OR^{10}$ wherein $R^{10}$ represents a hydrocarbyl group.

The term "ether", as used herein, refers to a hydrocarbyl group linked through an oxygen to another hydrocarbyl group. Accordingly, an ether substituent of a hydrocarbyl group may be hydrocarbyl-O—. Ethers may be either symmetrical or unsymmetrical. Examples of ethers include, but are not limited to, heterocycle-O-heterocycle and aryl-O-heterocycle. Ethers include "alkoxyalkyl" groups, which may be represented by the general formula alkyl-O-alkyl.

The terms "halo" and "halogen" as used herein means halogen and includes chloro, fluoro, bromo, and iodo.

The term "heteroalkyl", as used herein, refers to a saturated or unsaturated chain of carbon atoms and at least one heteroatom, for example, wherein no two heteroatoms are adjacent.

The terms "heteroaralkyl" and "hetaralkyl", as used herein, refers to an alkyl group substituted with a hetaryl group.

The terms "heteroaryl" and "hetaryl" include substituted or unsubstituted aromatic single ring structures, preferably 5- to 7-membered rings, more preferably 5- to 6-membered rings, whose ring structures include at least one heteroatom, preferably one to four heteroatoms, more preferably one or two heteroatoms. The terms "heteroaryl" and "hetaryl" also include polycyclic ring systems having two or more cyclic rings in which two or more carbons are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls. Heteroaryl groups include 5- to 10-membered cyclic or polycyclic ring systems, such as pyrrole, furan, thiophene, imidazole, oxazole, thiazole, pyrazole, pyridine, pyrazine, pyridazine, and pyrimidine, and the like.

The term "heteroatom" as used herein means an atom of any element other than carbon or hydrogen. Preferred heteroatoms are nitrogen, oxygen, and sulfur.

The terms "heterocyclyl", "heterocycle", and "heterocyclic" refer to substituted or unsubstituted non-aromatic ring structures, preferably 3- to 10-membered rings, preferably 3- to 7-membered rings, more preferably 5- to 6-membered rings, in some instances, most preferably a 5-membered ring, in other instances, most preferably a 6-membered ring, which ring structures include at least one heteroatom, preferably one to four heteroatoms, more preferably one or two heteroatoms. The terms "heterocyclyl" and "heterocyclic" also include 5- to 10-membered polycyclic ring systems having two or more cyclic rings in which two or more carbons are common to two adjoining rings wherein at least one of the rings is heterocyclic, e.g., the other cyclic rings can be cycloalkyls, cycloalkenyls, cycloalkynyls, aryls, heteroaryls, and/or heterocyclyls. Heterocyclyl groups include, for example, pyrrolidine, piperidine, piperazine, pyrrolidine, tetrahydropyran, tetrahydrofuran, morpholine, lactones, lactams, oxazoles, imidazolines, and the like.

The term "heterocyclylalkyl", as used herein, refers to an alkyl group substituted with a heterocycle group.

The term "hydrocarbyl", as used herein, refers to a group that is bonded through a carbon atom that does not have a =O or =S substituent, and typically has at least one carbon-hydrogen bond and a primarily carbon backbone, but may optionally include heteroatoms. Thus, groups like methyl, ethoxyethyl, 2-pyridyl, and trifluoromethyl are considered to be hydrocarbyl for the purposes of this application, but substituents such as acetyl (which has a =O substituent on the linking carbon) and ethoxy (which is linked through oxygen, not carbon) are not. Hydrocarbyl groups include, but are not limited to aryl, heteroaryl, carbocycle, heterocyclyl, alkyl, alkenyl, alkynyl, and combinations thereof.

The term "hydroxyalkyl", as used herein, refers to an alkyl group substituted with a hydroxy group.

The term "lower" when used in conjunction with a chemical moiety, such as, acyl, acyloxy, alkyl, alkenyl, alkynyl, or alkoxy is meant to include groups where there are ten or fewer non-hydrogen atoms in the substituent, preferably six or fewer, more preferably three or fewer. A "lower alkyl", for example, refers to an alkyl group that contains ten or fewer carbon atoms, preferably six or fewer, more preferably three or fewer. In certain embodiments, acyl, acyloxy, alkyl, alkenyl, alkynyl, or alkoxy substituents defined herein are respectively lower acyl, lower acyloxy, lower alkyl, lower alkenyl, lower alkynyl, or lower alkoxy, whether they appear alone or in combination with other substituents, such as in the recitations hydroxyalkyl and aralkyl (in which case, for example, the atoms within the aryl group are not counted when counting the carbon atoms in the alkyl substituent).

The term "orthoester" as used herein is art-recognized and refers to a group $C(OR^4)_3$, wherein each $R^4$ independently represents hydrogen or a hydrocarbyl, such as alkyl, or any occurrence of $R^4$ taken together with another and the intervening atom(s) complete a heterocycle having from 4 to 8 atoms in the ring structure.

The term "phosphoester", as used herein, refers to a group —OP(=O)(OH)$_2$.

The term "phosphodiester", as used herein, refers to a group —OP(=O)(OR$^4$)$_2$ wherein $R^4$ represents a hydrocarbyl group.

The terms "polycyclyl", "polycycle", and "polycyclic" refer to two or more rings (e.g., cycloalkyls, cycloalkenyls, cycloalkynyls, aryls, heteroaryls, and/or heterocyclyls) in which two or more atoms are common to two adjoining rings, e.g., the rings are "fused rings". Each of the rings of the polycycle can be substituted or unsubstituted. In certain embodiments, each ring of the polycycle contains from 3 to 10 atoms in the ring, preferably from 5 to 7.

The term "pseudohalide," as used herein, means a polyatomic analogue of a halide. Preferred pseudohalides include sulfonates, e.g., arylsulfonates and alkylsulfonates, such as p-toluenesulfonate and trifluoromethanesulfonate.

The term "selenide", as used herein, is equivalent to an ether, wherein the oxygen is replaced with a selenium.

The term "selenoxide" is art-recognized and refers to the group —Se(O)—R$^4$, wherein R$^4$ represents a hydrocarbyl.

The term "siloxane" is art-recognized and refers to a group with an Si—O—Si linkage, such as the group —Si($R^4$)$_2$—O—Si—($R^4$)$_3$, wherein each $R^4$ independently represents hydrogen or hydrocarbyl, such as alkyl, or two $R^4$ taken together with the intervening atom(s) complete a heterocycle having from 4 to 8 atoms in the ring structure.

The term "silyl" refers to a silicon moiety with three hydrocarbyl moieties attached thereto.

The term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this disclosure, the heteroatoms such as nitrogen may have hydrogen substituents and/or any permissible substituents of organic compounds described herein which satisfy the valences of the heteroatoms. Substituents can include any substituents described herein, for example, a halogen, a hydroxyl, an oxo, a carbonyl (such as a carboxyl, an alkoxycarbonyl, a formyl, or an acyl), a thiocarbonyl (such as a thioester, a thioacetate, or a thioformate), an alkoxy, a phosphoryl, a phosphate, a phosphonate, a phosphinate, an alkyl, an amino, an amido, an amidine, an imine, an oxime, a cyano, a nitro, an azido, a silyl ether, a sulfhydryl, an alkylthio, a sulfate, a sulfonate, a sulfamoyl, a sulfonamido, a sulfonyl, a heterocyclyl, an aralkyl, or an aromatic or heteroaromatic moiety. In preferred embodiments, the substituents on substituted alkyls are selected from $C_1$-$C_6$ alkyl, $C_3$-$C_6$ cycloalkyl, halogen, carbonyl, cyano, or hydroxyl. In more preferred embodiments, the substituents on substituted alkyls are selected from fluoro, carbonyl, cyano, or hydroxyl. It will be understood by those skilled in the art that substituents can themselves be substituted, if appropriate. Unless specifically stated as "unsubstituted," references to chemical moieties herein are understood to include substituted variants. For example, reference to an "aryl" group or moiety implicitly includes both substituted and unsubstituted variants.

The term "sulfate" is art-recognized and refers to the group —OSO$_3$H, or a pharmaceutically acceptable salt thereof.

The term "sulfonamide" is art-recognized and refers to the group represented by the general formulae

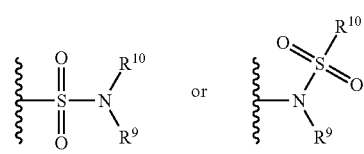

wherein $R^9$ and $R^{10}$ independently represents hydrogen or hydrocarbyl, such as alkyl, or $R^9$ and $R^{10}$ taken together with the intervening atom(s) complete a heterocycle having from 4 to 8 atoms in the ring structure.

The term "sulfoxide" is art-recognized and refers to the group —S(O)$_2$—R$^{10}$, wherein R$^{10}$ represents a hydrocarbyl.

The term "sulfonate" is art-recognized and refers to the group SO₃H, or a pharmaceutically acceptable salt thereof.

The term "sulfone" is art-recognized and refers to the group —S(O)₂—R¹⁰, wherein R¹⁰ represents a hydrocarbyl.

The term "thioalkyl", as used herein, refers to an alkyl group substituted with a thiol group.

The term "thioester", as used herein, refers to a group —C(O)SR¹⁰ or —SC(O)R¹⁰ wherein R¹⁰ represents a hydrocarbyl.

The term "thioether", as used herein, is equivalent to an ether, wherein the oxygen is replaced with a sulfur.

The term "urea" is art-recognized and may be represented by the general formula

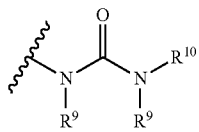

wherein each R⁹ and R¹⁰ independently represents hydrogen or a hydrocarbyl, such as alkyl, or either occurrence of R⁹ taken together with R¹⁰ or the other R⁹ and the intervening atom(s) complete a heterocycle having from 4 to 8 atoms in the ring structure.

"Protecting group" refers to a group of atoms that, when attached to a reactive functional group in a molecule, mask, reduce or prevent the reactivity of the functional group. Typically, a protecting group may be selectively removed as desired during the course of a synthesis. Examples of protecting groups can be found in Greene and Wuts, Protective Groups in Organic Chemistry, 3rd Ed., 1999, John Wiley & Sons, NY and Harrison et al., Compendium of Synthetic Organic Methods, Vols. 1-8, 1971-1996, John Wiley & Sons, NY. Representative nitrogen protecting groups include, but are not limited to, formyl, acetyl, trifluoroacetyl, anisoyl ("An"), benzyl ("Bn"), benzoyl ("Bz"), benzyloxycarbonyl ("CBZ"), tert-butoxycarbonyl ("Boc"), trimethylsilyl ("TMS"), 2-trimethylsilyl-ethanesulfonyl ("TES"), trityl and substituted trityl groups, allyloxycarbonyl, 9-fluorenylmethyloxycarbonyl ("FMOC"), nitro-veratryloxycarbonyl ("NVOC") and the like. Representative hydroxyl protecting groups include, but are not limited to, those where the hydroxyl group is either acylated (esterified) or alkylated such as benzyl and trityl ethers, as well as alkyl ethers, tetrahydropyranyl ethers, trialkylsilyl ethers (e.g., TMS or TIPS groups), glycol ethers, such as ethylene glycol and propylene glycol derivatives and allyl ethers.

The phrase "pharmaceutically acceptable" is art-recognized. In certain embodiments, the term includes compositions, excipients, adjuvants, polymers and other materials and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

"Pharmaceutically acceptable salt" or "salt" is used herein to refer to an acid addition salt or a basic addition salt that is suitable for or compatible with the treatment of patients.

The term "pharmaceutically acceptable acid addition salt" as used herein means any non-toxic organic or inorganic salt of any base compounds disclosed herein. Illustrative inorganic acids that form suitable salts include hydrochloric, hydrobromic, sulfuric and phosphoric acids, as well as metal salts such as sodium monohydrogen orthophosphate and potassium hydrogen sulfate. Illustrative organic acids that form suitable salts include mono-, di-, and tricarboxylic acids such as glycolic, lactic, pyruvic, malonic, succinic, glutaric, fumaric, malic, tartaric, citric, ascorbic, maleic, benzoic, phenylacetic, cinnamic and salicylic acids, as well as sulfonic acids such as p-toluene sulfonic and methanesulfonic acids. Either the mono or di-acid salts can be formed, and such salts may exist in either a hydrated, solvated or substantially anhydrous form. In general, the acid addition salts of compounds disclosed herein are more soluble in water and various hydrophilic organic solvents, and generally demonstrate higher melting points in comparison to their free base forms. The selection of the appropriate salt will be known to one skilled in the art. Other non-pharmaceutically acceptable salts, e.g., oxalates, may be used, for example, in the isolation of compounds of the invention for laboratory use, or for subsequent conversion to a pharmaceutically acceptable acid addition salt.

The term "pharmaceutically acceptable basic addition salt" as used herein means any non-toxic organic or inorganic base addition salt of any acid compounds of the invention, or any of their intermediates. Illustrative inorganic bases that form suitable salts include lithium, sodium, potassium, calcium, magnesium, or barium hydroxide. Illustrative organic bases which form suitable salts include aliphatic, alicyclic, or aromatic organic amines such as methylamine, trimethylamine and picoline or ammonia. The selection of the appropriate salt will be known to a person skilled in the art.

Many of the compounds useful in the methods and compositions of this disclosure have at least one stereogenic center in their structure. This stereogenic center may be present in a R or a S configuration, said R and S notation is used in correspondence with the rules described in Pure Appl. Chem. (1976), 45, 11-30. The disclosure contemplates all stereoisomeric forms such as enantiomeric and diastereoisomeric forms of the compounds, salts, prodrugs or mixtures thereof (including all possible mixtures of stereoisomers). See, e.g., WO 01/062726.

Furthermore, certain compounds which contain alkenyl groups may exist as Z (zusammen) or E (entgegen) isomers. In each instance, the disclosure includes both mixtures and separate individual isomers.

Some of the compounds may also exist in tautomeric forms. Such forms, although not explicitly indicated in the formulae described herein, are intended to be included within the scope of the present disclosure.

II. Description

General Description

This disclosure is based on the discovery of novel C-arylation and novel C-vinylation reactions that generate an α-quaternary substituted lactam. The methods comprise treating a lactam with a chiral nickel (Ni) or palladium (Pd) catalyst, and an aryl halide, heteroaryl halide or a vinyl halide. Use of a ligand, preferably a chiral ligand, enables the construction of quaternary stereocenters on α-substituted lactams to form β-aryl or β-vinyl lactams.

According to some embodiments of the present disclosure, a wide range of structurally-diverse, functionalized products are prepared by a stereoselective method of nickel or palladium-catalyzed enantioselective arylation or vinylation. This chemistry is useful in the synthesis of lactams, and for the construction of novel building blocks for medicinal and polymer chemistry.

This disclosure is also based, in part, on the discovery of novel decarboxylative asymmetric allylic alkylation reactions that generate α-quaternary substituted piperazinones, tetrahydropyrimidinones, and diazepanones. The methods comprise enolate functionalization of protected 3-(allyloxycarbonyl)piperazine-2-ones, 5-(allyloxycarbonyl)tetrahydropyrimidin-4-one, and 6-(allyloxycarbonyl)-1,4-diazepan-5-ones, followed by decarboxylative asymmetric allylic alkylation. This chemistry is useful in the construction of novel building blocks for medicinal chemistry, such as in the synthesis of β-lactams (such as in β-lactam antibiotics), hexahydropyrimidines, and benzodiazepines. For example, tetrahydropyrimidinones may be reductively transformed into hexahydropyrimidines, which are found in bioactive molecules such as the antibiotic hexetidine and the macrocyclic natural product verbamethine. [A. Guggisberg, K. Drandarov, M. Hesse, *Helvetica Chimica Acta* 2000, 83, 3035-3042; K. Drandarov, A. Guggisberg, M. Hesse, *Helvetica Chimica Acta* 2002, 85, 979-989.] In addition, diazepane heterocycles are also found in the antipsychotic clozapine and the anti-insomnia drug suvorexant.

Pharmaceutical Agents and Compositions

Also provided herein are methods of synthesizing a pharmaceutical agent and/or composition, comprising preparing a compound of formula (I), (Ia), (Ib), (IVa), or (IVb) as defined below, according to a method as described herein and synthesizing the pharmaceutical agent and/or composition from the compound of formula (I), (Ia), (Ib), (IVa), or (IVb), e.g., by carrying out one or more chemical reactions on the compound of formula (I), (Ia), (Ib), (IVa), or (IVb) and/or combining the pharmaceutical agent with one or more pharmaceutically acceptable carriers and/or excipients.

The pharmaceutical agent and/or composition prepared from the compound of formula (I), (Ia), (Ib), (IVa), or (IVb) may be utilized to treat an individual in need thereof. In certain embodiments, the individual is a mammal such as a human, or a non-human mammal. When administered to an animal, such as a human, the composition or the compound is preferably administered as a pharmaceutical composition comprising, for example, a compound of the invention and a pharmaceutically acceptable carrier. Pharmaceutically acceptable carriers are well known in the art and include, for example, aqueous solutions such as water or physiologically buffered saline or other solvents or vehicles such as glycols, glycerol, oils such as olive oil, or injectable organic esters. In preferred embodiments, when such pharmaceutical compositions are for human administration, particularly for invasive routes of administration (i.e., routes, such as injection or implantation, that circumvent transport or diffusion through an epithelial barrier), the aqueous solution is pyrogen-free, or substantially pyrogen-free. The excipients can be chosen, for example, to effect delayed release of an agent or to selectively target one or more cells, tissues or organs. The pharmaceutical composition can be in dosage unit form such as tablet, capsule (including sprinkle capsule and gelatin capsule), granule, lyophile for reconstitution, powder, solution, syrup, suppository, injection or the like. The composition can also be present in a transdermal delivery system, e.g., a skin patch. The composition can also be present in a solution suitable for topical administration, such as a lotion, cream, or ointment.

Methods of preparing these formulations or compositions include the step of bringing into association an active compound, such as a compound of the invention, with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

III. Methods of the Disclosure

In certain aspects, the present disclosure provides for the preparation of a compound of formula (I):

In certain embodiments, the invention relates to a method for the preparation of a compound of formula (I):

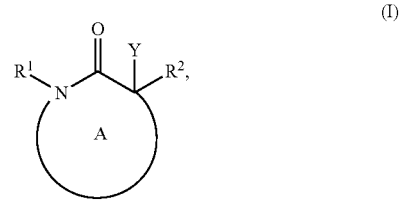

comprising treating a compound of formula (II):

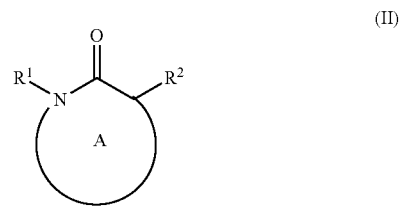

or a salt thereof;
with a Pd or Ni catalyst comprising a chiral ligand;
an optionally substituted aryl halide, optionally substituted aryl pseudohalide, optionally substituted heteroaryl halide, an optionally substituted heteroaryl pseudohalide, or

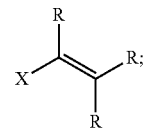

and
a base;
wherein, as valence and stability permit,
ring A represents an optionally substituted heterocycloalkyl, or heterocycloalkenyl group;
R in each occurrence independently represents optionally substituted alkyl, cycloalkyl, (cycloalkyl)alkyl, aryl, aralkyl, heteroaryl, heteroaralkyl, —OR$^{10}$, —SR$^{10}$, or —NR$^{10}$R$^{11}$;
R$^1$ represents hydrogen or optionally substituted alkyl, cycloalkyl, (cycloalkyl)alkyl, aryl, aralkyl, heteroaryl, heteroaralkyl, alkenyl, alkynyl, —C(O)alkyl, —C(O)aryl, —C(O)aralkyl, —C(O)heteroaryl, —C(O)heteroaralkyl, —C(O)O(alkyl), —C(O)O(aryl), —C(O)O(aralkyl), —C(O)O(heteroaryl), —C(O)O(heteroaralkyl), —S(O)$_2$(aryl), —S(O)$_2$(alkyl), —S(O)$_2$(haloalkyl), —OR$^{10}$, —SR$^{10}$, or —NR$^{10}$R$^{11}$;
or R$^1$ taken together with a substituent on ring A and the intervening atoms, form an optionally substituted aryl, heteroaryl, cycloalkyl, cycloalkenyl, heterocycloalkyl, or heterocycloalkenyl group;

or a substituent on ring A taken together with another substituent on ring A and the intervening atoms, form an optionally substituted aryl, heteroaryl, cycloalkyl, cycloalkenyl, heterocycloalkyl, or heterocycloalkenyl group;

$R^2$ represents substituted or unsubstituted alkyl, alkenyl, alkynyl, aralkyl, aralkenyl, aryl, heteroaralkyl, heteroaralkenyl, heteroaryl, (cycloalkyl)alkyl, cycloalkyl, (heterocycloalkyl)alkyl, heterocycloalkyl, alkoxy, amino, or halo;

$R^{10}$ and $R^{11}$ are independently selected for each occurrence from hydrogen or substituted or unsubstituted alkyl, aralkyl, aryl, heteroaralkyl, heteroaryl, (cycloalkyl)alkyl, cycloalkyl, (heterocycloalkyl)alkyl, heterocycloalkyl, alkenyl, and alkynyl;

X is a halogen or pseudohalide; and

Y represents optionally substituted aryl, optionally substituted heteroaryl, or

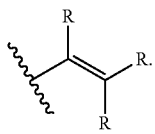

In certain embodiments, the compound of formula (I) is represented by formula (Ia):

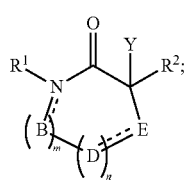

and the compound of formula (II) is represented by formula (IIa):

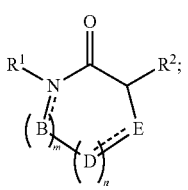

wherein:

B, D, and E independently for each occurrence represent, as valence permits, O, S, $NR^4$, $CR^5R^6$, —C(O), $CR^5$, or N; provided that no two adjacent occurrences of N, B, D, and E are $NR^4$, O, S, or N;

$R^4$ represents hydrogen or optionally substituted alkyl, cycloalkyl, (cycloalkyl)alkyl, aryl, aralkyl, heteroaryl, heteroaralkyl, alkenyl, alkynyl, —C(O)alkyl, —C(O)aryl, —C(O)aralkyl, —C(O)heteroaryl, —C(O)heteroaralkyl, —C(O)O(alkyl), —C(O)O(aryl), —C(O)O(aralkyl), —C(O)O(heteroaryl), —C(O)O(heteroaralkyl), —S(O)$_2$(aryl), —S(O)$_2$(alkyl), —S(O)$_2$(haloalkyl), —OR$^{10}$, —SR$^{10}$, or —NR$^{10}$R$^{11}$;

$R^5$ and $R^6$ each independently represent hydrogen, hydroxyl, halogen, nitro, alkyl, cycloalkyl, (cycloalkyl)alkyl, aryl, aralkyl, heteroaryl, heteroaralkyl, (heterocycloalkyl)alkyl, heterocycloalkyl, alkenyl, alkynyl, cyano, carboxyl, sulfate, amino, alkoxy, aryloxy, arylalkoxy, alkylamino, alkylthio, hydroxyalkyl, alkoxyalkyl, aminoalkyl, thioalkyl, haloalkyl, ether, thioether, ester, amido, thioester, carbonate, carbamate, urea, sulfonate, sulfone, sulfoxide, sulfonamide, acyl, acyloxy, or acylamino;

or any two occurrences of $R^1$, $R^4$, $R^5$, and $R^6$ on adjacent N, B, D, or E groups, taken together with the intervening atoms, form an optionally substituted aryl, heteroaryl, cycloalkyl, cycloalkenyl, heterocycloalkyl, or heterocycloalkenyl group;

each occurrence of ⹀ independently represents a double bond or a single bond as permitted by valence; and m and n are integers each independently selected from 0, 1, and 2.

In some embodiments, the sum of m and n is 0, 1, 2, or 3.

In exemplary embodiments, each occurrence of B, D, and E is independently —$CR^5R^6$—, —$CR^5$—, or —C(O)—.

In certain embodiments, E is —$CR^5$—; and the sum of m and n is 0.

In certain embodiments, $R^1$ is selected from optionally substituted alkyl, aryl, aralkyl, heteroaryl, heteroaralkyl, alkenyl, —C(O)alkyl, —C(O)aryl, —C(O)aralkyl, —C(O)heteroaryl, —C(O)heteroaralkyl, —C(O)O(alkyl), —C(O)O(aryl), —C(O)O(aralkyl), —C(O)O(heteroaryl), —C(O)O(heteroaralkyl), and —S(O)$_2$(aryl); and $R^5$ is selected from hydrogen, hydroxyl, halogen, alkyl, cycloalkyl, (cycloalkyl)alkyl, aryl, aralkyl, heteroaryl, heteroaralkyl, (heterocycloalkyl)alkyl, heterocycloalkyl, alkenyl, alkynyl, amino, alkoxy, aryloxy, alkylamino, amido, and acylamino; or $R^1$ and the occurrence of $R^5$ on E are taken together to form an optionally substituted heteroaryl, heterocycloalkyl, or heterocycloalkenyl group.

In certain embodiments, $R^1$ is selected from optionally substituted alkyl, aryl, aralkyl, alkenyl, —C(O)alkyl, —C(O)O(alkyl), —C(O)O(aryl), —C(O)O(aralkyl), and —S(O)$_2$(aryl), for example, substituted aryl.

In some embodiments, $R^1$ and the occurrence of $R^5$ on E are taken together to form an optionally substituted heteroaryl, heterocycloalkyl, or heterocycloalkenyl group, for example, $R^1$ and the occurrence of $R^5$ on E are taken together to form an optionally substituted heterocycloalkyl, or heterocycloalkenyl group.

In some embodiments, the compound of formula (I) is represented by formula (Ib):

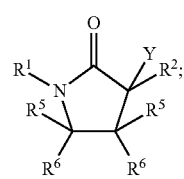

and the compound of formula (II) is represented by formula (IIb):

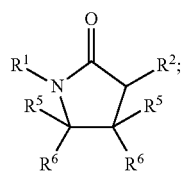

(IIb)

wherein:
R⁵ and R⁶ each independently represent hydrogen, hydroxyl, halogen, nitro, alkyl, cycloalkyl, (cycloalkyl)alkyl, aryl, aralkyl, heteroaryl, heteroaralkyl, (heterocycloalkyl)alkyl, heterocycloalkyl, alkenyl, alkynyl, cyano, carboxyl, sulfate, amino, alkoxy, aryloxy, arylalkoxy, alkylamino, alkylthio, hydroxyalkyl, alkoxyalkyl, aminoalkyl, thioalkyl, haloalkyl, ether, thioether, ester, amido, thioester, carbonate, carbamate, urea, sulfonate, sulfone, sulfoxide, sulfonamide, acyl, acyloxy, or acylamino;
or any two occurrences of R¹, R⁵, and R⁶, taken together with the intervening atoms, form an optionally substituted aryl, heteroaryl, cycloalkyl, cycloalkenyl, heterocycloalkyl, or heterocycloalkenyl group.

In certain embodiments,
R¹ is selected from optionally substituted alkyl, aryl, aralkyl, heteroaryl, heteroaralkyl, alkenyl, —C(O)alkyl, —C(O)aryl, —C(O)aralkyl, —C(O)heteroaryl, —C(O)heteroaralkyl, —C(O)O(alkyl), —C(O)O(aryl), —C(O)O(aralkyl), —C(O)O(heteroaryl), —C(O)O(heteroaralkyl), and —S(O)₂(aryl); and
R⁵ is selected from hydrogen, hydroxyl, halogen, alkyl, cycloalkyl, (cycloalkyl)alkyl, aryl, aralkyl, heteroaryl, heteroaralkyl, (heterocycloalkyl)alkyl, heterocycloalkyl, alkenyl, alkynyl, amino, alkoxy, aryloxy, alkylamino, amido, and acylamino; or
R¹ and R⁵ on E are taken together to form an optionally substituted heteroaryl, heterocycloalkyl, or heterocycloalkenyl group.

In certain embodiments, R¹ is selected from optionally substituted alkyl, aryl, aralkyl, alkenyl, —C(O)alkyl, —C(O)O(alkyl), —C(O)O(aryl), —C(O)O(aralkyl), and —S(O)₂(aryl), for example, substituted aryl.

In some embodiments, R¹ and the occurrence of R⁵ on E are taken together to form an optionally substituted heteroaryl, heterocycloalkyl, or heterocycloalkenyl group.

In exemplary embodiments, R² represents substituted or unsubstituted alkyl, alkenyl, alkynyl, aralkyl, aralkenyl, aryl, heteroaralkyl, heteroaralkenyl, heteroaryl, (cycloalkyl)alkyl, cycloalkyl, (heterocycloalkyl)alkyl, heterocycloalkyl, or halo.

In certain embodiments, R² is selected from alkyl, alkenyl, aryl, aralkyl, aralkenyl, and heteroaralkenyl, optionally substituted with halo, alkyl, haloalkyl, hydroxy, alkoxy, aryloxy, arylalkoxy, cyano, nitro, azido, —CO₂H, —C(O)O(alkyl), amino, alkylamino, arylamino, aralkylamino, or amido, for example, R² is selected from alkyl, alkenyl, aryl, aralkyl, aralkenyl, and heteroaralkenyl, optionally substituted with halo, alkyl, haloalkyl, alkoxy, aryloxy, or arylalkoxy.

In some embodiments, the Pd catalyst is Pd(dmdba)₂ or Pd₂(dmdba)₃.

In other embodiments, the Ni(0) catalyst is Ni(COD)₂.

In certain embodiments, the Pd or Ni catalyst is used in an amount from about 0.1 mol % to about 20 mol % relative to the compound of formula (II), for example, an amount from about 1 mol % to about 15 mol % relative to the compound of formula (II), preferably, an amount of about 1 mol %, about 2 mol %, about 3 mol %, about 4 mol %, about 5 mol %, about 6 mol %, about 7 mol %, about 8 mol %, about 9 mol %, about 10 mol %, about 11 mol %, about 12 mol %, about 13 mol %, or about 14 mol % relative to the compound of formula (II).

In some embodiments, the catalyst is a Pd catalyst and the chiral ligand is an enantioenriched ferrocelane ligand, or the catalyst is a Ni catalyst and the chiral ligand is an enantioenriched Josiphos ligand; for example, the enantioenriched ferrocelane ligand is 1,1'-bisR2S,5S)-2,5-diethyl-1-phospholanyliferrocene, 1,1'-bis[(2S,5S)-2,5-dimethyl-1-phospholanyl]ferrocene, or 1,1'-bis[(2S,5S)-2,5-diisopropyl-1-phospholanyl]ferrocene, preferably, the enantioenriched Josiphos ligand is (R)-1-[(S)-2-(dicyclohexylphosphino)ferrocenylethyl]diphenylphosphine.

In certain embodiments, the chiral ligand is used in an amount from about 0.5 mol % to about 50 mol % relative to the compound of formula (II), for example, the chiral ligand is used in an amount from about 1 mol % to about 20 mol % relative to the compound of formula (II), preferably, the chiral ligand is used in an amount of about 5 mol %, about 5.5 mol %, about 6 mol %, about 6.5 mol %, about 7 mol %, about 7.5 mol %, about 8 mol %, about 8.5 mol %, about 9 mol %, about 9.5 mol %, about 10 mol %, about 11 mol %, about 12 mol %, about 13 mol %, about 14 mol %, or about 15 mol % relative to the compound of formula (II).

In some embodiments, the aryl halide or aryl pseudohalide is selected from bromobenzene, chlorobenzene, iodobenzene, phenyl triflate, and chlorotoluene.

In certain embodiments, the base is selected from hexamethyldisilazane sodium salt (NaHMDS), KHMDS, LiHMDS, and lithium tert-butoxide (tBuOLi), preferably LiHMDS, or preferably NaHMDS.

In certain embodiments, the reaction includes dioxane, for example, the dioxane is used in an amount from about 0.01 M to about 0.4 M, preferably, the dioxane is used in an amount of about 0.01 M, about 0.05 M, about 0.1 M, about 0.15 M, about 0.2 M, about 0.25 M, about 0.3 M, about 0.35 M, or about 0.4 M.

In preferred embodiments, the compound of formula (I) is enantioenriched.

In certain preferred embodiments, no aryl nitrile is used in the method.

In certain embodiments, the invention relates to a compound of formula (I) made by any of the methods described herein.

In some embodiments, the invention relates to a method comprising
preparing a compound of formula (I) according to any of the methods described herein; and
synthesizing a medicinal product from the compound of formula (I).

In certain aspects, the invention relates to a compound of formula (III) or formula (IV):

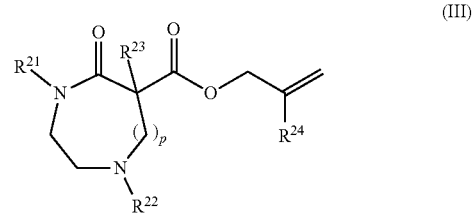

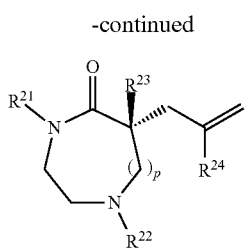

(IV)

wherein, as valence and stability permit, $R^{21}$ is —C(O)aryl or —C(O)heteroaryl, each optionally substituted with alkoxy, alkyl, or haloalkyl;

$R^{22}$ is —C(O)OR$^{22a}$, —C(O)aryl, or —C(O)heteroaryl, wherein each of aryl and heteroaryl are optionally substituted with alkoxy, alkyl, or haloalkyl;

$R^{22a}$ is $C_{1-6}$ alkyl, $C_{6-10}$ aryl, or $C_{5-9}$ heteroaryl, wherein each of aryl and heteroaryl are optionally substituted with alkoxy, alkyl, or haloalkyl;

$R^{23}$ is H, halogen, alkynyl, alkenyl, or $C_{1-6}$ alkyl, each optionally substituted with cyano, OH, alkoxy, aryloxy, acyl, alkoxycarbonyl, halogen, aryl, or —NHC(O)OR$^{23a}$;

$R^{23a}$ is $C_{1-6}$ alkyl, ($C_{6-10}$ aryl)alkyl, or ($C_{5-9}$ heteroaryl)alkyl;

$R^{24}$ is H or halogen; and p is 0 or 1.

In certain embodiments, p is 0, the compound of formula (III) is a compound of formula (IIIa):

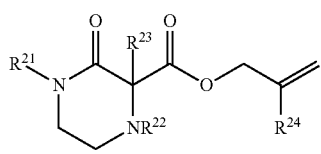

(IIIa)

and the compound of formula (IV) is a compound of formula (IVa):

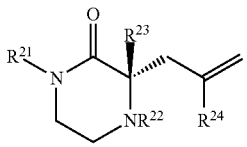

(IVa)

wherein, as valence and stability permit, $R^{21}$ is —C(O)aryl or —C(O)heteroaryl, each optionally substituted with alkoxy, alkyl, or haloalkyl;

$R^{22}$ is —C(O)OR$^{22a}$, —C(O)aryl, or —C(O)heteroaryl, wherein each of aryl and heteroaryl are optionally substituted with alkoxy, alkyl, or haloalkyl;

$R^{22a}$ is $C_{1-6}$ alkyl, $C_{6-10}$ aryl, or $C_{5-9}$ heteroaryl, wherein each of aryl and heteroaryl are optionally substituted with alkoxy, alkyl, or haloalkyl;

$R^{23}$ is H, or $C_{1-6}$ alkyl optionally substituted with cyano, OH, alkoxy, aryloxy, acyl, or NHC(O)OR$^{23a}$;

$R^{23a}$ is $C_{1-6}$ alkyl, ($C_{6-10}$ aryl)alkyl, or ($C_{5-9}$ heteroaryl)alkyl; and $R^{24}$ is H or halogen.

In certain embodiments, $R^{21}$ is Bz or An;

$R^{22}$ is Boc, Cbz, or Bz;

$R^{23}$ is H, CH$_3$, CH$_2$Ph, CH$_2$OBn, CH$_2$CH$_2$CN, CH$_2$CH$_2$C(O)CH$_3$, CH$_2$NHCbz, or CH$_2$NHBoc; and $R^{24}$ is H or Cl.

In certain embodiments, $R^{22}$ is Boc or Cbz.

In some such embodiments, $R^{22}$ is Boc.

In certain preferred embodiments, the compound is:

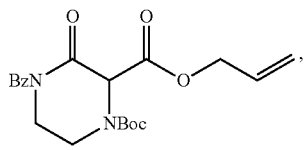

(3a)

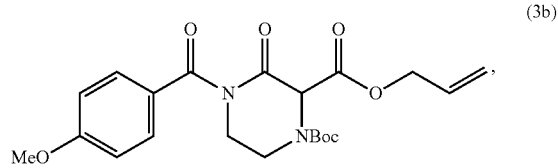

(3b)

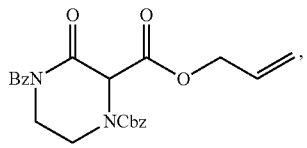

(3c)

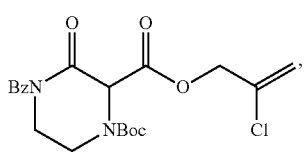

(3d)

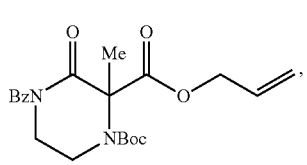

(3e)

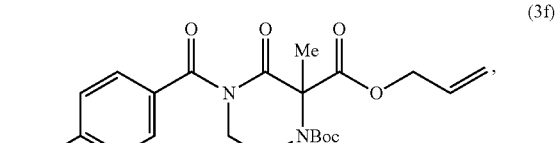

(3f)

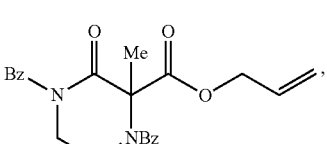

(3g)

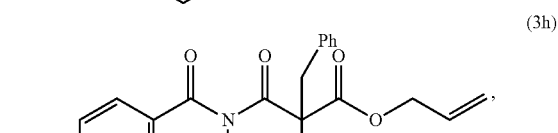

(3h)

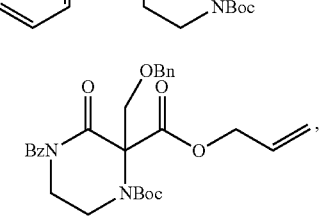

(3i)

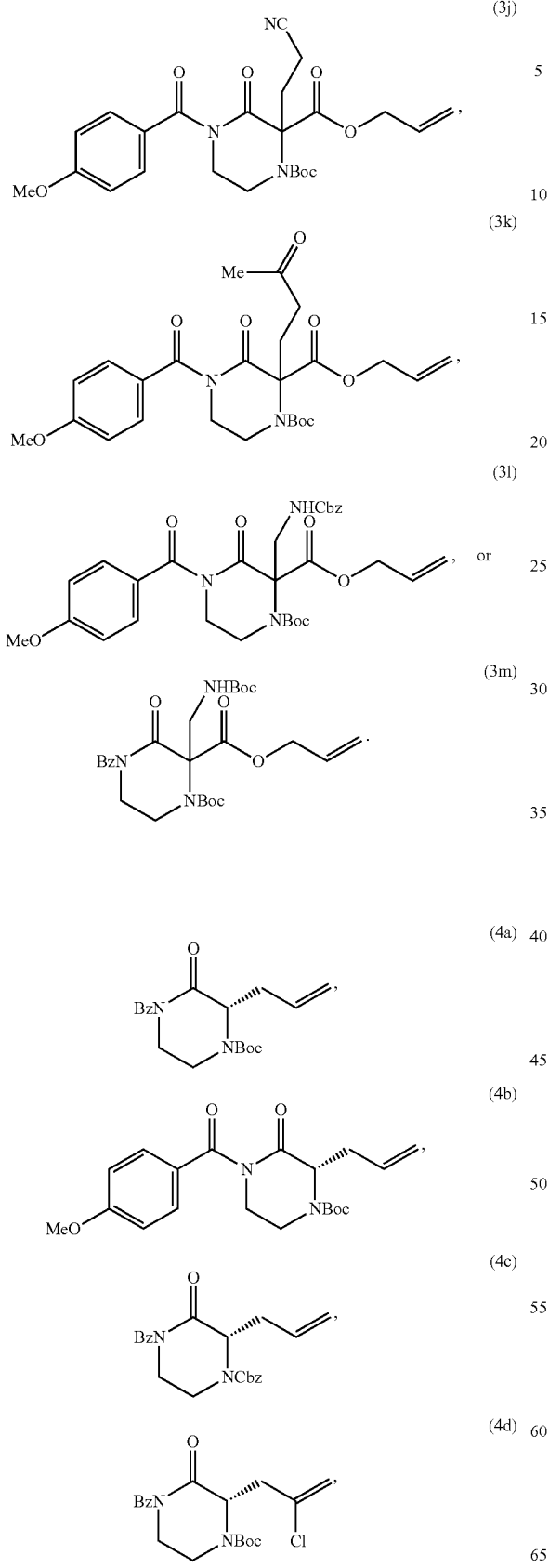

In other preferred embodiments, the compound is:

In certain other preferred embodiments, the compound is

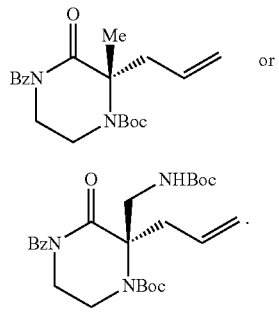

(4e)

or (4m)

In certain embodiments, p is 1, the compound of formula (III) is a compound of formula (IIIb):

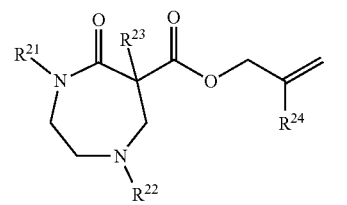

(IIIb)

the compound of formula (IV) is a compound of formula (IVb):

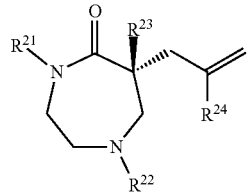

(IVb)

wherein, as valence and stability permit:

R$^{21}$ is —C(O)aryl or —C(O)heteroaryl, each optionally substituted with alkoxy, alkyl, or haloalkyl;

R$^{22}$ is —C(O)OR$^{22a}$;

R$^{22a}$ is C$_{1-6}$ alkyl;

R$^{23}$ is halogen, alkynyl, alkenyl, or C$_{1-6}$ alkyl, each optionally substituted with halogen, OH, cyano, alkoxy, aryloxy, alkoxycarbonyl, or —NHC(O)OR$^{23a}$;

R$^{23a}$ is C$_{1-6}$ alkyl; and

R$^{24}$ is H.

In certain embodiments,

R$^{21}$ is Bz, An, or pCF$_3$Bz;

R$^{22}$ is Boc; and

R$^{23}$ is CH$_3$, CHdPh, CH$_2$CCl=CH$_2$, F, CH$_2$CCH, CH$_2$CH$_2$CO$_2$CH$_3$, CH$_2$CH$_2$CN, or CH$_2$NHBoc.

In certain embodiments, the compound of formula (IIIb) is:

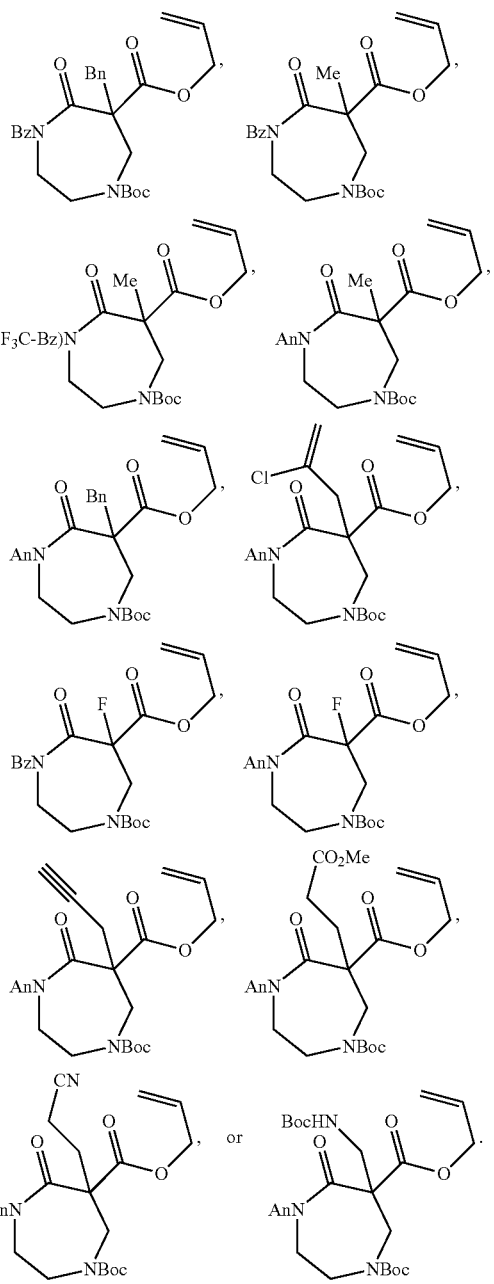

In certain embodiments, the compound of formula (IVb) is:

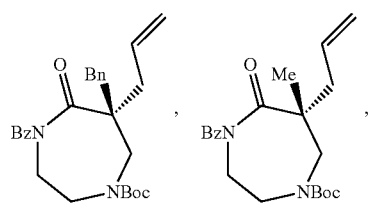

-continued

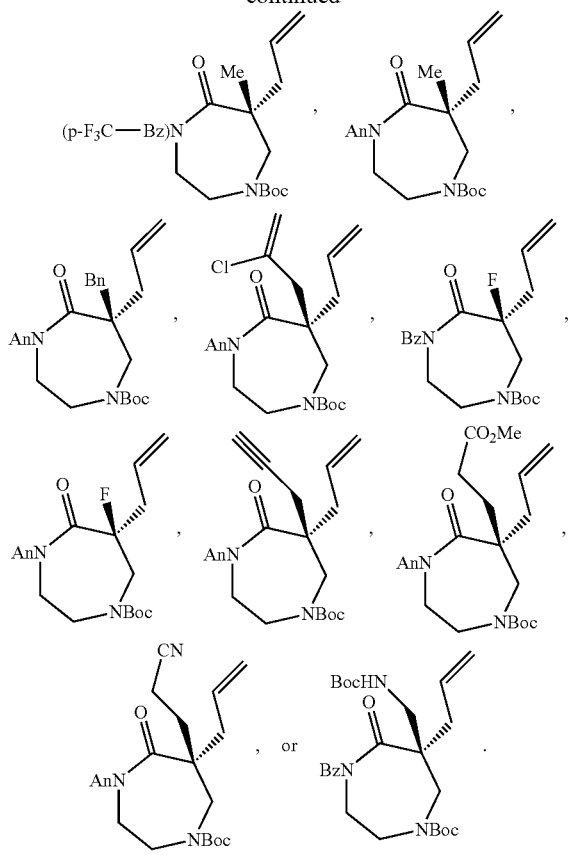

In certain preferred embodiments, the compound of formula (IVb) is

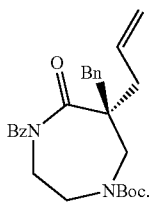

In certain aspects, the invention relates to a compound of formula (V), (VI), or (VII):

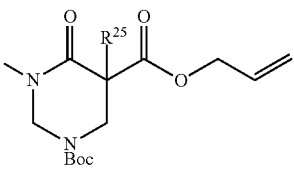

(V)

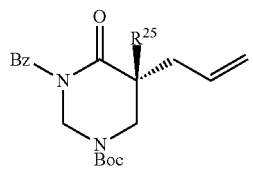

(VI)

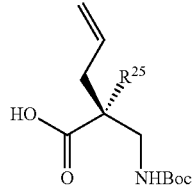

(VII)

wherein, as valence and stability permit, $R^{25}$ is $C_{1-6}$ alkyl, optionally substituted with halogen, OH, CN, aryl, heteroaryl, aryloxy, alkynyl, or —NHC(O)OR$^{25b}$; halogen; or allyl, optionally substituted with halogen;

$R^{25b}$ is $C_{1-6}$ alkyl, $(C_{6-10}$ aryl)alkyl, or $(C_{5-9}$ heteroaryl)alkyl.

In certain embodiments, the compound is:

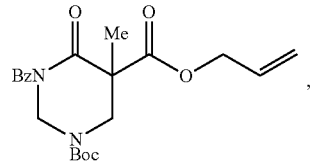

(5a)

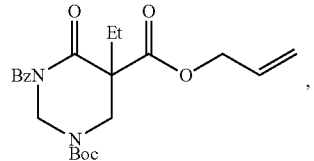

(5b)

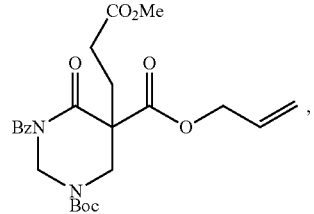

(5c)

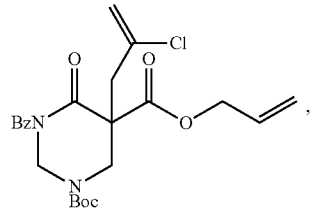

(5d)

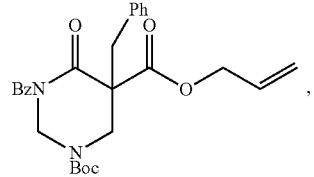

(5e)

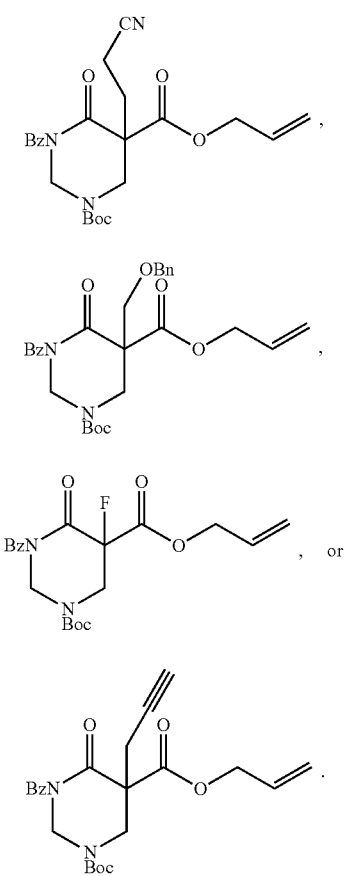
In other embodiments, the compound is:
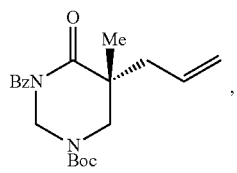
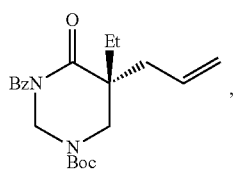
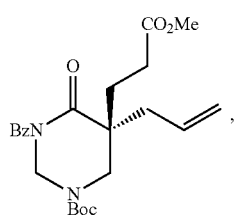
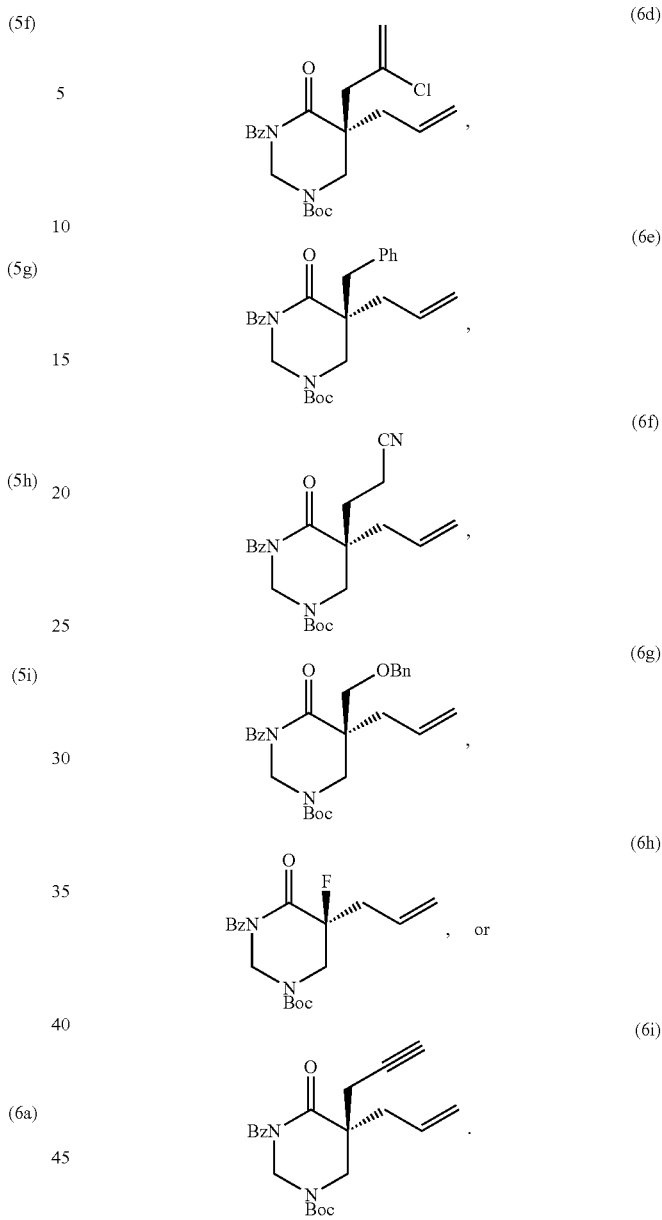
In some such embodiments, the compound is
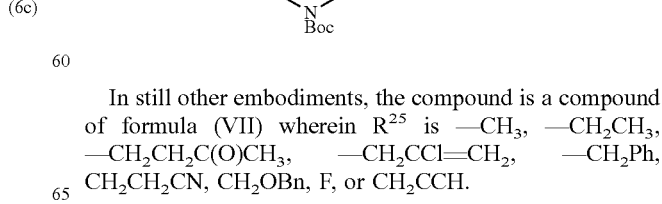
In still other embodiments, the compound is a compound of formula (VII) wherein $R^{25}$ is —CH$_3$, —CH$_2$CH$_3$, —CH$_2$CH$_2$C(O)CH$_3$, —CH$_2$CCl=CH$_2$, —CH$_2$Ph, CH$_2$CH$_2$CN, CH$_2$OBn, F, or CH$_2$CCH.
In certain aspects, the invention is directed to a compound selected from:

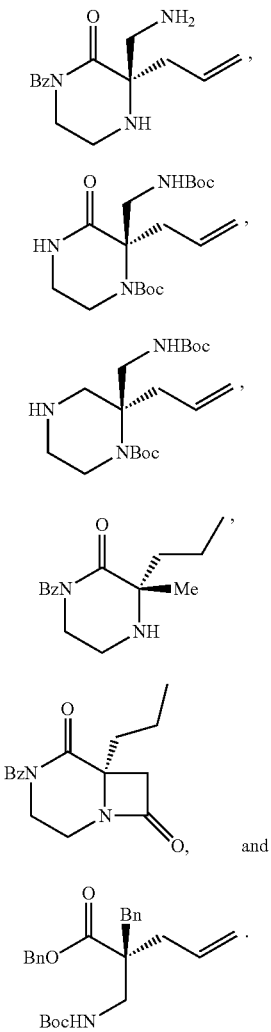

(8), (9), (10), (11), (12), (13)

In certain aspects, the invention relates to compound of formula V in).

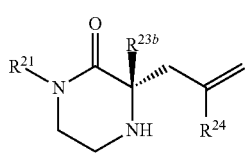

(VIII)

wherein, as valence and stability permit,
$R^{21}$ is —C(O)aryl or —C(O)heteroaryl, each optionally substituted with alkoxy, alkyl, or haloalkyl;
$R^{23b}$ is H, or $C_{1-6}$ alkyl optionally substituted with CN, OH, alkoxy, aryloxy, amino, acyl, or —NHC(O)$R^{23c}$;
$R^{23c}$ is $C_{1-6}$ alkyl, ($C_{6-10}$ aryl)alkyl or ($C_{5-9}$ heteroaryl)alkyl; and
$R^{24}$ is H or halogen.
In certain embodiments,
$R^{21}$ is Bz or An;
$R^{23b}$ is H, CH$_3$, CH$_2$Ph, CH$_2$NHCbz, CH$_2$OBn, CH$_2$CH$_2$CN, CH$_2$CH$_2$C(O)CH$_3$, CH$_2$NH$_2$; and
$R^{24}$ is H or Cl.

In some such embodiments, $R^{21}$ is Bz; $R^{23b}$ is CH$_2$NH$_2$; and $R^{24}$ is H.

In certain aspects, the invention relates to a compound of Formula (IX) or (X):

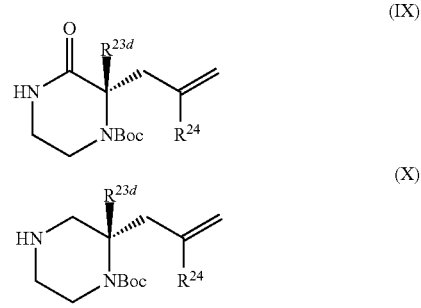

(IX), (X)

wherein, as valence and stability permit,
$R^{23d}$ is H, or is $C_{1-6}$ alkyl optionally substituted with cyano, OH, alkoxy, aryloxy, acyl, —NHC(O)OR$^{23a}$;
$R^{23a}$ is $C_{1-6}$ alkyl, ($C_{6-10}$ aryl)alkyl, or ($C_{5-9}$ heteroaryl)alkyl; and
$R^{24}$ is H or halogen.

In certain embodiments,
$R^{23d}$ is H, CH$_3$, CH$_2$Ph, CH$_2$OBn, CH$_2$CH$_2$OH, CH$_2$CH$_2$C(O)CH$_3$, CH$_2$CH$_2$CH(OH)CH$_3$, CH$_2$NHCBz, or CH$_2$NHBoc; and
$R^{24}$ is H or Cl.

In some such embodiments, $R^{23d}$ is CH$_2$NHBoc; and $R^{24}$ is H.

In certain aspects, the invention relates to a compound of formula (XI):

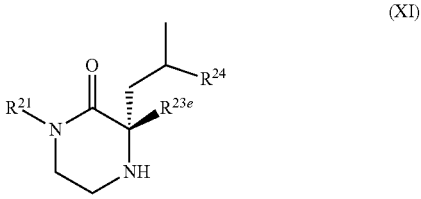

(XI)

wherein, as valence and stability permit,
$R^{21}$ is —C(O)aryl or —C(O)heteroaryl, each optionally substituted with alkoxy, alkyl, or haloalkyl;
$R^{24}$ is H or halogen; and
$R^{23e}$ is H, or is $C_{1-6}$ alkyl optionally substituted with halogen, OH, aryl, aryloxy, CN, acyl, or amino.

In certain embodiments,
$R^{21}$ is Bz or An;
$R^{24}$ is H or Cl; and
$R^{23e}$ is H, CH$_3$, CH$_2$Ph, CH$_2$OBn, CH$_2$CH$_2$CN, CH$_2$CH$_2$C(O)CH$_3$, or CH$_2$NH$_2$.

In some such embodiments, $R^{21}$ is Bz; $R^{23e}$ is CH$_3$; and $R^{24}$ is H.

In certain aspects, the invention relates to a compound of formula (XII):

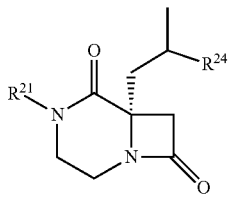

wherein, as valence and stability permit, $R^{21}$ is —C(O)aryl or —C(O)heteroaryl, each optionally substituted with alkoxy, alkyl, or haloalkyl; and $R^{24}$ is H or halogen.

In certain embodiments, $R^{21}$ is Bz or An; and $R^{24}$ is H or Cl.

In certain preferred embodiments, $R^{21}$ is Bz and $R^{24}$ is H.

In certain aspects, the invention relates to a compound of formula (XIII):

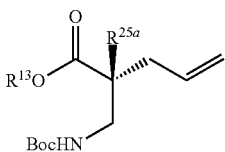

wherein, as valence and stability permit, $R^{25a}$ is $C_{1-6}$ alkyl, optionally substituted with CN, OH, aryl, heteroaryl, aryloxy, or alkynyl; halogen; or allyl, optionally substituted with halogen; and $R^{13}$ is aralkyl or hetaralkyl.

In certain embodiments, $R^{25a}$ is —CH$_3$, —CH$_2$CH$_3$, —CH$_2$CH$_2$C(O)CH$_3$, —CH$_2$CCl=CH$_2$, —CH$_2$Ph, CH$_2$CH$_2$CN, CH$_2$OBn, F, or CH$_2$CCH; and $R^{13}$ is Bn.

In certain preferred embodiments, wherein $R^{25a}$ is CH$_2$Ph and $R^{13}$ is Bn.

In certain aspects, the invention relates to a method for preparation of a compound of formula (IV):

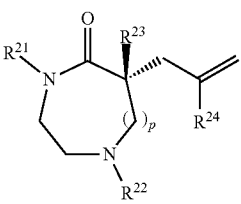

the method comprising:
treating a compound of formula (III)

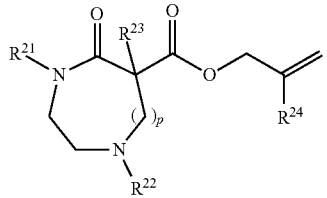

or a salt thereof, with a Pd(0) catalyst and a ligand L under alkylation conditions, wherein, as valence and stability permit, $R^{21}$ is —C(O)aryl or —C(O)heteroaryl, optionally substituted with alkoxy, alkyl, or haloalkyl;

$R^{22}$ is —C(O)OR$^{22a}$, —C(O)aryl, or —C(O)heteroaryl, wherein each of aryl and heteroaryl is optionally substituted with alkoxy, alkyl, or haloalkyl;

$R^{22a}$ is $C_{1-6}$ alkyl, $C_{6-10}$ aryl, or $C_{5-9}$ heteroaryl;

$R^{23}$ is H, halogen, alkynyl, alkenyl, or $C_{1-6}$ alkyl, each optionally substituted with cyano, OH, alkoxy, aryloxy, acyl, alkoxycarbonyl, halogen, aryl, or —NHC(O)OR$^{23a}$;

$R^{23a}$ is $C_{1-6}$ alkyl, ($C_{6-10}$ aryl)alkyl, or ($C_{5-9}$ heteroaryl)alkyl;

$R^{24}$ is H or halogen; and p is 0 or 1.

In certain embodiments, p is 0, the compound of formula (IV) is a compound of formula (IVa):

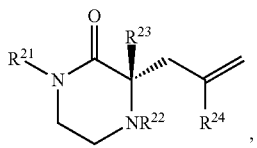

and the compound of formula (III) is a compound of formula (IIIa):

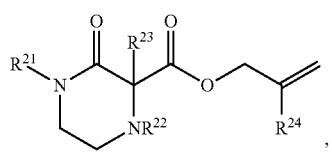

or a salt thereof, wherein, as valence and stability permit, $R^{21}$ is —C(O)aryl or —C(O)heteroaryl, optionally substituted with alkoxy, alkyl, or haloalkyl;

$R^{22}$ is —C(O)OR$^{22a}$, —C(O)aryl, or —C(O)heteroaryl, wherein each of aryl and heteroaryl is optionally substituted with alkoxy, alkyl, or haloalkyl;

$R^{22a}$ is $C_{1-6}$ alkyl, $C_{6-10}$ aryl, or $C_{5-9}$ heteroaryl;

$R^{23}$ is H, or $C_{1-6}$ alkyl optionally substituted with cyano, OH, alkoxy, aryloxy, acyl, or —NHC(O)OR$^{23a}$;

$R^{23a}$ is $C_{1-6}$ alkyl, ($C_{6-10}$ aryl)alkyl, or ($C_{5-9}$ heteroaryl)alkyl; and $R^{24}$ is H or halogen.

In certain embodiments, $R^{21}$ is Bz or An;

$R^{22}$ is Boc, Cbz, or Bz;

$R^{23}$ is H, $CH_3$, $CH_2Ph$, $CH_2OBn$, $CH_2CH_2CN$, $CH_2CH_2C(O)CH_3$, $CH_2NHCbz$, or $CH_2NHBoc$; and $R^{24}$ is H or Cl.

In certain preferred embodiments, $R^{22}$ is Boc or Cbz.

In certain more preferred embodiments, the compound of formula (IVa) is:

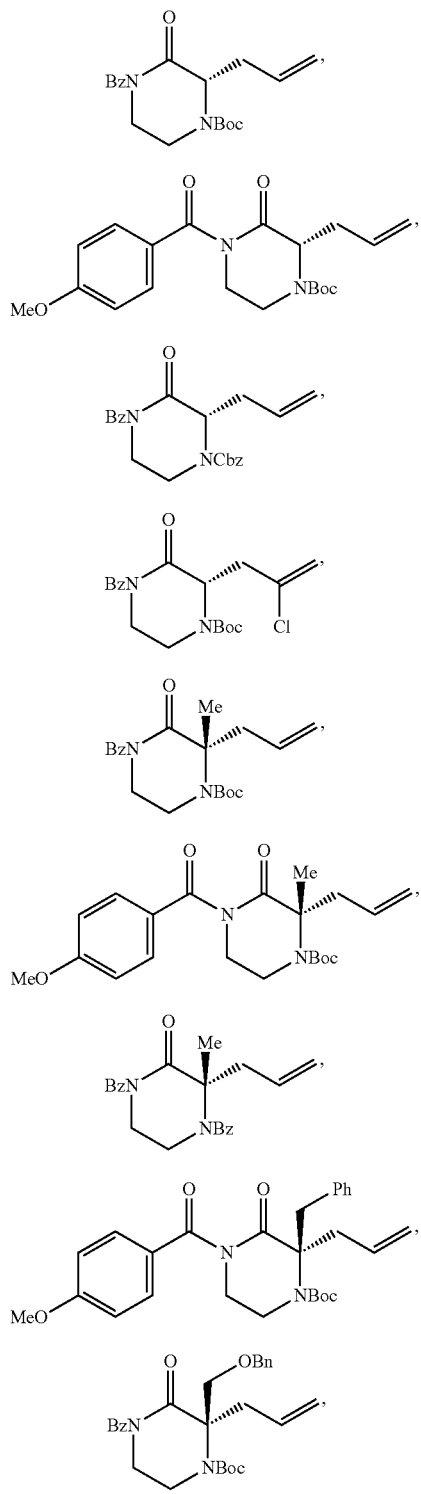

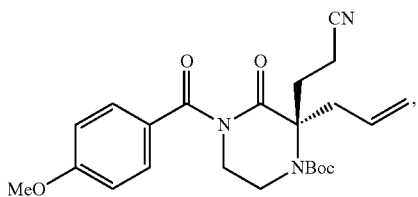

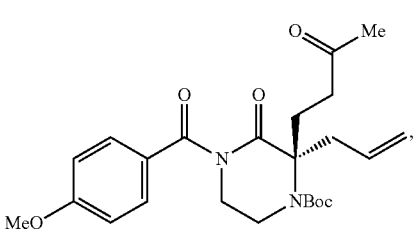

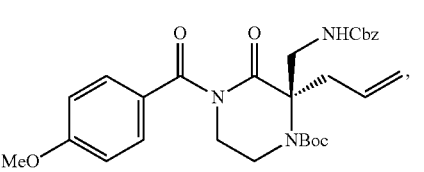

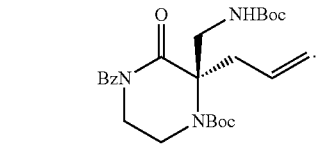

In certain embodiments, the alkylation conditions include reaction in toluene, THF, MTBE, or hexanes, or a combination thereof.

In certain embodiments, the Pd(0) catalyst is $Pd_2(pmdba)_3$ or $Pd_2(dba)_3$.

In certain preferred embodiments, the Pd(0) catalyst is $Pd_2(dba)_3$.

In certain embodiments, the Pd(0) catalyst is used in an amount from about 0.01 mol % to about 10 mol % relative to the compound of formula (IIIa). In certain embodiments, the Pd catalyst is used in an amount from about 0.1 mol % to about 20 mol % relative to the compound of formula (III), for example, an amount from about 1 mol % to about 15 mol % relative to the compound of formula (III), preferably, an amount of about 1 mol %, about 2 mol %, about 3 mol %, about 4 mol %, about 5 mol %, about 6 mol %, about 7 mol %, about 8 mol %, about 9 mol %, about 10 mol %, about 11 mol %, about 12 mol %, about 13 mol %, or about 14 mol % relative to the compound of formula (III).

In certain preferred embodiments, the Pd(0) catalyst is used in an amount of about 4 mol % relative to the compound of formula (IIIa).

In certain embodiments, the ligand L is:

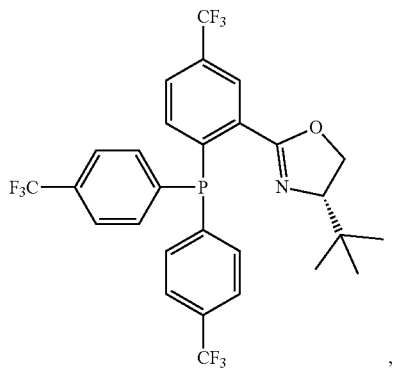
((S)-L1)

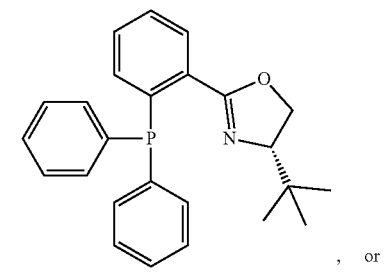
((S)-L2), or

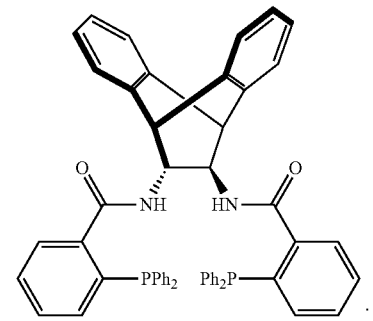
((S,S)-L3)

In certain such embodiments, the ligand L is (S)-L1.

In certain embodiments, the ligand L is used in an amount from about 0.1 mol % to about 100 mol % relative to the compound of formula (IIIa). In certain embodiments, the chiral ligand is used in an amount from about 0.5 mol % to about 50 mol % relative to the compound of formula (IIIa), for example, the chiral ligand is used in an amount from about 1 mol % to about 20 mol % relative to the compound of formula (IIIa), preferably, the chiral ligand is used in an amount of about 5 mol %, about 5.5 mol %, about 6 mol %, about 6.5 mol %, about 7 mol %, about 7.5 mol %, about 8 mol %, about 8.5 mol %, about 9 mol %, about 9.5 mol %, about 10 mol %, about 11 mol %, about 12 mol %, about 13 mol %, about 14 mol %, or about 15 mol % relative to the compound of formula (IIIa). In certain such embodiments, the ligand L is used in an amount of about 10 mol %.

In certain embodiments, the compound of formula (IVa) is enantioenriched.

In certain embodiments, the invention relates to a method of synthesizing a medicinal product, the method comprising:
preparing a compound of formula (IVa) according to any of the methods disclosed herein; and
synthesizing a medicinal product from the compound of formula (IVa).

In certain embodiments,
p is 1;
the compound of formula (IV) is a compound of formula (IVb)

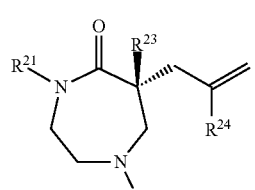
(IVb)

the compound of formula (III) is a compound of formula (IIIb)

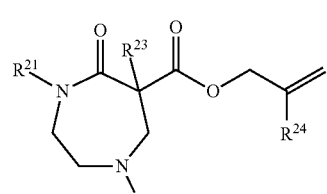
(IIIb)

or a salt thereof,
wherein, as valence and stability permit,
$R^{22}$ is —C(O)OR$^{22a}$;
$R^{22a}$ is $C_{1-6}$ alkyl;
$R^{23}$ is halogen, alkynyl, alkenyl, or $C_{1-6}$ alkyl, each optionally substituted with halogen, OH, cyano, alkoxy, aryloxy, alkoxycarbonyl, or —NHC(O)OR$^{23a}$;
$R^{23a}$ is $C_{1-6}$ alkyl; and
$R^{24}$ is H.

In certain embodiments,
$R^{21}$ is Bz, An, or pCF$_3$Bz;
$R^{22}$ is Boc; and
$R^{23}$ is CH$_3$, CH$_2$Ph, CH$_2$CCl=CH$_2$, F, CH$_2$CCH, CH$_2$CH$_2$CO$_2$CH$_3$, CH$_2$CH$_2$CN, or CH$_2$NHBoc.

In certain embodiments, the compound of formula (IIIb) is:

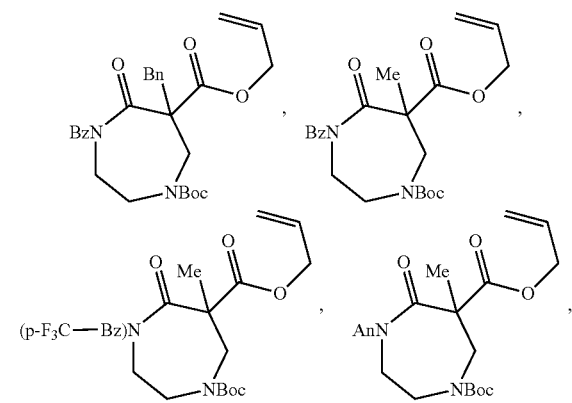

In certain embodiments, the compound of formula (IVb) is:

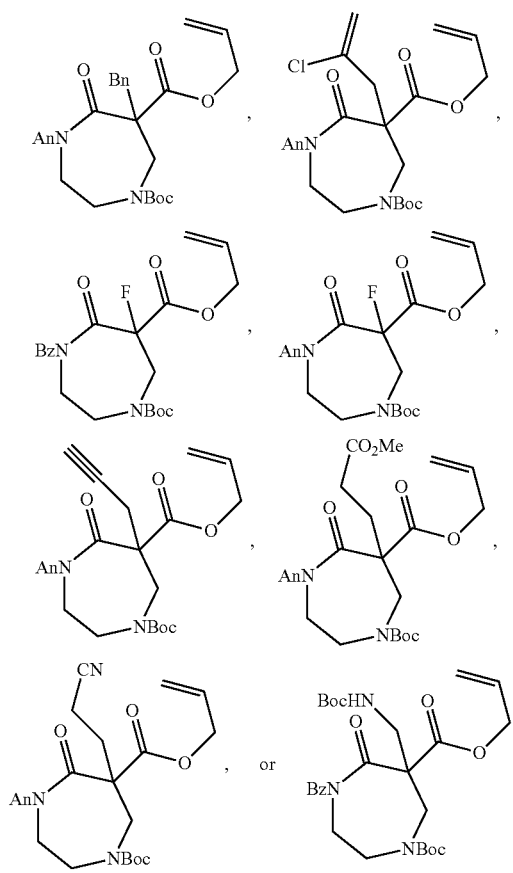
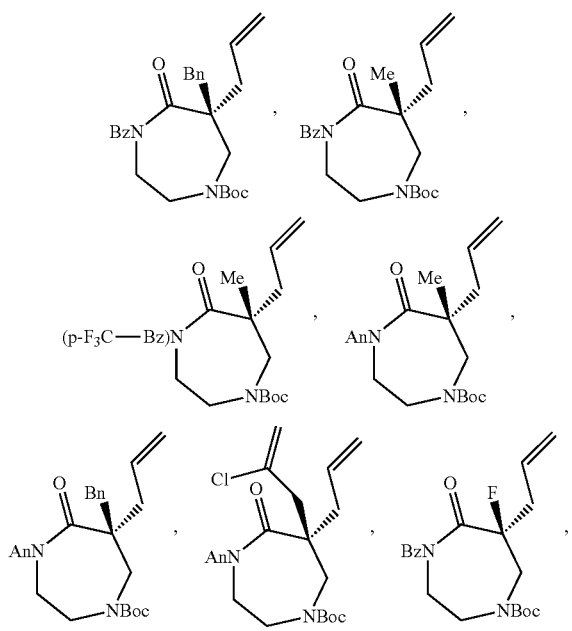

In certain embodiments, the compound of formula (IVb) is

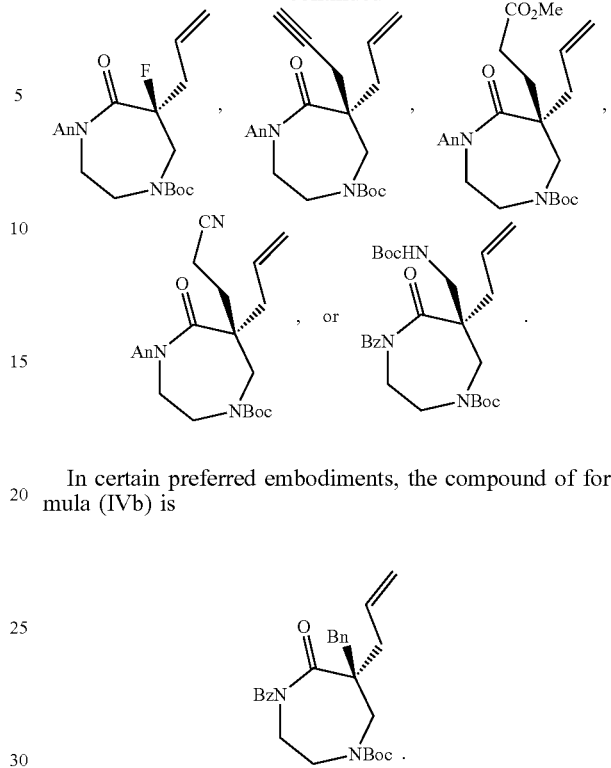

In certain preferred embodiments, the compound of formula (IVb) is

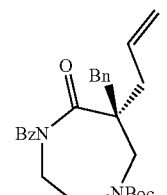

In certain embodiments, the alkylation conditions include reaction in THF, 1,4-dioxane, MTBE, toluene, cyclohexane, or methylcyclohexane, or a combination thereof. In certain preferred embodiments, the alkylation conditions include reaction in methylcyclohexane.

In certain embodiments, the Pd(0) catalyst is $Pd_2(pmdba)_3$ or $Pd_2(dba)_3$. In certain preferred embodiments, the Pd(0) catalyst is $Pd_2(pmdba)_3$.

In certain embodiments, the Pd(0) catalyst is used in an amount from about 0.01 mol % to about 10 mol % relative to the compound of formula (IIIb). In certain embodiments, the Pd(0) catalyst is used in an amount from about 0.1 mol % to about 20 mol % relative to the compound of formula (IIIb), for example, an amount from about 1 mol % to about 15 mol % relative to the compound of formula (IIIb), preferably, an amount of about 1 mol %, about 2 mol %, about 3 mol %, about 4 mol %, about 5 mol %, about 6 mol %, about 7 mol %, about 8 mol %, about 9 mol %, about 10 mol %, about 11 mol %, about 12 mol %, about 13 mol %, or about 14 mol % relative to the compound of formula (IIIb). In certain preferred embodiments, the Pd(0) catalyst is used in an amount of about 4 mol % relative to the compound of formula (IIIb).

In certain embodiments, the ligand L is:

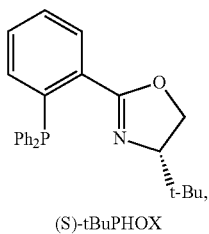

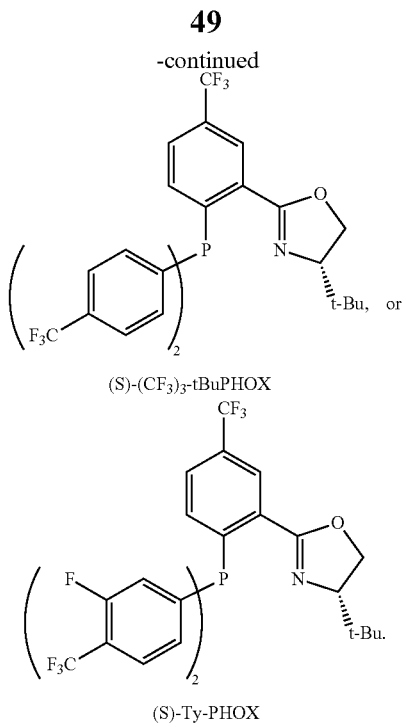

(S)-(CF₃)₃-tBuPHOX

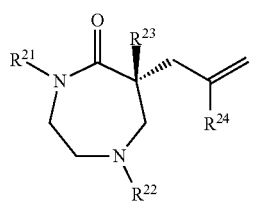

(S)-Ty-PHOX

In certain preferred embodiments, L is (S)—(CF₃)₃-tBu-PHOX.

In certain embodiments, the ligand L is used in an amount from about 0.5 mol % to about 50 mol % relative to the compound of formula (IIIb), for example, the chiral ligand is used in an amount from about 1 mol % to about 20 mol % relative to the compound of formula (IIIb), preferably, the chiral ligand is used in an amount of about 5 mol %, about 5.5 mol %, about 6 mol %, about 6.5 mol %, about 7 mol %, about 7.5 mol %, about 8 mol %, about 8.5 mol %, about 9 mol %, about 9.5 mol %, about 10 mol %, about 11 mol %, about 12 mol %, about 13 mol %, about 14 mol %, or about 15 mol % relative to the compound of formula (IIIb). In certain embodiments, the ligand L is used in an amount of about 4 mol % relative to the compound of formula (IIIb).

In certain embodiments, the compound of formula (IVb) is enantioenriched.

In certain embodiments, the invention is directed to a method of synthesizing a medicinal product, the method comprising:
preparing a compound of formula (IVb) according to a method as disclosed herein; and synthesizing a medicinal product from the compound of formula (IVb).

In some such embodiments, the synthesizing the medicinal product from the compound of formula (IVb) comprises: treating the compound of formula (IVb)

(IVb)

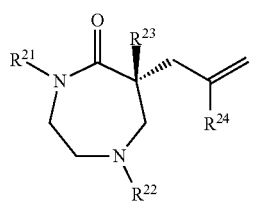

with lithium hydroxide and subsequently with lithium aluminum hydride, to form a product of formula (A)

(A)

treating the compound of formula (A) with a compound of formula (B)

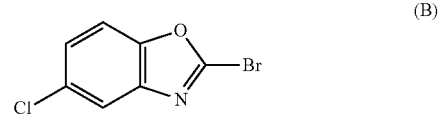 [SMILES: Clc1ccc2oc(Br)nc2c1]
(B)

and subsequently with acetyl chloride in methanol, to form a product of formula (C)

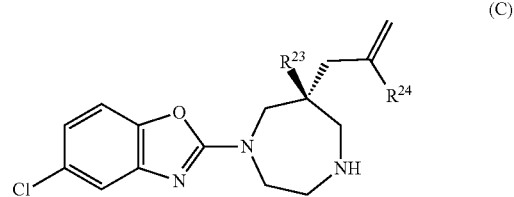
(C)

treating the compound of formula (C) with a compound of formula (D)

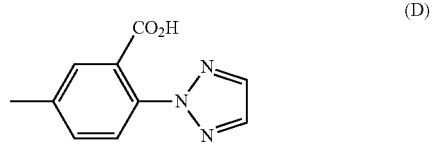
(D)

to form a compound of formula (E)

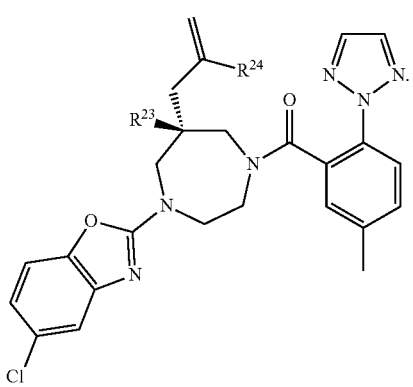
(E)

In certain preferred embodiments, $R^{23}$ is $CH_3$, $CH_2Ph$, $CH_2CCl=CH_2$, F, $CH_2CCH$, $CH_2CH_2CO_2CH_3$, $CH_2CH_2CN$, or $CH_2NHBoc$. In certain more preferred embodiments, $R^{23}$ is $CH_2Ph$.

In certain aspects, the invention relates to a compound of formula (E):

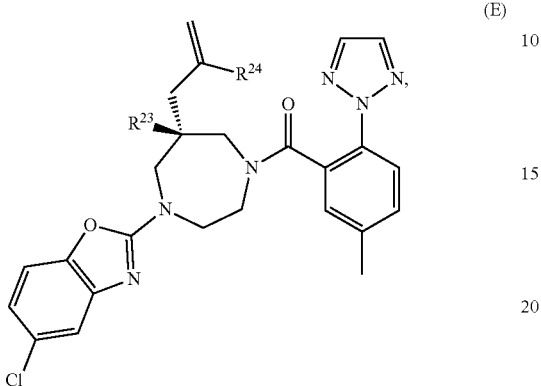
(E)

or a salt thereof,
wherein, as valence and stability permit,
$R^{23}$ is halogen, alkynyl, alkenyl, or $C_{1-6}$ alkyl, each optionally substituted with halogen, OH, cyano, alkoxy, aryloxy, alkoxycarbonyl, or $-NHC(O)OR^{23a}$;
$R^{23a}$ is $C_{1-6}$ alkyl; and
$R^{24}$ is H.

In certain embodiments, $R^{23}$ is $CH_3$, $CH_2Ph$, $CH_2Cl=CH_2$, F, $CH_2CCH$, $CH_2CH_2CO_2CH_3$, $CH_2CH_2CN$, or $CH_2NHBoc$. In certain preferred embodiments, $R^{23}$ is $CH_2Ph$.

In certain aspects, the invention relates to a method for preparation of a compound of formula (VI):

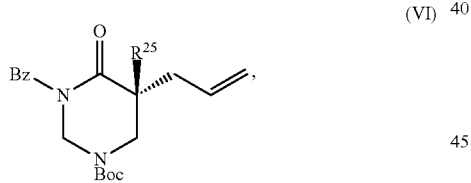
(VI)

the method comprising:
treating a compound of formula (V):

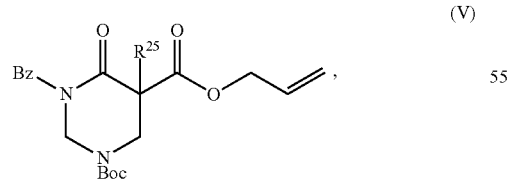
(V)

or a salt thereof,
with a Pd(0) catalyst and a ligand L, under alkylation conditions,
wherein, as valence and stability permit,
$R^{25}$ is $C_{1-6}$ alkyl, optionally substituted with halogen, OH, CN, aryl, heteroaryl, aryloxy, or alkynyl; halogen; or allyl, optionally substituted with halogen.

In certain embodiments, the compound of formula (VI) is:

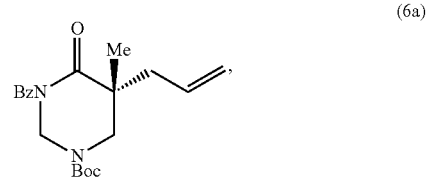
(6a)

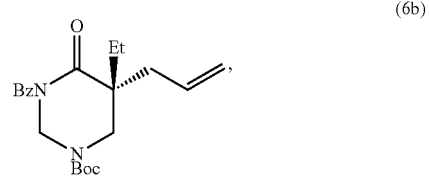
(6b)

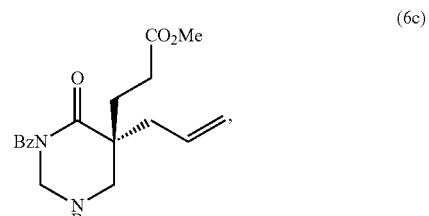
(6c)

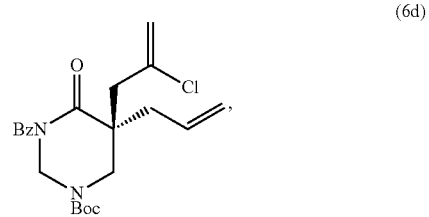
(6d)

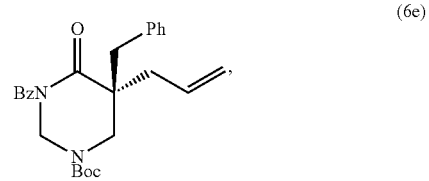
(6e)

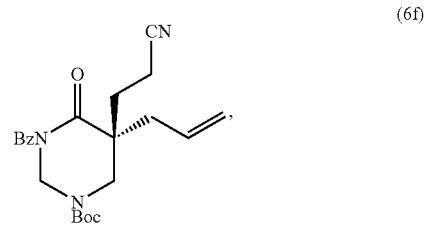
(6f)

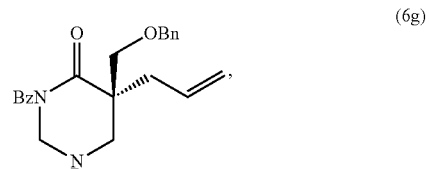
(6g)

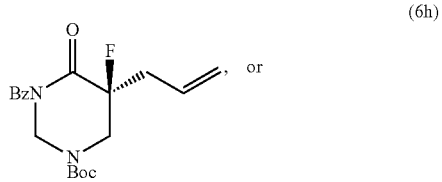
(6h)

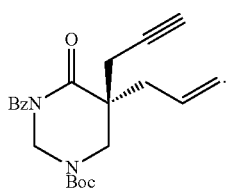
(6i)

In certain embodiments, alkylation conditions include reaction in hexanes, toluene, or a mixture thereof.

In certain embodiments, the Pd(0) catalyst is Pd$_2$(dba)$_3$ or Pd$_2$(pmdba)$_3$. In certain preferred embodiments, the Pd(0) catalyst is Pd$_2$(pmdba)$_3$.

In certain embodiments, the Pd(0) catalyst is used in an amount from about 0.01 mol % to about 10 mol %. In certain embodiments, the Pd catalyst is used in an amount from about 0.1 mol % to about 20 mol % relative to the compound of formula (V), for example, an amount from about 1 mol % to about 15 mol % relative to the compound of formula (V), preferably, an amount of about 1 mol %, about 2 mol %, about 3 mol %, about 4 mol %, about 5 mol %, about 6 mol %, about 7 mol %, about 8 mol %, about 9 mol %, about 10 mol %, about 11 mol %, about 12 mol %, about 13 mol %, or about 14 mol % relative to the compound of formula (V). In certain preferred embodiments, the Pd(0) catalyst is used in an amount of about 4 mol %.

In certain embodiments, L is:

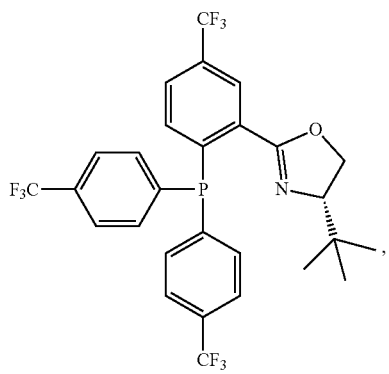
((S)-L1)

((S)-L2)

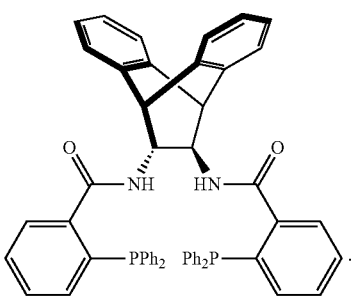
((S,S)-L3)

In certain preferred embodiments, L is (S)-L1.

In certain embodiments, L is used in an amount of from about 0.1 mol % to about 100 mol %. In certain embodiments, the ligand is used in an amount from about 0.5 mol % to about 50 mol % relative to the compound of formula (V), for example, the ligand is used in an amount from about 1 mol % to about 20 mol % relative to the compound of formula (V), preferably, the chiral ligand is used in an amount of about 5 mol %, about 5.5 mol %, about 6 mol %, about 6.5 mol %, about 7 mol %, about 7.5 mol %, about 8 mol %, about 8.5 mol %, about 9 mol %, about 9.5 mol %, about 10 mol %, about 11 mol %, about 12 mol %, about 13 mol %, about 14 mol %, or about 15 mol % relative to the compound of formula (V). In certain preferred embodiments, L is used in an amount of about 10 mol %.

In certain embodiments, the compound of formula (VI) is enantioenriched.

In certain embodiments, the method further comprises hydrolyzing the compound of formula (VI), to form a compound of formula (VII):

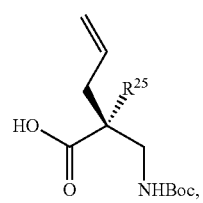
(VII)

or a salt thereof.

In certain aspects, the invention relates to a method for preparation of a compound of formula (VIII):

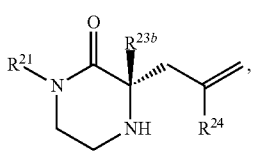
(VIII)

the method comprising:
treating a compound of formula (IVa):

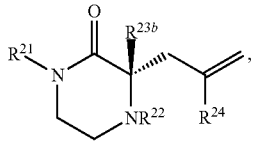

with TFA in a solvent;
wherein, as valence and stability permit,
$R^{21}$ is —C(O)aryl or —C(O)heteroaryl, optionally substituted with alkoxy, alkyl, or haloalkyl;
$R^{22}$ is Boc;
$R^{23}$ is H, or is $C_{1-6}$ alkyl optionally substituted with CN, OH, alkoxy, aryloxy, acyl, or —NHC(O)O$R^{23a}$;
$R^{23a}$ is $C_{1-6}$ alkyl, ($C_{6-10}$ aryl)alkyl, or ($C_{5-9}$ heteroaryl)alkyl;
$R^{24}$ is H or halogen;
$R^{23b}$ is H; or is $C_{1-6}$ alkyl optionally substituted with halogen, OH, CN, alkoxy, aryloxy, amino, acyl, or —NHC(O)O$R^{23e}$; and
$R^{23c}$ is ($C_{6-10}$ aryl)alkyl or ($C_{5-9}$ heteroaryl)alkyl.
In certain embodiments,
$R^{21}$ is Bz or An;
$R^{22}$ is Boc;
$R^{23}$ is H, $CH_3$, $CH_2Ph$, $CH_2OBn$, $CH_2CH_2CN$, $CH_2CH_2C(O)CH_3$, $CH_2NHCbz$, or $CH_2NHBoc$;
$R^{24}$ is H or Cl; and
$R^{23b}$ is H, $CH_3$, $CH_2Ph$, $CH_2OBn$, $CH_2CH_2CN$, $CH_2CH_2C(O)CH_3$, $CH_2NHCbz$, or $CH_2NH_2$.
In certain such embodiments, $R^{21}$ is Bz; $R^{22}$ is Boc; $R^{23}$ is $CH_2NHBoc$; $R^{24}$ is H; and $R^{23b}$ is $CH_2NH_2$.
In certain embodiments, the solvent is $CH_2Cl_2$.
In certain aspects, the invention relates to a method for the preparation of a compound of formula (IX):

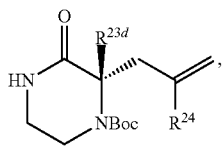

the method comprising:
treating a compound of formula (IVa):

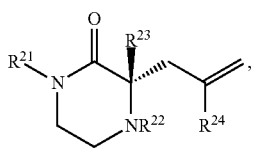

or a salt thereof,
with LiOH in a first solvent,
wherein, as valence and stability permit,
$R^{21}$ is —C(O)aryl or —C(O)heteroaryl, optionally substituted with alkoxy, alkyl, or haloalkyl;
$R^{22}$ is Boc;
$R^{23}$ is H, or $C_{1-6}$ alkyl optionally substituted with halogen, OH, cyano, alkoxy, aryloxy, acyl, or —NHC(O)O$R^{23a}$;

$R^{23a}$ is $C_{1-6}$ alkyl, ($C_{6-10}$ aryl)alkyl, or ($C_{5-9}$ heteroaryl)alkyl;
$R^{23d}$ is H, or is $C_{1-6}$ alkyl optionally substituted with halogen, OH, alkoxy, aryloxy, acyl, or —NHC(O)O$R^{23a}$; and
$R^{24}$ is H or halogen.
In certain embodiments,
$R^{21}$ is Bz or An;
$R^{23d}$ is H, $CH_3$, $CH_2Ph$, $CH_2OBn$, $CH_2OH$, $CH_2CH_2C(O)CH_3$, $CH_2CH_2CH(OH)CH_3$, $CH_2NHCbz$, $CH_2NHBoc$; and
$R^{24}$ is H or Cl.
In certain such embodiments, $R^{21}$ is Bz; $R^{22}$ is Boc; $R^{23}$ is $CH_2NHBoc$; $R^{23d}$ is $CH_2NHBoc$; and $R^{24}$ is H.
In certain embodiments, the first solvent comprises methanol, water, or a mixture thereof. In certain such embodiments, the first solvent comprises methanol and water.
In certain embodiments, the method further comprises preparing a compound of formula (X):

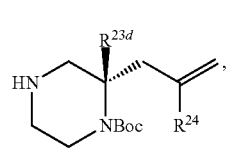

the method comprising:
treating the compound of formula (IX) with $LiAlH_4$ in a second solvent.
In certain embodiments, the second solvent comprises THF.
In certain embodiments, $R^{22}$ is Boc; $R^{23d}$ is $CH_2NHBoc$; and $R^{24}$ is H.
In certain aspects, the invention relates to a method of preparation of a compound of formula (XI):

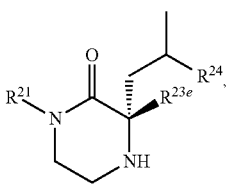

the method comprising:
treating a compound of formula (IVa):

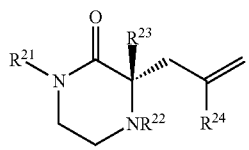

or a salt thereof,
with hydrogen gas in the presence of a Pd/C catalyst in a first solvent, to form a first product mixture;
filtering the first product mixture, to form a crude first product; and
treating the crude first product with TFA in a second solvent;
wherein, as valence and stability permit, $R^{21}$ is —C(O)aryl or —C(O)heteroaryl, optionally substituted with alkoxy, alkyl, or haloalkyl;

$R^{22}$ is Boc;

$R^{23}$ is H, or is $C_{1-6}$ alkyl optionally substituted with halogen, OH, alkoxy, aryloxy, CN, aryl, or —NHC(O)OR$^{23a}$;

$R^{23a}$ is $C_{1-6}$ alkyl, ($C_{6-10}$ aryl)alkyl, or ($C_{5-9}$ heteroaryl)alkyl;

$R^{23e}$ is H, or is $C_{1-6}$ alkyl optionally substituted with halogen, OH, aryl, aryloxy, CN, acyl, or amino; and $R^{24}$ is H or halogen.

In certain embodiments, $R^{21}$ is Bz or An;

$R^{22}$ is Boc;

$R^{23}$ is H, $CH_3$, $CH_2Ph$, $CH_2OBn$, $CH_2CH_2CN$, $CH_2CH_2C(O)CH_3$, or $CH_2NHBoc$;

$R^{23e}$ is H, $CH_3$, $CH_2Ph$, $CH_2OBn$, $CH_2CH_2CN$, $CH_2CH_2C(O)CH_3$, or $CH_2NH_2$;

$R^{24}$ is H or Cl.

In certain embodiments, $R^{21}$ is Bz; $R^{23}$ is $CH_3$; $R^{23e}$ is $CH_3$; and $R^{24}$ is H.

In certain embodiments, the first solvent comprises methanol.

In certain embodiments, the second solvent comprises $CH_2Cl_2$, ethyl acetate, or a mixture thereof.

In certain embodiments, the method further comprises preparation of a compound of formula (XII):

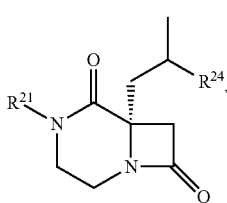

(XII)

the method comprising:
treating a compound of formula (XI):

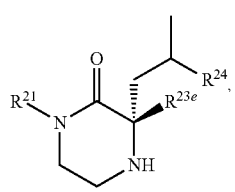

(XI)

or a salt thereof,
with Pd(OPiv)$_2$, xantphos, AgOPiv, and benzoquinone in the presence of CO$_{(g)}$ in a third solvent;
wherein, as valence and stability permit,
$R^{21}$ is —C(O)aryl or —C(O)heteroaryl;
$R^{23e}$ is methyl; and
$R^{24}$ is H or halogen.

In certain embodiments, $R^{24}$ is H.

In certain preferred embodiments, $R^{21}$ is Bz or An.

In certain more preferred embodiments, $R^{21}$ is Bz; $R^{23e}$ is $CH_3$; and $R^{24}$ is H.

In certain embodiments, the third solvent comprises toluene.

In certain aspects, the invention relates to a method of preparation of a compound of formula (XIII):

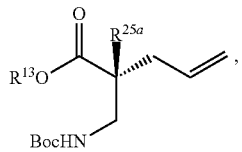

(XIII)

the method comprising:
treating a compound of formula (VI):

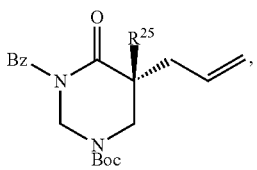

(VI)

or a salt thereof,
with TFA in a first solvent, to form a first product;
treating the first product with lithium hydroxide in a second solvent, to form a second product;
treating the second product with Boc$_2$O in the presence of a base, to form a third product;
treating the third product with $K_2CO_3$ and $R^{13}$—$X^{21}$ in a third solvent, to form a compound of formula (XIII);
wherein, as valence and stability permit,
$R^{25}$ is $C_{1-6}$ alkyl, optionally substituted with halogen, OH, CN, aryl, heteroaryl, aryloxy, or alkynyl; halogen; or allyl, optionally substituted with halogen;
$R^{25a}$ is $C_{1-6}$ alkyl, optionally substituted with halogen, OH, CN, aryl, heteroaryl, aryloxy, or alkynyl; halogen; or allyl, optionally substituted with halogen;
$R^{13}$ is aralkyl or hetaralkyl; and
$X^{21}$ is halogen.

In certain embodiments,
$R^{25}$ is $CH_3$, $CH_2CH_3$, $CH_2CH_2CO_2CH_3$, $CH_2CCl=CH_2$, $CH_2Ph$, $CH_2CH_2CN$, $CH_2OBn$, F, or $CH_2CCH$;
$R^{25a}$ is $CH_3$, $CH_2CH_3$, $CH_2CH_2CO_2CH_3$, $CH_2CCl=CH_2$, $CH_2Ph$, $CH_2CH_2CN$, $CH_2OBn$, F, or $CH_2CCH$; and
$R^{13}$ is Bn.

In certain embodiments, $R^{25}$ is $CH_2Ph$; $R^{25a}$ is $CH_2Ph$; and $X^{21}$ is Br.

In certain embodiments, the first solvent comprises dichloromethane.

In certain embodiments, the second solvent comprises methanol.

In certain embodiments, the third solvent comprises DMF.

Figure 2:
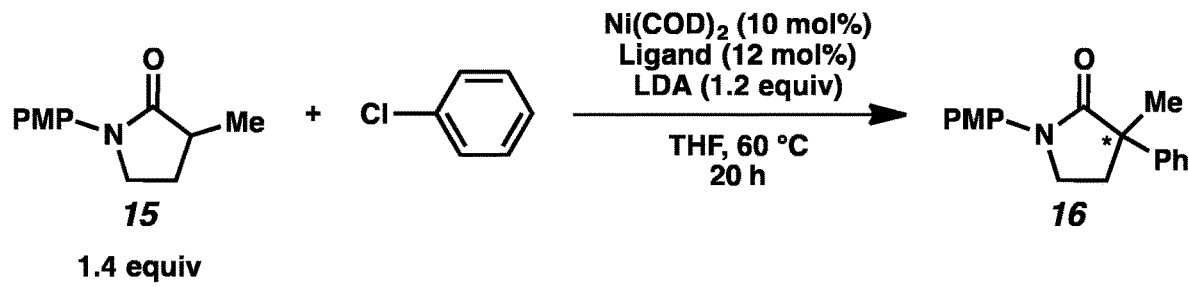
FIG. 2 shows initial evaluation of ligands in Ni catalyzed coupling of lactam 15 with chlorobenzene as described in Example 1.
Figure 2:
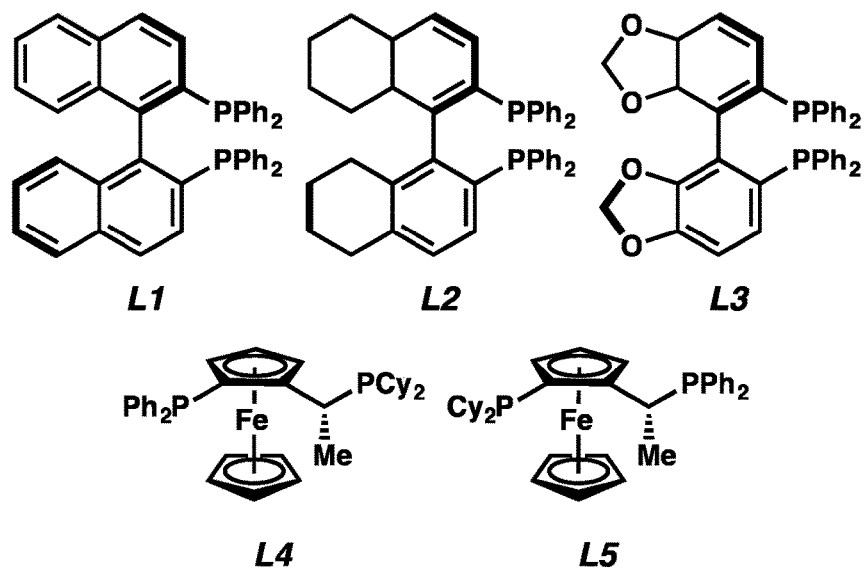

In certain embodiments, the invention relates to a method as described in FIG. 2. In certain embodiments, the invention relates to a method as described in FIG. 3. In certain embodiments, the invention relates to a method as described in FIG. 4. In certain embodiments, the invention relates to a method as described in FIG. 5. In certain embodiments, the invention relates to a method as described in FIG. 6. In certain embodiments, the invention relates to a method as described in FIG. 7. In certain embodiments, the invention relates to a method as described in Table 1. In certain embodiments, the invention relates to a method as described in Table 2. In certain embodiments, the invention relates to a method as described in FIG. 8. In certain embodiments, the invention relates to a method as described in FIG. 9. In certain embodiments, the invention relates to a method as described in Table 3. In certain embodiments, the invention relates to a method as described in Table 4. In certain embodiments, the invention relates to a method as described in FIG. 10. In certain embodiments, the invention relates to a method as described in FIG. 11. In certain embodiments, the invention relates to a method as described in Table 5. In certain embodiments, the invention relates to a method as described in Table 6. In certain embodiments, the invention relates to a method as described in Table 7. In certain embodiments, the invention relates to a method as described in Table 8. In certain embodiments, the invention relates to a method as described in Table 9. In certain embodiments, the invention relates to a method as described in Table 10. In certain embodiments, the invention relates to a method as described in Table 11. In certain embodiments, the invention relates to a method as described in Table 12. In certain embodiments, the invention relates to a method as described in Table 13. In certain embodiments, the invention relates to a method as described in Table 14. In certain embodiments, the invention relates to a method as described in Table 15. In certain embodiments, the invention relates to a method as described in Table 16. In certain embodiments, the invention relates to a method as described in Table 17. In certain embodiments, the invention relates to a method as described in Table 18. In certain embodiments, the invention relates to a method as described in Table 19. In certain embodiments, the invention relates to a method as described in Table 20. In certain embodiments, the invention relates to a method as described in Table 21. In certain embodiments, the invention relates to a method as described in Table 22. In certain embodiments, the invention relates to a method as described in Table 23. In certain embodiments, the invention relates to a method as described in Table 24. In certain embodiments, the invention relates to a method as described in Table 25. In certain embodiments, the invention relates to a method as described in Table 26. In certain embodiments, the invention relates to a method as described in FIG. 12. In certain embodiments, the invention relates to a method as described in the table in Example 35. In certain embodiments, the invention relates to a method as described in Table 27. In certain embodiments, the invention relates to a method as described in Table 28.

Transition Metal Catalysts

Preferred transition metal catalysts of the disclosure are complexes of nickel or palladium comprising a chiral ligand. In certain embodiments, the complex is of Ni(0) comprising a chiral ligand. In other embodiments, the complex is of Ni(II) comprising a chiral ligand. In other embodiments, the complex is of Pd(0) comprising a chiral ligand. In yet other embodiments, the complex is of Pd(II) comprising a chiral ligand.

It should be appreciated that typical transition metal catalysts having a low oxidation state (e.g., (0) or (I)) suffer from air- and moisture-sensitivity, such that these complexes of transition metals necessitate appropriate handling precautions. This may include the following precautions without limitation: minimizing exposure of the reactants to air and water prior to reaction; maintaining an inert atmosphere within the reaction vessel; properly purifying all reagents; and removing water from reaction vessels prior to use. In certain embodiments, the Ni(0) catalyst is a precatalyst. In other embodiments, the Pd(0) catalyst is a precatalyst. In yet other embodiments, the Pd(II) catalyst is a precatalyst.

Example Ni(0) catalysts that may be used in the methods of the disclosure include $Ni[(1,5\text{-cyclooctadiene})_2]$, which is also referred to herein as $Ni(COD)_2$.

In certain embodiments, the transition metal catalysts of the disclosure are complexes of Ni(0) or Ni(II), such as $Ni(COD)_2$, $NiCl$, and $NiBr_2$.

In certain embodiments, the transition metal catalysts of the disclosure are complexes of Pd(0) or Pd(II). In certain embodiments, Pd(II) catalysts are typically robust, and are less sensitive to air and moisture than their lower-oxidation state counterparts.

Examples of Pd(0) catalysts that may be used in the methods of the invention include $Pd(PPh_3)_4$, $Pd(dm\text{-}dba)_2$, $Pd(dba)_2$, $Pd_2(dba)_3 \cdot CHCl_3$, $Pd_2(dba)_3$, and $Pd_2(pm\text{-}dba)_3$. In preferred embodiments, the transition metal catalyst is $Pd(PPh_3)_4$. In other preferred embodiments, the transition metal catalyst is $Pd(dm\text{-}dba)_2$. In other preferred embodiments, the transition metal catalyst is $Pd(dba)_2$. In other preferred embodiments, the transition metal catalyst is $Pd_2(dba)_3 \cdot CHCl_3$. In yet other preferred embodiments, the transition metal catalyst is $Pd_2(dba)_3$. In other preferred embodiments, the transition metal catalyst is $Pd_2(pm\text{-}dba)_3$.

Examples of Pd(II) catalysts that may be used in the methods of the invention include $Pd(OC(O)R^c)_2$, wherein $R^c$ is optionally substituted alkyl, alkenyl, alkynyl, aryl, heteroaryl, aralkyl, heteroaralkyl, cycloalkyl, heterocycloalkyl, (cycloalkyl)alkyl, or (heterocycloalkyl)alkyl. Further examples of Pd(II) catalysts include $Pd(OC(O)R^c)_2$, $Pd(OC(=O)CH_3)_2$ (i.e., $Pd(OAc)_2$), $Pd(TFA)_2$, $Pd(acac)_2$, $PdCl$, $PdBr_2$, $PdCl(R^{23}CN)_2$ (e.g., $Pd(PhCN)_2Cl$ and $Pd(CH_3CN)_2Cl)$, $PdCl(PR^{24}R^{25}R^{26})_2$, $[Pd(\eta3\text{-allyl})Cl]_2$, and pre-formed Pd(II)-ligand complex, wherein $R^{23}$, $R^{24}$, $R^{25}$, and $R^{26}$ are independently selected from hydrocarbyl, substituted hydrocarbyl, heteroatom-containing hydrocarbyl, and substituted heteroatom-containing hydrocarbyl. Alternatively, the transition metal catalyst is $Pd(OC(O)R^c)_2$, wherein $R^c$ is defined above, For example, $R^c$ may be alkyl, substituted by one or more halo or cyano groups. In preferred embodiments, the transition metal catalyst is $Pd(OAc)_2$. In other preferred embodiments, the transition metal catalyst is $[Pd(cinnamyl)Cl]_2$.

To improve the effectiveness of the catalysts discussed herein, additional reagents may be employed in the methods of the invention, including, without limitation, salts, solvents, and other small molecules, such as a chiral ligand (see below). In some preferred embodiments, additives include salts. These additives are preferably used in an amount that is in the range of about 0.1 equivalents to about 15 equivalents relative to the amount of the reactant, more preferably in the range of about 0.5 equivalents to about 10 equivalents relative to the reactant, and most preferably in the range of about 2 equivalents to about 7 equivalents relative to the reactant.

In certain embodiments, additives include one or more of $Mn^0$, $Zn^0$, LiCl, LiBr, NaCl, NaBr, NaI, KCl, KBr, CsCl, $ZnCl_2$, CuI, $AlCl_3$, HMDS, COD, LiOt-Bu, NaOt-Bu, and KOt-Bu. These additives are preferably used in an amount that is in the range of about 1 equivalent to about 5 equivalents relative to the amount of the catalyst.

A low oxidation state of a transition metal, i.e., an oxidation state sufficiently low to undergo oxidative addition, can be obtained in situ, by the reduction of transition metal complexes that have a high oxidation state. Reduction of the transition metal complex can optionally be achieved by adding nucleophilic reagents including, without limitation, tetrabutyl ammonium hydroxide, tetrabutyl ammonium difluorotriphenylsilicate (TBAT), tetrabutylammonium fluoride (TBAF), 4-dimethylaminopyridine (DMAP), tetramethylammonium hydroxide (e.g., as the pentahydrate), KOH/1,4,7,10,13,16-hexaoxacyclooctadecane, sodium ethoxide, TBAT/trimethyl-(2-methyl-cyclohex-1-enyloxy)-silane, and combinations thereof. When a nucleophilic reagent is needed for the reduction of the metal complex, the nucleophilic reagent is used in an amount in the range of about 1 mol % to about 20 mol % relative to the reactant, more preferably in the range of about 1 mol % to about 10 mol % relative to the substrate, and most preferably in the range of about 5 mol % to about 8 mol % relative to the substrate.

For example, a Pd(II) complex can be reduced in situ to form a Pd(0) catalyst. Exemplary transition metal complexes that may be reduced in situ, include, without limitation, allylchloro[1,3-bis(2,6-di-iso-propylphenyl)imidazol-2-ylidene]palladium(II), ([2S,3S]-bis[diphenylphosphino]butane)($\eta^3$-allyl)palladium(II) perchlorate, [S]-4-tert-butyl-2-(2-diphenylphosphanyl-phenyl)-4,5-dihydro-oxazole($\eta^3$-allyl)palladium(II) hexafluorophosphate (i.e., [Pd(S-tBu-PHOX)(allyl)]PF$_6$), and cyclopentadienyl($\eta^3$-allyl)palladium(II).

The effectiveness of the catalysts discussed herein can be improved by adding nucleophilic reagents including, without limitation, NaHMDS, KHMDS, LiHMDS, tBuOLi, tetrabutyl ammonium hydroxide, tetrabutyl ammonium difluorotriphenylsilicate (TBAT), tetrabutylammonium fluoride (TBAF), 4-dimethylaminopyridine (DMAP), tetramethylammonium hydroxide (e.g., as the pentahydrate), KOH/1,4,7,10,13,16-hexaoxacyclooctadecane, sodium ethoxide, TBAT/trimethyl-(2-methyl-cyclohex-1-enyloxy)-silane, and combinations thereof. When a nucleophilic reagent is added, the nucleophilic reagent is used in an amount in the range of about range of about 0.1 equivalents to about 10 equivalents relative to the amount of the reactant, more preferably in the range of about 0.1 equivalents to about 5 equivalents relative to the reactant, and most preferably in the range of about 0.5 equivalents to about 2 equivalents relative to the reactant.

Accordingly, when describing the amount of transition metal catalyst used in the methods of the disclosure, the following terminology applies. The amount of transition metal catalyst present in a reaction is alternatively referred to herein as "catalyst loading". Catalyst loading may be expressed as a percentage that is calculated by dividing the moles of catalyst complex by the moles of the substrate present in a given reaction. Catalyst loading is alternatively expressed as a percentage that is calculated by dividing the moles of total transition metal (for example, nickel) by the moles of the substrate present in a given reaction.

In certain embodiments, the transition metal catalyst is present under the conditions of the reaction from an amount of about 0.1 mol % to about 20 mol % total transition metal relative to the substrate, which is the compound of formula (II), (IIIa), (IIIb), or (V). In certain embodiments, the catalyst loading is from about 1 mol % to about 15 mol % total transition metal relative to the substrate. In certain embodiments, the catalyst loading is from about 1 mol % to about 14 mol %, about 1 mol % to about 12%, about 1 mol % to about 10%, about 2 mol % to about 9 mol %, about 2.5 mol % to about 8 mol %, about 3 mol % to about 7 mol %, about 3.5 mol % to about 6.5 mol %, or about 4 mol % to about 6 mol % total transition metal relative to the substrate. For example, in certain embodiments, the catalyst loading is about 3 mol %, about 4 mol %, about 5 mol %, about 6 mol %, about 7 mol %, about 8 mol %, about 9 mol %, about 10 mol %, about 11 mol %, about 12 mol %, about 13 mol %, or about 14 mol % total transition metal. In certain embodiments, the catalyst loading is about 2 mol %, about 2.5 mol %, about 3 mol %, about 3.5 mol %, about 4 mol %, about 4.25 mol %, about 4.5 mol %, about 4.75 mol %, about 5 mol %, about 5.25 mol %, about 5.5 mol %, about 5.75 mol %, about 6 mol %, about 6.5 mol %, about 7 mol %, about 7.5 mol %, about 8 mol %, about 8.5 mol %, or about 9% total transition metal.

Ligands

In certain embodiments, the methods disclosed herein use a Ni(0) catalyst comprising a chiral ligand. In certain embodiments, the methods disclosed herein use a Pd(0) catalyst comprising a chiral ligand. In certain embodiments, the methods disclosed herein use a Pd(II) catalyst comprising a chiral ligand.

One aspect of the disclosure relates to the enantioselectivity of the methods. Enantioselectivity results from the use of chiral ligands during the arylation or vinylation reaction. Without being bound by theory, the asymmetric environment that is created around the metal center by the presence of chiral ligands produces an enantioselective reaction. The chiral ligand forms a complex with the transition metal (e.g., nickel), thereby occupying one or more of the coordination sites on the metal and creating an asymmetric environment around the metal center. This complexation may or may not involve the displacement of achiral ligands already complexed to the metal. When displacement of one or more achiral ligands occurs, the displacement may proceed in a concerted fashion, i.e., with both the achiral ligand decomplexing from the metal and the chiral ligand complexing to the metal in a single step. Alternatively, the displacement may proceed in a stepwise fashion, i.e., with decomplexing of the achiral ligand and complexing of the chiral ligand occurring in distinct steps. Complexation of the chiral ligand to the transition metal may be allowed to occur in situ, i.e., by admixing the ligand and metal before adding the substrate. Alternatively, the ligand-metal complex can be formed separately, and the complex isolated before use in the arylation or vinylation reactions of the present disclosure.

Once coordinated to the transition metal center, the chiral ligand influences the orientation of other molecules as they interact with the transition metal catalyst. Coordination of the metal center with an aryl halide and reaction of the substrate with the aryl halide-metal complex are dictated by the presence of the chiral ligand. The orientation of the reacting species determines the stereochemistry of the products.

Chiral ligands of the disclosure may be bidentate or monodentate or, alternatively, ligands with higher denticity (e.g., tridentate, tetradentate, etc.) can be used. Preferably, the ligand will be substantially enantiopure. By "enantiopure" is meant that only a single enantiomer is present. In many cases, substantially enantiopure ligands (e.g., ee>99%, preferably >99.5%, even more preferably >99.9%) can be purchased from commercial sources, obtained by successive recrystallizations of an enantioenriched substance, or by other suitable means for separating enantiomers.

Examples of chiral ligands used in certain embodiments may be found in U.S. Pat. No. 10,040,784, the entirety of which is incorporated herein by reference. In certain embodiments, the chiral ligand is an enantioenriched phosphine ligand. In certain embodiments, the enantioenriched phosphine ligand is a ferrocenyl ligand such as a Mandyphos-type ligand, a Josiphos-type ligand, a Taniaphos-type ligand, or a Walphos-type ligand. Preferred chiral ligands of the disclosure include a Mandyphos-type ligand a Josiphos-type ligand, or a ferrocenyl-type ligand. In certain embodiments, the Mandyphos-type ligand or the Josiphos-type ligand is selected from SL-M001-2, SL-M003-2, SL-M004-1, SL-M004-2, SL-M009-1, SL-M009-2, SL-J001-1, SL-J002-1, SL-J003-1, SL-J004-1, SL-J006-1, SL-J007-1, SL-J013-1, SL-J212-1, and SL-J418-1. In some embodiments, the ferrocenyl-type ligand is selected from (2S,5S)—Me-ferocelane, (2S,5S)-Et-ferocelane, and (2S,5S)-iPr-ferocelane. In some embodiments, the enantioenriched phosphine ligand is selected from (R)-BINAP, (R)-DM-BINAP, (S)-DTBM-SEGPHOS, (R)-BTFM-Garphos, (S)—C3-TunePhos, (R)—P-Phos, (2S,5S)—Me-ferocelane, (2S,5S)-Et-ferocelane, (2S,5S)-iPr-ferocelane, (2S,5S)—Me-f-

Ketalphos, SL-M001-2, SL-M003-2, SL-M004-1, SL-M004-2, SL-M009-1, SL-M009-2, SL-J001-1, SL-3002-1, SL-J003-1, SL-J004-1, SL-J006-1, SL-J007-1, SL-J013-1, SL-J212-1, SL-J418-1, SL-W001-1, SL-W002-1, SL-W005-1, SL-W006-1, SL-WOOS-1, SL-W009-1, and SL-W022-1. In some embodiments, the enantioenriched phosphine ligand is selected from (R)-BINAP, (R)-DM-BINAP, (S)—C3-TunePhos, SL-M001-2, SL-M003-2, SL-M004-1, SL-M004-2, SL-M009-1, SL-M009-2, SL-J001-1, SL-J002-1, SL-J003-1, SL-J004-1, SL-J006-1, SL-J013-1, SL-J212-1, SL-W001-1, SL-W002-1, SL-W005-1, SL-W006-1, SL-WOOS-1, and SL-W009-1. In some embodiments, the enantioenriched phosphine ligand is selected from (S)-DTBM-SEGPHOS, (R)-BTFM-Garphos, (R)—P-Phos, (2S,5S)—Me-ferocelane, (2S,5S)-Et-ferocelane, (2S,5S)—Me-f-Ketalphos, SL-J007-1, SL-J418-1, and SL-W022-1. Exemplary ligand structures are depicted in FIG. 1.

Generally, the chiral ligand is present in an amount in the range of about 0.1 equivalents to about 10 equivalents relative to the amount of total metal from the catalyst, preferably in the range of about 0.1 to about 6 equivalents relative to the amount of total metal from the catalyst, and most preferably in the range of about 0.5 to about 4.5 equivalents relative to the amount of total metal from the catalyst. Alternatively, the amount of the chiral ligand can be measured relative to the amount of the substrate.

In certain embodiments, the ligand is present under the conditions of the reaction from an amount of about 0.1 mol % to about 100 mol % relative to the substrate, which is the compound of formula (II), (Ma), (Mb), or (V). The amount of ligand present in the reaction is alternatively referred to herein as "ligand loading" and is expressed as a percentage that is calculated by dividing the moles of ligand by the moles of the substrate present in a given reaction. In certain embodiments, the ligand loading is from about 0.5 mol % to about 50 mol %. For example, in certain embodiments, the ligand loading is about 9 mol %, about 10 mol %, about 11 mol %, about 12 mol %, about 13 mol %, about 14 mol %, or about 15 mol %. In certain embodiments, the ligand is in excess of the transition metal catalyst. In certain embodiments, the ligand loading is about 10 times the transition metal catalyst loading.

Where a chiral ligand is used, the reactions of the disclosure may enrich the stereocenter bearing $R^2$ in the product relative to the enrichment at this center, if any, of the starting material. In certain embodiments, the chiral ligand used in the methods of the disclosure yields a compound of formula (I) that is enantioenriched. The level of enantioenrichment of a compound may be expressed as enantiomeric excess (ee). The ee of a compound may be measured by dividing the difference in the fractions of the enantiomers by the sum of the fractions of the enantiomers. For example, if a compound is found to comprise 98% (S)-enantiomer, and 2% (R)-enantiomer, then the ee of the compound is (98−2)/(98+2), or 96%. In certain embodiments, the compound of formula (I) has about 5% ee or greater, 10% ee or greater, 15% ee or greater, 20% ee or greater, 25% ee or greater, 30% ee or greater, 40% ee or greater, 50% ee or greater, 60% ee or greater, 70% ee or greater, about 80% ee, about 85% ee, about 88% ee, about 90% ee, about 91% ee, about 92% ee, about 93% ee, about 94% ee, about 95% ee, about 96% ee, about 97% ee, about 98% ee, about 99% ee, or above about 99% ee, even where this % ee is greater than the % ee of the starting material, such as 0% ee (racemic). In certain embodiments, the compound of formula (I) is enantioenriched. In certain embodiments, the compound of formula (I) is enantiopure. In embodiments where the starting material has more than one stereocenter, reactions of the disclosure may enrich the stereocenter bearing $R^2$ relative to the enrichment at this center, if any, of the starting material, and substantially independently of the stereochemical disposition/enrichment (de) of any other stereocenters of the molecule. For example, a product of the methods described herein may have 5% de or greater, 10% de or greater, 15% de or greater, 20% de or greater, 25% de or greater, 30% de or greater, 40% de or greater, 50% de or greater, 60% de or greater, 70% de or greater, 80% de or greater, 90% de or greater, 95% de or greater, or even 98% de or greater at the stereocenter of the product bearing $R^2$.

Arylation and Vinylation Conditions

In certain embodiments, the methods of the disclosure include treating a compound of formula (II) with a palladium or nickel catalyst comprising a chiral ligand, and an aryl halide or a heteroaryl halide under arylation conditions. In certain embodiments, the methods of the disclosure include treating a compound of formula (II) with a palladium or nickel catalyst comprising a chiral ligand, and a vinyl halide under vinylation conditions. In certain embodiments, the palladium catalyst under arylation or vinylation conditions is a Pd(0) catalyst comprising a chiral ligand. In certain embodiments, the palladium catalyst under arylation or vinylation conditions is a Pd(II) catalyst comprising a chiral ligand. In certain embodiments, the nickel catalyst under arylation or vinylation conditions is a Ni(0) catalyst comprising a chiral ligand. In certain embodiments, the palladium catalyst under arylation or vinylation conditions is a Ni(II) catalyst comprising a chiral ligand. In certain embodiments, arylation and vinylation conditions further comprise a base, such as NaHMDS, KHMDS, and LiHMDS. In certain embodiments, the base is LiHMDS. In certain embodiments, the base is NaHMDS. In certain embodiments, arylation and vinylation conditions of the reaction include one or more additives, such as a salt. In certain embodiments, the salt is one or more of LiCl, NaCl, NaBr, NaI, KCl, KBr, CsCl, CuI, LiOt-Bu, and KOt-Bu.

In certain embodiments, arylation, vinylation, and alkylation conditions of the reaction include one or more organic solvents. In certain embodiments, organic solvents include aromatic or non-aromatic hydrocarbons, ethers, alkylacetates, nitriles, or combinations thereof. In certain embodiments, organic solvents include hexane, pentane, benzene, toluene, xylene, cyclohexane, methylcyclohexane, cyclic ethers such as optionally substituted tetrahydrofuran and dioxane, acyclic ethers such as dimethoxyethane, diethyl ether, methyl tertbutyl ether, and cyclopentyl methyl ether, acetonitrile, isobutyl acetate, ethyl acetate, isopropyl acetate, or combinations thereof. In certain preferred embodiments, the solvent is toluene, tetrahydrofuran, dioxane, methyl tert-butyl ether, cyclohexane, methylcyclohexane, dimethoxyethane, or a mixture of toluene and tetrahydrofuran. In some embodiments, the solvent is a mixture of two organic solvents. In some such embodiments, the solvent is a mixture of two organic solvents in a ratio of 1:5, 1:2, 1:1, 2:1, 3:1, 4:1, 5:1, 6:1, 7:1, 8:1, 9:1, 10:1, 11:1, 12:1, 13:1, 14:1, or 15:1. In preferred embodiments, the solvent is dioxane. In certain other embodiments, the solvent is a mixture of toluene and tetrahydrofuran. In certain embodiments, the mixture of toluene and tetrahydrofuran is in a ratio of 1:5, 1:2, 1:1, 2:1, 3:1, 4:1, 5:1, 6:1, 7:1, 8:1, 9:1, 10:1, 11:1, 12:1, 13:1, 14:1, or 15:1. In certain embodiments, the mixture of toluene and tetrahydrofuran is in a ratio of 5:1 or 10:1. In certain other embodiments, the solvent is a mixture of toluene and hexanes. In certain embodiments, the mixture of toluene and hexanes is in a ratio of 1:5, 1:2, 1:1, 2:1, 3:1, 4:1, 5:1, 6:1, 7:1, 8:1, 9:1, 10:1, 11:1, 12:1, 13:1, 14:1, or 15:1. In certain embodiments, the mixture of toluene and hexanes is in a ratio of 5:1 or 10:1. In certain embodiments, the solvent is methylcyclohexane.

In certain embodiments, arylation, vinylation, and alkylation conditions of the reaction include a reaction temperature. In certain embodiments, the reaction temperature is ambient temperature (about 20° C. to about 26° C.). In preferred embodiments, the reaction temperature is about 60° C. to about 100° C. In preferred embodiments, the reaction temperature is higher than ambient temperature, such as, for example, about 30° C., about 35° C., about 40° C., about 45° C., about 50° C., about 55° C., about 60° C., about 65° C., about 70° C., about 75° C., about 80° C., about 85° C., about 90° C., about 95° C., or about 100° C. Reaction temperature may be optimized per each substrate.

EXEMPLIFICATION

The disclosure described generally herein will be more readily understood by reference to the following examples, which are included merely for purposes of illustration of certain aspects and embodiments of the present disclosure, and are not intended to limit the disclosure.

I. Ni-Catalyzed Lactam α-Arylation

Example 1: Initial Evaluation of Ligands and Bases for Ni-Catalyzed Lactam α-Arylation Chlorobenzene and the lithium enolate derived from lactam 15 generated a small amount of arylated product 16 in high enantioselectivity in the presence of Ni(COD)$_2$ and a Josiphos ligand (L5) (FIG. 2, entry 5). A variety of other ligand classes resulted in unreacted aryl chloride.

Figure 3:
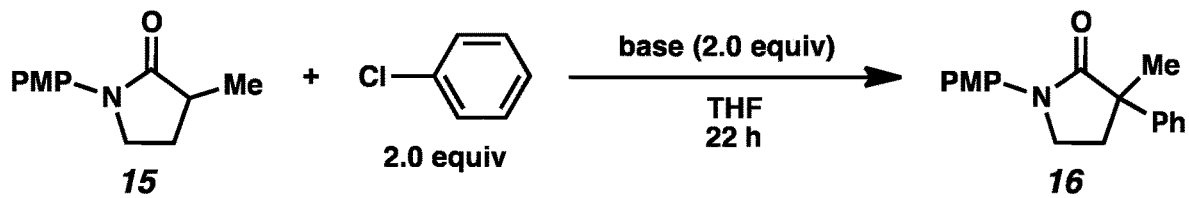
FIG. 3 shows initial evaluation of bases in the Ni catalyzed coupling of lactam 15 with chlorobenzene as described in Example 1.
Figure 4:
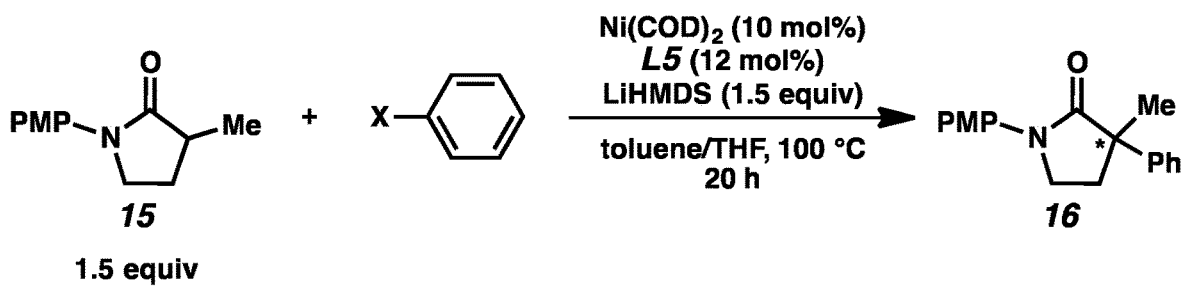
FIG. 4 shows the effect of aryl (pseudo)halide leaving group on conversion and enantioselectivity as described in Example 1.

Reactions in the absence of Ni and ligand revealed a significant background reaction resulting from the direct reaction of the enolate with chlorobenzene. Direct reaction was observed in the presence of LDA, NaHMDS, or KHMDS but not in the presence of LiHMDS (FIG. 3). Weaker bases resulted in little to no product formation. When bromo- or iodobenzene was used instead of chlorobenzene, enantioselectivity decreased significantly (FIG. 4, entries 2 and 3). Phenyl triflate and phenyl tosylate were unreactive under the reaction conditions (entries 4 and 5).

Figure 5:
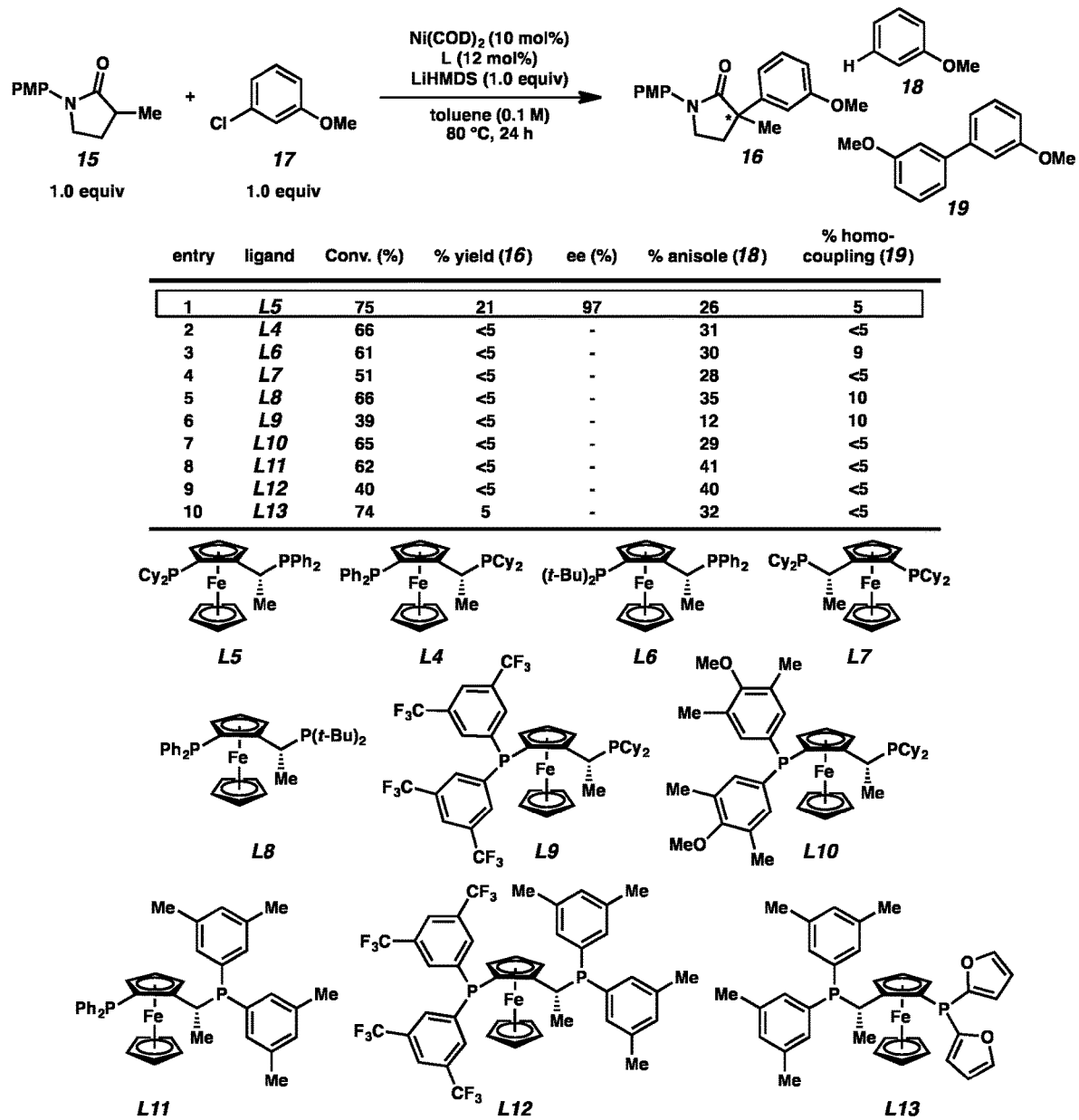
FIG. 5 shows the evaluation of Josiphos ligands as described in Example 1.

Although a number of Josiphos ligands were evaluated, only L5 resulted in >5% α-arylation (FIG. 5, entry 1). Anisole (18) and homocoupled electrophile (19) were consistently formed under the reaction conditions.

Figure 6:
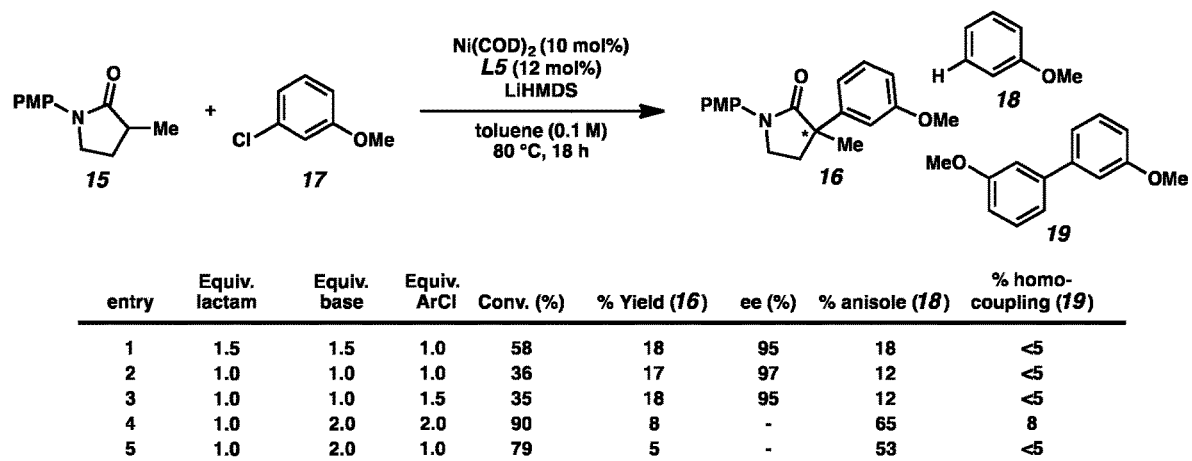
FIG. 6 shows the effect of stoichiometry on yield, enantioselectivity, and side product formation as described in Example 2.
Figure 7:
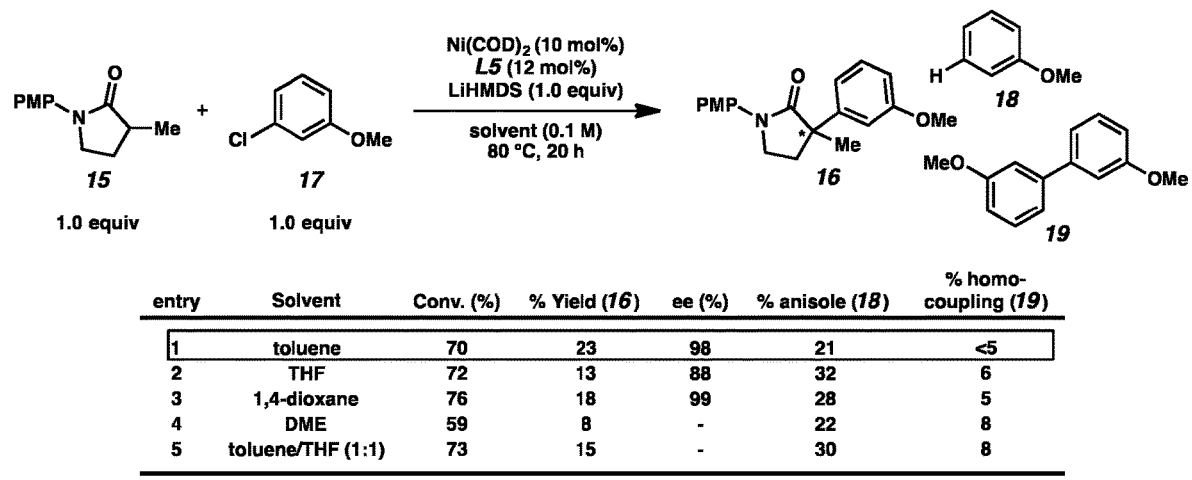
FIG. 7 shows the effect of solvent as described in Example 2.
Figure 8:
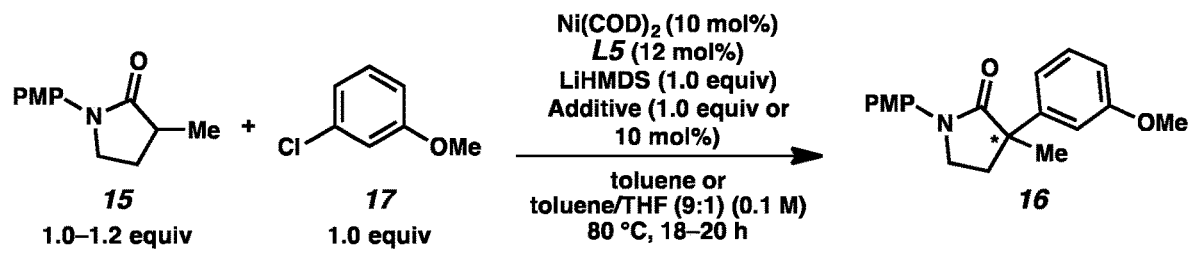
FIG. 8 shows the effect of additives as described in Example 4.

Example 2: Evaluation of Reaction Parameters for Ni-Catalyzed Lactam α-Arylation A variety of reaction parameters were evaluated in the α-arylation of lactam 15 with 3-chloroanisole (17). Neither an excess of enolate relative to aryl chloride nor an excess of aryl chloride relative to enolate provided an improvement in yield or enantioselectivity relative to a 1:1 ratio (FIG. 6, entries 1-3). Ethereal solvents provided equivalent or slightly diminished yields as compared to toluene (FIG. 7). Ni(COD)$_2$ was found to be a preferred Ni source, as other Ni$^0$ or Ni$^{II}$ salts resulted in decreased yields (Table 1).

TABLE 1

Effect of Ni source

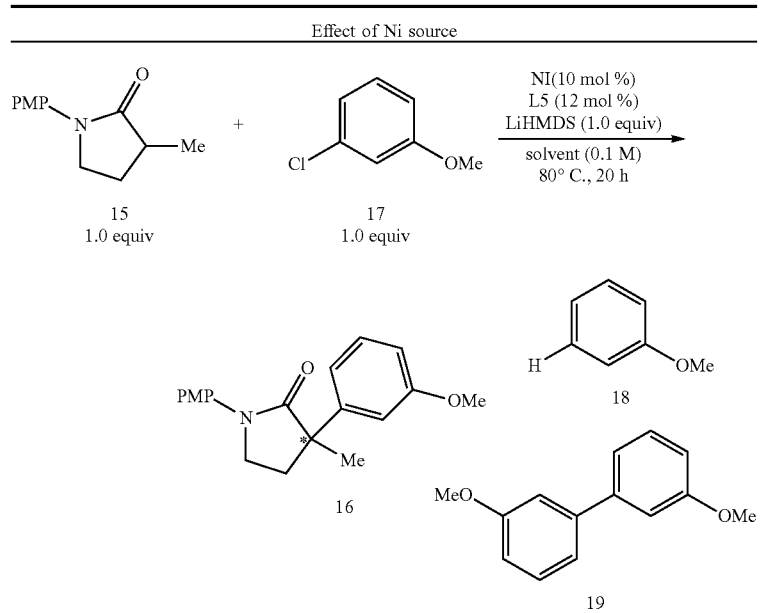

| entry | Ni source | Additive | Conv. (%) | % Yield (16) | % anisole (18) | % homo-coupling (19) |
|---|---|---|---|---|---|---|
| 1[a] | Ni(COD)$_2$ | Mn$^0$ | 38 | 14 | 10 | <5 |
| 2[a] | Ni(COD)$_2$ | Zn$^0$ | 29 | 3 | 9 | <5 |
| 3 | NiCl$_2$•glyme | — | 33 | 9 | 14 | <5 |
| 4[a] | NiCl$_2$•glyme | Mn$^0$ | <5 | <5 | <5 | <5 |
| 5[a] | NiCl$_2$•glyme | Zn$^0$ | 9 | 5 | <5 | <5 |
| 6 | NiBr$_2$•glyme | — | 22 | <5 | 7 | <5 |
| 7 | NiBr$_2$•diglyme | — | 18 | 6 | 6 | <5 |
| 8 | Ni(acac)$_2$ | — | 51 | <5 | 4 | <5 |
| 9 | NiBr$_2$(PPh$_3$)$_2$ | — | 53 | 5 | 27 | <5 |
| 10 | Ni(PPh$_3$)$_4$ | — | 80 | 11 | 33 | <5 |

[a]The reaction was run for 2 h instead of 20 h

Example 3: Evaluation of N-Protecting Groups for Ni-Catalyzed Lactam α-Arylation A number of N-protecting groups were evaluated. Generally low yields were observed for N-aryl and N-benzyl lactams (Table 2, 15a-15f). Little to no improvement in yield was observed for benzoyl or tosyl protected substrates (15g, 15h), an oxindole (15i), a δ-lactam (15j), and an ε-lactam (15k). Both an α-Et-substituted (15l) and an unsubstituted lactam (15m) resulted in low product to internal standard ratios.

TABLE 2

Effect of N-protecting groups

| Substrate | Conv. (%) | Yield (%) |
|---|---|---|
| 15a R = H | 63 | 22 |
| 15 OMe | 61 | 19 |
| 15b CF₃ | 28 | 9 |
| 15c | 73 | <5 |
| 15d | 54 | 12 |
| 15e | 84 | 25 |

TABLE 2-continued

Effect of N-protecting groups

[Reaction scheme: 15-15m (1.0-1.2 equiv) + 17 (1.0 equiv), Ni(COD)₂ (10 mol %), L5 (12 mol %), LiHMDS (1.0 equiv), toluene (0.1 M), 80° C., 20 h → 16-16m]

| Substrate | Conv. (%) | Yield (%) |
|---|---|---|
| 15f (N-CHPh₂, 3-Me pyrrolidinone) | 85 | <5 |
| 15g (N-Cbz, 3-Me pyrrolidinone) | 14 | <5 |
| 15h (N-Ts, 3-Me pyrrolidinone) | 17 | <5 |
| 15i (N-PMP, 3-Me oxindole) | 3 | <5 |
| 15j (N-PMP, 3-Me piperidinone) | 33 | <5 |

TABLE 2-continued

Effect of N-protecting groups

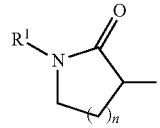

| Substrate | Conv. (%) | Yield (%) |
|---|---|---|
| 15k 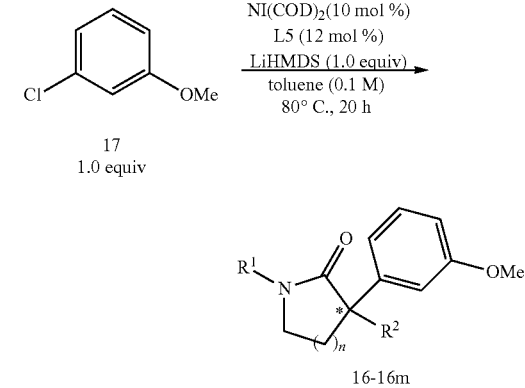 | 57 | <5 |
| 15l 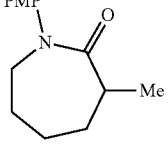 | 79 | P/IS = 0.32 |
| 15m 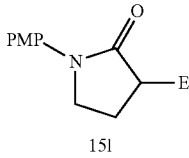 | 33 | P/IS = 0.21 |

Example 4: Evaluation of Additives for Ni-Catalyzed Lactam α-Arylation

Although additives have been beneficial in several examples of Ni-catalyzed cross-coupling, neither alkali metal halides (FIG. 8, entries 2-10) nor Lewis acids (entries 11-16) provided a boost in yield. The expected byproducts of this reaction, HMDS and COD, did not have a significant detrimental effect when added to the reaction (entries 17-18).

Example 5: Evaluation of Ni Loading for Ni-Catalyzed Lactam α-Arylation

Figure 9:
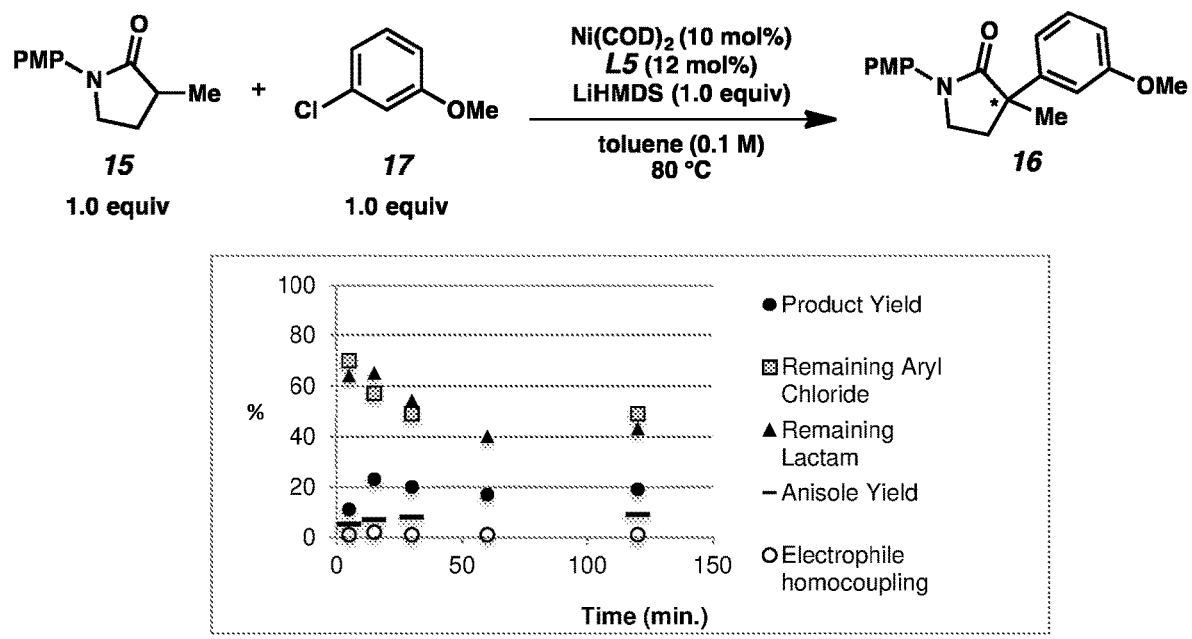
FIG. 9 shows the Ni-catalyzed α-arylation of lactam 15 over time as described in Example 5.

Monitoring the reaction over time revealed that a low terminal yield of α-arylation product 16 is generated within 1 h at 80° C. (FIG. 9). At 40° C. or 60° C., lower terminal yields were obtained. Increasing the Ni loading to 20% led to a somewhat decreased yield (Table 3, entries 7 and 8).

TABLE 3

Effect of Ni loading

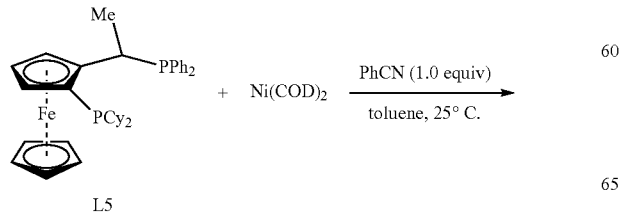

| entry | mol % Ni | mol % L5 | time (h) | % conv | % Yield (16) | % anisole (18) | % homo-coupling (19) |
|---|---|---|---|---|---|---|---|
| 1 | 2.5 | 3 | 1 | 17 | 5 | 1 | <5 |
| 2 | 2.5 | 3 | 16 | 40 | 12 | 14 | <5 |
| 3 | 5 | 6 | 1 | 29 | 9 | 4 | <5 |
| 4 | 5 | 6 | 16 | 57 | 13 | 16 | <5 |
| 5 | 10 | 12 | 1 | 48 | 14 | 9 | <5 |
| 6 | 10 | 12 | 16 | 70 | 22 | 14 | <5 |
| 7 | 20 | 40 | 1 | 68 | 11 | 12 | <5 |
| 8 | 20 | 40 | 26 | 83 | 11 | 17 | <5 |

Example 6: Evaluation of Josiphos-Ligated Ni⁰ (PhCN) Complex for Ni-Catalyzed Lactam α-Arylation Nitrile-/Josiphos-ligated Ni complexes have been demonstrated to be particularly reactive toward oxidative addition of aryl halides. Complex 20 was synthesized according to a literature procedure (Scheme 1) and used as a precatalyst in the coupling of lactam 15 with 3-chloroanisole (17). Complex 20 did not result in improved reactivity as compared to Ni(COD)$_2$ (Table 4).

Scheme 1 Synthesis of a Josiphos-ligated Ni⁰(PhCN) complex

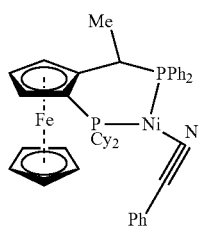

20
71% yield

TABLE 4

Use of a Ni⁰(PhCN) complex as a precatalyst

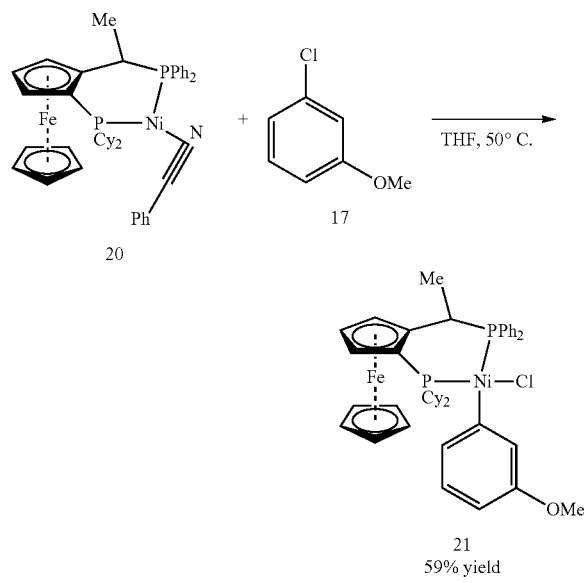

| entry | mol % Ni | temp. | % added L5 | % Yield (16) |
|---|---|---|---|---|
| 1 | 5 | 80 °C. | — | 14 |
| 2 | 10 | 80° C. | — | 13 |
| 3 | 5 | 50 °C. | 5 | 12 |
| 4 | 10 | 50° C. | 10 | 15 |

Example 7: Evaluation of Josiphos-Ligated Ni$^{II}$ ArCl Complex for Ni-Catalyzed Lactam α-Arylation Complex 20 was subjected to literature conditions for the synthesis of a Josiphos-ligated Ni$^{II}$ArCl species (21, Scheme 2). When a 1:1 ratio of Ni$^{II}$ complex 21, lactam 15, and LiHMDS was reacted in THF at 80° C., a 50% yield of homocoupled aryl chloride (19) and only 5% product 16 were obtained (Scheme 3).

Scheme 2 Synthesis of a Josiphos-ligated Ni$^{II}$ArCl complex

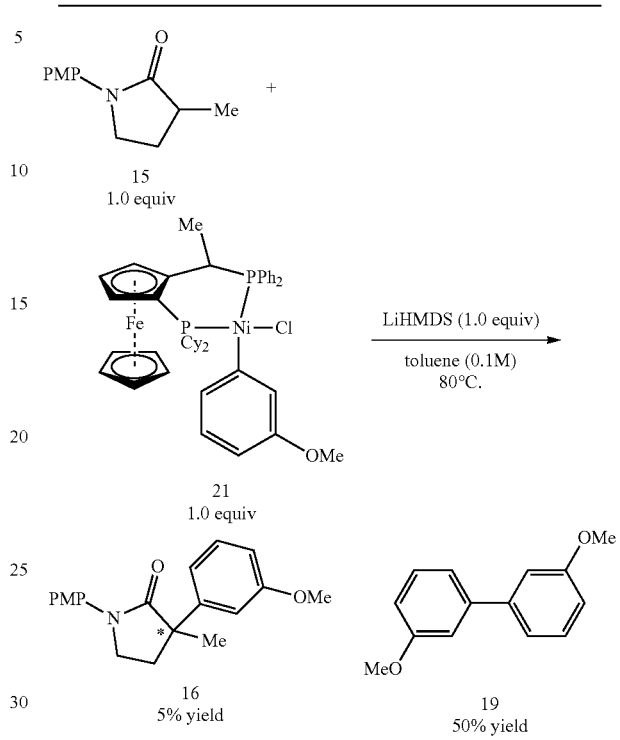

Scheme 3 Stoichiometric reaction of a lithium enolate and a Josiphos-ligated Ni$^{II}$ArCl complex The Ni-catalyzed α-arylation of lactam 15 with an aryl chloride may be achieved with high enantioselectivity but low yield. Both lower yields and levels of enantioselectivity were observed for an aryl bromide or an aryl iodide. Product formation was found to terminate within 1 hour, and increasing the Ni loading decreased yield. The stoichiometric reaction of an isolated Ni$^{II}$ArCl complex and the lithium enolate derived from 15 resulted in predominant aryl chloride homocoupling.

II. Pd-Catalyzed Lactam α-Arylation

Figure 10:
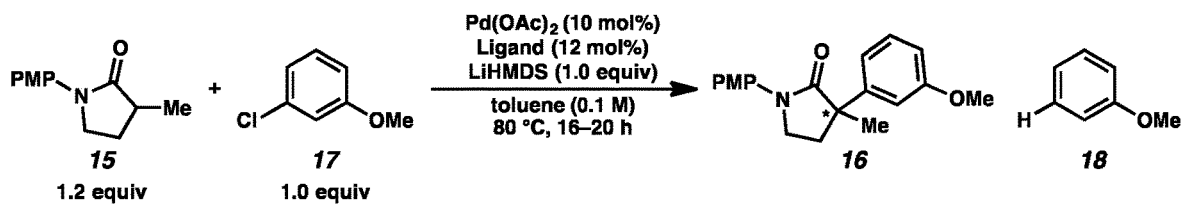
FIG. 10 shows the effect of ligands on Pd-catalyzed coupling of lactam 15 and 3-chloroanisole as described in Example 8.
Figure 10:
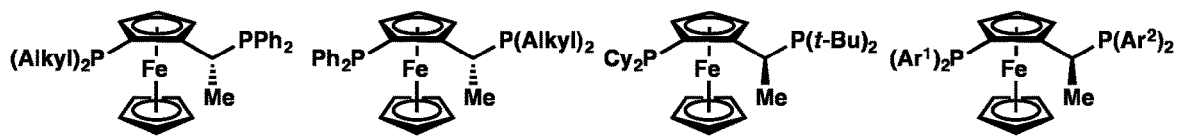
Figure 10:
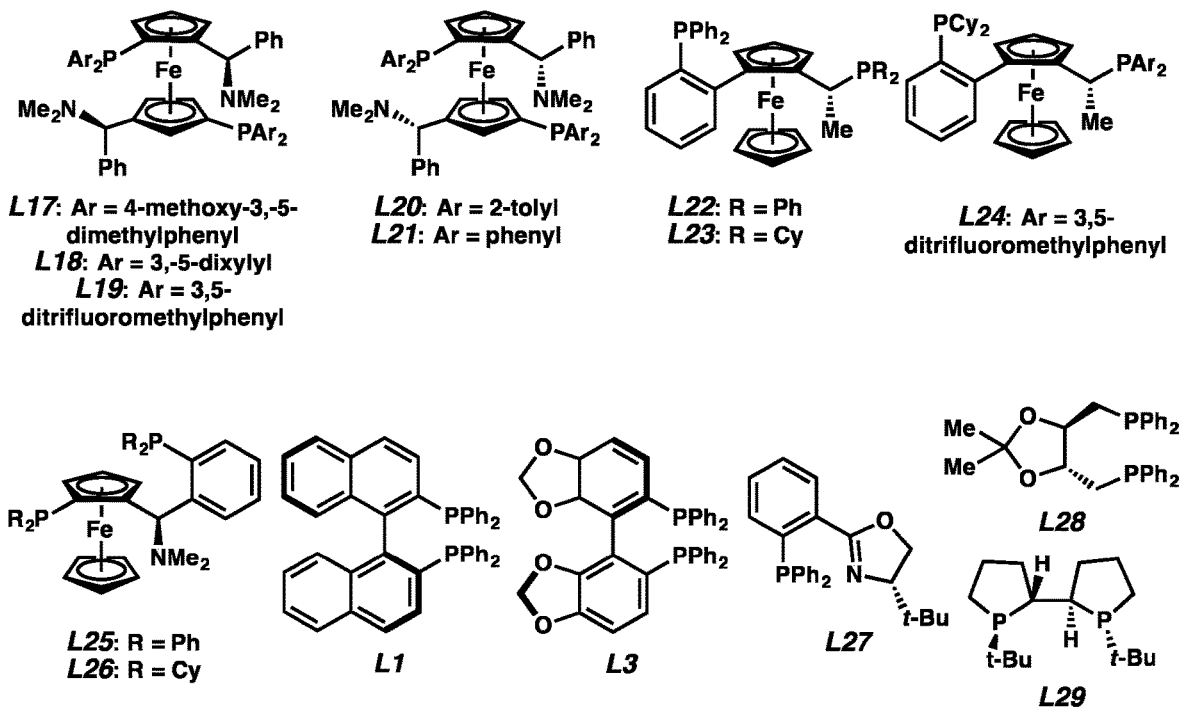

Example 8: Evaluation of Ligands and Bases for Pd-Catalyzed Lactam α-Arylation with 3-Chloroanisole and Chlorobenzene α-Arylation of lactam 15 with 3-chloroanisole (17) was achieved in the presence of LiHMDS and catalytic Pd(OAc)$_2$. In contrast to the Ni-catalyzed process, α-arylation was observed with several ferrocene-based ligands, including Josiphos and Mandyphos ligand classes. Moderate yields of product were obtained with Mandyphos ligands L17 and L18 (FIG. 10, entries 8 and 9). Moderate levels of enantioselectivity were achieved with a Josiphos ligand (L5, entry 1) and several Mandyphos ligands (L18, entry 9; L19, entry 10; L21, entry 12).

Figure 11:
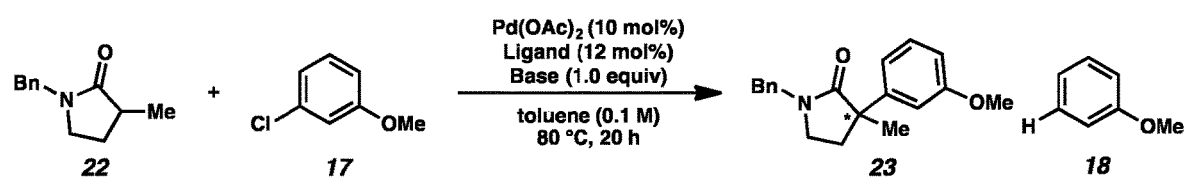
FIG. 11 shows the effect of bases in combination with Josiphos and Mandyphos ligands as described in Example 8. The ligand numbers in FIG. 11 refer to those in FIG. 10.

In an investigation of various lactam substrates, an N-benzyl protected lactam (22) provided the highest levels of enantioselectivity (FIG. 11, entries 1 and 4). However, lower yields were observed compared to those observed for the N-PMP protected lactam 15.

α-Arylation of lactam 1a with chlorobenzene was achieved in the presence of LiHMDS and catalytic Pd(dmdba)$_2$ using various ligands (Table 5).

TABLE 5

Effect of ligands on Pd-catalyzed coupling of lactam 15 and chlorobenzene

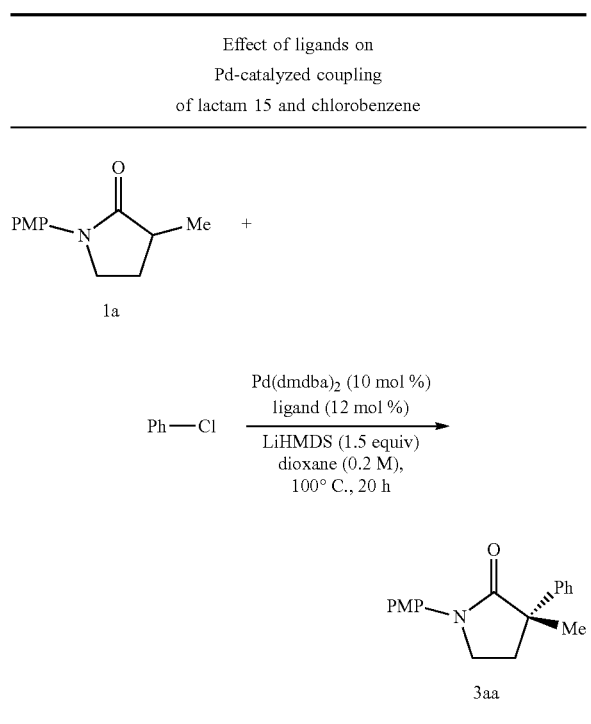

| entry | ligand | yield(%)[b] | ee(%)[c] |
|---|---|---|---|
| 1 | L1 | — | — |
| 2 | L2 | 29 | 5 |
| 3 | L3 | 65 | 93 |
| 4 | L4 | 69 | 94 |
| 5 | L5 | 19 | 2 |
| 6 | L6 | 6 | 0 |

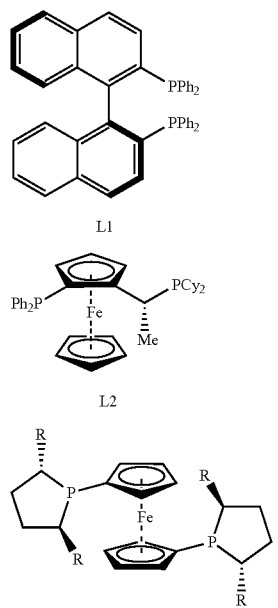

TABLE 5-continued

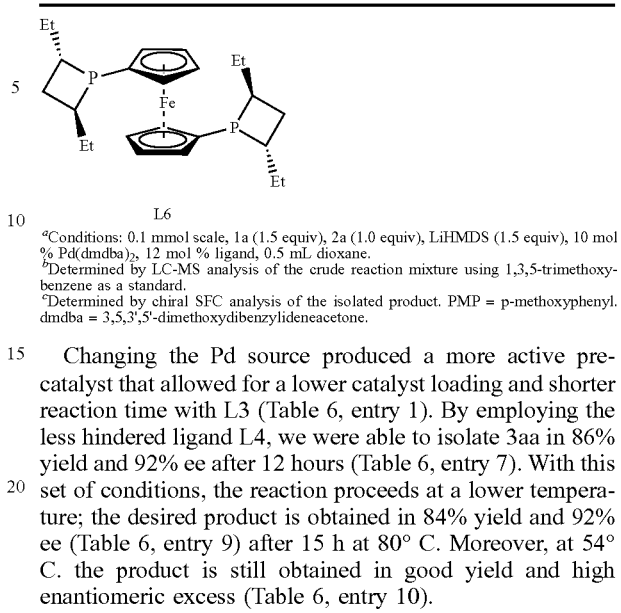

[a]Conditions: 0.1 mmol scale, 1a (1.5 equiv), 2a (1.0 equiv), LiHMDS (1.5 equiv), 10 mol % Pd(dmdba)₂, 12 mol % ligand, 0.5 mL dioxane.
[b]Determined by LC-MS analysis of the crude reaction mixture using 1,3,5-trimethoxybenzene as a standard.
[c]Determined by chiral SFC analysis of the isolated product. PMP = p-methoxyphenyl. dmdba = 3,5,3',5'-dimethoxydibenzylideneacetone.

Changing the Pd source produced a more active precatalyst that allowed for a lower catalyst loading and shorter reaction time with L3 (Table 6, entry 1). By employing the less hindered ligand L4, we were able to isolate 3aa in 86% yield and 92% ee after 12 hours (Table 6, entry 7). With this set of conditions, the reaction proceeds at a lower temperature; the desired product is obtained in 84% yield and 92% ee (Table 6, entry 9) after 15 h at 80° C. Moreover, at 54° C. the product is still obtained in good yield and high enantiomeric excess (Table 6, entry 10).

TABLE 6

Optimization of reaction conditions for arylation of lactam 1a

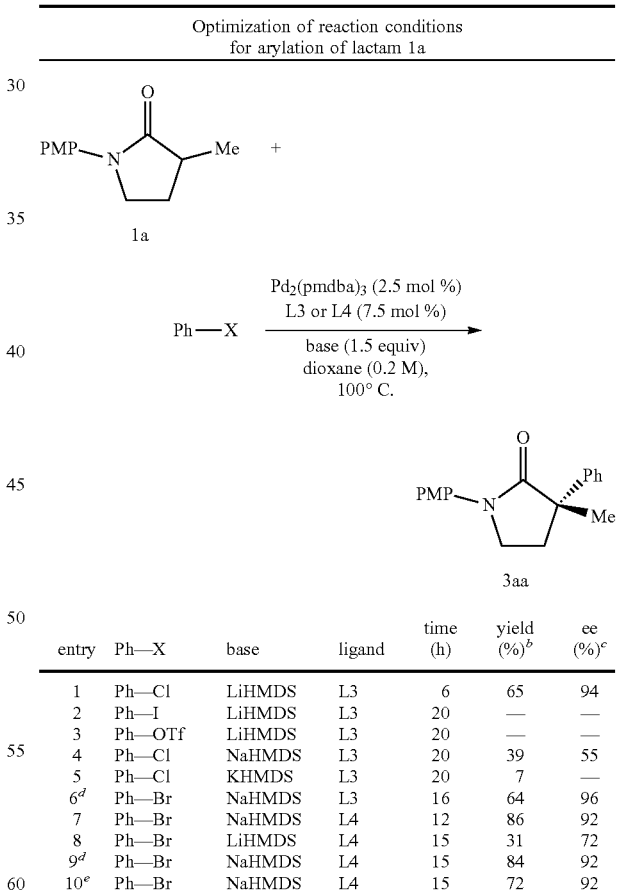

| entry | Ph—X | base | ligand | time (h) | yield (%)[b] | ee (%)[c] |
|---|---|---|---|---|---|---|
| 1 | Ph—Cl | LiHMDS | L3 | 6 | 65 | 94 |
| 2 | Ph—I | LiHMDS | L3 | 20 | — | — |
| 3 | Ph—OTf | LiHMDS | L3 | 20 | — | — |
| 4 | Ph—Cl | NaHMDS | L3 | 20 | 39 | 55 |
| 5 | Ph—Cl | KHMDS | L3 | 20 | 7 | — |
| 6[d] | Ph—Br | NaHMDS | L3 | 16 | 64 | 96 |
| 7 | Ph—Br | NaHMDS | L4 | 12 | 86 | 92 |
| 8 | Ph—Br | LiHMDS | L4 | 15 | 31 | 72 |
| 9[d] | Ph—Br | NaHMDS | L4 | 15 | 84 | 92 |
| 10[e] | Ph—Br | NaHMDS | L4 | 15 | 72 | 92 |

[a]Conditions: 0.1 mmol scale, 1a (1.5 equiv), Ph—X (1.0 equiv), base 1.5 equiv), Pd₂(pmdba)₃ (2.5 mol %), ligand (7.5 mol %), 0.5 mL dioxane.
[b]yield determined by LCMS analysis of the crude reaction mixture using 1,3,5-trimethoxybenzene as a standard.
[c]Determined by chiral SFC analysis of the isolated product.
[d]Reaction performed at 80° C.
[e]Reaction performed at 54° C. PMP = p-methoxyphenyl. pmdba = 4,4'-dimethoxydibenzylideneacetone.

Example 9: Evaluation of N-Protecting Groups for Pd-Catalyzed Lactam α-Arylation A number of different N-protecting groups were tolerated (Table 7). Bis-methoxyphenyl lactam 1b performs just as well as 1a with Method B, but a slight decrease in yield and enantioselectivity is observed when subjected to Method A (3ba). Switching to ortho-methoxy phenyl substituted 1c or electron-deficient trifluoromethylphenyl 1e led to diminished yield and enantioselectivity (3ca and 3ea). Although N-phenyl 1d does not outperform 1a in Method A, it does exhibit higher reactivity and enantioselectivity when exposed to Method B, furnishing the desired product in 91% yield and 93% ee (3da). Benzyl-protected lactam 1f affords α-quaternary lactam 3fa in high levels of enantiomeric excess across both Methods.

TABLE 7

Evaluation of N-protecting groups in arylation of lactams 1a-f[a]

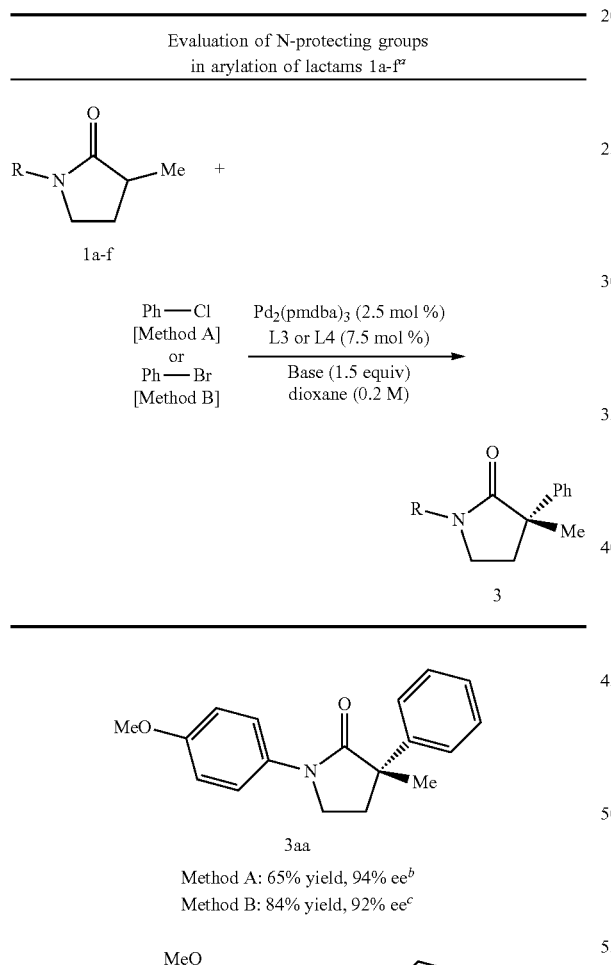

3aa
Method A: 65% yield, 94% ee[b]
Method B: 84% yield, 92% ee[c]

3ba
Method A: 53% yield, 89% ee
Method B: 85% yield, 92% ee

TABLE 7-continued

Evaluation of N-protecting groups in arylation of lactams 1a-f[a]

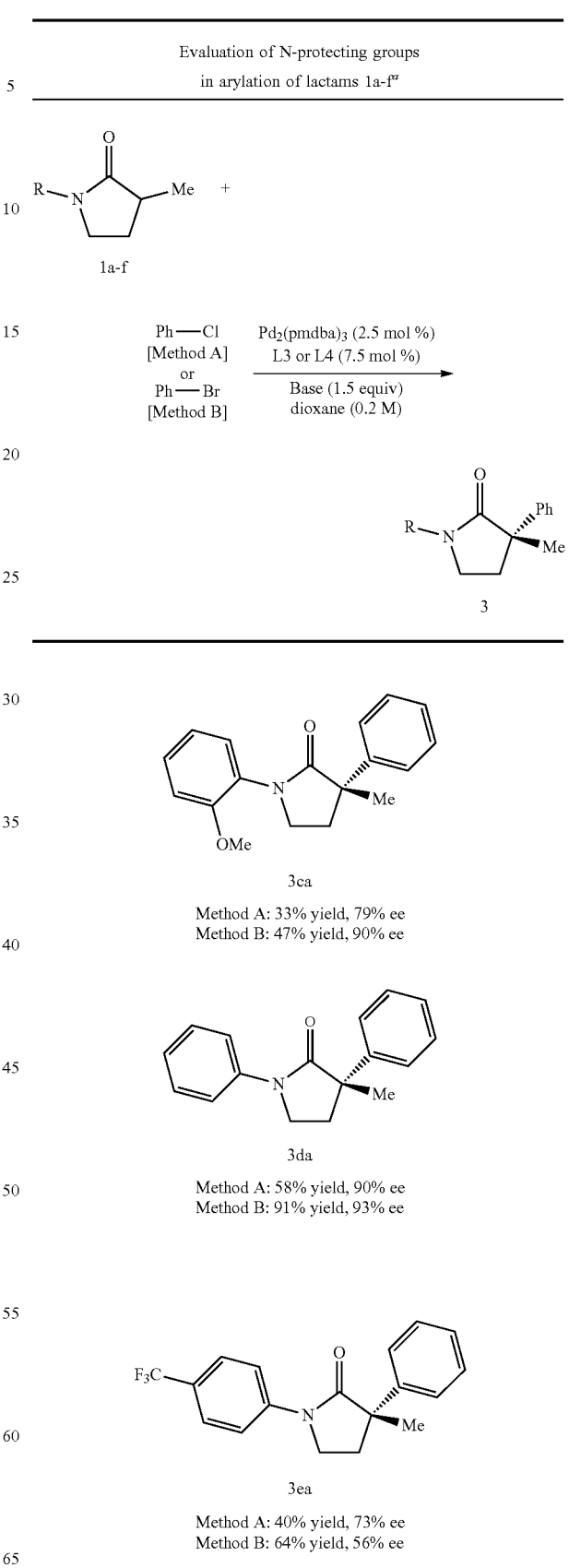

3ca
Method A: 33% yield, 79% ee
Method B: 47% yield, 90% ee

3da
Method A: 58% yield, 90% ee
Method B: 91% yield, 93% ee

3ea
Method A: 40% yield, 73% ee
Method B: 64% yield, 56% ee

TABLE 7-continued

Evaluation of N-protecting groups in arylation of lactams 1a-f[a]

1a-f

Ph—Cl [Method A] or Ph—Br [Method B]

Pd$_2$(pmdba)$_3$ (2.5 mol %)
L3 or L4 (7.5 mol %)
Base (1.5 equiv)
dioxane (0.2 M)

3

3fa

Method A: 43% yield, 95% ee
Method B: 55% yield, 92% ee

[a]Conditions for each method are as follows: Method A: lactam (1.5 equiv), Ph—Cl (1.0 equiv), Pd$_2$(pmdba)$_3$ (2.5 mol %), L3 (7.5 mol %) LiHMDS (1.5 equiv), dioxane (0.2 M), 100° C., 20 h. Method B: lactam (1.5 equiv), Ph—Br(1.0 equiv), Pd$_2$(pmdba)$_3$ (2.5 mol %), L4 (7.5 mol %), NaHMDS (1.5 equiv), dioxane (0.2 M), 80° C., 20 h.
[b]6 h.
[c]15 h. pmdba = 4,4'-dimethoxydibenzylideneacetone.

Example 10: Evaluation of Reaction Time, Temperature and Pd Sources for Pd-Catalyzed Lactam α-Arylation When the reaction was monitored over time, the yield did not significantly increase between 30 minutes and 8 hours (Table 8). At 60° C., a lower yield was obtained. Other Pd sources resulted in similarly low yields (Table 9).

TABLE 8

Effect of time on Pd-catalyzed lactam α-arylation 22 (1.2 equiv) + 17 (1.0 equiv)

Pd(OAc)$_2$ (10 mol %)
Ligand (12 mol %)
Base (1.0 equiv)
toluene (0.1 M)
80° C., 20 h

| Entry | Ligand | Reaction time | Conv. (%) | % Yield (22) | % anisole (18) | ee (%) |
|---|---|---|---|---|---|---|
| 1 | L18 | 30 min | 36 | 24 | 19 | −79 |
| 2 | L18 | 1 h | 64 | 23 | 17 | −79 |
| 3 | L18 | 8 h | 76 | 33 | 25 | −79 |
| 4 | L17 | 30 min | 65 | 23 | 16 | −79 |
| 5 | L17 | 1 h | 71 | 24 | 17 | −78 |
| 6 | L17 | 8 h | 81 | 28 | 26 | |

TABLE 9

Effect of Pd sources on Pd-catalyzed lactam α-arylation 22 (1.2 equiv) + 17 (1.0 equiv)

[Pd] (10 mol %)
L18 (12 mol %)
Additive (1.0 equiv)
LiHMDS (1.0 equiv)
toluene (0.1 M)
60-80° C.

23 + 18

| Entry | [Pd] | Additive | Conv. (%) | % Yield (22) | % anisole (18) |
|---|---|---|---|---|---|
| 1 | [Pd(cinnamyl)Cl]$_2$ | — | 55 | 27 | 24 |
| 2 | [Pd(cinnamyl)Cl]$_2$ | LiOt-Bu | 59 | 20 | 23 |
| 3 | [Pd(cinnamyl)Cl]$_2$ | NaOt-Bu | 76 | 12 | 18 |
| 4 | [Pd(cinnamyl)Cl]$_2$ | KOt-Bu | 93 | 25 | 14 |
| 5 | Pd(PPh$_3$)$_4$ | — | 52 | 16 | 5 |
| 6 | Pd(Cp)(allyl) | — | 40 | 13 | 17 |

Example 11: Scope of Aryl Halides and Lactams for Pd-Catalyzed Lactam α-Arylation Aryl bromides and aryl chlorides with a variety of substitution patterns are accommodated in the arylation (Table 10). Aryl halides possessing electron-deficient (see products 3ab, 3ad, 3ah, 3ae) and electron-rich (3af, 3ag) substituents at the para position led to products with excellent enantioselectivites using Method A and B, respectively. Aryl halides possessing substituents at the meta position are also permissible in both Method A and B, although slightly diminished enantioselectivity is observed when 3-chloroanisole is used as the electrophile (3ai). Trace product is observed when ortho-substituted aryl halides are exposed to the reaction conditions. An N-methyl indole was also well tolerated. 5-indolyl lactam 3al was obtained in moderate yield and excellent enantioselectivity.

TABLE 10

Scope of aryl halide[a]

1a

Ar—Cl [Method A] or Ar—Br [Method B]    2a-l

Pd$_2$(pmdba)$_3$ (2.5 mol %)
L3 or L4 (7.5 mol %)
base (1.5 equiv)
dioxane (0.2 M)

3

3aa
Method A: 65% yield, 94% ee
Method B: 83% yield, 92% ee

3ab[b]
Method A: 83% yield, 95% ee
Method B: 75% yield, 93% ee

3ac
Method A: 88% yield, 94% ee

3ad
Method A: 33% yield, 93% ee

3ae
Method A: 78% yield, 97% ee

TABLE 10-continued

Scope of aryl halide[a]

1a: PMP-N-pyrrolidinone with Me at 3-position

Ar—Cl [Method A] or Ar—Br [Method B]  2a-l

Pd$_2$(pmdba)$_3$ (2.5 mol %)
L3 or L4 (7.5 mol %)
base (1.5 equiv)
dioxane (0.2 M)

→ 3: PMP-N-pyrrolidinone with Ar and Me at 3-position

3af (4-methylphenyl)
Method A: 49% yield, 91% ee
Method B: 57% yield, 95% ee

3ag (4-t-Bu-phenyl)
Method A: 60% yield, 91% ee

3ah (4-(pyrrolidine-1-carbonyl)phenyl)
Method A: 87% yield, 81% ee

3ai (3-OMe-phenyl)
Method A: 69% yield, 86% ee

3aj (3-CF$_3$-phenyl)
Method A: 75% yield, 96% ee

3ak (3-methylphenyl)
Method B: 70% yield, 97% ee

TABLE 10-continued

Scope of aryl halide[a]

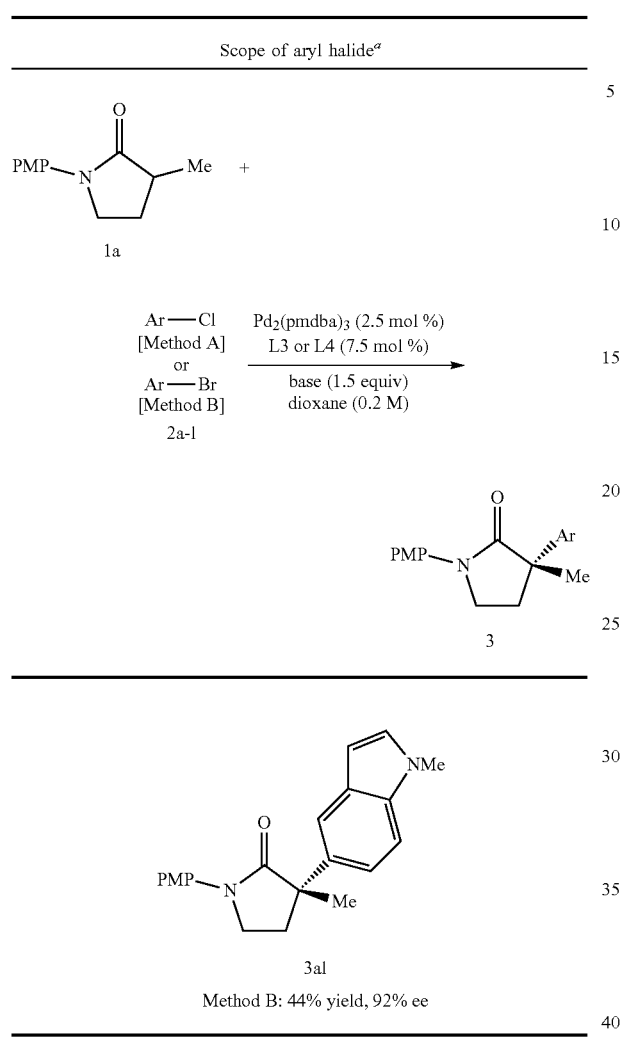

3al
Method B: 44% yield, 92% ee

[a]Conditions for each method are as follows: Method A: 1a (1.5 equiv), Ar—Cl (1.0 equiv), Pd₂(pmdba)₃ (2.5 mol %), L3 (7.5 mol %), LiHMDS (1.5 equiv), dioxane (0.2 M), 100° C., 6 h. Method B: lactam (1.5 equiv), Ar—Br (1.0 equiv), Pd₂(pmdba)₃ (2.5 mol %), L4 (7.5 mol %) NaHMDS (1.5 equiv), dioxane (0.2 M), 80° C., 15 h.
[b]Absolute configuration determined via single crystal X-ray analysis. PMP = p-methoxyphenyl. pmdba = 4,4'-dimethoxydibenzylideneacetone.

Sterically demanding α-substituents are well tolerated in both Methods (Table 11). Although the yields are slightly diminished, the high levels of enantioselectivity are retained. Examples having ethyl (3ha, 3hb), benzyl (3ga, 3gb), propyl (3ia), phenethyl (3ja), and 2-naphthylmethyl (3ka) substitution all furnish the α-arylated products in good enantioselectivity. α-Benzyl substituted lactam 1g was also employed in the reaction with a number of different electrophilic coupling partners using both Methods. Even with a more hindered substrate, similar patterns of reactivity and selectivity to α-methyl substituted 1a were observed. When an electron-deficient aryl chloride coupling partner is used in Method A or m-bromotoluene is used in Method B with 1g, the desired product is formed in high enantioselectivity and good yield (3gc and 3gk).

TABLE 11

Scope of the lactam[a]

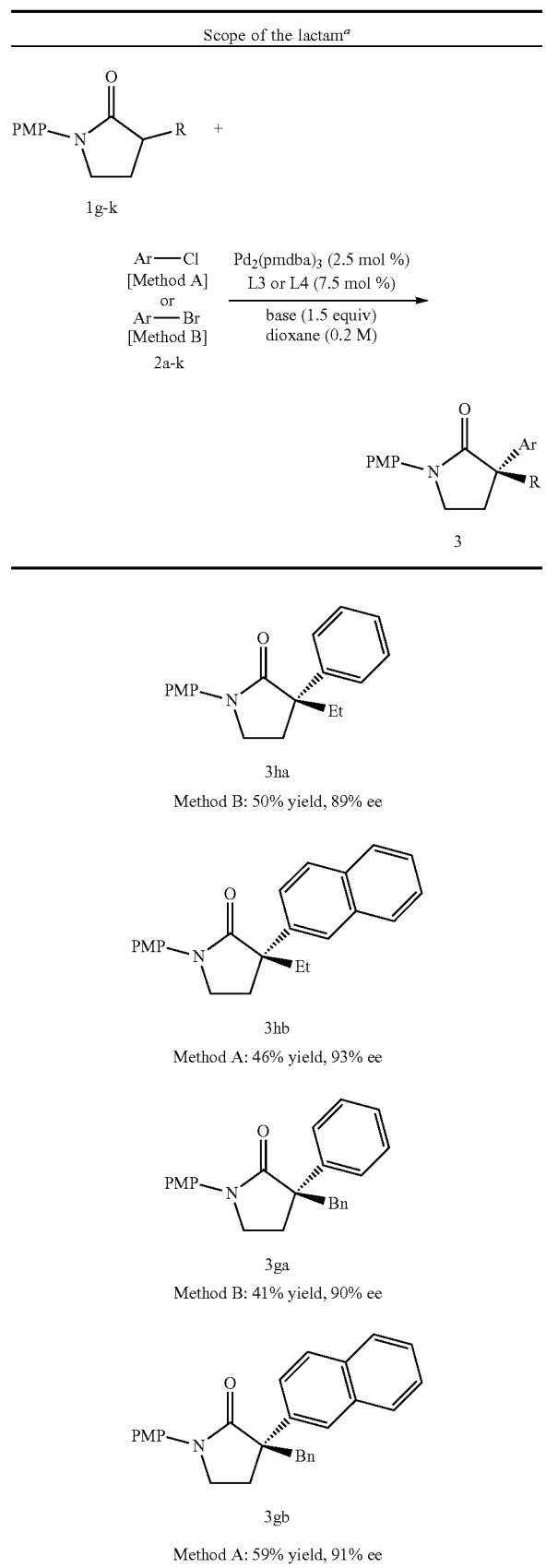

3ha
Method B: 50% yield, 89% ee

3hb
Method A: 46% yield, 93% ee

3ga
Method B: 41% yield, 90% ee

3gb
Method A: 59% yield, 91% ee

TABLE 11-continued

Scope of the lactam[a]

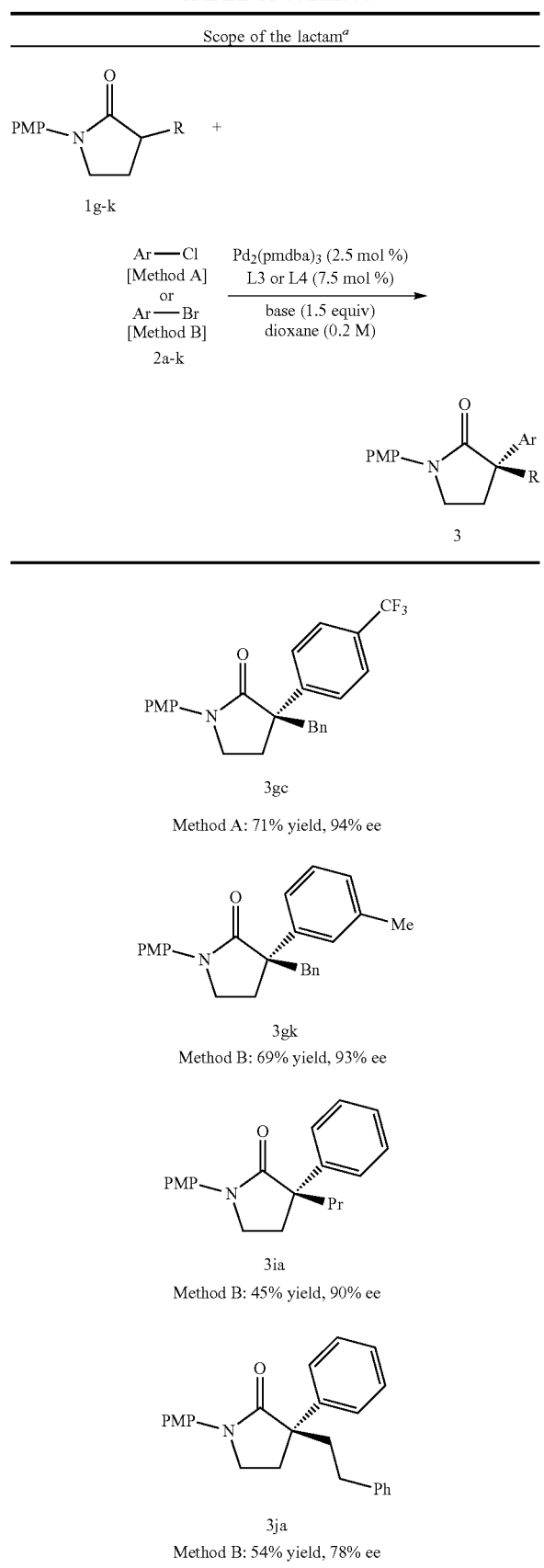

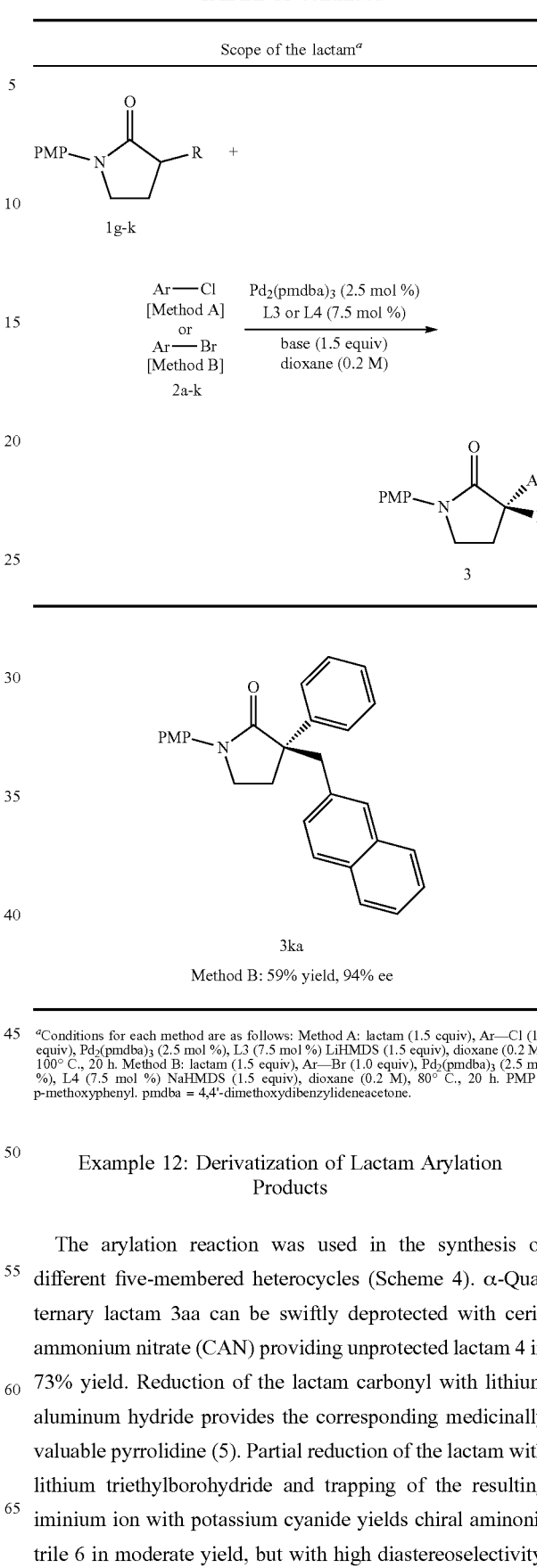

[a]Conditions for each method are as follows: Method A: lactam (1.5 equiv), Ar—Cl (1.0 equiv), Pd₂(pmdba)₃ (2.5 mol %), L3 (7.5 mol %) LiHMDS (1.5 equiv), dioxane (0.2 M), 100° C., 20 h. Method B: lactam (1.5 equiv), Ar—Br (1.0 equiv), Pd₂(pmdba)₃ (2.5 mol %), L4 (7.5 mol %) NaHMDS (1.5 equiv), dioxane (0.2 M), 80° C., 20 h. PMP = p-methoxyphenyl. pmdba = 4,4'-dimethoxydibenzylideneacetone.

Example 12: Derivatization of Lactam Arylation Products

The arylation reaction was used in the synthesis of different five-membered heterocycles (Scheme 4). α-Quaternary lactam 3aa can be swiftly deprotected with ceric ammonium nitrate (CAN) providing unprotected lactam 4 in 73% yield. Reduction of the lactam carbonyl with lithium aluminum hydride provides the corresponding medicinally valuable pyrrolidine (5). Partial reduction of the lactam with lithium triethylborohydride and trapping of the resulting iminium ion with potassium cyanide yields chiral aminonitrile 6 in moderate yield, but with high diastereoselectivity.

Scheme 4 Derivatization of arylation products

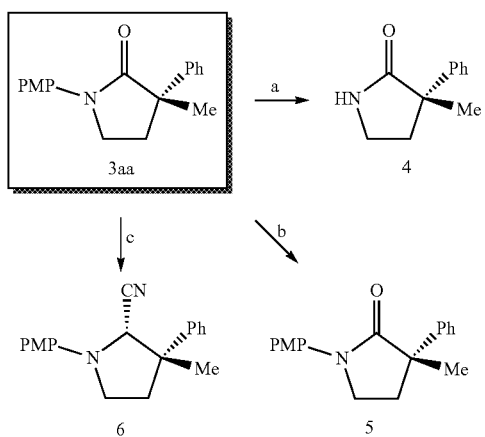

<sup>a</sup>Conditions: (a) CAN, MeCN/H₂O, 0° C., 30 min, 73% yield; (b) LAH, Et₂O, 0° C. to 23° C., 16 h, 93% yield; (c) LiBEt₃H, -78° C. to 23° C., then AcOH, KCN, 0° C., 5 h, 43% yield, 93:7 dr.

III. Pd-Catalyzed α-Vinylation of Lactams

Example 13: Evaluation of Pd Sources for Pd-Catalyzed Lactam α-Vinylation

α-Vinylation of lactam 15 with 2-chloroprop-1-ene (25) was achieved in the presence of LiHMDS and various palladium sources (Table 12).

TABLE 12

Effect of various palladium sources on α-vinylation of lactam 15 with vinyl 25

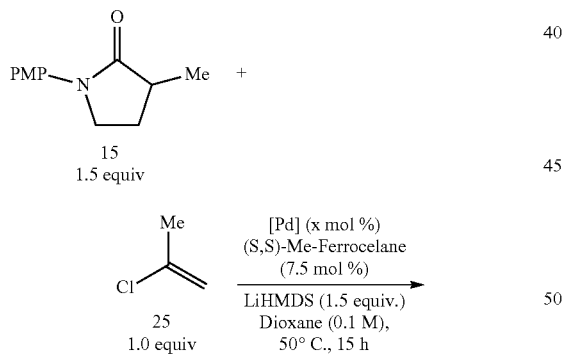

| Entry | [Pd] (x) | % Yield (26) | ee (%) |
|---|---|---|---|
| 1 | Pd₂(pm-dba)₃ (2.5) | 21 | 91 |
| 2 | Pd₂(dba)₃ (2.5) | 34 | 95 |
| 3 | Pd(OAc)₂ (5) | trace | — |

α-Vinylation of lactam 15 with 1-chloro-2-methylprop-1-ene (27) was achieved in the presence of LiHMDS and various palladium sources (Table 13).

TABLE 13

Effect of various palladium sources on α-vinylation of lactam 15 with vinyl 27

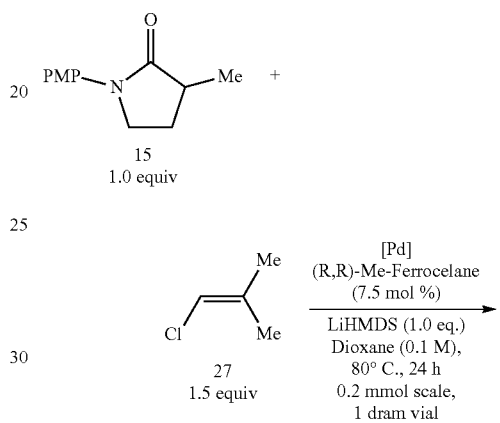

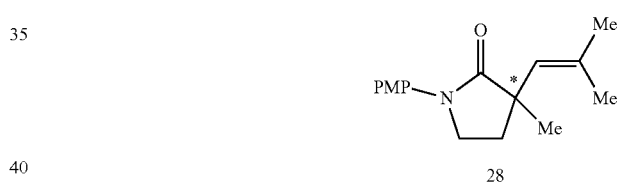

| Entry | [Pd] | % Yield (28) | % ee |
|---|---|---|---|
| 1 | Pd(dba)₂ (5 mol %) | 40 | 94 |
| 2 | Pd(dba)₂ (10 mol %) | 24 | — |
| 3 | Pd(dm-dba)₂ (5 mol %) | 8 | — |

Example 14: Evaluation of Ligands for Pd-Catalyzed Lactam α-Vinylation

α-vinylation of lactam 15 with vinyl 25 was achieved in the presence of LiHMDS and catalytic Pd₂(pm-dba)₃ using various ligands (Table 14).

TABLE 14
Effect of ligand on α-vinylation of lactam 15 with vinyl 25
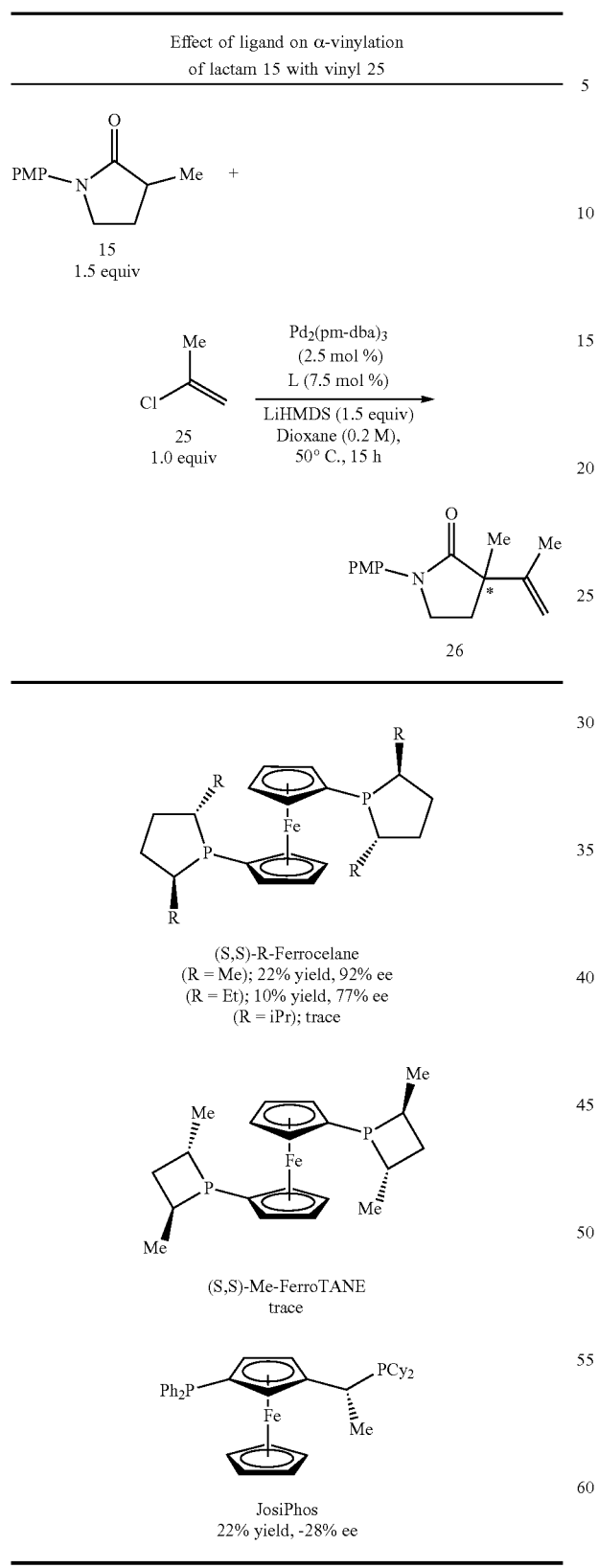
TABLE 15
Effect of ligand on α-vinylation of lactam 15 with vinyl 27
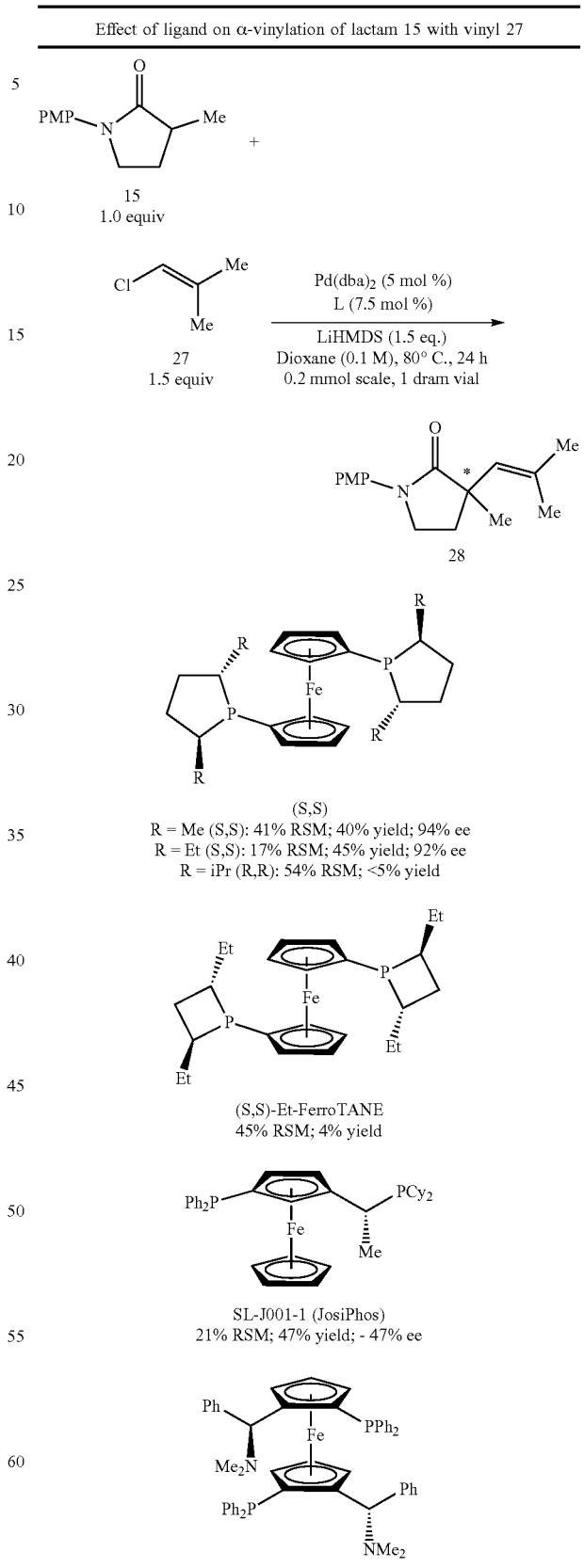
α-vinylation of lactam 15 with vinyl 27 was achieved in the presence of LiHMDS and catalytic Pd(dba)$_2$ using various ligands (Table 15).

TABLE 15-continued

Effect of ligand on α-vinylation of lactam 15 with vinyl 27

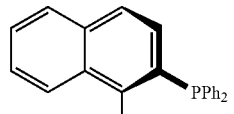

(R)-BINAP
37% RSM; 4% yield

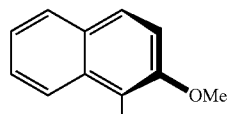

(R)-MOP
24% RSM; <1% yield

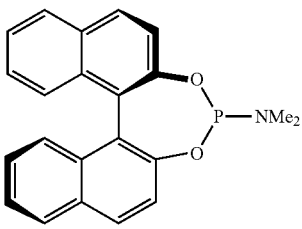

(R)-MonoPhos
35% RSM; 5% yield

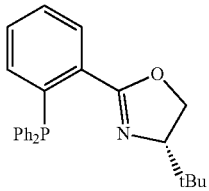

(S)-tBu-PHOX
30% RSM; 4% yield

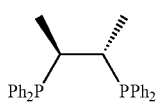

(R,R)-ChiraPhos
46% RSM; 4% yield

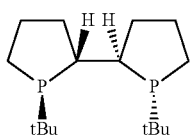

(S,S,R,R)-TangPhos
37% RSM; 10% yield

TABLE 15-continued

Effect of ligand on α-vinylation of lactam 15 with vinyl 27

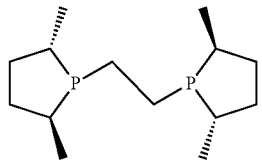

(S,S)-Me-BPE
87% RSM; 5% yield

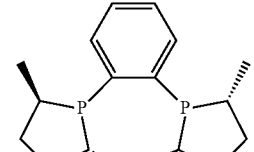

(R,R)-Me-DuPhos
29% RSM; 5% yield

Example 15: Evaluation of Temperature for Pd-Catalyzed Lactam α-Vinylation

α-Vinylation of lactam 15 with vinyl 25 was achieved in the presence of LiHMDS and catalytic Pd$_2$(pm-dba)$_3$ at various temperatures (Table 16).

TABLE 16

Effect of temperature on α-vinylation of lactam 15 with vinyl 25

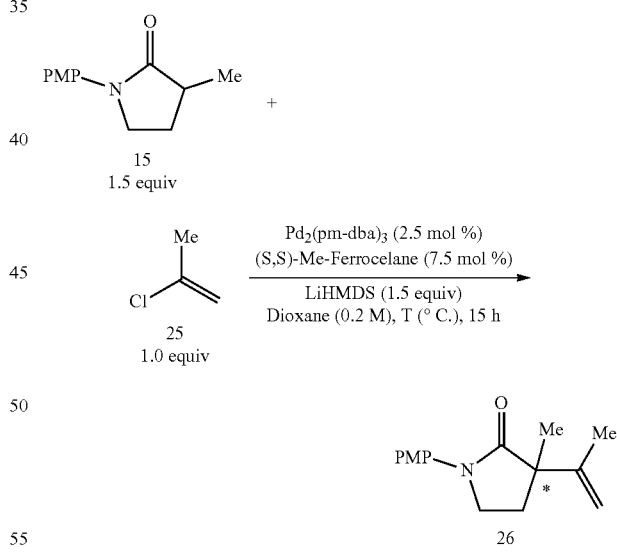

| Entry | T | % RSM$^a$ | % Yield (26)$^a$ | % ee |
|---|---|---|---|---|
| 1 | 60 | 23 | 37 | 88 |
| 2 | 50 | 31 | 42 | 86 |
| 3 | 40 | 67 | 8 | — |
| 4 | 60 | — | 36$^b$ | 86 |

$^a$Internal standard trimethoxybenzene (TMB) was used for measurements.
$^b$Isolated yield.

α-Vinylation of lactam 15 with vinyl 27 was achieved in the presence of LiHMDS and catalytic Pd$_2$(dba)$_3$ at various temperatures (Table 17).

TABLE 17

Effect of temperature on α-vinylation of lactam 15 with vinyl 27

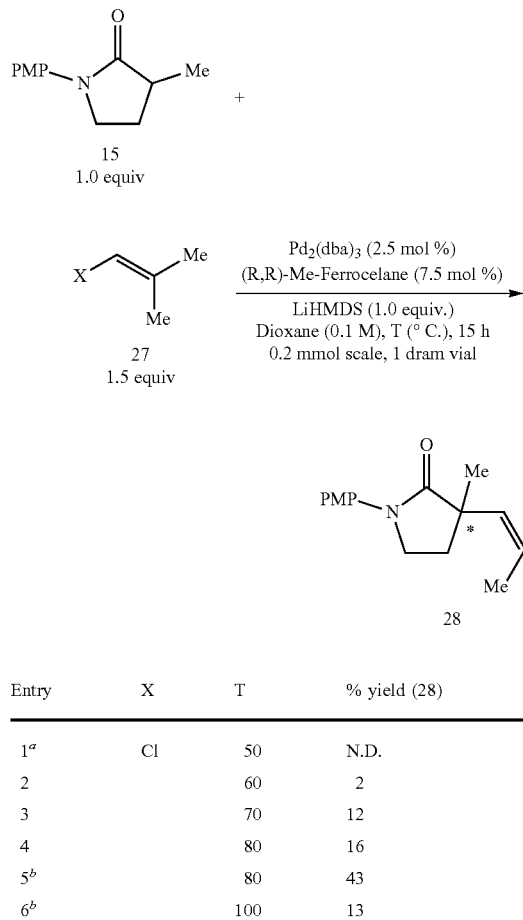

| Entry | X | T | % yield (28) |
|---|---|---|---|
| 1[a] | Cl | 50 | N.D. |
| 2 | | 60 | 2 |
| 3 | | 70 | 12 |
| 4 | | 80 | 16 |
| 5[b] | | 80 | 43 |
| 6[b] | | 100 | 13 |
| 7[a] | Br | r.t. | trace |
| 8[a] | | 40 | 7 |
| 9[a] | | 50 | 8 |
| 10[a] | | 80 | 13 |

[a](S,S)-Me-ferrocelane
[b]24 h

Example 16: Evaluation of Solvents and Solvent Concentration for Pd-Catalyzed Lactam α-Vinylation α-Vinylation of lactam 15 with vinyl 25 was achieved in the presence of LiHMDS and catalytic $Pd_2$(pm-dba)$_3$ at various concentrations of dioxane (Table 18).

TABLE 18

Effect of Dioxane concentration on α-vinylation of lactam 15 with vinyl 25

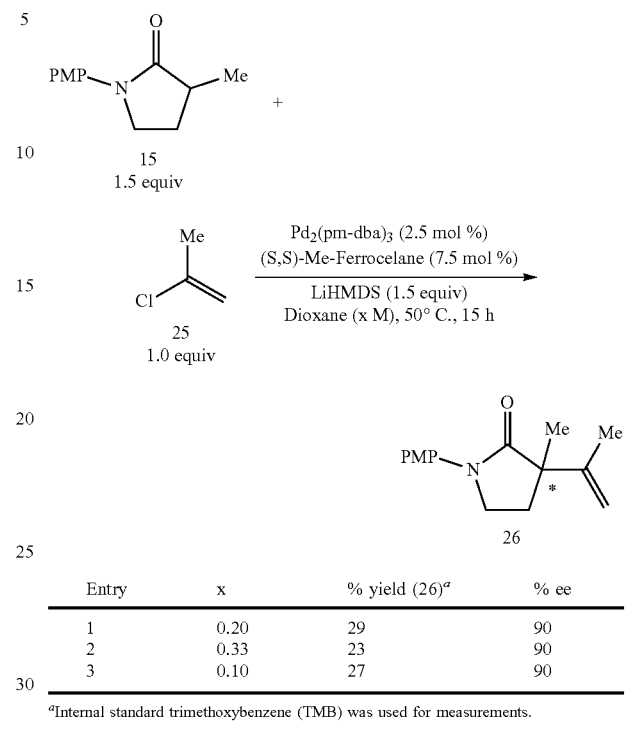

| Entry | x | % yield (26)[a] | % ee |
|---|---|---|---|
| 1 | 0.20 | 29 | 90 |
| 2 | 0.33 | 23 | 90 |
| 3 | 0.10 | 27 | 90 |

[a]Internal standard trimethoxybenzene (TMB) was used for measurements.

α-Vinylation of lactam 15 with vinyl 27 was achieved in the presence of LiHMDS and catalytic $Pd_2$(dba)$_3$ with a solvent mixture or Toluene alone (Table 19).

TABLE 19

Effect of Dioxane/Toluene mixture or Toluene alone on α-vinylation of lactam 15 with vinyl 27

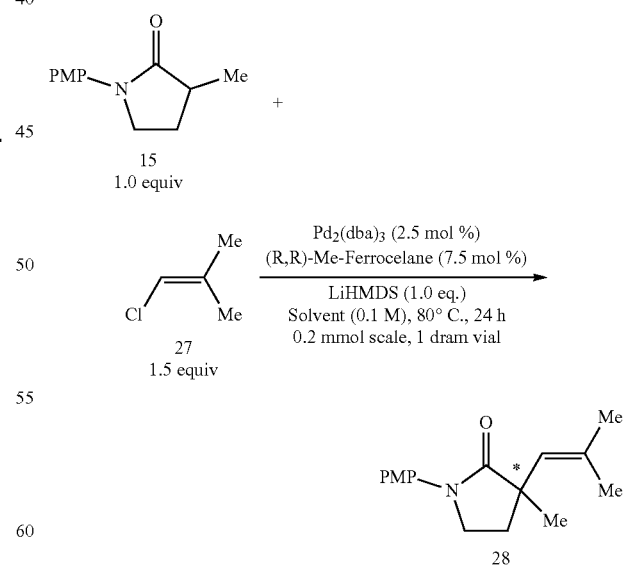

| Entry | Solvent | % yield | % ee |
|---|---|---|---|
| 1 | Dioxane/Toluene (1:1) | 23 | 83 |
| 2 | Toluene | 30 | 84 |

Example 17: Evaluation of Stoichiometry for Pd-Catalyzed Lactam α-Vinylation

α-Vinylation of lactam 15 with vinyl 25 was achieved in the presence of LiHMDS and catalytic $Pd_2(pm\text{-}dba)_3$ with a variation of the stoichiometry of 15 and 25 (Table 20, entry 1), and α-vinylation of lactam 15 with vinyl 27 was achieved in the presence of LiHMDS and catalytic $Pd(dba)_2$ with several variations in the stoichiometry of 15 and 27 (Table 20, entries 2-6).

TABLE 20

Effect of stoichiometry on α-vinylation of lactam 15

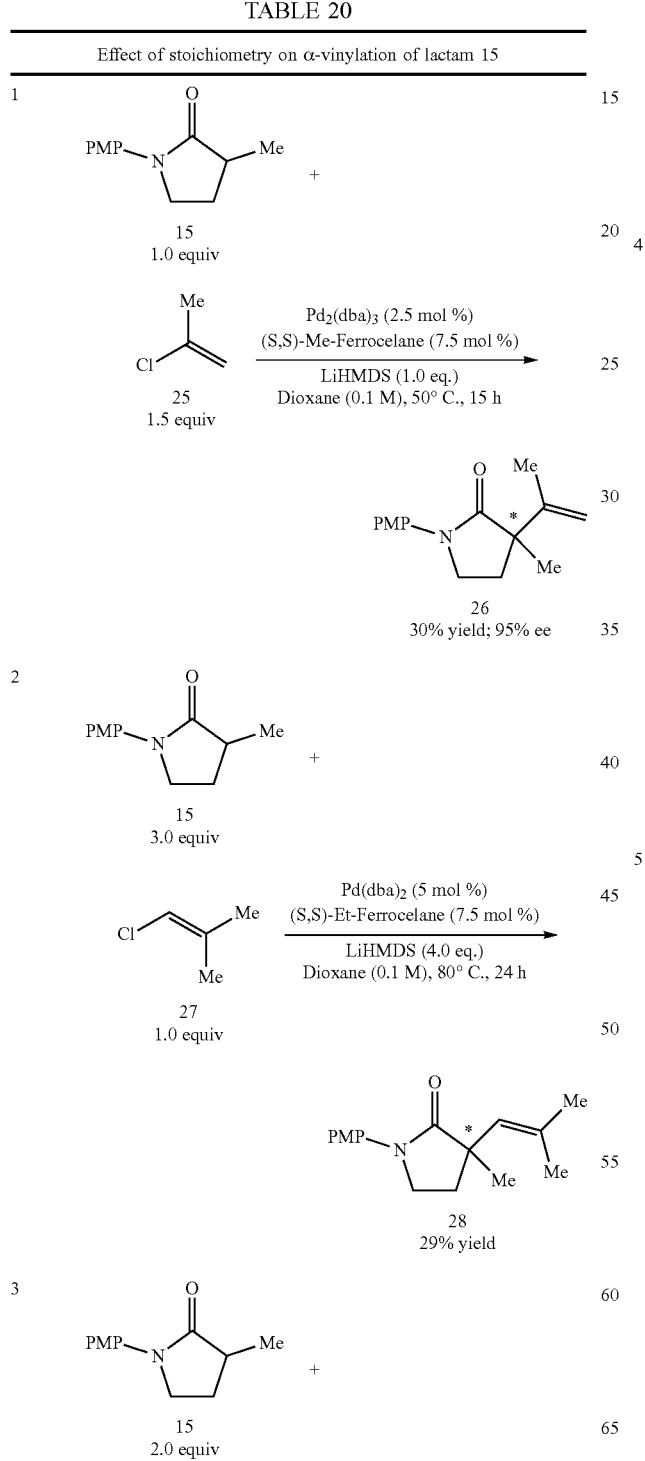

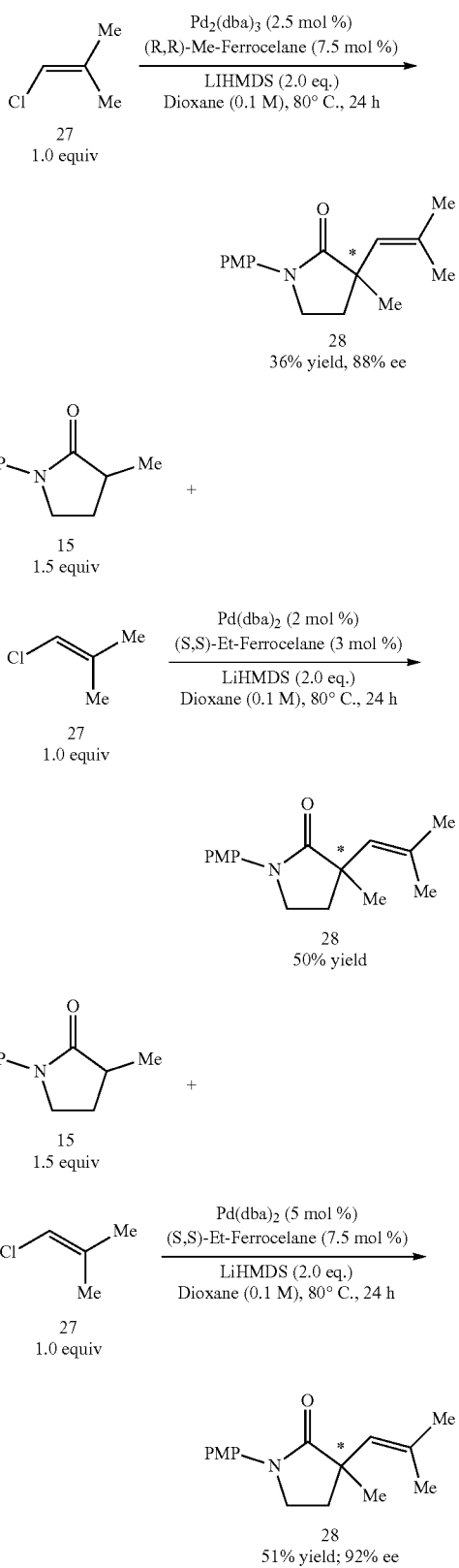

TABLE 20-continued

Effect of stoichiometry on α-vinylation of lactam 15

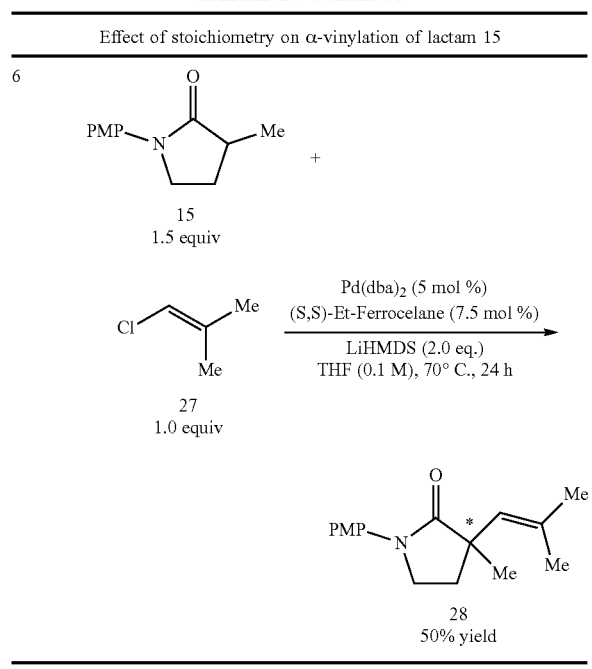

Example 18: Evaluation of N-Protecting Groups for Pd-Catalyzed Lactam α-Vinylation α-Vinylation of lactam 15 with various N-protecting groups was achieved in the presence of LiHMDS and catalytic Pd$_2$(dba)$_3$ (Table 21) using vinyl 27.

TABLE 21

Effect of N-protecting group on α-vinylation of lactam 15 with vinyl 27

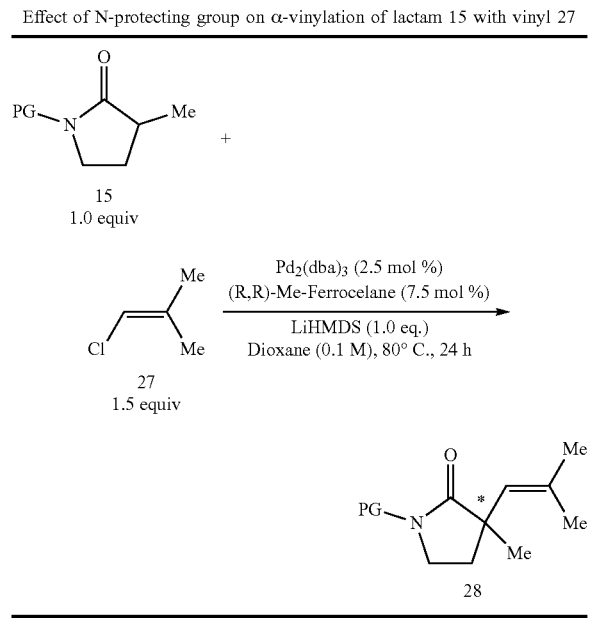

PG =

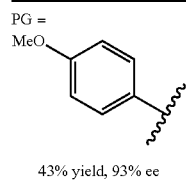

43% yield, 93% ee

TABLE 21-continued

Effect of N-protecting group on α-vinylation of lactam 15 with vinyl 27

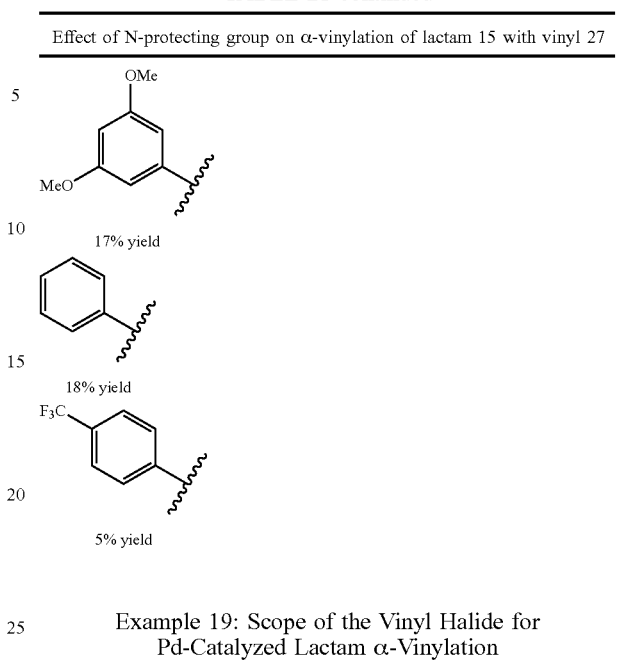

Example 19: Scope of the Vinyl Halide for Pd-Catalyzed Lactam α-Vinylation

α-Vinylation of lactam 15 with 2-chlorovinylbenzene (29) was achieved in the presence of LiHMDS and catalytic Pd(dba)$_2$ (Table 22).

TABLE 22

Scope of vinyl halide for α-vinylation of lactam 15

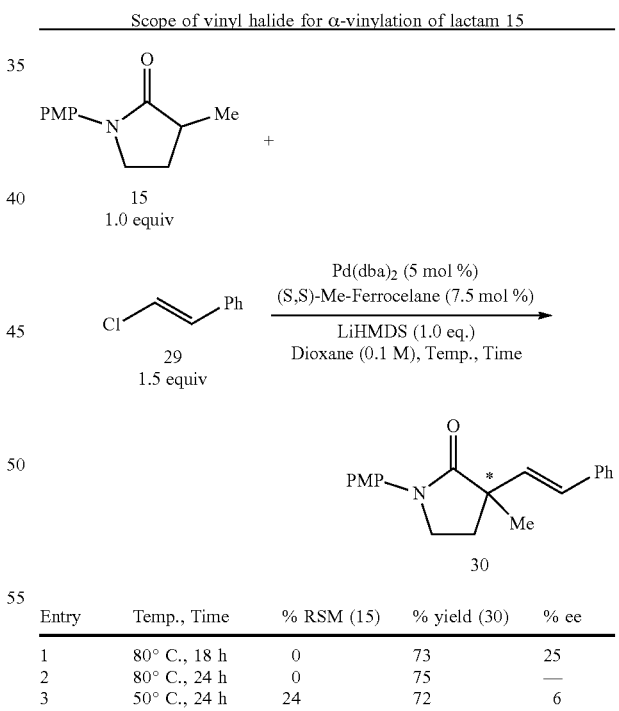

| Entry | Temp., Time | % RSM (15) | % yield (30) | % ee |
|---|---|---|---|---|
| 1 | 80° C., 18 h | 0 | 73 | 25 |
| 2 | 80° C., 24 h | 0 | 75 | — |
| 3 | 50° C., 24 h | 24 | 72 | 6 |

IV. Experimental Procedures

General Information

Unless otherwise stated, reactions were performed in flame-dried or oven-dried glassware under an argon or nitrogen atmosphere using dry, deoxygenated solvents.

Reaction temperatures were controlled by an IKAmag temperature modulator unless otherwise indicated. Glovebox manipulations were performed under a $N_2$ atmosphere. TLC was performed using E. Merck silica gel 60 F254 precoated glass plates (0.25 mm) and visualized by UV fluorescence quenching or $KMNO_3$ staining. Silicycle SiliaFlash P60 Academic Silica gel (particle size 0.040-0.064 mm) was used for flash column chromatography. Analytical chiral HPLC was performed with an Agilent 1100 Series HPLC utilizing a Chiralcel OD-H column (4.6 mm×25 cm) obtained from Daicel Chemical Industries, Ltd. with visualization at 254 nm. Analytical SFC was performed with a Mettler SFC supercritical $CO_2$ analytical chromatography system utilizing a Chiralcel AD column (4.6 mm×25 cm) obtained from Daicel Chemical Industries, Ltd. with visualization at 254 nm. $^1$H-NMR spectroscopic data were collected on a Varian 500 MHz spectrometer at ambient temperature. GC analyses were obtained on an Agilent 6890 Series GC system with a DB-1 column (length 30 m, internal diameter 0.25 mm).

THF, $Et_2O$, $CH_2Cl_2$, toluene, $CH_3CN$, TBME and dioxane were dried by passage through an activated alumina column under argon. Purified water was obtained using a Barnstead NANOpure Infinity UV/UF system. Commercially available reagents were purchased.

N-aryl lactam substrates, Ni benzonitrile complex 20, and $Ni^{II}ArCl$ complex 21 were prepared according to previously reported procedures.

Example 20: Preparation of Authentic Product 16

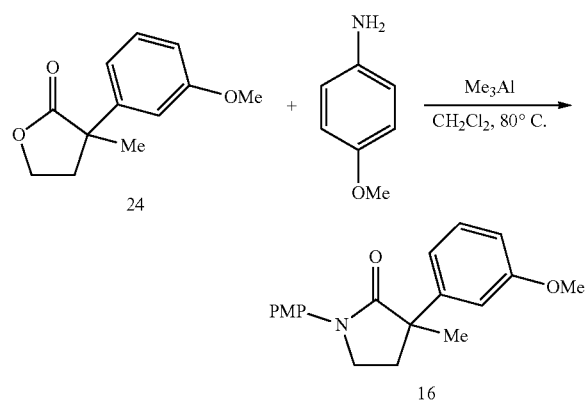

This procedure was adapted from a previously reported procedure. In a Schlenk-tube, to a solution of p-anisidine (219 mg, 1.78 mmol, 3.07 equiv) in $CH_2Cl_2$ (2.0 mL) cooled to 0° C. was added dropwise via syringe a trimethylalumnium-solution (2.0 M in heptane, 0.330 mL, 0.660 mmol, 1.13 equiv). The solution was allowed to warm to room temperature. Lactone 24 (121 mg, 0.580 mmol, 1.00 equiv) was added in $CH_2Cl_2$ (1.9 mL). The Schlenk-tube was closed with a Teflon screw-cap and the reaction mixture was heated to 80° C. for 20 h. After 20 h, the reaction was allowed to cool to room temperature. After quenching with MeOH, followed by the addition of aqueous, saturated $NH_4Cl$-solution and vigorous stirring, the layers were separated and the aqueous phase extracted with ethyl acetate (3×20 mL). The combined organic extracts were dried over $Na_2SO_4$ and the volatiles were removed under reduced pressure. Chromatography of the crude mixture on silica eluting with 50% ethyl acetate/hexane yielded the title compound as an off-white solid. $^1$H-NMR ($CDCl_3$, 500 MHz): δ 7.59-7.55 (m, 2H), 7.27-7.23 (m, 1H), 7.03-6.99 (m, 2H), 6.93-6.89 (m, 2H), 6.79 (m, 1H), 3.81 (s, 3H), 3.80 (s, 3H), 2.57 (ddd, 1H, J=12.6, 6.6, 4.1 Hz), 2.26 (dt, 1H, J=12.7, 8.0 Hz), 1.62 (s, 3H).

Example 21: Representative Procedure for Evaluating Ligands in the Ni-Catalyzed α-Arylation of Lactam with Aryl Halide n=the number of reactions in the screen. In a glovebox, $Ni(COD)_2$ (1.38n mg, 0.005n mmol, 0.100 equiv), toluene (0.25n mL), and a stir bar were added to a 4-mL vial A. To a separate 4-mL vial B was added LiHMDS (8.37n mg, 0.050 n mmol, 1.00 equiv), lactam (10.3n mg, 0.050 n mmol, 1.00 equiv), toluene (0.25n mL), and a stir bar. The contents of A and B were stirred for ~2 minutes. To a separate vial was added the ligand (0.006 mmol, 0.120 equiv) and a stir bar followed by 0.25 mL of solution A. The ligand/Ni mixture was then stirred for 10 minutes and aryl halide (7.1 mg, 6.1 μL, 0.050 mmol, 1.00 equiv) and 0.25 mL of solution B were added. The vial was then sealed with a PTFE-lined cap and removed from the glovebox. The reaction mixture was then heated at and stirred for 16-20 h. The vial was then cooled to room temperature and opened to air. A solution of 1,3,5-trimethoxybenzene (8.41 mg, 0.050 mmol, 1.00 equiv) in $Et_2O$ (0.1 mL) was added as an internal standard. The reaction mixture was then filtered through a short silica plug, eluting with $Et_2O$ (2 mL). An aliquot of the eluate was then removed for GC determination of aryl halide conversion with respect to 1,3,5-trimethoxybenzene. The remaining eluate was then concentrated by rotary evaporator and dissolved in $CDCl_3$ to determine an $^1$HNMR yield with respect to 1,3,5-trimethoxybenzene. Then, the sample was concentrated and purified by preparative TLC (EtOAc/hexanes). The purified product was then dissolved in hexanes for HPLC analysis on a Chiralcel OD column (20% IPA/hexanes, 1.0 mL/min).

Example 22: Representative Procedure for Evaluating Ligands in the Pd-Catalyzed α-Arylation of Lactam with Aryl Halide n=the number of reactions in the screen. In a glovebox, $Pd(OAc)_2$ (1.10 n mg, 0.005n mmol, 0.100 equiv), toluene (0.25n mL), and a stir bar were added to a 4-mL vial A. To a separate 4-mL vial B was added LiHMDS (8.37n mg, 0.050 n mmol, 1.00 equiv), lactam (12.3n mg, 0.060 n mmol, 1.20 equiv), toluene (0.25n mL), and a stir bar. The contents of A and B were stirred for ~2 minutes. To a separate vial was added the ligand (0.006 mmol, 0.120 equiv) and a stir bar followed by 0.25 mL of solution A. The ligand/Pd mixture was then stirred for 10 minutes and aryl halide (7.1 mg, 6.1 μL, 0.050 mmol, 1.00 equiv) and 0.25 mL of solution B were added. The vial was then sealed with a PTFE-lined cap and removed from the glovebox. The reaction mixture was then heated at 80° C. and stirred for 16-20 h. The vial was then cooled to room temperature and opened to air. A solution of 1,3,5-trimethoxybenzene (8.41 mg, 0.050 mmol, 1.00 equiv) in $Et_2O$ (0.1 mL) was added as an internal standard. The reaction mixture was then filtered through a short silica plug, eluting with $Et_2O$ (2 mL). An aliquot of the eluate was then removed for GC determination of aryl halide conversion with respect to 1,3,5-trimethoxybenzene. The remaining eluate was then concentrated by rotary evaporator and dissolved in $CDCl_3$ to determine an $^1$HNMR yield with respect to 1,3,5-trimethoxybenzene. Then, the sample was concentrated and purified by preparative TLC (EtOAc/hexanes). The purified product was then dissolved in hexanes for SFC analysis on a Chiralcel AD column (40% IPA/hexanes, 2.5 mL/min).

V. Pd-Catalyzed Enantioselective Synthesis of Gem-disubstituted N-Boc Diazaheterocycles via Decarboxylative Asymmetric Allylic Alkylation

Example 23: Optimizing Reaction Conditions for Decarboxylative Asymmetric Allylic Alkylation of Piperazin-2-ones With model substrate 3m, conditions based on our previous report (Korch et al., *Angew. Chem. Int. Ed.,* 2015, 54, 179-183) using 10 mol % (S)—(CF$_3$)$_3$-t-BuPHOX ligand and 4 mol % Pd$_2$(pmdba)$_3$ in 0.014 M toluene gave the product 3m in only 76% ee (Table 23, entry 1). Other commonly used allylic alkylation ligands such as (S)-t-BuPHOX (L2) and (S,S)-ANDEN-Ph Trost (L3) were also tested (entries 2-3). We then examined the effect of solvent on the enantioselectivity (entries 4-6), ultimately finding that 2:1 hexanes-toluene provided high yield and ee.

TABLE 23

Optimization of reaction conditions$^a$

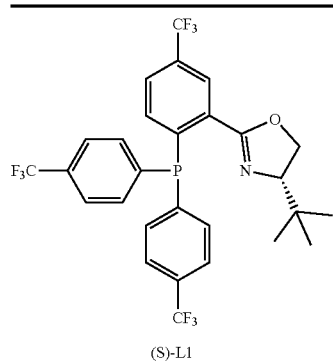

| Entry | L  | Solvent     | Yield (%)$^b$ | ee (%)$^c$ |
|-------|----|-------------|---------------|------------|
| 1     | L1 | Tol         | 75            | 76         |
| 2     | L2 | Tol         | 70            | 1          |
| 3     | L3 | Tol         | 83            | 52         |
| 4     | L1 | THF         | —             | 13         |
| 5     | L1 | MTBE        | —             | 80         |
| 6     | L1 | 2:1 Hex/Tol | 93            | 93         |

(S)-L1

TABLE 23-continued

Optimization of reaction conditions$^a$

| Entry | L | Solvent | Yield (%)$^b$ | ee (%)$^c$ |
|-------|---|---------|---------------|------------|

(S)-L2

(S,S)-L3

$^a$Screens performed on a 0.04 mmol scale. All reported yields are for isolated products. The ee values were determined by chiral SFC analysis. Bz = benzoyl, Boc = tert-butoxycarbonyl, pmdba = bis(4-methoxybenzylidene)acetone

Example 24: Substrate Scope for Decarboxylative Asymmetric Allylic Alkylation of Piperazin-2-Ones The substrate scope of the decarboxylative alkylation of various N4-Boc protected piperazinones was also explored (Table 24). We first tested the α-monosubstituted piperazinone 3a, finding that typical conditions in a 0.033 M solution of toluene afforded the product 4a in high yield and enantioselectivity. Another monosubstituted piperazinone 4b with a N1-anisoyl protecting group, was also obtained in high yield and ee. Furthermore, replacement of the N4-Boc protecting group with Cbz (3c), and 2-chloro substitution of the allyl group (3d) provided similar results.

Next, we examined α,α-disubstituted substrates, finding that for the simple cases of methyl substitution (3e, 3f), performing the reaction at 0.033 M concentration in toluene gave high yields and ee, with no improvement with the use of 2:1 hexanes-toluene at 0.014 M concentration. The exception was N4-benzoyl protected substrate 3g, which in our previous work gave 52% ee in toluene (Korch et al., *Angew.*

*Chem. Int. Ed.,* 2015, 54, 179-183); under our optimized conditions in 2:1 hexanes-toluene, the substrate gave an improved albeit modest ee of 70%. Larger substituents such as α-benzylated compound 3h or benzyloxymethyl ether 3i required the use of 2:1 hexanes-toluene to achieve high enantioselectivity. This unique mixed-solvent requirement was observed in all substituents other than methyl. A wide range of functional groups was tolerated: notably, the nitrile, ketone, and methylcarbamate substrates, which could not be accessed in our previously described efforts, gave high ee and yields (3j-*m*).

TABLE 24

Substrate scope exploration[a]

3a-n → 4a-n

Pd$_2$(dba)$_3$ (4 mol %)
(S)-(CF$_3$)$_3$-tBuPHOX (10 mol %)
2:1 hexanes-toluene
40° C.

4a[c]: R$^1$ = Bz, 90% yield, 92% ee
4b[c]: R$^1$ = An, 90% yield, 96% ee

4c[c]
75% yield
99% ee

4d[b,c]
85% yield
98% ee

TABLE 24-continued

Substrate scope exploration[a]

4e[b,c]
90% yield
96% ee

4f[b,c]
85% yield
96% ee 4g
80% yield
70% ee

4h[b]
70% yield
96% ee

4i[b]
87% yield
92% ee

TABLE 24-continued

Substrate scope exploration[a]

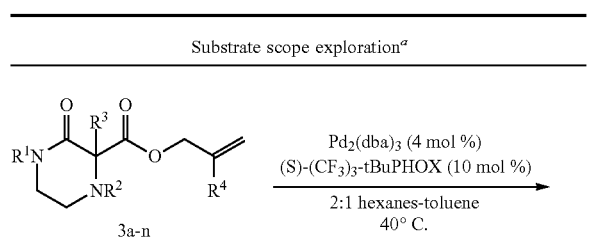

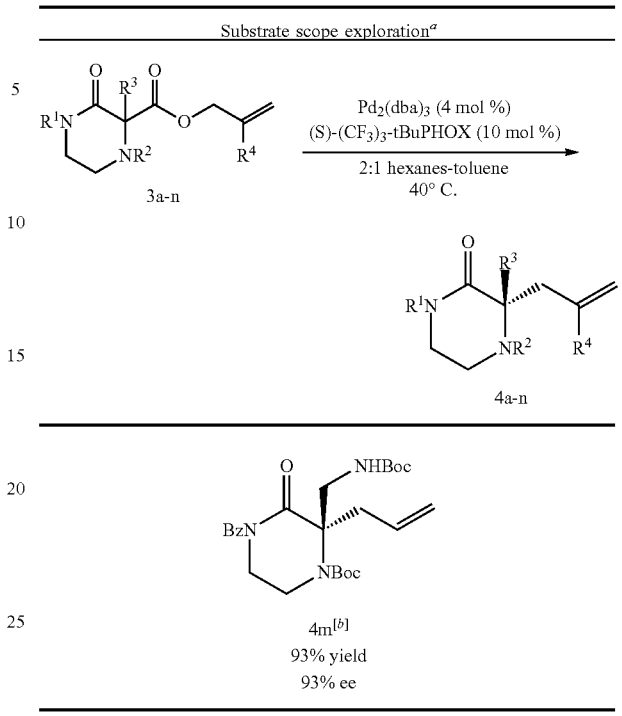

[a]Conditions: piperazin-2-one 3 (1.0 equiv), Pd₂(dba)₃ (4 mol %), (S)-(CF₃)₃-tBuPHOX (10 mol %), in 2:1 hexanes/toluene (0.014 M) at 40° C. for 12-24 h.
[b]Pd₂(pmdba)₃ (4 mol %) instead of Pd₂(dba)₃.
[c]Toluene (0.033 M) instead of 2:1 hexanes/toluene. All reported yields are for isolated products. The ee values were determined by chiral SFC analysis. An = 4-methoxybenzoyl, dba = dibenzylideneacetone.

Example 25: Scope of α-Substituents for Pd-Catalyzed Decarboxylative Alkylation of Tetrahydropyrimidin-4-Ones If decarboxylative alkylation could be achieved with the versatile tetrahydropyrimidin-2-one scaffold, a broader range of chiral β$^{2,2}$-amino acids might be accessible:

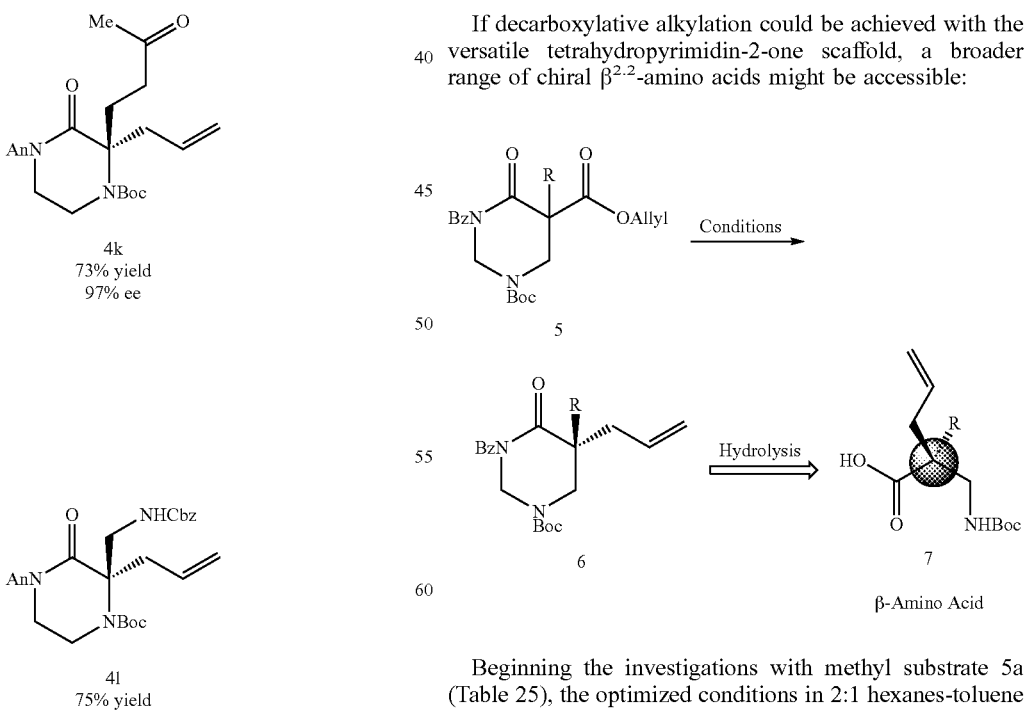

Beginning the investigations with methyl substrate 5a (Table 25), the optimized conditions in 2:1 hexanes-toluene furnished the decarboxylative alkylation product 6a in high yield and ee. The reaction proved amenable to a variety of α-substituents, including ethyl (6b), methyl ester (6c), 2-chloroallyl (6d), and benzyl (6e). Furthermore, the reaction is scalable, as shown for the benzyl substrate 5e in a 1 gram reaction. In contrast, the nitrile and benzyloxymethyl ether products 6f and 6g were isolated with reduced enantioselectivities. The fluorine and propargyl substrates 5h and 5i were also able to be used, and may serve as a precursor to a novel fluorinated $\beta^{2.2}$-amino acid, or for biorthogonal click reactions, respectively.

TABLE 25

Scope of α-substituents for Pd-catalyzed decarboxylative alkylation of tetrahydropyrimidin-4-ones[a]

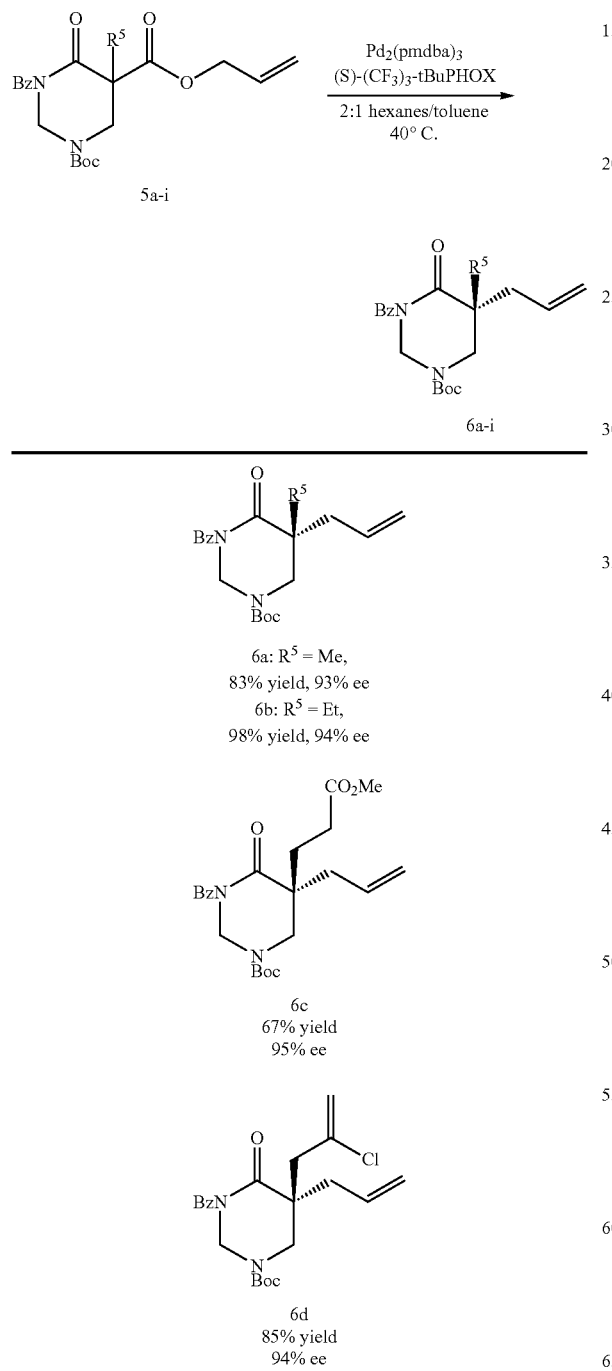

6a: $R^5$ = Me,
83% yield, 93% ee
6b: $R^5$ = Et,
98% yield, 94% ee 6c
67% yield
95% ee 6d
85% yield
94% ee TABLE 25-continued Scope of α-substituents for Pd-catalyzed decarboxylative alkylation of tetrahydropyrimidin-4-ones[a]

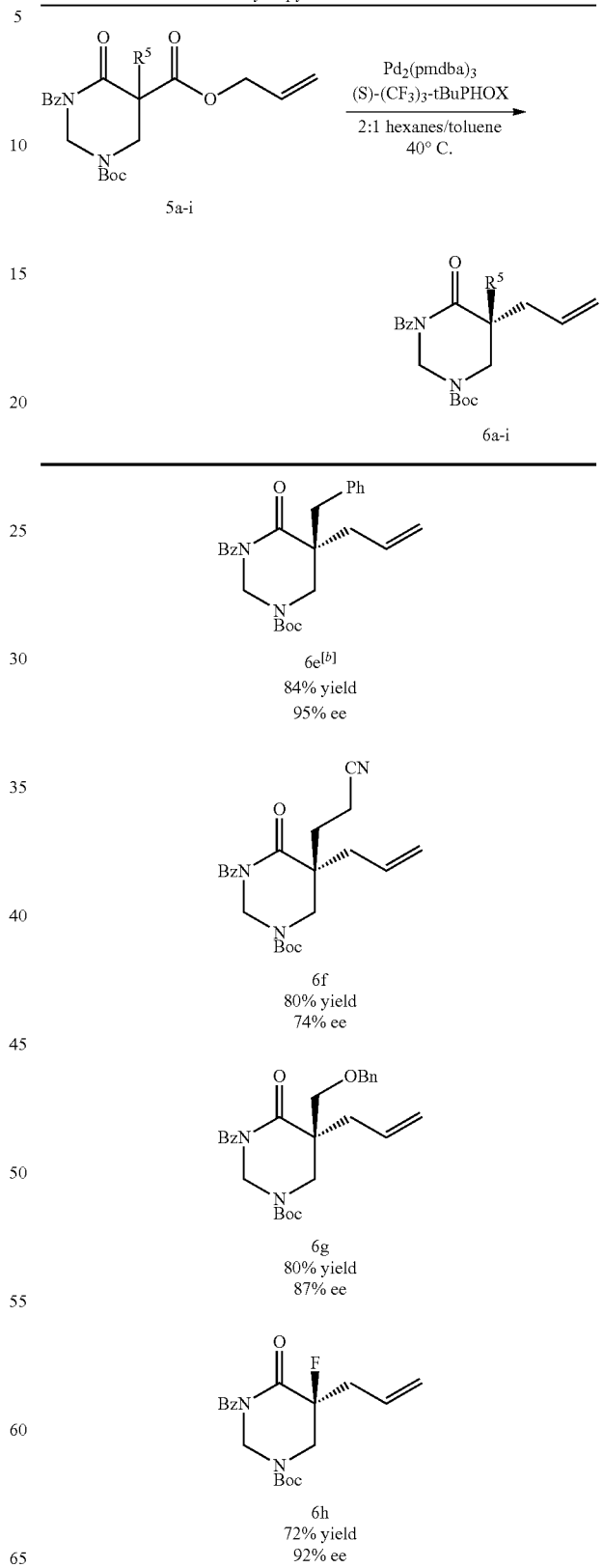

6e[b]
84% yield
95% ee 6f
80% yield
74% ee 6g
80% yield
87% ee 6h
72% yield
92% ee

TABLE 25-continued

Scope of α-substituents for Pd-catalyzed decarboxylative alkylation of tetrahydropyrimidin-4-ones[a]

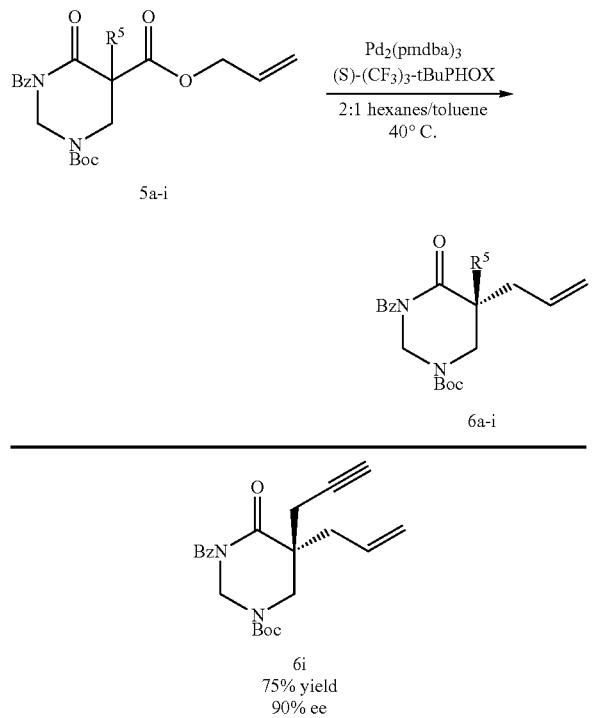

6i
75% yield
90% ee

[a]Conditions: tetrahydropyrimidinone 5 (1.0 equiv), Pd₂(pmdba)₃ (4 mol %), (S)-(CF₃)₃-tBuPHOX (10 mol %), in 2:1 hexanes/toluene (0.014 M) at 40° C. for 12-24 h. All reported yields are for isolated products.
[b]Reaction performed with 1 gram of substrate 5e. The ee values were determined by chiral SFC analysis.

Example 26: Synthetic Utility of Compounds 4a-m and Compounds 6a-i

Both Boc groups of 4m could be removed by treatment with excess TFA to give aminopiperazinone 8 (Table 26, row a). With LiOH, the benzoyl group could be orthogonally removed to provide the free amide 9 (Table 26, row b). The amide 9 could then be reduced with LiAlH₄ to the corresponding chiral aminopiperazine 10. To further illustrate the synthetic versatility realized by Boc-deprotection of N4, we hydrogenated the allyl olefin of methyl piperazinone 4e before cleaving the Boc group to obtain 11. We then applied Gaunt's method of CH carbonylation on the aliphatic amine of 11 to forge the fused β-lactam 12, which bears resemblance to the core of various β-lactam antibiotics and β-lactamase inhibitors (Table 26, row c). [J. R. Cabrera-Pardo, A. Trowbridge, M. Nappi, K. Ozaki, M. J. Gaunt, *Angew. Chem. Int. Ed.* 2017, 56, 11958-11962]. Lastly, we transformed four tetrahydropyrimidinone substrates, 6c-e and 6h, into their corresponding acyclic forms (Table 26, rows d-e). Using a two-step protocol involving TFA-mediated Boc cleavage followed by saponification with LiOH, we successfully obtained the crude $\beta^{2,2}$-amino acid (Table 26, row d); to facilitate silica gel chromatographic isolation, we chose to mask the free amine and carboxylic acid with Boc and benzyl groups, respectively, resulting in protected $\beta^{2,2}$-amino acid 13. We note that in this four step sequence, we only performed one chromatographic separation to isolate the protected β-amino acid. In contrast, novel unprotected $\beta^{2,2}$-amino acids 14-16 bearing pendant carboxylic acid, chloroallyl, and fluorine atom functional groups could be obtained directly by purification with reverse phase preparatory HPLC following the two-step deprotection sequence (Table 26, row e).

TABLE 26

Product Derivatization a)

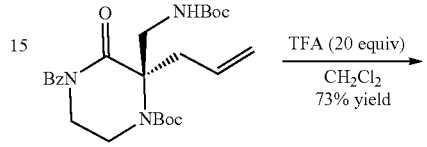

b)

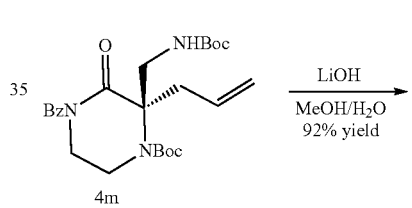

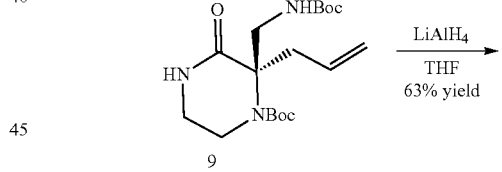

c)

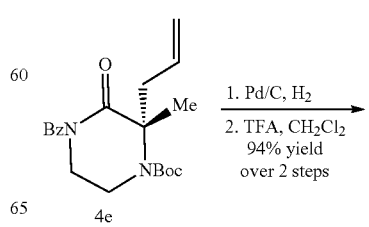

TABLE 26-continued

Product Derivatization

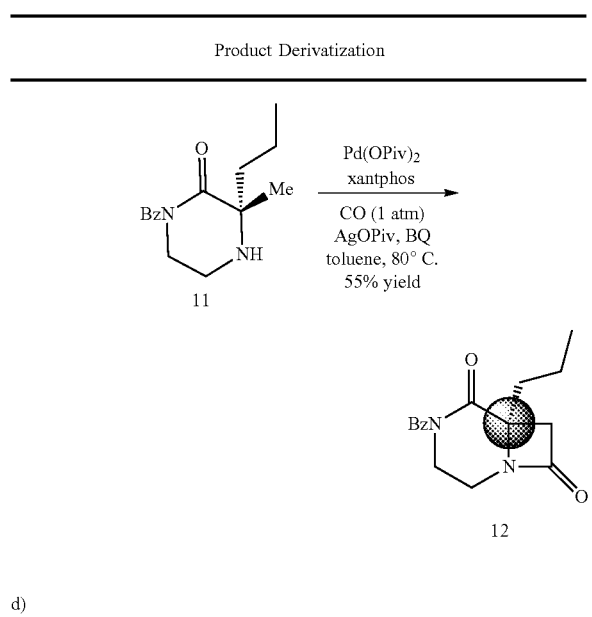

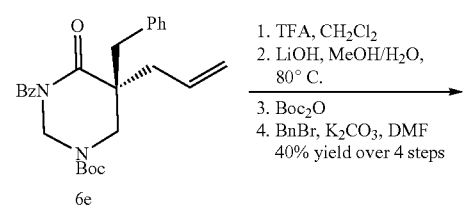

d)

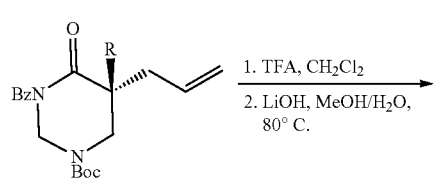

e)

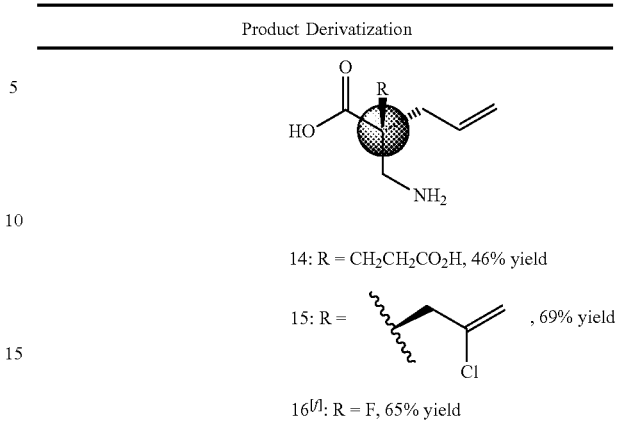

14: R = CH$_2$CH$_2$CO$_2$H, 46% yield

15: R = [allyl with Cl substituent], 69% yield

16[f]: R = F, 65% yield a) Boc cleavage to the free amine.
b) Benzoyl cleavage and reduction to the piperazine.
c) Boc cleavage, allyl hydrogenation, and C—H carbonylation of the free amine.
d, e) hydrolysis and subsequent protection of the β$^{2,2}$-amino acid.
[f] KOH, 1:1 MeOH/H$_2$O, rt; then, HCl, MeOH, rt.
BQ = benzoquinone.
Piv = pivalate.

VI. Experimental Procedures

General Information

Unless otherwise stated, reactions were performed in flame-dried glassware under an argon or nitrogen atmosphere using dry, deoxygenated solvents. Solvents were dried by passage through an activated alumina column under argon. tert-Butyl 3-oxopiperazine-1-carboxylate 1 was obtained from Combi-Blocks. Commercially obtained reagents were used as received. Chemicals were purchased from Sigma Aldrich/Strem/Alfa Aesar/Combi-Blocks and used as received. Reaction temperatures were controlled by an IKAmag temperature modulator. Glove box manipulations were performed under a nitrogen atmosphere. Thin-layer chromatography (TLC) was performed using E. Merck silica gel 60 F254 precoated plates (0.25 mm) and visualized by UV fluorescence quenching, iodine on silica, or KMnO4 staining. SiliaFlash P60 Academic Silica gel (particle size 0.040-0.063 mm) was used for flash chromatography. Analytical SFC was performed with a Mettler SFC supercritical CO2 analytical chromatography system utilizing a Chiralpak IC column (4.6 mm×25 cm) obtained from Daicel Chemical Industries, Ltd. with visualization at 254 nm. $^1$H NMR spectra were recorded on a Varian Inova 500 MHz spectrometer or a Bruker Avance HD 400 MHz spectrometer and are reported relative to residual CHCl3 (δ 7.26 ppm). $^{13}$C NMR spectra were recorded on a Varian Inova 500 MHz spectrometer or a Bruker Avance HD 400 MHz spectrometer and are reported relative to residual CDCl3 (δ 77.16 ppm). Data for $^1$H NMR are reported as follows: s=singlet, d=doublet, t=triplet, q=quartet, p=pentet, sept=septuplet, m=multiplet, br s=broad singlet. Data for $^{13}$C NMR are reported in terms of chemical shifts (S ppm). Some reported spectra include minor solvent impurities of water (δ 1.56 ppm), ethyl acetate (δ 4.12, 2.05, 1.26 ppm), methylene chloride (δ 5.30 ppm), acetone (δ 2.17 ppm), grease (δ 1.26, 0.86 ppm), and/or silicon grease (δ 0.07 ppm), which do not impact product assignments. IR spectra were obtained using a Perkin Elmer Paragon 1000 spectrometer using thin films deposited on NaCl plates and reported in frequency of absorption (cm$^{-1}$). High resolution mass spectra (HRMS)

were obtained from an Agilent 6200 Series TOF with an Agilent G1978A Multimode source in electrospray ionization (ESI+), atmospheric pressure chemical ionization (APCI+), or mixed ionization mode (MM: ESI-APCI+). Optical rotations were measured with a Jasco P-2000 polarimeter operating on the sodium D-line (589 nm), using a 100 mm pathlength cell and are reported as: [a]D$^T$ (concentration in g/100 mL, solvent). Stereochemistry is assigned by analogy to previous results.[1] (a) D. C. Behenna, B. M. Stoltz, J. Am. Chem. Soc. 2004, 126, 15044-15045; b) J. T. Mohr, D. C. Behenna, A. M. Hamed, B. M. Stoltz, Angew. Chem. Int. Ed. 2005, 44, 6924-6927; Angew. Chem. 2005, 117, 7084-7087; c) M. Seto, J. L. Roizen, B. M. Stoltz, Angew. Chem. Int. Ed. 2008, 47, 6873-6876; Angew. Chem. 2008, 120, 6979-6982; d) J. Streuff, D. E. White, S. C. Virgil, B. M. Stoltz, Nat. Chenz. 2010, 2, 192-196; e) D. C. Behenna, Y. Liu, T. Yurino, J. Kim, D. E. White, S. C. Virgil, B. M. Stoltz, Nat. Chem. 2012, 4, 130-133; f) C. M. Reeves, C. Eidamshaus, J. Kim, B. M. Stoltz, Angew. Chem. Int. Ed. 2013, 52, 6718-6721; Angew. Chem. 2013, 125, 6850-6853)

List of Abbreviations: An—Anisoyl, Boc—tert-Butyloxycarbonyl, BRSM—based on recovered starting material, Bz—benzoyl, $CH_2Cl_2$—methylene chloride, Cbz—carboxybenzyl, ee—enantiomeric excess, $Et_2O$—diethyl ether, EtOAc—ethyl acetate, IPA—isopropanol, LHMDS—lithium hexamethyldisilazide, MeCN—acetonitrile, MeOH—methanol, SFC—supercritical fluid chromatography, THF—tetrahydrofuran, TLC—thin-layer chromatography.

Example 27: Preparation of Known Compounds

Allyl cyanoformate was prepared according to the method of Weber. [M. E. Childs, W. P. Weber, J. Org. Chem. 1976, 41, 3486-3487.] Phosphinooxazoline (PHOX) ligands (S)-L1, (S)-L2, and achiral GlyPhox were prepared by methods described in our previous work. [(a) D. C. Behenna, B. M. Stoltz, J. Am. Chem. Soc. 2004, 126, 15044-15045. (b) K. Tani, D. C. Behenna, R. M. McFadden, B. M. Stoltz, Org. Lett. 2007, 9, 2529-2531. (c) M. R. Krout, J. T. Mohr, B. M. Stoltz, Org. Synth. 2009, 86, 181-193.] Di-benzoylated allylic alkylation substrate 3g was prepared according to the method of Korch. [K. M. Korch, C. Eidamshaus, D. C. Behenna, S. Nam, D. Home, B. M. Stoltz, Angew. Chem. Int. Ed. 2015, 54, 179-183.] Tris(4,4'-methoxydibenzylideneacetone)dipalladium(0) [$Pd_2(pmdba)_3$] was prepared according to the method of Ibers [J. Organomet. Chem. 1999, 65, 253-266] or Fairlamb [Org. Lett. 2004, 6, 4435-4438]. AgOPiv was prepared using Grubbs' procedure [J. Am. Chem. Soc. 2011, 133, 8525-8527]. tert-Butyl ((phenylsulfonyl)methyl)carbamate and benzyl ((phenylsulfonyl)methyl) carbamate were prepared according to the method of Zwierzak or Dikshit [(a) Klepacz, A.; Zwierzak, A. Tetrahedron Len. 2002, 43, 1079. (b) Sikriwal, D.; Kant, R.; Maulik, P. R.; Dikshit, D. K. Tetrahedron 2010, 66, 6167]. Benzyl 3-oxopiperazine-1-carboxylate was prepared according to the method of Batey. [Tetrahedron 2010, 66, 3370-3377]. 2-chloroallyl chloroformate was prepared according to the method of Stoltz. [J. Am. Chem. Soc. 2008, 130, 810-811.]

Example 28: Synthesis of Piperazinone Allylic Alkylation Substrates

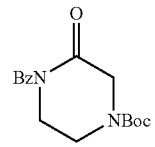

tert-butyl 4-benzoyl-3-oxopiperazine-1-carboxylate (SI-1). To a solution of tert-butyl 3-oxopiperazine-1-carboxylate 1 (5.0 g, 24.9 mmol, 1 equiv) in THF (250 mL) at −78° C. was added dropwise nBuLi (11.4 mL, 2.4M solution in hexane, 27.5 mmol, 1.1 equiv) over 20 minutes. The resulting yellow solution was stirred for 10 min at −78° C. Benzoyl chloride (3.48 mL, 30.0 mmol, 1.2 equiv) was then added dropwise at −78° C., giving an orange solution. The reaction was stirred for 2.5 h at −78° C., quenched by addition of saturated aqueous $NH_4Cl$ (100 mL), and diluted with ethyl acetate (100 mL). The layers were separated and the aqueous layer was extracted with ethyl acetate (3×100 mL). The combined organic layers were dried over anhydrous $Na_2SO_4$, decanted, and concentrated under reduced pressure onto silica gel. The silica-loaded crude reaction mixture was purified by silica gel flash column chromatography (10%→15%→20% EtOAc/hexanes) to give protected ketopiperazine SI-1 as a white solid (3.2 g, 42.1% yield). Product identity was confirmed by comparison to previously reported characterization data. [A. Chollet, G. Mori, C. Menendez, F. Rodriguez, I. Fabing, M. R. Pasca, J. Madacki, J. Korduláková, P. Constant, A. Quemard, et al., Eur. J. Med. Chem. 2015, 101, 218-235.]

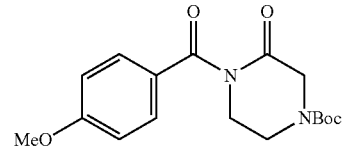

tert-butyl 4-(4-methoxybenzoyl)-3-oxopiperazine-1-carboxylate (SI-2). To a solution of tert-Butyl 3-oxopiperazine-1-carboxylate (5.0 g, 24.9 mmol, 1 equiv) in THF (250 mL) at −78° C. was added dropwise nBuLi (11.4 mL, 2.4M solution in hexane, 27.5 mmol, 1.1 equiv) over 20 minutes. The resulting yellow solution was stirred for 10 min at −78° C. Anisoyl chloride (4.1 mL, 30.0 mmol, 1.2 equiv) was then added dropwise at −78° C., giving a bright orange solution. The reaction was stirred for 2 h at −78° C., quenched by addition of saturated aqueous $NH_4Cl$ (100 mL), and diluted with ethyl acetate (100 mL). The layers were separated and the aqueous layer was extracted with ethyl acetate (3×100 mL). The combined organic layers were dried over anhydrous $Na_2SO_4$, decanted, and concentrated under reduced pressure onto silica gel. The silica-loaded crude reaction mixture was filtered through a plug of silica (1%→2% MeOH/$CH_2Cl_2$) to give crude anisoyl protected ketopiperazine SI-2 as a white foam, which was directly used without further purification in subsequent acylation reactions with allyl cyanoformate.

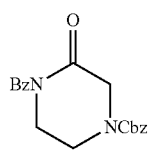

benzyl 4-benzoyl-3-oxopiperazine-1-carboxylate (SI-3). To a solution of benzyl 3-oxopiperazine-1-carboxylate [Tetrahedron 2010, 66, 3370-3377] (1.0 g, 4.3 mmol, 1.0 equiv) in THF (42 mL) at −78° C. was added dropwise nBuLi (1.96 mL, 2.4M solution in hexane, 4.7 mmol, 1.1 equiv) over 20 minutes. The solution was stirred for 10 min at −78° C. Benzoyl chloride (0.595 mL, 5.1 mmol, 1.2 equiv) was then added dropwise at −78° C., giving a light yellow solution. The reaction was stirred for 1 h at −78° C., quenched by addition of saturated aqueous NH$_4$Cl (50 mL), and diluted with ethyl acetate (50 mL). The layers were separated and the aqueous layer was extracted with ethyl acetate (3×50 mL). The combined organic layers were dried over anhydrous Na$_2$SO$_4$, decanted, and concentrated under reduced pressure onto silica gel. The silica-loaded crude reaction mixture was purified by silica gel flash column chromatography (33% EtOAc/hexanes) to give Bz-Cbz-protected ketopiperazine SI-3 as a white solid (1.0 g, 70.0% yield); $^1$H NMR (500 MHz, CDCl$_3$) δ 7.61-7.56 (m, 2H), 7.54-7.49 (m, 1H), 7.44-7.31 (m, 7H), 5.21 (s, 2H), 4.30 (s, 2H), 3.95 (dd, J=6.8, 4.4 Hz, 2H), 3.83 (dd, J=6.9, 4.3 Hz, 2H); $^{13}$C NMR (126 MHz, CDCl$_3$) δ (a mixture of two rotamers) 172.8, 168.0, 167.6, 154.5, 136.0, 135.0, 132.3, 128.7, 128.5, 128.4, 128.3, 128.3, 68.0, 48.5, 43.3, 41.7, 41.4; IR (Neat Film, NaCl) 3386, 3063, 3033, 2954, 2894, 1706, 1600, 1584, 1498, 1449, 1422, 1394, 1367, 1302, 1231, 1177, 1162, 1123, 1060, 1028, 1010, 944, 857, 796, 765, 731, 699, 639, 612 cm$^{-1}$; HRMS (MM: ESI-APCI) m/z calc'd for C$_{19}$H$_{19}$N$_2$O$_4$ [M+H]$^+$: 339.1339, found 339.1338.

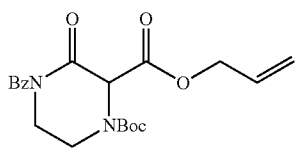

2-allyl 1-(tert-butyl) 4-benzoyl-3-oxopiperazine-1,2-dicarboxylate. To a solution of Bz-protected oxopiperazine SI-1 (1.5 g, 4.9 mmol, 1.0 equiv) in THF (40 mL) at −78° C. was added LiHMDS (907 mg, 5.42 mmol, 1.10 equiv.) in THF (10 mL) dropwise. The resulting orange reaction mixture was stirred for 15 min at −78° C. Then, allyl cyanoformate (590 μL, 5.2 mmol, 1.05 equiv) was added dropwise at −78° C., giving a yellow solution. After stirring for 1.5 h at −78° C., the reaction was quenched with saturated aqueous NH$_4$Cl (20 mL) and diluted with ethyl acetate (50 mL). The aqueous phase was extracted with ethyl acetate (3×100 mL). The combined organic layers were dried over anhydrous Na$_2$SO$_4$, decanted, and concentrated under reduced pressure onto silica. The silica-loaded crude mixture was purified by silica gel flash chromatography (10%→20% EtOAc/hexanes) to give the allyl ester 2 as a white solid (1.3 g, 68% yield); $^1$H NMR (500 MHz, CDCl$_3$) δ (a mixture of two rotamers) 7.59 (d, J=7.7 Hz, 2H), 7.52 (t, J=7.6 Hz, 1H), 7.40 (t, J 7.6 Hz, 2H), 5.92 (m, 1H), 5.44-5.07 (m, 3H), 4.84-4.57 (m, 2H), 4.28-3.61 (m, 4H), 1.43 (br s, 9H); $^{13}$C NMR (126 MHz, CDCl$_3$) δ (a mixture of two rotamers) 172.7, 166.9, 164.4, 154.1, 153.5, 134.6, 132.6, 131.0, 128.6, 128.4, 119.9, 119.4, 82.2, 82.0, z67.1, 62.7, 61.7, 43.2, 42.6, 41.5, 40.2, 29.4, 28.3; IR (Neat Film, NaCl) 2978 1746 1695 1600 1450 1393 1367 1310 1277 1231 1177 1158 1127 1088 1059 1009 958 861 794 770 728 694 623 cm$^{-1}$; HRMS (MM: ESI-APCI) m/z calc'd for C$_{16}$H$_{17}$N$_2$O$_6$ [(M-tBu)+H]$^+$: 333.1081, found 333.1075.

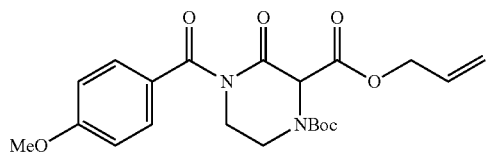 [SMILES: C=CCOC(=O)C1C(=O)N(C(=O)c2ccc(OC)cc2)CCN1C(=O)OC(C)(C)C]

2-allyl 1-(tert-butyl) 4-(4-methoxybenzoyl)-3-oxopiperazine-1,2-dicarboxylate (3b). Following the procedure described for the preparation of 2, anisoyl protected oxopiperazine SI-2 (1.0 g, 3.0 mmol, 1.0 equiv) was treated with LiHMDS (550 mg, 3.3 mmol, 1.1 equiv) and acylated with allyl cyanoformate (336 μL, 3.1 mmol, 1.05 equiv) to give, after purification by silica gel flash chromatography (Dry load SiO$_2$, 18% EtOAc/hexanes), allyl ester 3b as a white solid (566 mg, 45% yield): $^1$H NMR (400 MHz, CDCl$_3$) δ (a mixture of two rotamers) 7.61 (d, J=8.6 Hz, 2H), 6.86 (d, J=8.8 Hz, 2H), 5.91 (ddt, J=16.4, 10.8, 5.8 Hz, 1H), 5.46-5.12 (m, 3H), 4.70 (s, 2H), 4.13-3.65 (m, 4H), 3.81 (s, 3H), 1.46 (m, 9H); $^{13}$C NMR (101 MHz, CDCl$_3$) δ (a mixture of two rotamers) 171.9, 171.8, 167.0, 164.4, 164.2, 163.4, 154.0, 153.4, 131.4, 131.0, 126.3, 119.6, 119.2, 113.6, 82.0, 81.8, 66.9, 62.5, 61.6, 55.5, 43.3, 42.8, 41.5, 40.1, 28.2; IR (Neat Film, NaCl) 3384, 3060, 2978, 2843, 2568, 2049, 1732, 1605, 1580, 1513, 1456, 1372, 1258, 1088, 1059, 959, 844, 769, 736, 706, 634 cm$^{-1}$; HRMS (MM: ESI-APCI) m/z calc'd for C$_{21}$H$_{27}$N$_2$O$_7$ [M+H]$^+$: 419.1813, found 419.1815.

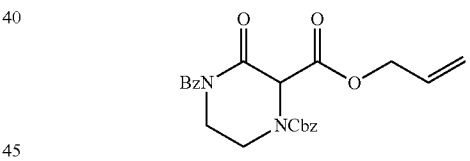

2-allyl 1-benzyl 4-benzoyl-3-oxopiperazine-1,2-dicarboxylate (3c). Following the procedure described for the preparation of 2, Cbz protected oxopiperazine SI-3 (1.0 g, 3.0 mmol, 1.0 equiv) was treated with LiHMDS (544 mg, 3.3 mmol, 1.1 equiv) and acylated with allyl cyanoformate (331 μL, 3.1 mmol, 1.05 equiv) to give, after purification by silica gel flash chromatography (dry load SiO$_2$, 20→25% EtOAc/hexanes), allyl ester 3a as a white solid (720 mg, 58% yield): $^1$H NMR (500 MHz, CDCl$_3$) δ (a mixture of two rotamers) 7.65-7.56 (m, 2H), 7.56-7.46 (m, 1H), 7.46-7.28 (m, 7H), 5.87 (dtd, J. 47.5, 10.7, 5.4 Hz, 1H), 5.55-5.04 (m, 5H), 4.84-4.48 (m, 2H), 4.24-3.99 (m, 2H), 3.99-3.66 (m, 2H); $^{13}$C NMR (126 MHz, CDCl$_3$) δ (a mixture of two rotamers) 172.4, 172.3, 166.5, 164.0, 163.8, 154.8, 154.2, 135.7, 135.6, 134.4, 132.5, 130.9, 130.8, 128.7, 128.6, 128.5, 128.5, 128.4, 128.3, 128.2, 128.1, 119.6, 119.5, 68.3, 68.2, 67.2, 67.1, 62.1, 61.9, 42.8, 42.3, 41.3, 40.8; IR (Neat Film, NaCl) 3386, 3064, 3033, 2955, 2897, 1746, 1713, 1694, 1651, 1600, 1584, 1498, 1450, 1417, 1368, 1304, 1278, 1229, 1195, 1178, 1160, 1124, 1088, 1061, 1014, 985, 951, 860, 794, 768, 729, 696, 675, 623 cm$^{-1}$; HRMS (MM: ESI-APCI) m/z calc'd for $C_{23}H_{23}N_2O_6$ [M+H]$^+$: 423.1551, found 423.1547.

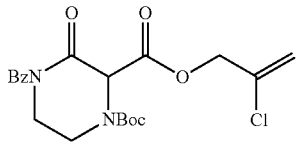

1-(tert-butyl) 2-(2-chloroallyl) 4-benzoyl-3-oxopiperazine-1,2-dicarboxylate (3d). Following the procedure described for the preparation of 2, benzoyl protected oxopiperazine SI-1 (440 mg, 1.5 mmol, 1.0 equiv) was treated with LiHMDS (267 mg, 1.6 mmol, 1.1 equiv) and acylated with 2-chloroallyl chloroformate (235 mg, 1.5 mmol, 1.05 equiv) [J. Am. Chem. Soc. 2008, 130, 810-811] to give, after purification by silica gel flash chromatography (Dry load SiO$_2$, 15% EtOAc/hexanes), 2-chloroallyl ester 3d as an off-white solid (431 mg, 70% yield): $^1H$ NMR (500 MHz, CDCl$_3$): δ (a mixture of two rotamers) 7.59-7.54 (m, 2H), 7.50-7.44 (m, 1H), 7.43-7.37 (m, 2H), 6.67 (m, 1H), 5.42-5.33 (m, 2H), 4.54 (m, 2H), 3.95-3.89 (m, 2H), 3.72 (t, J=5.2 Hz, 2H), 1.51 (s, 9H); $^{13}$C NMR (101 MHz, CDCl$_3$): δ (a mixture of two rotamers) 167.5, 167.3, 152.4, 152.2, 151.1, 151.0, 135.1, 134.9, 134.3, 131.3, 131.2, 128.5, 128.4, 128.0, 127.9, 126.7, 115.9, 115.7, 107.9, 107.6, 82.3, 82.2, 69.9, 69.8, 44.2, 43.1, 42.3, 41.7, 28.3; IR (Neat Film, NaCl) 3396, 3129, 3062, 2979, 2936, 2253, 1770, 1691, 1372, 1242, 1050, 987, 950, 922, 859, 839, 764, 731, 707, 647 cm$^{-1}$; HRMS (MM: ESI-APCI) m/z calculated for $C_{20}H_{24}ClN_2O_6$ [M+H]$^+$: 423.1317, found 423.1316.

2-allyl 1-(tert-butyl) 4-(4-methoxybenzoyl)-2-methyl-3-oxopiperazine-1,2-dicarboxylate (3e). Sodium hydride (60% in mineral oil, 25 mg, 0.62 mmol, 1.2 equiv) was added to a solution of allyl ester 2 (200 mg, 0.52 mmol, 1.0 equiv) in THF (5 mL) at 0° C. After stirring for 30 min at 0° C., MeI (160 µL, 2.57 mmol, 5.0 equiv) was added. The reaction mixture was allowed to warm to room temperature and stirred for 16 h. The reaction was quenched with aqueous NH$_4$Cl (10 mL) and extracted with EtOAc (3×5 mL). The combined organic phases were dried over anhydrous Na$_2$SO$_4$, decanted, and concentrated under reduced pressure onto silica gel. The silica-loaded residue was purified by silica gel flash chromatography (20% EtOAc/hexanes) to give methylated allyl ester 3e as a colorless oil (180 mg, 85% yield): $^1$H NMR (400 MHz, CDCl$_3$): δ 7.59-7.46 (m, 3H), 7.46-7.32 (m, 2H), 5.92 (ddt, J=17.2, 10.4, 5.8 Hz, 1H), 5.41-5.19 (m, 2H), 4.66 (d, J=5.8 Hz, 2H), 4.24-4.09 (m, 1H), 4.05-3.90 (m, 2H), 3.81-3.64 (m, 1H), 1.84 (s, 3H), 1.46 (s, 9H); $^{13}$C NMR (101 MHz, CDCl$_3$): δ (a mixture of two rotamers) 172.5, 169.2, 168.0, 153.2, 134.8, 132.4, 131.5, 128.4, 128.0, 88.7, 66.9, 43.7, 40.9, 28.3, 21.5; IR (Neat Film, NaCl) 3384, 3064, 2980, 2939, 2876, 1962, 1766, 1694, 1600, 1584, 1451, 1394, 1368, 1306, 1270, 1232, 1206, 1164, 1096, 1060, 1032, 1016, 993, 968, 936, 854, 795, 770, 727, 696, 675, 633, 618 cm$^{-1}$; HRMS (MM: ESI-APCI) m/z calculated for $C_{16}H_{19}N_2O_4$ [(M-Boc)+H]$^+$: 303.1341, found 303.1339.

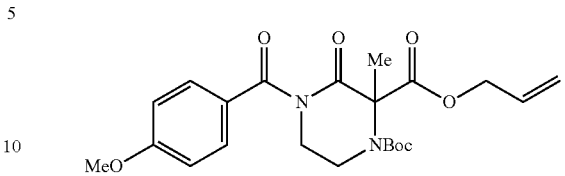

2-allyl 1-(tert-butyl) 4-(4-methoxybenzoyl)-2-methyl-3-oxopiperazine-1,2-dicarboxylate (3f). Following the procedure described for the preparation of 3e, anisoyl protected oxopiperazine 3b (120 mg, 0.29 mmol, 1.0 equiv) was treated with NaH (60% in mineral oil, 13 mg, 0.32 mmol, 1.1 equiv) and methylated with MeI (90 µL, 1.43 mmol, 5.0 equiv) to give, after purification by silica gel flash chromatography (dry load SiO$_2$, 15%-20%-25%-30% EtOAc/hexanes), methylated allyl ester 3f as a colorless oil (110 mg, 89% yield): $^1$H NMR (400 MHz, CDCl$_3$) δ 7.56 (d, J=8.8 Hz, 2H), 6.85 (d, J=8.9 Hz, 2H), 5.92 (ddt, J=17.2, 10.4, 5.8 Hz, 1H), 5.40-5.17 (m, 2H), 4.66 (d, J=5.8 Hz, 2H), 4.15-4.02 (m, 1H), 4.02-3.87 (m, 2H), 3.83 (s, 3H), 3.80-3.67 (m, 1H), 1.84 (s, 3H), 1.46 (s, 9H); $^{13}$C NMR (101 MHz, CDCl$_3$) δ 171.8, 169.0, 168.1, 163.4, 153.2, 131.5, 131.0, 126.6, 119.0, 113.7, 82.6, 68.5, 66.8, 55.5, 43.8, 41.0, 28.3, 21.6; IR (Neat Film, NaCl) 3081, 2978, 2938, 2842, 1766, 1702, 1604, 1579, 1512, 1460, 1394, 1368, 1308, 1287, 1259, 1235, 1208, 1169, 1114, 1095, 1060, 1021, 1004, 969, 933, 845, 789, 770, 733, 706, 648, 634 cm$^{-1}$; HRMS (MM: ESI-APCI) m/z calculated for $C_{18}H_{21}N_2O_7$ [(M-tBu)+H]$^+$: 377.1343, found 377.1339.

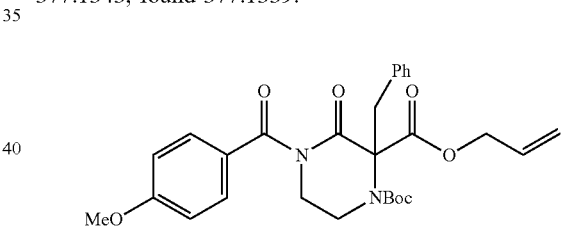

2-allyl 1-(tert-butyl) 2-benzyl-4-(4-methoxybenzoyl)-3-oxopiperazine-1,2-dicarboxylate (3h). Following the procedure described for the preparation of 3e, anisoyl-protected allyl ester 3b (200 mg, 0.48 mmol, 1.0 equiv) was treated with potassium hydride (23 mg, 0.57 mmol, 1.2 equiv) and alkylated with benzyl bromide (170 µL, 1.43 mmol, 3.0 equiv) to give, after purification by silica gel flash chromatography (Dry load SiO$_2$, 20%-25% EtOAc/hexanes), the benzyl ester 3h as a colorless oil (100 mg, 41% yield) (Note: attempts using sodium hydride as a base failed to give conversion of starting material. Instead, potassium hydride resulted in conversion to the desired product): $^1$H NMR (400 MHz, CDCl$_3$) δ (a mixture of two rotamers) 7.52 (m, 2H), 7.42-7.23 (m, 3H), 7.11 (m, 2H), 6.92-6.75 (m, 2H), 5.97 (ddt, J=17.2, 10.4, 5.8 Hz, 1H), 5.50-5.17 (m, 2H), 4.87-4.57 (m, 2H), 3.86 (s, 3H), 3.79-3.56 (m, 4H), 2.95 (ddd, J=13.3, 7.4, 3.0 Hz, 1H), 2.86 (br s, 1H), 1.55 (s, 9H); $^{13}$C NMR (101 MHz, CDCl$_3$) δ (a mixture of two rotamers) 172.1, 168.0, 167.4, 166.9, 163.4, 153.6, 153.4, 136.0, 135.3, 131.8, 131.3, 130.7, 128.8, 128.7, 128.2, 127.8, 127.7, 127.5, 126.6, 119.4, 118.9, 113.7, 82.9, 81.8, 72.7, 67.0, 66.5, 55.6, 44.5, 43.0, 42.2, 41.4, 40.8, 40.0, 38.8, 28.5; IR (Neat Film, NaCl) 2978, 1764, 1698, 1604, 1512, 1496, 1455, 1394, 1366, 1307, 1282, 1256, 1196, 1155, 1078, 1020, 1000, 921, 844, 768 733, 704 cm$^{-1}$; HRMS (MM: ESI-APCI) m/z calculated for C$_{28}$H$_{33}$N$_2$O$_7$ [M+H]$^+$: 509.2282, found 509.2285.

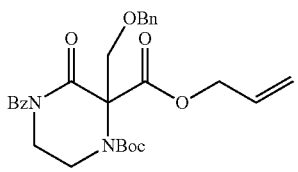

2-allyl 1-(tert-butyl) 4-benzoyl-2-((benzyloxy)methyl)-3-oxopiperazine-1,2-dicarboxylate (3i). Following the procedure described for the preparation of 3e, allyl ester 2 (150 mg, 0.39 mmol, 1.00 equiv) was treated with sodium hydride (17 mg, 0.42 mmol, 1.1 equiv) and alkylated with benzyl chloromethyl ether (107 μL, 0.77 mmol, 2.0 equiv) to give, after purification by silica gel flash chromatography (Dry load SiO$_2$, 10%-15% EtOAc/hexanes), benzyloxy methyl ether 3i as a colorless oil (50 mg, 55% yield BRSM): $^1$H NMR (500 MHz, CDCl$_3$) δ (a mixture of two rotamers) 7.64-7.55 (m, 2H), 7.51-7.44 (m, 114), 7.41-7.27 (m, 7H), 5.88 (ddt, J=17.3, 10.4, 5.8 Hz, 1H), 5.40-5.17 (m, 2H), 4.74-4.47 (m, 4H), 4.38 (m, 1H), 4.17 (m, 1H), 4.08-3.84 (m, 4H), 1.42 (m, 9H); 13C NMR (126 MHz, CDCl$_3$) δ (a mixture of two rotamers) 173.0, 167.4, 167.2, 166.5, 153.6, 153.1, 141.0, 137.9, 137.5, 134.8, 132.4, 131.6, 131.1, 128.7, 128.7, 128.6, 128.4, 128.3, 128.0, 127.7, 127.6, 127.1, 119.5, 118.9, 82.7, 81.9, 73.9, 73.3, 72.6, 71.2, 71.1, 66.8, 65.4, 43.6, 43.4, 42.5, 41.7, 28.4, 28.3; IR (Neat Film, NaCl) 3528, 3064, 3031, 2978, 2934, 1762, 1694, 1600, 1496, 1453, 1394, 1366, 1314, 1270, 1231, 1205, 1161, 1094, 1055, 1014, 972, 941, 854, 795, 770, 730, 696, 674, 624 cm$^{-1}$; HRMS (MM: ESI-APCI) m/z calculated for C$_{24}$H$_{25}$N$_2$O$_7$ [(M-tBu)+H]$^+$: 453.1656, found 453.1649.

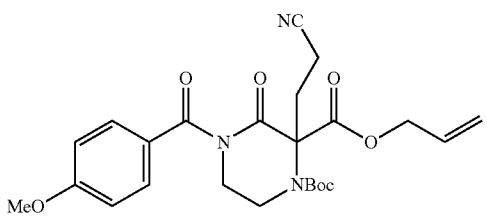 [SMILES: C=CCOC(=O)C1(CCC#N)C(=O)N(C(=O)c2ccc(OC)cc2)CCN1C(=O)OC(C)(C)C]

1-(tert-butyl) 2-(2-cyanoethyl)-4-(4-methoxybenzoyl)-3-oxopiperazine-1,2-dicarboxylate (3j). DBU (7.1 μL, 0.048 mmol, 0.10 equiv) was added to a solution of allyl ester 3b (200 mg, 0.478 mmol, 1.0 equiv) and acrylonitrile (94 μL, 1.43 mmol, 3.0 equiv) in DMF (2.4 mL) at room temperature. After stirring for 2 h at 70° C. and 24 h at 55° C., additional DBU (14 μL, 0.1 mmol, 0.2 equiv) was added and the orange solution was maintained at 70° C. for 4 h. Then, additional DBU (21 μL, 0.143 mmol, 0.30 equiv) was added and the mixture was stirred at 70° C. for 3 h. After allowing the reaction mixture to cool to room temperature, the reaction was quenched with saturated aqueous NH$_4$Cl (2 mL) and diluted with EtOAc (6 mL). The aqueous phase was extracted with EtOAc (3×5 mL). The combined organic layers were dried over anhydrous Na$_2$SO$_4$, decanted, and concentrated under reduced pressure onto silica gel. The silica-loaded residue was purified by flash chromatography (20% EtOAc/hexanes) to give the α-cyanoethylated allyl ester 3j as a pale yellow oil (77.6 mg, 34% yield): $^1$H NMR (400 MHz, CDCl$_3$) δ 7.54 (s, 2H), 6.85 (d, J=8.9 Hz, 2H), 5.92 (ddt, J=17.2, 10.4 Hz, 5.9 Hz, 1H), 5.36 (dd, J=17.2, 1.4 Hz, 1H), 5.29 (d, J=10.5 Hz, 1H), 4.69 (d, J=5.8 Hz, 2H), 4.25 (s, 1H), 4.06 (ddd, J=13.1, 5.7, 3.1 Hz, 1H), 3.96 (ddd, J=13.1, 8.6, 3.4 Hz, 1H), 3.83 (s, 3H), 3.64-3.49 (m, 1H), 2.77 (s, 2H), 2.49 (m, 1H), 2.44-2.31 (m, 1H), 1.47 (s, 9H); $^{13}$C NMR (101 MHz, CDCl$_3$) δ 171.7, 167.24, 166.3, 163.5, 153.4, 131.1, 126.2, 119.6, 119.1, 113.8, 82.9, 70.5, 67.3, 55.5, 43.9, 42.3, 29.8, 28.2, 12.8; IR (Neat Film, NaCl) 2978, 2249, 1760, 1694, 1604, 1579, 1512, 1462, 1394, 1368, 1311, 1258, 1160, 1018, 933, 846, 769, 737, 704 cm$^{-1}$; HRMS (MM: ESI-APCI): m/z calc'd for C$_{24}$H$_{30}$N$_3$O$_7$ [M+H]$^+$: 472.2078, found 472.2078.

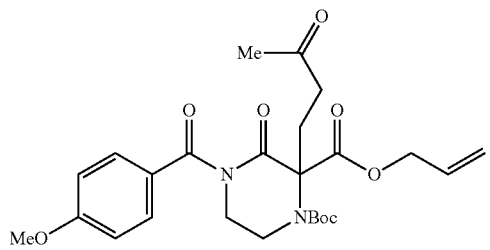 [SMILES: C=CCOC(=O)C1(CCC(C)=O)C(=O)N(C(=O)c2ccc(OC)cc2)CCN1C(=O)OC(C)(C)C]

2-allyl 1-(tert-butyl) 4-(4-methoxybenzoyl)-3-oxo-2-(3-oxobutyl)piperazine-1,2-dicarboxylate (3k). To a solution of allyl ester 3b (200 mg, 0.5 mmol, 1.0 equiv) and methyl vinyl ketone (80 μL, 0.96 mmol, 2.0 equiv) in acetone (2 mL) at room temperature was added DBU (7.1 μL, 0.05 mmol, 0.1 equiv). After stirring for 24 h at 55° C., additional DBU (7.1 μL, 0.05 mmol, 0.1 equiv) was added and the orange solution was maintained at 55° C. for an additional 24 h. The reaction mixture was allowed to cool to ambient temperature and concentrated under reduced pressure onto silica gel. The silica-loaded crude reaction mixture was purified by silica gel flash column chromatography (33% EtOAc/hexanes) to afford the ketone 3k as a pale yellow oil (90 mg, 39% yield): $^1$H NMR (400 MHz, CDCl$_3$) δ 7.56 (d, J=8.8 Hz, 2H), 6.84 (d, J=8.9 Hz, 2H), 5.92 (ddt, J=17.2, 10.4, 5.8 Hz, 1H), 5.35 (dd, J=17.2, 1.5 Hz, 1H), 5.26 (d, J=10.4 Hz, 1H), 4.71-4.60 (m, 2H), 4.11-3.93 (m, 3H), 3.82 (s, 3H), 3.71-3.59 (m, 1H), 2.72 (q, J=9.3, 8.1 Hz, 1H), 2.60 (dt, J=9.6, 6.2 Hz, 2H), 2.10 (s, 3H), 1.45 (s, 9H); $^{13}$C NMR (101 MHz, CDCl$_3$) δ 207.9, 172.0, 167.9, 167.4, 163.4, 153.5, 131.5, 131.1, 126.6, 119.2, 113.7, 82.4, 70.6, 66.9, 55.5, 43.5, 42.1, 38.8, 29.8, 28.7, 28.3; IR (Neat Film, NaCl): 2977, 2934, 1761, 1704, 1604, 1512, 1456, 1394, 1367, 1312, 1257, 1199, 1168, 1090, 1018, 845, 768 cm$^{-1}$; HRMS (MM: ESI-APCI): m/z calc'd for C$_{25}$H$_{33}$N$_2$O$_8$ [M+H]$^+$: 489.2231, found: 489.2228.

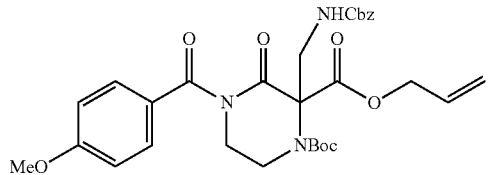 [SMILES: C=CCOC(=O)C1(CNC(=O)OCc2ccccc2)C(=O)N(C(=O)c2ccc(OC)cc2)CCN1C(=O)OC(C)(C)C]

2-allyl 1-(tert-butyl) 2-((((benzyloxy)carbonyl)amino)methyl)-4-(4-methoxybenzoyl)-3-oxopiperazine-1,2-dicarboxylate (3l). Following the procedure described for the preparation of 3m, anisoyl-protected allyl ester 3b (400 mg, 0.96 mmol, 1.0 equiv) was treated with Cs$_2$CO$_3$ (779 mg, 02.39 mmol, 2.5 equiv) and alkylated with benzyl ((phenylsulfonyl)methyl)carbamate[8] (350 mg, 1.15 mmol, 2.5 equiv) to give, after purification by silica gel flash chromatography (Dry load SiO$_2$, 10%-15%-20% EtOAc/hexanes), the aminomethyl allyl ester 3l as a white foam (300 mg, 54% yield): $^1$H NMR (400 MHz, CDCl$_3$) δ (a mixture of two rotamers) 7.69-7.50 (m, 2H), 7.41-7.25 (m, 5H), 6.95-6.72 (m, 2H), 5.92 (ddt, J=17.3, 10.4, 5.9 Hz, 1H), 5.49-4.96 (m, 5H), 4.85-4.53 (m, 2H), 4.27-3.87 (m, 5H), 3.83 (d, J=14.6 Hz, 3H), 3.60 (d, J=22.7 Hz, 1H), 1.47 (s, 9H); $^{13}$C NMR (101 MHz, CDCl$_3$) δ (a mixture of two rotamers) 171.7, 167.3, 166.5, 163.4, 156.8, 153.7, 152.7, 136.4, 134.21, 132.5, 131.5, 131.2, 129.4, 129.3, 128.9, 128.6, 128.3, 126.5, 119.8, 119.3, 113.7, 83.1, 82.1, 71.4, 70.6, 68.3, 67.8, 67.0, 55.5, 45.0, 44.2, 43.7, 42.9, 41.9, 28.3; IR (Neat Film, NaCl) 3366, 2977, 1704, 1604, 1513, 1456, 1394, 1367, 1313, 1257, 1232, 1169, 1091, 1018, 1002, 845, 767, 698 cm$^{-1}$; HRMS (MM: ESI-APCI): m/z calc'd for C$_{30}$H$_{36}$N$_3$O$_9$ [M+H]$^+$: 582.2446, found 582.2438.

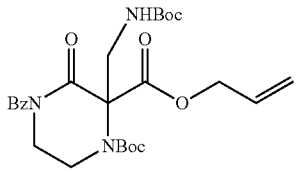

2-allyl 1-(tert-butyl) 4-benzoyl-2-(((tert-butoxycarbonyl)amino)methyl)-3-oxopiperazine-1,2-dicarboxylate (3m). To a suspension of allyl ester 2 (200 mg, 0.5 mmol, 1.0 equiv) and tert-butyl ((phenylsulfonyl)methyl)carbamate (168 mg, 0.6 mmol, 1.2 equiv), in dichloromethane (2.5 mL) at room temperature was added Cs$_2$CO$_3$ (419 mg, 1.3 mmol, 2.5 equiv). [(a) Klepacz, A.; Zwierzak, A. *Tetrahedron Lett.* 2002, 43, 1079. (b) Sikriwal, D.; Kant, R.; Maulik, P. R.; Dikshit, D. K. *Tetrahedron* 2010, 66, 6167.] After stirring for 3 h, saturated aqueous NH$_4$Cl (1 mL) was added and the biphasic mixture was vigorously stirred for 20 min. The aqueous phase was extracted with dichloromethane (3×3 mL). The combined organic phases were dried over anhydrous Na$_2$SO$_4$, decanted, and concentrated under reduced pressure onto silica gel. The silica-loaded crude reaction mixture was purified by silica gel flash column chromatography (15% EtOAc/hexanes) to give methylcarbamate allyl ester 3m as a white foam (202 mg, 76% yield): $^1$H NMR (400 MHz, CDCl$_3$) δ (a mixture of two rotamers) 7.55 (d, J=7.5 Hz, 2H), 7.49 (t, J=7.5 Hz, 1H), 7.36 (t, J=7.7 Hz, 2H), 5.91 (ddt, J=16.5, 10.4, 5.8 Hz, 1H), 5.34-5.27 (m, 2H), 4.96 (m, 1H), 4.66 (br s, 2H), 4.19-3.85 (m, 5H), 3.79-3.64 (m, 1H), 1.48 (s, 9H), 1.40 (s, 9H); $^{13}$C NMR (101 MHz, CDCl$_3$) δ (a mixture of two rotamers) 172.4, 167.3, 166.8, 156.1, 153.6, 152.9, 134.9, 132.4, 131.7, 131.1, 128.3, 128.3, 119.6, 119.0, 83.1, 82.1, 79.9, 71.4, 70.6, 67.0, 44.3, 43.8, 43.2, 42.2, 41.6, 28.4, 28.3; IR (Neat Film, NaCl) 3386, 2978, 1760, 1698, 1601, 1505, 1451, 1394, 1367, 1314, 1232, 1203, 1164, 1092, 1067, 1012, 915, 854, 766, 730, 696 cm$^{-1}$; HRMS (MM: ESI-APCI): m/z calc'd for C$_{26}$H$_{36}$N$_3$O$_8$ [M+H]$^+$: 518.2497, found 518.2496.

Example 29: Synthesis of Tetrahydropyrimidinone Allylic Alkylation Substrates

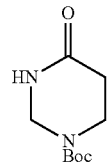

tert-Butyl 4-oxotetrahydropyrimidine-1(2H)-carboxylate (SI-4). A solution of 3-aminopropanamide hydrochloride (5 g, 40.1 mmol, 1.0 equiv), potassium hydroxide (3.38 g, 60.2 mmol, 1.5 equiv), and formaldehyde (37% in water, 5.97 mL, 80.3 mmol, 2.0 equiv) in ethanol (13 mL) was stirred at reflux for 4 h. The suspension was then maintained at 55° C. while triethylamine (5.5 mL, 40.1 mmol, 1 equiv) and di-tert-butyl dicarbonate (9.2 g, 42.1 mmol, 1.05 equiv) were added successively. The reaction was stirred for 2 h at 55° C. and then allowed to cool to ambient temperature. The precipitate was filtered off, the filtrate was concentrated under reduced pressure, and was then purified by silica gel flash chromatography (1→3% MeOH/CH$_2$Cl$_2$) to afford Boc-protected tetrahydropyrimidinone SI-4 as a white solid (4.09 g, 51% yield over two steps): $^1$H NMR (500 MHz, CDCl$_3$) δ 8.14-7.60 (m, 1H), 4.77-4.61 (m, 2H), 3.58 (t, J=6.5 Hz, 2H), 2.41 (t, J=6.5 Hz, 2H), 1.41 (s, 9H); $^{13}$C NMR (126 MHz, CDCl$_3$) δ (a mixture of two rotamers) 171.5, 153.8, 153.4, 81.1, 54.8, 54.0, 40.4, 39.4, 31.4, 28.3; IR (Neat Film, NaCl) 3193, 2970, 1710, 1643, 1488, 1404, 1366, 1326, 1276, 1245, 1210, 1159, 1136, 1020, 949, 776 cm$^{-1}$; HRMS (MM: ESI-APCI): m/z calc'd for C$_9$H$_{17}$N$_2$O$_3$ [M+H]+: 201.1234, found 201.1231.

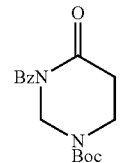

tert-Butyl 3-benzoyl-4-oxotetrahydropyrimidine-1(2H)-carboxylate (SI-5). To a solution of tetrahydropyrimidinone SI-4 (2.07 g, 10.4 mmol, 1.0 equiv) in THF (100 mL) at −78° C. was added n-butyllithium (2.2 M in hexanes, 4.94 mL, 10.9 mmol, 1.05 equiv) dropwise over 10 min. After stirring the solution at −78° C. for 20 min, benzoyl chloride (1.43 mL, 12.4 mmol, 1.2 equiv) was added dropwise at −78° C. The reaction solution was stirred at −78° C. for 40 min, allowed to warm up to room temperature, and was then quenched with saturated aqueous NH$_4$Cl (50 mL). The mixture was diluted with EtOAc (100 mL) and the aqueous phase was extracted with EtOAc (3×80 mL). The combined organic phases were dried over anhydrous Na$_2$SO$_4$, filtered and concentrated under reduced pressure onto silica gel. The silica-loaded residue was purified by silica gel flash chromatography (30% EtOAc/hexanes) to give Bz-protected tetrahydropyrimidinone SI-5 as a white solid (2.72 g, 86% yield): $^1$H NMR (400 MHz, Chloroform-d) δ 7.55 (dt, J=8.3, 1.4 Hz, 2H), 7.50 (t, J=7.4 Hz, 1H), 7.39 (t, J=7.6 Hz, 2H), 5.28 (s, 2H), 3.74 (t, J=6.6 Hz, 2H), 2.68 (t, J=6.6 Hz, 2H), 1.49 (s, 9H); $^{13}$C NMR (101 MHz, CDCl$_3$) δ 172.3, 170.7, 153.8, 135.0, 132.2, 128.4, 128.2, 81.7, 57.0, 40.4, 33.4, 28.3; IR (Neat Film, NaCl) 2978, 1698, 1480, 1450, 1408, 1367, 1304, 1266, 1239, 1141, 1015, 936, 863, 797, 700, 618 cm$^{-1}$; HRMS (MM: ESI-APCI): m/z calc'd for $C_{16}H_{21}N_2O_4$ [M+H]$^+$: 305.1496, found 305.1500.

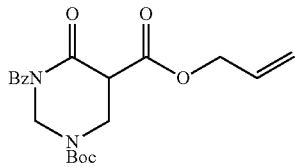

5-Allyl 1-(tert-butyl) 3-benzoyl-4-oxotetrahydropyrimidine-1,5(2H)-dicarboxylate (SI-6). To a solution of diisopropylamine (224 µL, 1.59 mmol, 1.2 equiv) in THF (3 mL) at –78° C. was added n-butyllithium (2.2 M in hexanes, 664 µL, 1.46 mmol, 1.1 equiv). The solution was maintained at –78° C. for 15 min and then cannulated over 10 min into a solution of Bz-protected tetrahydropyrimidine SI-5 (404 mg, 1.33 mmol, 1.0 equiv) in THF (10 mL) at –78° C. After stirring the solution at –78° C. for 25 min, allyl cyanoformate (156 µL, 1.46 mmol, 1.1 equiv) was added dropwise at –78° C. The reaction mixture was maintained at –78° C. for 50 min and was then quenched with saturated aqueous NH$_4$Cl (10 mL). The reaction mixture was diluted with EtOAc (10 mL) and allowed to warm to room temperature. The aqueous phase was extracted with EtOAc (3×15 mL) and the combined organic phases were dried over anhydrous Na$_2$SO$_4$, decanted, and concentrated under reduced pressure onto silica gel. The silica-loaded residue was purified by silica gel flash chromatography (18→20→30% EtOAc/hexanes) to give re-isolated starting material SI-5 (154 mg, 38% yield) and allyl ester SI-6 as a white crystalline solid (310 mg, 60% yield, 97% yield based on recovered starting material): $^1$H NMR (400 MHz, CDCl$_3$) δ 7.70 (d, J=7.2 Hz, 2H), 7.51 (t, J=7.4 Hz, 1H), 7.40 (t, J=7.6 Hz, 2H), 5.95 (ddt, J=17.2, 10.4, 5.9 Hz, 1H), 5.37 (dq, J=17.2, 1.5 Hz, 1H), 5.36 (m, 1H), 5.30 (dd, J=10.4, 1.3 Hz, 1H), 5.17 (d, J=12.6 Hz, 1H), 4.69 (d, J=6.0 Hz, 2H), 4.27 (ddd, J=13.7, 5.4, 1.2 Hz, 1H), 3.85 (dd, J=13.7, 6.2 Hz, 1H), 3.63 (t, J=5.7 Hz, 1H), 1.49 (s, 9H); $^{13}$C NMR (101 MHz, CDCl$_3$) θ 172.9, 167.8, 167.0, 153.4, 134.6, 132.5, 131.3, 128.7, 128.3, 119.7, 82.3, 67.0, 58.5, 50.1, 43.9, 28.3; IR (Neat Film, NaCl) 3406, 3064, 2978, 2935, 1714, 1601, 1480, 1450, 1416, 1369, 1287, 1148, 1072, 1017, 934, 859, 796, 768, 736, 703, 626 cm$^{-1}$; HRMS (MM: ESI-APCI): m/z calc'd for $C_{20}H_{25}N_2O_6$ [M+H]$^+$: 389.1707, found 389.1708.

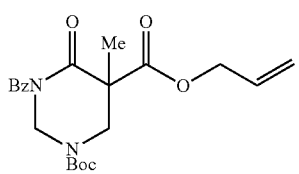

1-(tert-butyl) 3-benzoyl-5-methyl-4-oxotetrahydropyrimidine-1,5(2H)-dicarboxylate (5a). To a solution of allyl ester SI-6 (100 mg, 0.26 mmol, 1.0 equiv) in acetonitrile (2.6 mL) at 0° C. was added cesium carbonate (168 mg, 0.52 mmol, 2.0 equiv). After stirring the suspension for 30 min at 0° C., methyl iodide (48 µL, 0.77 mmol, 3.0 equiv) was added. The reaction mixture was stirred for 3 h at 0° C. and diluted with saturated aqueous NH$_4$Cl (2 mL) and EtOAc (2 mL). The aqueous phase was extracted with EtOAc (4×3 mL) and the combined organic phases were dried over anhydrous Na$_2$SO$_4$, decanted, and concentrated under reduced pressure onto silica gel. The residue was purified by silica gel flash chromatography (15% EtOAc/hexanes) to give methylated allyl ester 5a as a colorless oil (100 mg, 95% yield): $^1$H NMR (500 MHz, CDCl$_3$) δ (a mixture of two rotamers) 7.71 (d, J=15.3 Hz, 2H), 7.51 (t, J=7.4 Hz, 1H), 7.39 (t, J=6.8 Hz, 2H), 5.96 (ddt, J=16.6, 10.4, 6.0 Hz, 1H), 5.48-5.17 (m, 4H), 4.71 (d, J=6.1 Hz, 2H), 4.43 (m, 1H), 3.38 (m, 1H), 1.49 (s, 9H), 1.47 (s, 3H); $^{13}$C NMR (101 MHz, CDCl$_3$) δ (a mixture of two rotamers) 173.2, 170.9, 170.7, 153.2, 135.0, 132.3, 131.3, 128.4, 128.2, 119.7, 82.1, 67.1, 58.9, 58.1, 52.8, 50.6, 50.3, 28.3, 19.3; IR (Neat Film, NaCl) 3406, 3065, 2980, 2939, 1714, 1602, 1450, 1423, 1369, 1288, 1251, 1162, 1134, 1104, 1028, 984, 938, 902, 857, 804, 765, 732, 697, 657, 635 cm$^{-1}$; HRMS (MM: ESI-APCI): m/z calc'd for $C_{21}H_{27}N_2O_6$ [M+H]$^+$: 403.1864, found 403.1868.

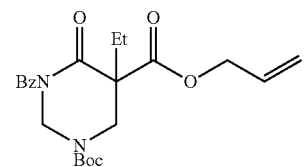

5-allyl 1-(tert-butyl) 3-benzoyl-5-ethyl-4-oxotetrahydropyrimidine-1,5(2H)-dicarboxylate (5b). Following the procedure described for the preparation of 5a, allyl ester SI-6 (200 mg, 0.52 mmol, 1.0 equiv) was treated with cesium carbonate (336 mg, 1.03 mmol, 2.0 equiv) and alkylated with ethyl iodide (124 µL, 1.54 mmol, 3.0 equiv) to give, after purification by silica gel flash chromatography (dry load SiO$_2$, 15% EtOAc/hexanes), ethylated allyl ester 5b as a colorless oil (182 mg, 85% yield): $^1$H NMR (400 MHz, CDCl$_3$) δ (a mixture of two rotamers) 7.70 (d, J 8.0 Hz, 2H), 7.50 (t, J=7.4 Hz, 1H), 7.38 (t, J=7.7 Hz, 2H), 5.95 (ddt, J=16.6, 10.4, 6.0 Hz, 1H), 5.38 (dd, J=17.2, 1.5 Hz, 1H), 5.31 (d, J=10.3 Hz, 2H), 5.20 (d, J=12.5 Hz, 1H), 4.70 (t, J=5.5 Hz, 2H), 4.47-4.26 (m, 1H), 3.49 (d, J=13.5 Hz, 1H), 1.96 (q, J=7.5 Hz, 2H), 1.49 (s, 9H), 0.96 (t, J=7.4 Hz, 3H); $^{13}$C NMR (101 MHz, CDCl$_3$) δ (a mixture of two rotamers) 172.9, 170.4, 170.1, 169.8, 153.2, 135.0, 132.3, 131.2, 128.4, 128.2, 119.8, 81.9, 66.9, 57.9, 57.4, 56.7, 47.8, 47.4, 28.3, 26.4, 9.1; IR (Neat Film, NaCl) 2976, 1703, 1450, 1422, 1367, 1288, 1247, 1156, 1134, 1015, 942, 894, 802, 766, 718, 696 cm$^{-1}$; HRMS (MM: ESI-APCI): m/z calc'd for $C_{22}H_{29}N_2O_6$ [M+H]$^+$: 417.2020, found 417.2019.

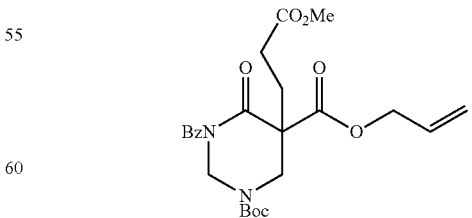

5-allyl 1-(tert-butyl) 3-benzoyl-5-(3-methoxy-3-oxopropyl)-4-oxotetrahydropyrimidine-1,5(2H)-dicarboxylate (5c). To a suspension of allyl ester SI-6 (100 mg, 0.26 mmol, 1.0 equiv) and potassium carbonate (178 mg, 1.29 mmol, 5.0 equiv) in acetone (1.0 mL) at room temperature was added methyl acrylate (47 µL, 0.52 mmol, 2.0 equiv). The reaction mixture was stirred for 3.5 h at 55° C., allowed to cool to room temperature, and filtered through a cotton plug. The filter cake was washed with acetone (3×1 mL) and the combined organic phases were concentrated by under reduced pressure onto silica gel. The silica-loaded residue was purified by silica gel flash chromatography (19% EtOAc/hexanes) to give pyrimidinone 5c as a colorless oil (101 mg, 83% yield): $^1H$ NMR (400 MHz, CDCl$_3$) δ (a mixture of two rotamers) 7.70 (br s, 2H), 7.50 (t, J=7.4 Hz, 1H), 7.38 (t, J=7.7 Hz, 2H), 5.95 (ddt, J=16.6, 10.3, 6.0 Hz, 1H), 5.38 (dd, J=17.1, 1.6 Hz, 1H), 5.32 (d, J=10.4 Hz, 1H), 5.25 (m, 2H), 4.70 (d, J=6.0 Hz, 2H), 4.41 (m, 1H), 3.62 (s, 3H), 3.47 (m, 1H), 2.58 (ddd, J=16.0, 9.5, 6.4 Hz, 1H), 2.46-2.33 (m, 1H), 2.21 (ddd, J=10.0, 6.3, 3.2 Hz, 2H), 1.48 (s, 9H); $^{13}$C NMR (101 MHz, CDCl$_3$) δ (a mixture of two rotamers) 173.0, 172.9, 169.7, 153.1, 134.9, 132.4, 131.1, 128.4, 128.3, 120.1, 82.2, 67.2, 58.3, 57.6, 55.6, 51.9, 48.7, 48.2, 29.7, 28.3; IR (Neat Film, NaCl) 2978, 1704, 1423, 1368, 1248, 1153, 987, 803, 722, 696 cm$^{-1}$; HRMS (MM: ESI-APCI): m/z calc'd for C$_{24}$H$_{31}$N$_2$O$_8$ [M+H]$^+$: 475.2075, found 475.2074.

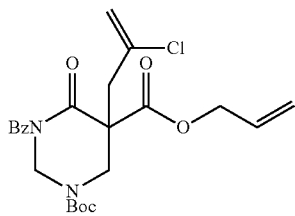

5-allyl 1-(tert-butyl) 3-benzoyl-5-(2-chloroallyl)-4-oxotetrahydropyrimidine-1,5(2H)-dicarboxylate (5d). To a suspension of allyl ester SI-6 (200 mg, 0.51 mmol, 1.0 equiv) and tetrabutylammonium iodide (17 mg, 0.05 mmol, 0.1 equiv), in THF (5.1 mL) at 0° C. was added NaH (60% in mineral oil, 25 mg, 0.62 mmol, 1.2 equiv). After stirring for 30 min at 0° C., 2,3-dichloro-1-propene (95 µL, 1.02 mmol, 2 equiv) was added and the reaction mixture heated at 40° C. for 16 h. The reaction was quenched with aqueous NH$_4$Cl (10 mL) and extracted with EtOAc (3×5 mL). The combined organic phases were dried over anhydrous Na$_2$SO$_4$, decanted, and concentrated under reduced pressure onto silica gel. The silica-loaded residue was purified by silica gel flash chromatography (10% 15% EtOAc/hexanes) to give 2-chloro-allyl allyl ester 5d as a colorless oil (140 mg, 59% yield): $^1$H NMR (400 MHz, CDCl$_3$) δ 7.75 (d, J=8.6 Hz, 2H), 7.51 (s, 1H), 7.39 (t, J=7.5 Hz, 2H), 6.07-5.90 (m, 1H), 5.71-5.48 (m, 1H), 5.33 (m, 4H), 5.03 (d, J=12.5 Hz, 1H), 4.85-4.43 (m, 3H), 3.58 (mz, 1H), 3.32 (d, J=15.1 Hz, 1H), 3.03 (d, J=15f.1 Hz, 1H), 1.48 (s, 9H); $^{13}$C NMR (101 MHz, CDCl$_3$) δ (a mixture of two rotamers) 173.3, 169.9, 168.7, 153.4, 136.3, 134.9, 132.4, 131.2, 128.7, 128.2, 120.1, 118.8, 82.1, 67.7, 58.5, 57.8, 55.1, 47.7, 47.2, 41.0, 28.3; IR (Neat Film, NaCl) 2978, 1703, 1632, 1478, 1450, 1423, 1368, 1289, 1246, 1137, 902, 803, 721, 695, 633 cm$^{-1}$; HRMS (MM: ESI-APCI): m/z calc'd for C$_{23}$H$_{28}$ClN$_2$O$_6$ [M+H]$^+$: 463.1630, found 463.1641.

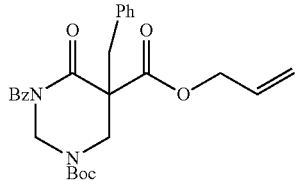

5-Allyl 1-(tert-butyl) 3-benzoyl-5-benzyl-4-oxotetrahydropyrimidine-1,5(2H)-dicarboxylate (5e). To a solution of allyl ester SI-6 (100 mg, 0.26 mmol, 1.0 equiv) in THF (2.6 mL) at room temperature was added sodium hydride (11 mg, 0.28 mmol, 1.1 equiv). After stirring for 15 min, benzyl bromide (37 µL, 0.31 mmol, 1.2 equiv) was added. The reaction mixture was maintained at room temperature for 22 h and at 55° C. for 24 h. The reaction was quenched with aqueous NH$_4$Cl (2 mL) and diluted with EtOAc (2 mL). The aqueous phase was extracted with EtOAc (3×3 mL) and the combined organic phases were dried over anhydrous Na$_2$SO$_4$, decanted, and concentrated under reduced pressure onto silica gel. The silica-loaded residue was purified by silica gel flash chromatography (15% EtOAc/hexanes) to give benzylated allyl ester 5e as a colorless oil (94 mg, 76% yield): $^1$H NMR (400 MHz, CDCl$_3$) δ 7.71 (d, J=7.6 Hz, 2H), 7.52 (t, J=7.5 Hz, 1H), 7.39 (t, J=7.5 Hz, 2H), 7.29-7.19 (m, 3H), 7.14 (dd, J=7.4, 2.2 Hz, 2H), 5.95 (ddt, J=16.6, 10.4, 6.0 Hz, 1H), 5.44-5.19 (m, 3H), 4.73 (m, 3H), 4.56-4.37 (m, 1H), 3.50 (d, J=14.0 Hz, 1H), 3.33 (d, J=13.9 Hz, 1H), 3.14 (d, J=14.0 Hz, 1H), 1.45 (s, 9H); $^{13}$C NMR (101 MHz, CDCl$_3$) δ (a mixture of two rotamers) 173.1, 170.4, 169.3, 153.2, 135.0, 134.9, 132.4, 131.3, 130.9, 128.7, 128.7, 128.2, 127.5, 119.9, 81.9, 67.3, 58.0, 57.5, 57.3, 47.8, 47.2, 38.1, 28.3; IR (Neat Film, NaCl) 3063, 2978, 2935, 1704, 1602, 1479, 1451, 1418, 1368, 1287, 1251, 1152, 1093, 1002, 927, 902, 857, 804, 764, 727, 697, 635 cm$^{-1}$; HRMS (MM: ESI-APCI): m/z calc'd for C$_{27}$H$_{31}$N$_2$O$_6$ [M+H]$^+$: 479.2177, found 479.2180.

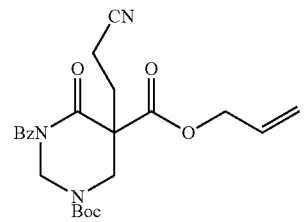

5-allyl 1-(tert-butyl) 3-benzoyl-5-(2-cyanoethyl)-4-oxotetrahydropyrimidine-1,5(2H)-dicarboxylate (5f). To a solution of allyl ester SI-6 (100 mg, 0.26 mmol, 1.0 equiv) and acrylonitrile (34 µL, 0.52 mmol, 2.0 equiv) in acetonitrile (1.3 mL) at room temperature was added DBU (1.9 µL, 0.013 mmol, 0.05 equiv). After 22 h at room temperature, the reaction mixture was heated to 70° C. for 32 h, allowed to cool to room temperature, and treated with additional DBU (1.9 µL, 0.013 mmol, 0.05 equiv). After 2 h at 70° C., the reaction mixture was allowed to cool to room temperature, directly concentrated onto silica gel, and purified by silica gel flash chromatography (22% EtOAc/hexanes) to give cyanoethylated pyrimidinone 5f as a colorless oil (71.5 mg, 63% yield): $^1$H NMR (400 MHz, CDCl$_3$) δ 7.72 (d, J=7.7 Hz, 2H), 7.53 (t, J=7.4 Hz, 1H), 7.41 (t, J=7.6 Hz, 2H), 5.97 (ddt, J=16.7, 10.3, 6.1 Hz, 1H), 5.41 (dd, J=17.4, 1.5 Hz, 1H), 5.36 (d, J=10.5 Hz, 1H), 5.28 (m, 2H), 4.74 (m, 2H), 4.41 (d, J=13.8 Hz, 1H), 3.49 (d, J=13.8 Hz, 1H), 2.72 (dt, J=16.2, 7.9 Hz, 1H), 2.50 (dt, J=16.6, 7.8 Hz, 1H), 2.20 (t, J=7.9 Hz, 2H), 1.49 (s, 9H); $^{13}$C NMR (101 MHz, CDCl$_3$) δ (a mixture of two rotamers) 173.0, 169.4, 169.0, 153.1, 134.6, 132.7, 130.8, 128.4, 128.4, 120.6, 118.9, 82.6, 67.6, 67.6, 58.8, 57.9, 55.1, 49.0, 48.4, 29.2, 28.4, 13.6; IR (Neat Film, NaCl) 2979, 2250, 1698, 1450, 1423, 1369, 1286, 1250, 1155, 1030, 939, 857, 803, 718, 696, 635 cm$^{-1}$; HRMS (MM: ESI-APCI): m/z calc'd for C$_{23}$H$_{31}$N$_4$O$_6$ [M+NH$_4$]$^+$: 459.2238, found 459.2243.

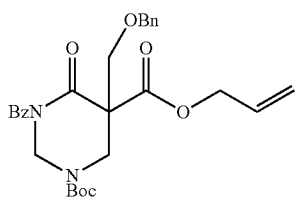

5-allyl 1-(tert-butyl) 3-benzoyl-5-((benzyloxy)methyl)-4-oxotetrahydropyrimidine-1,5(2H)-dicarboxylate (5g). Following the procedure described for the preparation of 5a, allyl ester SI-6 (200 mg, 0.52 mmol, 1.0 equiv) was treated with sodium hydride (29 mg, 0.72 mmol, 1.4 equiv) and alkylated with benzyl chloromethyl ether (127 µL, 0.93 mmol, 1.8 equiv) to give, after two rounds of purification by silica gel flash chromatography (dry load SiO$_2$, 16 25% EtOAc/hexanes), BOM-alkylated allyl ester 5g as a colorless oil (57 mg, 22% yield): III NMR (400 MHz, CDCl$_3$) δ 7.73 (t, J=8.3 Hz, 2H), 7.50 (t, J=7.9 Hz, 1H), 7.41-7.24 (m, 7H), 5.94 (ddt, J=16.5, 10.3, 6.0 Hz, 1H), 5.63 (d, J=12.2 Hz, 1H), 5.43-5.25 (m, 2H), 4.95 (d, J=12.4 Hz, 1H), 4.74 (dd, J=13.0, 5.9 Hz, 1H), 4.70-4.36 (m, 4H), 4.07 (d, J=9.2 Hz, 1H), 3.96-3.80 (m, 1H), 3.74 (d, J=9.3 Hz, 1H), 1.48 (s, 9H); $^{13}$C NMR (101 MHz, CDCl$_3$) δ (a mixture of two rotamers) 173.2, 169.0, 168.7, 168.3, 153.6, 153.3, 137.5, 134.9, 132.2, 131.3, 131.0, 128.6, 128.1, 128.0, 127.7, 119.9, 119.7, 81.9, 73.9, 70.0, 67.1, 58.7, 57.9, 57.0, 47.0, 46.7, 28.3; IR (Neat Film, NaCl) 2978, 2360, 1704, 1453, 1418, 1368, 1290, 1248, 1153, 1128, 1072, 1003, 904, 857, 803, 735, 697, 633 cm$^{-1}$; HRMS (MM: ESI-APCI): m/z calc'd for C$_{28}$H$_{33}$N$_2$O$_7$ [M+H]+: 509.2282, found 509.2279.

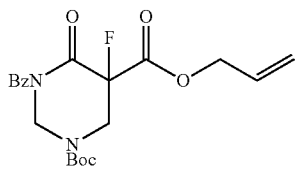

5-allyl 1-(tert-butyl) 3-benzoyl-5-fluoro-4-oxotetrahydropyrimidine-1,5(2H)-dicarboxylate (5h). To a solution of allyl ester SI-6 (100 mg, 0.257 mmol, 1.0 equiv) in THF (2.6 mL) at room temperature was added sodium hydride (11 mg, 0.28 mmol, 1.1 equiv). After stirring for 15 min, Selectfluor (109 mg, 0.31 mmol, 1.2 equiv) was added and the reaction mixture was stirred for 1.5 h at room temperature. The reaction was quenched with aqueous NH$_4$Cl (2 mL) and diluted with EtOAc (2 mL). The aqueous phase was extracted with EtOAc (3×3 mL) and the combined organic phases were dried over anhydrous Na$_2$SO$_4$, filtered and concentrated by reduced pressure onto silica gel. The residue was purified by silica gel flash chromatography (4:1 hexanes/EtOAc) to give fluorinated allyl ester 5h as a colorless oil (92 mg, 0.226 mmol, 88%); $^1$H NMR (400 MHz, CDCl$_3$) δ (a mixture of two rotamers) 7.67 (s, 2H), 7.52 (t, J=7.5 Hz, 1H), 7.39 (t, J=7.6 Hz, 2H), 5.95 (ddt, J=16.6, 10.3, 6.0 Hz, 1H), 5.63-5.07 (m, 4H), 4.88-4.77 (m, 1H), 4.75 (s, 1H), 4.43 (m, 1H), 3.99 (m, 1H), 1.49 (s, 9H); $^{13}$C NMR (101 MHz, CDCl$_3$) δ (a mixture of two rotamers) 172.4, 165.3, 164.4, 153.1, 133.8, 132.9, 130.5, 128.6, 128.5, 120.4, 89.3 (d, J$_{CF}$=192.9 Hz, appears as four peaks due to the presence of two rotamers and coupling with fluorine), 82.8, 67.8, 59.0, 58.4, 49.2, (d, J$_{CF}$=28.3 Hz), 48.4 (d, J$_{CF}$=27.3 Hz), 28.2; IR (Neat Film, NaCl) 2979, 2360, 1770, 1715, 1601, 1478, 1450, 1418, 1369, 1287, 1252, 1157, 1134, 1072, 1018, 907, 857, 829, 803, 764, 730, 695, 658, 633 cm$^{-1}$; HRMS (MM: ESI-APCI): m/z calc'd for C$_{20}$H$_{27}$FN$_3$O$_6$ [M+NH$_4$]$^+$: 424.1878, found 424.1877.

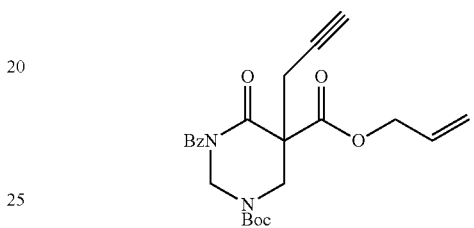

5-allyl 1-(tert-butyl) 3-benzoyl-4-oxo-5-(prop-2-yn-1-yl) tetrahydropyrimidine-1,5(2H)-dicarboxylate (5i). To a solution of allyl ester SI-6 (200 mg, 0.51 mmol, 1.0 equiv) in THF (5 mL) at 0° C. was quickly added sodium hydride (23 mg, 0.57 mmol, 1.1 equiv). After stirring at 0° C. for 30 minutes, propargyl bromide (111 µL, 1.03 mmol, 2 equiv) was added and the reaction mixture was heated to 50° C. After three hours, more propargyl bromide (111 µL, 1.03 mmol, 2 equiv) was added and the reaction was allowed to continue for 16 h at 50° C. The reaction was quenched with aqueous NH$_4$Cl (10 mL) and extracted with EtOAc (3×5 mL). The combined organic phases were dried over anhydrous Na$_2$SO$_4$, decanted, and concentrated under reduced pressure. The crude residue was purified by silica gel flash chromatography (50% CH$_2$Cl$_2$/hexanes—70% CH$_2$Cl$_2$/hexanes—20% EtOAc/hexanes) to afford the propargylated allyl ester 5i as a colorless oil (160 mg, 73% yield): $^1$H NMR (400 MHz, CDCl$_3$) δ 7.74 (s, 2H), 7.50 (d, J=7.4 Hz, 1H), 7.38 (t, J=7.5 Hz, 2H), 5.96 (dd, J=17.0, 10.6 Hz, 1H), 5.64 (dd, J=12.4, 2.1 Hz, 1H), 5.39 (d, J=17.2 Hz, 1H), 5.33 (d, J=10.4 Hz, 1H), 5.16-4.88 (m, 1H), 4.82-4.32 (m, 3H), 4.01-3.63 (m, 1H), 3.03 (d, J=18.2 Hz, 1H), 2.71 (dd, J=17.0, 2.7 Hz, 1H), 2.09 (t, J=2.6 Hz, 1H), 1.49 (s, 9H); $^{13}$C NMR (101 MHz, CDCl$_3$) δ (a mixture of two rotamers) 173.3, 169.6, 168.6, 153.5, 134.9, 132.4, 131.2, 130.9, 128.6, 128.2, 120.0, 82.2, 78.8, 72.6, 67.5, 58.9, 58.2, 55.2, 48.2, 28.3, 23.0; IR (Neat Film, NaCl) 3280, 2978, 1704, 1600, 1479, 1450, 1422, 1368, 1287, 1245, 1155, 1140, 1073, 1016, 929, 904, 856, 803, 765, 733 695, 656 cm$^{-1}$; HRMS (MM: ESI-APCI): m/z calc'd for C$_{23}$H$_{27}$N$_2$O$_6$ [M+H]$^+$: 427.1864, found 427.1859.

Figure 12:
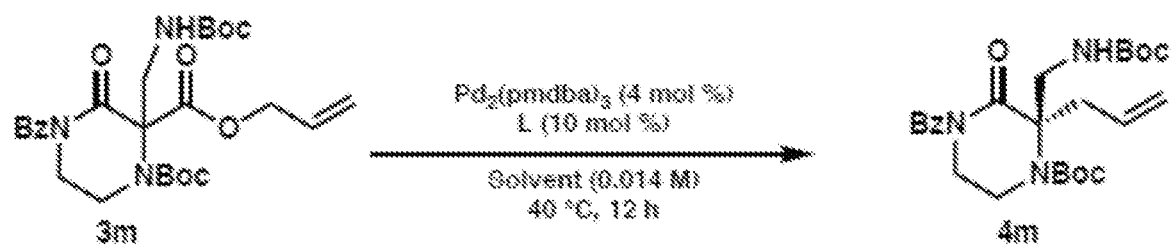
FIG. 12 shows optimization of reaction parameters as described in Example 30. [a] Screens performed on a 0.04 mmol scale. All reported yields are for isolated products. The ee values were determined by chiral SFC analysis. Bz=benzoyl, Boc=tert-butoxycarbonyl, pmdba=bis(4-methoxybenzylidene)acetone.
Figure 12:
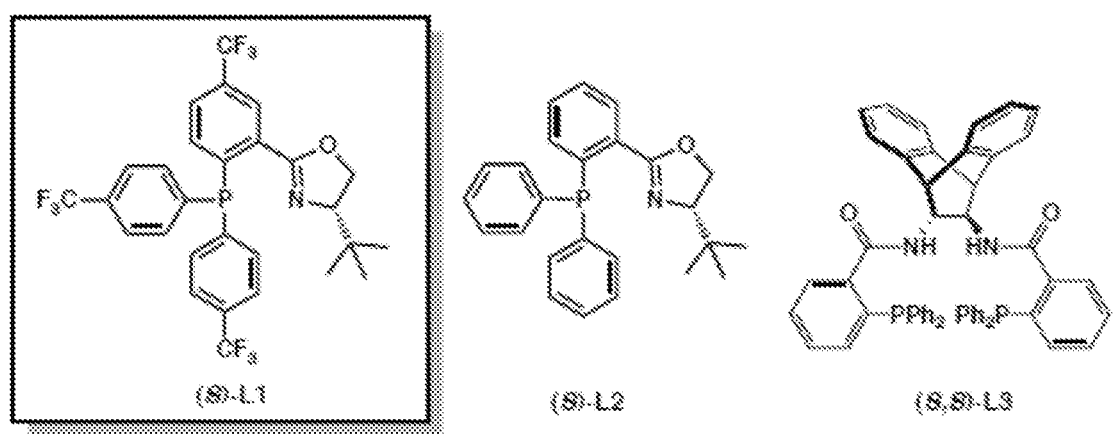

Example 30: General Procedure for Allylic Alkylation Optimization Screen (FIG. 12)

In a nitrogen-filled glovebox, an oven-dried 1 dram vial was charged with Pd$_2$(pmdba)$_3$ (1.7 mg, 0.0015 mmol, 4 mol %), ligand (10 mol %), solvent (1 mL), and a magnetic stir bar. The vial was stirred at ambient glovebox temperature (27° C.) for 30 min and then substrate 3m (20 mg, 0.04 mmol, 1.0 equiv) was added as a solution in solvent (1.8 mL, total concentration 0.014 M). The vial was sealed with a teflon cap and heated to 40° C. When complete consumption of the starting material was observed by thin layer chromatography, the reaction mixture was removed from the glovebox and concentrated under reduced pressure. The residue was purified by silica gel flash chromatography to afford the oxopiperazine 4m.

Example 31: General Procedure for Pd-Catalyzed Decarboxylative Allylic Alkylation Reactions Absolute configuration for all other products has been inferred by analogy. [a] D. C. Behenna, B. M. Stoltz, *J. Am. Chem. Soc.* 2004, 126, 15044-15045; b) J. T. Mohr, D. C. Behenna, A. M. Harned, B. M. Stoltz, *Angew. Chem. Int. Ed.* 2005, 44, 6924-6927; *Angew. Chem.* 2005, 117, 7084-7087; c) M. Seto, J. L. Roizen, B. M. Stoltz, *Angew. Chem. Int. Ed.* 2008, 47, 6873-6876; *Angew. Chem.* 2008, 120, 6979-6982; d) J. Streuff, D. E. White, S. C. Virgil, B. M. Stoltz, *Nat. Chem.* 2010, 2, 192-196; e) D. C. Behenna, Y. Liu, T. Yurino, J. Kim, D. E. White, S. C. Virgil, B. M. Stoltz, *Nat. Chem.* 2012, 4, 130-133; f) C. M. Reeves, C. Eidamshaus, J. Kim, B. M. Stoltz, *Angew. Chem. Int. Ed.* 2013, 52, 6718-6721; *Angew. Chem.* 2013, 125, 6850-6853.] Respective SFC conditions are described below under Determination of Enantiomeric Excess.

In a nitrogen-filled glovebox, an oven-dried 1-dram vial or 20 mL scintillation vial was charged with $Pd_2(pmdba)_3$ or $Pd_2(dba)_3$ (4 mol %), (S)—$(CF_3)_3$-tBu-PHOX (10 mol %), hexane/toluene (2:1), and a magnetic stir bar. The vial was stirred at ambient glovebox temperature (27° C.) for 30 min and then the substrate (1.0 equiv) was added as a solution in hexane/toluene (2:1, total concentration 0.014 M or 0.033 M). The vial was sealed with a teflon cap and heated to 40° C. When complete consumption of the starting material was observed by thin layer chromatography, the reaction mixture was removed from the glovebox and concentrated under reduced pressure. The residue was purified by silica gel flash chromatography to afford the desired oxopiperazine.

Example 32: Experimental Procedures and Spectroscopic Data for the Pd-Catalyzed Decarboxylative Asymmetric Allylic Alkylation of Piperazinone Substrates

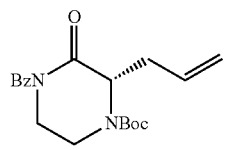

tert-butyl (S)-2-allyl-4-benzoyl-3-oxopiperazine-1-carboxylate (4a). Following the general procedure, allyl ester 3a (25 mg, 0.064 mmol, 1.0 equiv) in toluene (1.45 mL) was added to a solution of $Pd_2(dba)_3$ (2.3 mg, 0.0026 mmol, 4 mol %) and (S)—$(CF_3)_3$-tBu-PHOX (3.8 mg, 0.0064 mmol, 10 mol %) in toluene (0.5 mL). Purification by flash chromatography (20% EtOAc/hexanes) gave monosubstituted oxopiperazine 4a as a yellow oil (21 mg, 90% yield, 92% ee). $^1$H NMR (400 MHz, CDCl$_3$) δ (a mixture of two rotamers) 7.64-7.46 (m, 3H), 7.41 (m, 2H), 5.83 (ddt, J=17.2, 10.0, 7.3 Hz, 1H), 5.22-5.07 (m, 2H), 4.70 (m, 1H), 4.45-3.99 (m, 1H), 3.99-3.70 (m, 2H), 3.42 (m, 1H), 2.90- 2.52 (m, 2H), 1.50 (s, 9H); $^{13}$C NMR (101 MHz, CDCl$_3$) δ (a mixture of two rotamers) 173.6, 170.6, 153.8, 135.3, 133.2, 132.2, 128.3, 128.3, 119.0, 81.3, 58.4, 44.5, 38.1, 37.2, 28.5. IR (Neat Film, NaCl) 2977, 2930, 1692, 1600, 1450, 1413, 1392, 1366, 1300, 1231, 1159, 1130, 1008, 973, 920, 856, 795, 762, 729, 696, 656 cm$^{-1}$; HRMS (MM: ESI-APCI): m/z calc'd for $C_{19}H_{25}N_2O_4$ [M+H]$^+$: 345.1809, found 345.1810; [α]$D^{23.0}$+49.5 (c 1.00, CHCl3); SFC conditions: 15% IPA, 2.5 mL/min, Chiralpak AD-H column, X=210 nm, $t_R$ (min): major=3.741, minor=2.682.

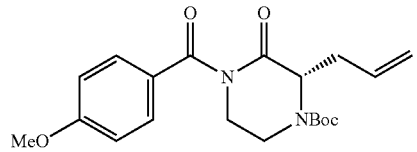 [SMILES: C=CC[C@H]1C(=O)N(C(=O)c2ccc(OC)cc2)CCN1C(=O)OC(C)(C)C]

tert-butyl (S)-2-allyl-4-(4-methoxybenzoyl)-3-oxopiperazine-1-carboxylate (4b). Following the general procedure, anisoyl-protected allyl ester 3b (15 mg, 0.036 mmol, 1.0 equiv) in toluene (0.6 mL) was added to a solution of $Pd_2(dba)_3$ (1.7 mg, 0.0014 mmol, 4 mol %) and (S)—$(CF_3)_3$-tBu-PHOX (2.8 mg, 0.0036 mmol, 10 mol %) in toluene (0.5 mL). Purification by flash chromatography (20% EtOAc/hexanes) gave monosubstituted oxopiperazine 4b as a light yellow oil (12 mg, 92% yield, 96% ee): $^1$H NMR (400 MHz, CDCl$_3$) S (a mixture of two rotamers) 7.60 (d, J=8.9 Hz, 2H), 6.89 (d, J=8.9 Hz, 2H), 5.85 (ddt, J=17.1, 10.0, 7.3 Hz, 1H), 5.24-5.04 (m, 2H), 4.69 (m, 1H), 4.19 (m, 1H), 3.85 (m, 5H), 3.42 (m, 1H), 2.89-2.56 (m, 2H), 1.49 (s, 9H); $^{13}$C NMR (101 MHz, CDCl$_3$) δ 173.0, 170.6, 163.3, 153.9, 133.4, 131.2, 127.1, 118.9, 113.7, 81.3, 58.4, 55.6, 44.6, 38.3, 37.4, 28.5; IR (Neat Film, NaCl) 2976, 1694, 1605, 1512, 1462, 1416, 1366, 1315, 1257, 1234, 1170, 1130, 1003, 973, 842, 770 cm$^{-1}$; HRMS (MM: ESI-APCI): m/z calc'd for $C_{20}H_{27}N_2O_5$ [M+H]$^+$: 375.1914, found 375.1931; [α]$D^{23.0}$+41.7 (c 1.00, CHCl3); SFC conditions: 15% IPA, 2.5 mL/min, Chiralpak AD-H column, X=210 nm, $t_R$ (min): major=4.708, minor=3.998.

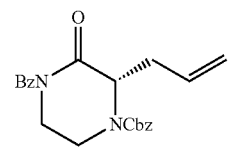

benzyl (S)-2-allyl-4-benzoyl-3-oxopiperazine-1-carboxylate (4c). Following the general procedure, Cbz-protected allyl ester 3c (20 mg, 0.047 mmol, 1.0 equiv) in toluene (0.9 mL) was added to a solution of $Pd_2(dba)_3$ (2.2 mg, 0.0019 mmol, 4 mol %) and (S)—$(CF_3)_3$-tBu-PHOX (3.5 mg, 0.0047 mmol, 10 mol %) in toluene (0.5 mL). Purification by flash chromatography (20% EtOAc/hexanes) gave monosubstituted oxopiperazine 4c as a colorless oil (15 mg, 83% yield, 99% ee): $^1$H NMR (500 MHz, CDCl$_3$) δ (a mixture of two rotamers) 7.62-7.46 (m, 3H), 7.44-7.29 (m, 7H), 5.79 (m, 1H), 5.16 (m, 4H), 4.83 (m, 1H), 4.26 (m, 1H), 3.97 (m, 1H), 3.87 (m, 1H), 3.49 (m, 1H), 2.89-2.53 (m, 2H); 13C NMR (126 MHz, CDCl$_3$) δ (a mixture of two rotamers) 173.5, 170.2, 154.7, 136.0, 135.2, 132.9, 132.3, 128.8, 128.6, 128.6, 128.4, 128.3, 119.3, 68.0, 58.4, 44.3, 39.6, 38.9, 37.2, 36.9; IR (Neat Film, NaCl) 3065, 2951, 1702, 1600, 1449, 1427, 1395, 1362, 1302, 1228, 1163, 1127, 1015, 975, 922, 796, 761, 730, 697, 656 cm$^{-1}$; HRMS (MM: ESI-APCI): m/z calc'd for C22H23N2O4 [M+H]$^+$: 379.1652, found 379.1659; [α]D$^{23.0}$+66.0 (c 1.0, CHCl3); SFC conditions: 30% IPA, 2.5 mL/min, Chiralpak IC column, λ=210 nm, $t_R$ (min): major=4.873, minor=6.748.

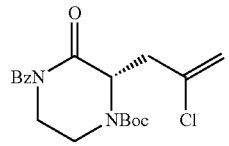

tert-butyl (S)-4-benzoyl-2-(2-chloroallyl)-3-oxopiperazine-1-carboxylate (4d). Following the general procedure, 2-chloroallyl ester 3d (20 mg, 0.047 mmol, 1.0 equiv.) in hexanes/toluene (2:1, 1.9 mL) was added to a solution of Pd$_2$(pmdba)$_3$ (2.1 mg, 0.0019 mmol, 4 mol %) and (S)—(CF$_3$)$_3$-tBu-PHOX (2.8 mg, 0.0047 mmol, 10 mol %) in hexanes/toluene (2:1, 1.5 mL). Purification by silica gel flash chromatography (15% EtOAc/hexanes) gave oxopiperazine 4d as a light yellow oil (15 mg, 85% yield, 98% ee). NMR (400 MHz, CDCl$_3$) δ (A mixture of two rotamers) 7.56 (d, J=7.8 Hz, 2H), 7.51 (t, J=7.4 Hz, 1H), 7.41 (t, J=7.5 Hz, 2H), 5.30 (s, 1H), 5.24 (s, 1H), 5.06-4.88 (m, 1H), 4.40-4.06 (m, 1H), 3.94 (m, 1H), 3.84 (m, 1H), 3.55-3.29 (m, 1H), 2.95 (dd, J=13.1, 7.4 Hz, 2H), 1.51 (s, 9H); $^{13}$C NMR (101 MHz, CDCl$_3$) δ 173.5, 169.8, 153.7, 137.5, 135.3, 132.3, 128.4, 128.3, 116.8, 81.9, 57.0, 44.6, 41.8, 37.7, 28.4. IR (Neat Film, NaCl) 2977, 2359, 1694, 1635, 1456, 1418, 1394, 1367, 1284, 1232, 1200, 1158, 1007, 971, 892, 856, 796, 730, 696 cm$^{-1}$; HRMS (MM: ESI-APCI): m/z calc'd for C$_{19}$H$_{24}$ClN$_2$O$_4$ [M+H]$^+$: 379.1419, found 379.1416; [α]D$^{23.1}$+33.8 (c 1.00, CHCl$_3$); SFC conditions: 15% IPA, 2.5 mL/min, Chiralpak AD-H column, k=254 nm, $t_R$ (min): major=4.482, minor=3.224.

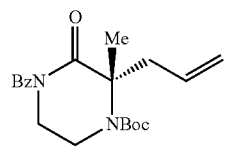

tert-butyl (S)-2-allyl-4-benzoyl-2-methyl-3-oxopiperazine-1-carboxylate (4e). Following the general procedure, methylated allyl ester 3e (23 mg, 0.057 mmol, 1.0 equiv) in toluene (1.2 mL) was added to a solution of Pd$_2$(pmdba)$_3$ (2.7 mg, 0.0023 mmol, 4 mol %) and (S)—(CF$_3$)$_3$-tBu-PHOX (3.7 mg, 0.0057 mmol, 10 mol %) in toluene (0.5 mL). Purification by flash chromatography (15% EtOAc/hexanes) gave di-substituted oxopiperazine 4e as a light yellow oil (17 mg, 85% yield, 96% ee). $^1$H NMR (500 MHz, CDCl$_3$) δ 7.57-7.46 (m, 3H), 7.40 (t, J=7.6 Hz, 2H), 5.81-5.67 (m, 1H), 5.17-5.13 (m, 1H), 5.12 (d, J=1.1 Hz, 1H), 4.16-4.02 (m, 1H), 4.03-3.91 (m, 1H), 3.79 (ddd, J=12.9, 9.0, 3.0 Hz, 1H), 3.53 (ddd, J=14.1, 9.0, 2.8 Hz, 1H), 3.11 (m, 1H), 2.84-2.70 (m, 1H), 1.77 (s, 3H), 1.53 (s, 9H); $^{13}$C NMR (126 MHz, CDCl$_3$) δ 174.3, 172.8, 135.8, 133.1, 131.8, 128.3, 127.6, 119.5, 81.2, 67.3, 44.2, 42.7, 41.0, 28.6, 25.5; IR (Neat Film, NaCl) 3076, 2977, 2934, 1692, 1641, 16001, 102, 1450, 1392, 1366, 1301, 1230, 1166, 1106, 1047, 1016, 955, 922, 852, 790, 757, 727, 695 cm$^{-1}$; HRMS (MM: ESI-APCI): m/z calc'd for C$_{20}$H$_{27}$N$_2$O$_4$ [M+H]$^+$: 359.1965, found 359.1966; [α]D$^{22.8}$+6.5 (c 2.0, CHCl$_3$); SFC conditions: 7% IPA, 2.5 ml/min, Chiralpak AD-H column, λ=210 nm, $t_R$ (min): major=7.208, minor=4.714.

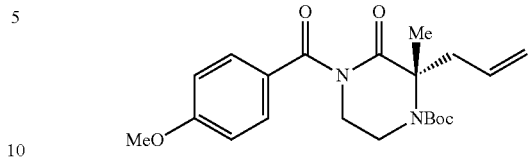

tert-butyl (S)-2-allyl-4-(4-methoxybenzoyl)-2-methyl-3-oxopiperazine-1-carboxylate (4f). Following the general procedure, anisoyl-protected allyl ester 3f (25 mg, 0.058 mmol, 1.0 equiv) in toluene (1.3 mL) was added to a solution of Pd$_2$(pmdba)$_3$ (2.5 mg, 0.0023 mmol, 4 mol %) and (S)—(CF$_3$)$_3$-tBu-PHOX (3.4 mg, 0.0058 mmol, 10 mol %) in toluene (0.5 mL). Purification by flash chromatography (20% EtOAc/hexanes) gave di-substituted oxopiperazine 4f as a light pink oil (19 mg, 86% yield, 96% ee). $^1$H NMR (400 MHz, CDCl$_3$) δ 7.70-7.53 (m, 2H), 6.99-6.82 (m, 2H), 5.86-5.67 (m, 1H), 5.23-5.04 (m, 2H), 4.01 (dddd, J=33.5, 13.9, 5.8, 2.8 Hz, 2H), 3.85 (s, 3H), 3.74 (ddd, J=12.7, 9.0, 2.8 Hz, 1H), 3.52 (ddd, J=13.9, 9.0, 2.7 Hz, 1H), 3.20 (s, 1H), 2.80 (ddt, J=14.0, 7.1, 1.2 Hz, 1H), 1.77 (s, 3H), 1.52 (s, 9H); $^{13}$C NMR (101 MHz, CDCl$_3$) δ 174.1, 172.4, 163.0, 153.9, 133.2, 130.6, 127.5, 119.4, 113.6, 81.2, 67.1, 55.5, 44.2, 42.8, 41.1, 28.6, 25.6; IR (Neat Film, NaCl) 3076, 2977, 2934, 1692, 1641, 16001, 102, 1450, 1392, 1366, 1301, 1230, 1166, 1106, 1047, 1016, 955, 922, 852, 790, 757, 727, 695 cm$^{-1}$; HRMS (MM: ESI-APCI): m/z calc'd for C$_{21}$H$_{29}$N$_2$O$_5$ [M+H]$^+$: 389.2071, found 389.2083; [α]D$^{22.0}$+75.6 (c 2.9, CHCl$_3$); SFC conditions: 10% IPA, 2.5 mL/min, Chiralpak AD-H column, X=210 nm, $t_R$ (min): major=5.370, minor=4.278.

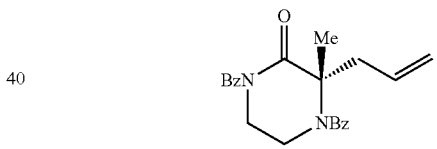

tert-butyl (S)-2-allyl-4-(4-methoxybenzoyl)-2-methyl-3-oxopiperazine-1-carboxylate (4g). Following the general procedure, di-Bz-protected allyl ester 3g (10 mg, 0.025 mmol, 1.0 equiv) in toluene (1.3 mL) was added to a solution of Pd$_2$(dba)$_3$ (0.9 mg, 0.00098 mmol, 4 mol %) and (S)—(CF$_3$)$_3$-tBu-PHOX (1.5 mg, 0.0025 mmol, 10 mol %) in toluene (0.5 mL). Purification by flash chromatography (20% EtOAc/hexanes) gave di-substituted oxopiperazine 4f as a colorless oil (8 mg, 89% yield, 70% ee). Product identity matched previously reported characterization data. [K. M. Korch, C. Eidamshaus, D. C. Behenna, S. Nam, D. Horne, B. M. Stoltz, Angew. Chem. Int. Ed. 2015, 54, 179-183]. SFC conditions: 10% MeOH, 2.5 mL/min, Chiralpak OJ-H column, X=254 nm, $t_R$ (min): major=5.574, minor=6.659.

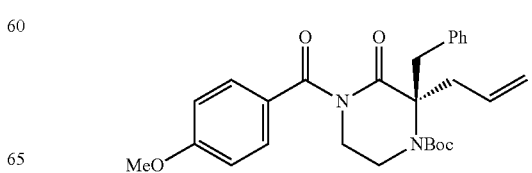

tert-butyl (R)-2-allyl-2-benzyl-4-(4-methoxybenzoyl)-3-oxopiperazine-1-carboxylate (4h). Following the general procedure, benzylated allyl ester 3h (10 mg, 0.02 mmol, 1.0 equiv) in hexanes/toluene (2:1, 0.9 mL) was added to a solution of $Pd_2(pmdba)_3$ (0.86 mg, 0.00078 mmol, 4 mol %) and (S)—$(CF_3)_3$-tBu-PHOX (1.2 mg, 0.002 mmol, 10 mol %) in hexanes/toluene (2:1, 0.5 mL). Purification by flash chromatography (5%-10%-15% EtOAc/hexanes) gave di-substituted oxopiperazine 4h as a colorless oil (7 mg, 77% yield, 96% ee): $^1$H NMR (400 MHz, $CDCl_3$) δ (A mixture of two rotamers) 7.57 (t, J=8.5 Hz, 2H), 7.29 (d, J=5.7 Hz, 3H), 7.22 7.07 (m, 2H), 6.91 (d, J=8.3 Hz, 2H), 5.82 (ddt, J=17.0, 9.6, 7.1 Hz, 1H), 5.29-5.13 (m, 2H), 3.88 (m, 4H), 3.74-3.45 (m, 2H), 3.31 (m, 1H), 3.16 (d, J=12.0 Hz, 2H), 2.98-2.57 (m, 2H), 1.57 (s, 9H); $^{13}$C NMR (101 MHz, $CDCl_3$) δ (A mixture of two rotamers) 172.7, 172.3, 172.0, 163.2, 154.7, 153.4, 137.1, 136.4, 133.1, 132.6, 131.3, 130.4, 128.7, 128.5, 127.5, 127.2, 119.9, 119.7, 113.5, 82.2, 80.6, 71.7, 55.6, 43.6, 43.3, 42.9, 42.6, 41.8, 29.8, 28.9, 28.6; IR (Neat Film, NaCl) 2975, 1691, 1604, 1512, 1454, 1365, 1309, 1282, 1258, 1167, 1104, 1077, 1021, 993, 925, 839, 768, 740, 704 $cm^{-1}$; HRMS (MM: ESI-APCI): m/z calc'd for $C_{27}H_{33}N_2O_5$ $[M+H]^+$: 465.2384, found 465.2390; $[α]_D^{23.4}$+31.0 (c 0.47, CHCl3); SFC conditions: 15% IPA, 2.5 ml/min, Chiralpak AD-H column, λ=254 nm, $t_R$ (min): major=7.471, minor=5.802.

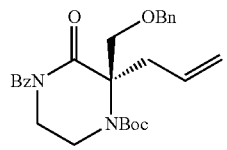

tert-butyl (R)-2-allyl-4-benzoyl-2-((benzyloxy)methyl)-3-oxopiperazine-1-carboxylate (4i). (Following the general procedure, benzyloxy methyl ether allyl ester 3i (25 mg, 0.049 mmol, 1.0 equiv) in hexanes/toluene (2:1, 3.0 mL) was added to a solution of $Pd_2(pmdba)_3$ (2.2 mg, 0.0020 mmol, 4 mol %) and (S)—$(CF_3)_3$-tBu-PHOX (2.9 mg, 0.0049 mmol, 10 mol %) in hexanes/toluene (2:1, 0.5 mL). Purification by flash chromatography (15% EtOAc/hexanes) gave di-substituted oxopiperazine 4i as a colorless oil (20 mg, 87% yield, 92% ee): $^1$H NMR (500 MHz, $CDCl_3$) δ (A mixture of two rotamers) 7.61 (dd, J=8.2, 1.4 Hz, 2H), 7.51-7.43 (m, 1H), 7.38-7.26 (m, 7H), 5.72 (ddt, J=17.6, 10.3, 7.4 Hz, 1H), 5.21-5.09 (m, 2H), 4.57 (t, J=13.3 Hz, 3H), 4.32-3.63 (m, 5H), 3.25-2.93 (m, 1H), 2.60 (br s, 1H), 1.50 (s, 9H); $^{13}$C NMR (126 MHz, $CDCl_3$) δ 173.3, 172.5, 153.4, 135.6, 132.1, 131.9, 128.6, 128.3, 128.2, 127.9, 127.5, 120.0, 75.1, 74.2, 73.7, 70.6, 43.5, 38.5, 37.0, 28.6; IR (Neat Film, NaCl) 3064, 2976, 2931, 1692, 1601, 1474, 1452, 1392, 1365, 1317, 1286, 1251, 1232, 1164, 1102, 1062, 1016, 969, 924, 857, 730, 696, 671 $cm^{-1}$; HRMS (MM: ESI-APCI): m/z calc'd for $C_{27}H_{33}N_2O_5$ $[M+H]^+$: 465.2384, found 465.2388; $[α]D^{23.8}$−13.9 (c 0.33, $CHCl_3$); SFC conditions: 7% IPA, 2.5 mL/min, Chiralpak OJ-H column, X=254 nm, $t_R$ (min): major=3.737, minor=4.398.

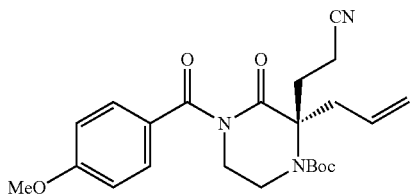 [SMILES: C=CC[C@@]1(CCC#N)C(=O)N(C(=O)c2ccc(OC)cc2)CCN1C(=O)OC(C)(C)C]

tert-butyl (S)-2-allyl-2-(2-cyanoethyl)-4-(4-methoxybenzoyl)-3-oxopiperazine-1-carboxylate (4j). Following the general procedure, α-cyanoethylated allyl ester 3j (25 mg, 0.053 mmol, 1.0 equiv) in hexanes/toluene (2:1, 2.8 mL) was added to a solution of $Pd_2(dba)_3$(1.9 mg, 0.0021 mmol, 4 mol %) and (S)—$(CF_3)_3$-tBu-PHOX (3.1 mg, 0.0053 mmol, 10 mol %) in hexanes/toluene (2:1, 1.0 mL). Purification by silica gel flash chromatography (dry load $SiO_2$, 3:1 hexanes/EtOAc) gave oxopiperazine 4j as a colorless oil (20 mg, 88% yield, 97% ee): $^1$H NMR (400 MHz, $CDCl_3$) δ 7.63 (d, J=8.8 Hz, 2H), 6.92 (d, J=8.9 Hz, 2H), 5.79 (ddt, J=16.6, 10.4, 7.5 Hz, 1H), 5.24 (d, J=1.7 Hz, 1H), 5.20 (dd, J=9.9, 1.9 Hz, 1H), 3.98-3.87 (m, 2H), 3.86 (s, 3H), 3.84-3.71 (m, 2H), 3.27 (m, 1H), 2.82 (m, 1H), 2.69 (dd, J=13.8, 7.4 Hz, 1H), 2.47 (dt, J=14.1, 7.4 Hz, 1H), 2.32 (t, J=7.2 Hz, 2H), 1.53 (s, 9H); $^{13}$C NMR (101 MHz, $CDCl_3$) δ 172.4, 171.5, 163.4, 153.6, 132.0, 131.2, 127.0, 120.6, 119.1, 113.7, 82.0, 69.0, 55.6, 43.8, 43.2, 42.0, 32.3, 28.5, 13.1; IR (Neat Film, NaCl) 2976, 2933, 2359, 2247, 1694, 1605, 1579, 1512, 1456, 1366, 1281, 1258 1168, 1113, 1020, 974, 928, 843, 768, 614 $cm^{-1}$; HRMS (MM: ESI-APCI): m/z calc'd for $C_{23}H_{30}N_3O_5$ $[M+H]^+$: 428.2180, found 428.2182; $[α]D^{23.2}$−4.3 (c 1.0, $CHCl_3$); SFC conditions: 15% IPA, 2.5 mL/min, Chiralpak OD-H column, X=210 nm, $t_R$ (min): major=6.049, minor=5.143.

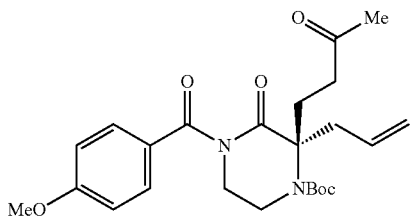 [SMILES: C=CC[C@@]1(CCC(C)=O)C(=O)N(C(=O)c2ccc(OC)cc2)CCN1C(=O)OC(C)(C)C]

tert-butyl (S)-2-allyl-4-(4-methoxybenzoyl)-3-oxo-2-(3-oxobutyl)piperazine-1-carboxylate (4k). Following the general procedure, ketone 3k (25 mg, 0.051 mmol, 1.0 equiv) in hexanes/toluene (2:1, 2.2 mL) was added to a solution of $Pd_2(dba)_3$ (1.9 mg, 0.002 mmol, 4 mol %) and (S)—$(CF_3)_3$-tBu-PHOX (3.0 mg, 0.0051 mmol, 10 mol %) in hexanes/toluene (2:1, 1.5 mL). Purification by silica gel flash chromatography (dry load $SiO_2$, 30% EtOAc/hexanes) gave ketone 4k as a pale yellow oil (17 mg, 73% yield, 97% ee); $^1$H NMR (400 MHz, CDCb) δ 7.59 (d, J=8.9 Hz, 2H), 6.89 (d, J=8.9 Hz, 2H), 5.79 (ddt, J=14.6, 9.4, 7.5 Hz, 1H), 5.18 (dd, J=13.8, 1.9 Hz, 2H), 3.92-3.81 (m, 6H), 3.80-3.66 (m, 1H), 3.22 (s, 1H), 2.74 (dd, J=13.8, 7.3 Hz, 1H), 2.72, (m, 1H), 2.50-2.27 (m, 3H), 2.13 (s, 3H), 1.51 (s, 9H); $^{13}$C NMR (101 MHz, $CDCl_3$) δ 207.5, 172.6, 172.4, 163.2, 132.8, 131.0, 127.3, 120.0, 113.6, 81.6, 69.5, 55.6, 43.9, 43.2, 39.1, 32.3, 30.0, 28.6, 24.8; IR (Neat Film, NaCl) 2975, 1694, 1605, 1512, 1456, 1392, 1366, 1282, 1258, 1168, 1113, 1062, 1019, 974, 923, 841, 768 $cm^{-1}$; HRMS (MM: ESI-APCI): m/z calc'd for $C_{24}H_{33}N_2O_6$ $[M+H]^+$: 445.2333, found 445.2335; [α]D²³·²+25.1 (c 0.97, CHCl₃); SFC conditions: 7% IPA, 2.5 mL/min, Chiralpak OD-H column, X=235 nm, t_R (min): major=9.712, minor=10.434.

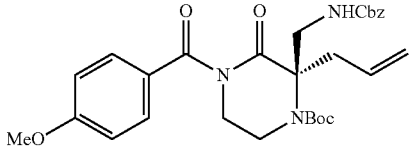 [SMILES: C=CC[C@@]1(CNC(=O)OCc2ccccc2)C(=O)N(C(=O)c2ccc(OC)cc2)CCN1C(=O)OC(C)(C)C]

tert-butyl (R)-2-allyl-2-((((benzyloxy)carbonyl)amino)methyl)-4-(4-methoxybenzoyl)-3-oxopiperazine-1-carboxylate (4l). Following the general procedure, aminomethyl allyl ester 3l (100 mg, 0.17 mmol, 1.0 equiv) in hexanes/toluene (2:1, 10 mL) was added to a solution of Pd₂(dba)₃ (6.3 mg, 0.0069 mmol, 4 mol %) and (S)—(CF₃)₃-tBu-PHOX (10 mg, 0.017 mmol, 10 mol %) in hexanes/toluene (2:1, 2 mL). Purification by silica gel flash chromatography (15%-20%-30% EtOAc/hexanes) gave di-substituted oxopiperazine 4l as a yellow oil (60 mg, 65% yield, 92% ee); ¹H NMR (400 MHz, CDCl₃) δ (a mixture of two rotamers) 7.64 (t, J. 8.9 Hz, 2H), 7.44-7.23 (m, 5H), 6.89 (d, J=8.5 Hz, 2H), 5.79 (dq, J=16.8, 7.8 Hz, 1H), 5.32-4.93 (m, 5H), 4.31-3.97 (m, 1H), 3.95-3.64 (m, 7H), 3.64-3.45 (m, 1H), 3.45-2.87 (m, 1H), 2.64 (dd, J. 14.0, 7.3 Hz, 1H), 1.48 (s, 9H); ¹³C NMR (101 MHz, CDCl₃) δ 172.6, 172.3, 163.1, 156.4, 153.7, 136.6, 132.2, 131.1, 128.6, 128.4, 128.3, 127.3, 120.1, 113.6, 70.2, 67.0, 55.6, 46.9, 43.8, 43.2, 39.6, 28.6; IR (Neat Film, NaCl) 3357, 2975, 2361, 1694, 1605, 1512, 1456, 1366, 1317, 1283, 1255, 1169, 1094, 1061, 1020, 923, 841, 768, 699 cm⁻¹; HRMS (MM: ESI-APCI): m/z calc'd for C₂₉H₃₆N₃O₇ [M+H]⁺: 538.2548, found 538.2543; [α]D²²·⁸+3.74 (c 2.0, CHCl₃); SFC conditions: 15% IPA, 2.5 mL/min, Chiralpak OD-H column, λ=280 nm, t_R (min): major=8.425, minor=7.817.

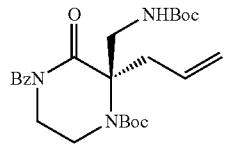

tert-Butyl (R)-2-allyl-4-benzoyl-2-(((tert-butoxycarbonyl)amino)methyl)-3-oxopiperazine-1-carboxylate (4m). Following the general procedure, allyl ester 3m (100 mg, 0.19 mmol, 1.0 equiv) in hexanes/toluene (2:1, 8.0 mL) was added to a solution of Pd₂(pmdba)₃ (8.5 mg, 0.0077 mmol, 4 mol %) and (S)—(CF₃)₃-tBu-PHOX (11.4 mg, 0.019 mmol, 10 mol %) in hexanes/toluene (2:1, 4.0 mL). Purification by flash chromatography (15% EtOAc/hexanes) gave di-substituted oxopiperazine 4m as a pale yellow foam (85 mg, 93% yield, 93% ee); ¹H NMR (400 MHz, CDCl₃) δ (a mixture of two rotamers) 7.61 (d, J=7.6 Hz, 2H), 7.51 (tt, J=7.5, 2.1 Hz, 1H), 7.41 (t, J=7.5 Hz, 2H), 5.91-5.66 (m, 1H), 5.19 (d, J=15.6 Hz, 2H), 4.73 (s, 1H), 4.09-3.72 (m, 5H), 3.67 (dd, J=14.0, 7.0 Hz, 1H), 3.43-2.97 (m, 1H), 2.72-2.51 (m, 1H), 1.54 (s, 9H), 1.43 (s, 9H); ¹³C NMR (101 MHz, CDCl₃) 172.9, 172.8, 155.7, 153.6, 135.8, 132.3, 131.9, 128.2, 128.0, 120.1, 81.2, 79.7, 70.5, 46.5, 43.7, 43.2, 39.4, 28.6, 28.5; IR (Neat Film, NaCl): =3374, 2977, 1694, 1504, 1454, 1392, 1366, 1317, 1286, 1231, 1165, 1094, 1060, 1014, 921, 855, 765, 729, 696 cm⁻¹; HRMS (MM: ESI-APCI): m/z calc'd for C₂₅H₃₆N₃O₆ [M+H]⁺: 474.2599, found: 474.2602; [α]D²³·²+2.7 (c 1.00, CH₃Cl); SFC conditions: 10% IPA, 2.5 mL/min, Chiralpak OD-H column, k=254 nm, t_R (min): major=4.429, minor=3.910.

Example 33: Experimental Procedures and Spectroscopic Data for the Pd-Catalyzed Decarboxylative Asymmetric Allylic Alkylation of Tetrahydropyrimidinone Substrates

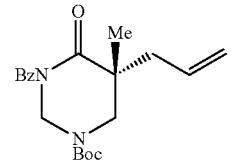

tert-butyl (R)-5-allyl-3-benzoyl-5-methyl-4-oxotetrahydropyrimidine-1(2H)-carboxylate (6a). Following the general procedure, methylated pyrimidinone 5a (15 mg, 0.037 mmol, 1.0 equiv) in hexanes/toluene (2:1, 1.0 mL) was added to a solution of Pd₂(pmdba)₃ (1.6 mg, 0.0015 mmol, 4 mol %) and (S)—(CF₃)₃-tBu-PHOX (2.2 mg, 0.0037 mmol, 10 mol %) in hexanes/toluene (2:1, 1.7 mL). Purification by silica gel flash chromatography (13% EtOAc/hexanes) gave α-methyl pyrimidinone 6a as a colorless oil (11 mg, 83% yield, 93% ee): ¹H NMR (500 MHz, CDCl₃) δ 7.57-7.46 (m, 3H), 7.40 (t, J=7.6 Hz, 2H), 5.78 (dq, J=16.9, 8.0 Hz, 1H), 5.31 (d, J=8.4 Hz, 1H), 5.25-5.09 (m, 3H), 3.69 (d, J=13.8 Hz, 1H), 3.55 (m, 1H), 2.52 (m, 1H), 2.31 (dd, J=13.9, 8.0 Hz, 1H), 1.51 (s, 9H), 1.26 (s, 3H); ¹³C NMR (101 MHz, CDCl₃) δ (a mixture of two rotamers) 176.8, 176.5, 173.9, 153.7, 135.6, 132.5, 132.1, 128.3, 127.9, 120.0, 81.8, 59.4, 59.0, 50.6, 49.7, 45.2, 41.0, 28.4, 22.4; IR (Neat Film, NaCl) 2976, 2932, 1698, 1426, 1367, 1286, 1246, 1136, 1027, 924, 858, 802, 750, 719, 695, 635 cm⁻¹; HRMS (MM: ESI-APCI): m/z calc'd for C₂₀H₂₇N₂O₄ [M+H]⁺: 359.1965, found 359.1963; [α]D²³·²–25.7 (c 1.0, CHCl₃); SFC conditions: 7% IPA, 2.5 mL/min, Chiralpak OJ-H column, X=254 nm, t_R (min): major=3.209, minor=2.569.

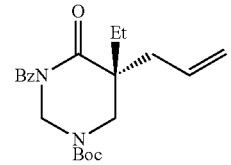

tert-butyl (R)-5-allyl-3-benzoyl-5-ethyl-4-oxotetrahydropyrimidine-1(2H)-carboxylate (6b). Following the general procedure, ethylated allyl ester 5b (15 mg, 0.036 mmol, 1.0 equiv) in hexanes/toluene (2:1, 1.0 mL) was added to a solution of Pd₂(pmdba)₃ (1.6 mg, 0.0014 mmol, 4 mol %) and (S)—(CF₃)₃-tBu-PHOX (2.1 mg, 0.0036 mmol, 10 mol %) in hexanes/toluene (2:1, 1.6 mL). Purification by silica gel flash chromatography (13% EtOAc/hexanes) gave α-ethyl tetrahydropyrimidinone 6b as a colorless oil (13 mg, 98% yield, 94% ee); ¹H NMR (400 MHz, CDCl₃) δ 7.57-7.45 (m, 3H), 7.39 (t, J=7.5 Hz, 2H), 5.87-5.62 (m, 1H), 5.48-5.24 (m, 1H), 5.20-5.03 (m, 3H), 3.75 (dd, J=14.0, 1.4 Hz, 1H), 3.65-3.52 (m, 1H), 2.50 (dd, J=14.2, 6.7 Hz, 1H), 2.27 (d, J=16.1 Hz, 1H), 1.79 (dq, J=14.9, 7.5 Hz, 1H), 1.68 (dq, J=14.6, 7.4 Hz, 1H), 1.51 (s, 9H), 0.95 (t, J=7.5 Hz, 3H);

$^{13}$C NMR (101 MHz, CDCl$_3$) δ (a mixture of two rotamers) 175.8, 174.1, 153.7, 135.8, 132.9, 132.0, 128.3, 128.0, 119.7, 81.7, 59.2, 58.8, 48.6, 48.0, 47.6, 39.1, 38.6, 28.7, 28.4, 8.4; IR (Neat Film, NaCl) 2976, 2927, 1698, 1426, 1367, 1286, 1263, 1246, 1136, 1017, 923, 859, 801, 738, 695, 635 cm$^{-1}$; HRMS (MM: ESI-APCI): m/z calc'd for C$_{21}$H$_{29}$N$_2$O$_4$ [M+H]$^+$: 373.2122, found: 373.2122; [α]$_D^{22.2}$−21.0 (c 1.0, CHCl$_3$); SFC conditions: 7% IPA, 2.5 mL/min, Chiralpak OJ-H column, λ=254 nm, $t_R$ (min): major=3.956, minor=2.585.

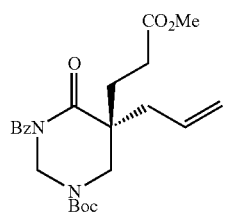

tert-butyl (R)-5-allyl-3-benzoyl-5-(3-methoxy-3-oxopropyl)-4-oxotetrahydropyrimidine-1(2H)-carboxylate (6c). Following the general procedure, methyl ester pyrimidinone 5c (15 mg, 0.032 mmol, 1.0 equiv) in hexanes/toluene (2:1, 1.0 mL) was added to a solution of Pd$_2$(pmdba)$_3$ (1.2 mg, 0.0013 mmol, 4 mol %) and (S)—(CF$_3$)$_3$-tBu-PHOX (1.9 mg, 0.0032 mmol, 10 mol %) in hexanes/toluene (2:1, 1.3 mL). Purification by silica gel flash chromatography (15% EtOAc/hexanes) gave methyl ester 6c as a colorless oil (9.1 mg, 67% yield, 95% ee): $^1$H NMR (400 MHz, CDCl$_3$) δ 7.50 (dd, J=13.1, 7.2 Hz, 3H), 7.38 (t, J=7.5 Hz, 2H), 5.73 (dq, J=16.6, 7.4 Hz, 1H), 5.47-5.22 (m, 1H), 5.22-5.04 (m, 3H), 3.66 (m, 5H), 2.49 (dt, J=12.9, 6.4 Hz, 1H), 2.37 (m, 2H), 2.31-2.19 (m, 1H), 2.14-1.91 (m, 2H), 1.51 (s, 9H); $^{13}$C NMR (101 MHz, CDCl$_3$) δ (a mixture of two rotamers) 175.2, 174.9, 173.9, 173.3, 153.5, 135.6, 132.1, 132.0, 128.4, 127.9, 120.3, 82.0, 59.2, 58.8, 51.1, 48.7, 47.7, 39.1, 38.8, 30.3, 28.9, 28.3; IR (Neat Film, NaCl) 2978, 1738, 1698, 1428, 1368, 1286, 1247, 1147, 925, 856, 802, 764, 696 cm$^{-1}$; HRMS (MM: ESI-APCI): m/z calc'd for C$_{23}$H$_{31}$N$_2$O$_6$ [M+H]$^+$: 431.2177, found 431.2173; [α]$_D^{23.1}$+5.5 (c 0.9, CHCl$_3$); SFC conditions: 10% IPA, 2.5 mL/min, Chiralpak AD-H column, λ=254 nm, $t_R$ (min): major=5.591, minor=6.372.

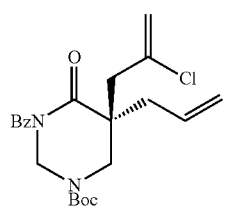

tert-butyl (S)-5-allyl-3-benzoyl-5-(2-chloroallyl)-4-oxotetrahydropyrimidine-1(2H)-carboxylate (6d). Following the general procedure, 2-chloropropenyl allyl ester 5d (20 mg, 0.049 mmol, 1.0 equiv) in hexanes/toluene (2:1, 3.0 mL) was added to a solution of Pd$_2$(pmdba)$_3$ (2.1 mg, 0.0020 mmol, 4 mol %) and (S)—(CF$_3$)$_3$-tBu-PHOX (2.9 mg, 0.0049 mmol, 10 mol %) in hexanes/toluene (2:1, 0.5 mL). Purification by flash chromatography (EtOAc/hexanes 15%) gave di-substituted oxopiperazine 6d as a yellow oil (17 mg, 94% yield, 94% ee); $^1$H NMR (400 MHz, CDCl$_3$) δ (a mixture of two rotamers) 7.65-7.45 (m, 3H), 7.40 (t, J=7.6 Hz, 2H), 5.95-5.76 (m, 1H), 5.76-5.47 (m, 1H), 5.31 (d, J=1.3 Hz, 1H), 5.30-5.16 (m, 2H), 4.92 (s, 1H), 4.05 (s, 1H), 3.61 (d, J=14.0 Hz, 1H), 3.06 (d, J=14.8 Hz, 1H), 2.69-2.55 (m, 1H), 2.45 (d, J=14.5 Hz, 2H), 1.52 (s, 9H); $^{13}$C NMR (101 MHz, CDCl$_3$) δ (a mixture of two rotamers) 174.4, 173.9, 153.6, 137.5, 135.6, 132.1, 132.0, 128.3, 128.1, 120.8, 118.1, 82.0, 59.1, 48.2, 47.6, 46.6, 42.8, 42.3, 41.7, 28.4; IR (Neat Film, NaCl) 2977, 1698, 1630, 1478, 1426, 1368, 1286, 1246, 1140, 902, 802, 765, 724, 695, 636 cm$^{-1}$; HRMS (MM: ESI-APCI): m/z calc'd for C$_{22}$H$_{28}$ClN$_2$O$_4$ [M+H]$^+$: 419.1732, found 419.1732; [α]$_D^{22.6}$+22.2 (c 1.0, CHCl$_3$); SFC conditions: 10% IPA, 2.5 mL/min, Chiralpak AD-H column, λ=210 nm, $t_R$ (min): major=4.679, minor=3.777.

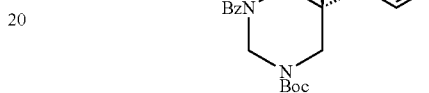

tert-butyl (S)-5-allyl-3-benzoyl-5-benzyl-4-oxotetrahydropyrimidine-1(2H)-carboxylate (6e). Following the general procedure, benzylated allyl ester 5e (15 mg, 0.031 mmol, 1.0 equiv) in hexanes/toluene (2:1, 1.0 mL) was added to a solution of Pd$_2$(pmdba)$_3$ (1.4 mg, 0.0013 mmol, 4 mol %) and (S)—(CF$_3$)$_3$-tBu-PHOX (1.9 mg, 0.0031 mmol, 10 mol %) in hexanes/toluene (2:1, 1.2 mL). Purification by silica gel flash chromatography (13% EtOAc/hexanes) gave benzyl tetrahydropyrimidinone 6e as a colorless oil (11.5 mg, 84% yield, 95% ee); $^1$H NMR (500 MHz, CDCl$_3$) δ 7.58-7.49 (m, 3H), 7.42 (t, J=7.7 Hz, 2H), 7.31-7.24 (m, 3H), 7.20 (d, J=7.2 Hz, 2H), 5.86 (dddd, J=16.8, 10.2, 7.9, 6.6 Hz, 1H), 5.48-5.25 (m, 1H), 5.22 (d, J=10.0 Hz, 1H), 5.21-5.14 (m, 1H), 4.87 (d, J=11.9 Hz, 1H), 3.89-3.72 (m, 1H), 3.55 (d, J=13.7 Hz, 1H), 3.37-3.21 (m, 1H), 2.80-2.68 (m, 1H), 2.65 (dd, J=14.0, 6.6 Hz, 1H), 2.32-2.19 (m, 1H), 1.52 (s, 9H); $^{13}$C NMR (101 MHz, CDCl$_3$) δ (a mixture of two rotamers) 175.4, 173.9, 153.6, 136.1, 135.6, 132.6, 132.1, 131.0, 128.5, 128.3, 128.1, 127.1, 120.2, 81.9, 58.8, 49.5, 47.2, 46.5, 41.1, 40.6, 28.4; IR (Neat Film, NaCl) 2978, 2930, 2360, 1698, 1424, 1368, 1288, 1245, 1142, 1029, 924, 856, 802, 718, 696, 636 cm$^{-1}$; HRMS (MM: ESI-APCI): m/z calc'd for C$_{26}$H$_{31}$N$_2$O$_4$ [M+H]$^+$: 435.2278, found: 435.2274; [α]$_D^{22.1}$−5.6 (c 1.0, CHCl$_3$); SFC conditions: 20% IPA, 2. mL/min, Chiralpak IC column, λ=254 nm, $t_R$ (min): major=4.096, minor=4.670.

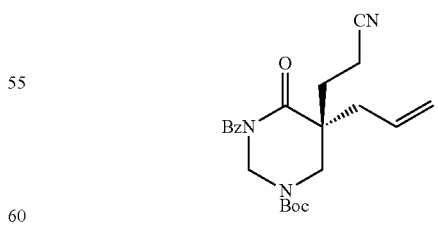

tert-butyl (R)-5-allyl-3-benzoyl-5-(2-cyanoethyl)-4-oxotetrahydropyrimidine-1(2H)-carboxylate (6f). Following the general procedure, cyanoethylated tetrahydropyrimidinone 5f (15 mg, 0.034 mmol, 1.0 equiv) in hexanes/toluene (2:1, 1.0 mL) was added to a solution of Pd$_2$(pmdba)$_3$ (1.2 mg, 0.0014 mmol, 4 mol %) and (S)—(CF$_3$)$_3$-tBu-PHOX (2.0 mg, 0.0034 mmol, 10 mol %) in hexanes/toluene (2:1, 1.4 mL). Purification by silica gel flash chromatography (20% EtOAc/hexanes) gave cyanoethylated tetrahydropyrimidinone 6f as a colorless oil (9.0 mg, 67% yield, 74% ee): $^1$H NMR (500 MHz, CDCl$_3$) δ 7.56-7.49 (m, 3H), 7.43 (t, J=7.6 Hz, 2H), 5.75 (dddd, J=16.8, 10.2, 7.9, 6.6 Hz, 1H), 5.35-5.13 (m, 4H), 3.86-3.55 (m, 2H), 2.57-2.51 (m, 1H), 2.44 (dd, J=10.0, 5.9 Hz, 2H), 2.32 (dd, J=14.1, 8.0 Hz, 1H), 2.09 (dt, J=14.6, 8.5 Hz, 1H), 1.96 (ddd, J=14.3, 9.8, 6.2 Hz, 1H), 1.53 (s, 9H); $^{13}$C NMR (101 MHz, CDCl$_3$) δ 174.6, 173.7, 153.4, 135.4, 132.4, 131.2, 128.5, 127.8, 121.2, 119.2, 82.5, 59.4, 48.3, 47.7, 39.1, 31.0, 28.4, 12.6; IR (Neat Film, NaCl) 2977, 2931, 2248, 1694, 1601, 1478, 1427, 1368, 1285, 1263, 1246, 1141, 1027, 926, 901, 857, 802, 763, 721, 696, 636, cm$^{-1}$; HRMS (MM: ESI-APCI): m/z calc'd for C$_{22}$H$_{28}$N$_3$O$_4$ [M+H]$^+$: 398.2074, found 398.2071; [α]D$^{23.2}$+10.0 (c 1.0, CHCl$_3$); SFC conditions: 30% IPA, 2.5 mL/min, Chiralpak IC column, X=254 nm, to (min): major=3.148, minor=4.927.

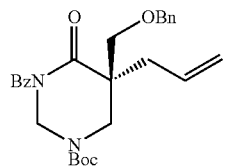

tert-butyl (R)-5-allyl-3-benzoyl-5-((benzyloxy)methyl)-4-oxotetrahydropyrimidine-1(2H)-carboxylate (6g). Following the general procedure, allyl ester 5g (15 mg, 0.029 mmol, 1.0 equiv) in hexanes/toluene (2:1, 1.6 mL) was added to a solution of Pd$_2$(pmdba)$_3$ (1.3 mg, 0.0012 mmol, 4 mol %) and (S)—(CF$_3$)$_3$-tBu-PHOX (1.7 mg, 0.0029 mmol, 10 mol %) in hexanes/toluene (2:1, 0.5 mL). Purification by flash chromatography (10-15% EtOAc/hexanes) gave di-substituted oxopiperazine 6g as a yellow oil (13 mg, 87% yield, 87% ee): $^1$H NMR (400 MHz, CDCl$_3$) δ 7.69-7.51 (m, 2H), 7.51-7.42 (m, 1H), 7.42-7.22 (m, 7H), 5.77 (ddt, J=15.0, 10.3, 7.4 Hz, 1H), 5.54-5.49 (m, 1H), 5.28-5.10 (m, 2H), 5.06 (d, J=12.1 Hz, 1H), 4.63-4.40 (m, 2H), 3.94 (m, 1H), 3.82 (d, J=13.9 Hz, 1H), 3.75 (d, J=8.9 Hz, 1H), 3.40 (d, J=9.0 Hz, 1H), 2.42 (m, 2H), 1.50 (s, 9H); $^{13}$C NMR (101 MHz, CDCl$_3$) δ 174.7, 173.5, 153.6, 137.8, 135.5, 132.0, 128.6, 128.3, 128.2, 127.9, 127.7, 112.0, 81.8, 73.8, 58.8, 50.0, 46.9, 46.3, 38.6, 28.4; IR (Neat Film, NaCl) 2977, 2926, 2283, 1698, 1641, 1478, 1451, 1426, 1367, 1287, 1246, 1151, 1028, 906, 857, 801, 740, 697, 635 cm$^{-1}$; HRMS (MM: ESI-APCI): m/z calc'd for C$_{27}$H$_{32}$N$_2$O$_5$ [M+H]$^+$: 465.2384, found 465.2378; [α]$_D^{23.4}$+11.9 (c 0.67, CHCl$_3$); SFC conditions: 20% IPA, 2.5 ml/min, Chiralpak IC column, λ=210 nm, t$_R$ (min): major=5.131, minor=4.419.

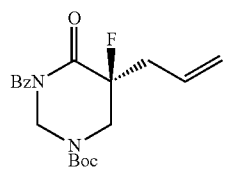

tert-butyl (S)-5-allyl-3-benzoyl-5-fluoro-4-oxotetrahydropyrimidine-1(2H)-carboxylate (6h). Following the general procedure, fluorinated tetrahydropyrimidinone 5h (15 mg, 0.037 mmol, 1.0 equiv) in hexanes/toluene (2:1, 1.0 mL) was added to a solution of Pd$_2$(pmdba)$_3$ (1.6 mg, 0.0015 mmol, 4 mol %) and (S)—(CF$_3$)$_3$-tBu-PHOX (2.2 mg, 0.0037 mmol, 10 mol %) in hexanes/toluene (2:1, 1.6 mL). Purification by silica gel flash chromatography (15% EtOAc/hexanes) gave fluorinated tetrahydropyrimidinone 6h as a pale yellow oil (9.6 mg, 72% yield, 92% ee); $^1$H NMR (400 MHz, CDCl$_3$) δ 7.59 (dd, J=8.3, 1.3 Hz, 2H), 7.54 (t, J=7.4 Hz, 1H), 7.42 (t, J=7.8 Hz, 2H), 5.82 (ddt, J=14.9, 9.6, 7.2 Hz, 1H). 5.66-5.34 (m, 1H), 5.29 (s, 1H), 5.25 (d, J=5.3 Hz, 1H), 5.24-5.13 (m, 1H), 4.13-3.72 (m, 2H), 2.81 (td, J=14.3, 6.9 Hz, 1H), 2.67 (ddd, J=22.4, 14.5, 7.6 Hz, 1H), 1.51 (s, 9H); $^{13}$C NMR (101 MHz, CDCl$_3$) δ (a mixture of two rotamers) 172.5, 168.23 (d, J$_{CF}$=23.6 Hz), 153.4, 134.3, 132.7, 129.7, 129.6, 128.5, 128.5, 128.3, 128.0, 121.4, 92.2 (d, J$_{CF}$=197.0 Hz, appears as four peaks due to the presence of two rotamers and coupling with fluorine), 82.4, 57.7, 49.4 (appears as four poorly resolved peaks due to the presence of two rotamers and coupling with fluorine), 38.2 (d, J$_{CF}$=22.8 Hz), 28.3; IR (Neat Film, NaCl) 2978, 1710, 1416, 1368, 1286, 1245, 1158, 1137, 906, 858, 801, 749, 723, 694, 662 cm$^{-1}$; HRMS (MM: ESI-APCI): m/z calc'd for C$_{19}$H$_{24}$N$_2$O$_4$ [M+H]$^+$: 363.1715, found: 363.1713; [α]D$^{21.8}$–28.6 (c 0.96, CHCl$_3$); SFC conditions: 10% IPA, 2.5 mL/min, Chiralpak IC column, X=254 nm, t$_R$ (min): major=6.226, minor=5.041.

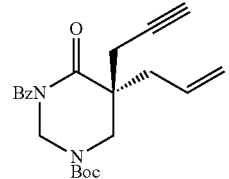

tert-butyl (S)-5-allyl-3-benzoyl-4-oxo-5-(prop-2-yn-1-yl) tetrahydropyrimidine-1(2H)-carboxylate (6i). Following the general procedure, propargylated allyl ester 5i (20 mg, 0.047 mmol, 1.0 equiv) in hexanes/toluene (2:1, 2.8 mL) was added to a solution of Pd$_2$(pmdba)$_3$ (2.1 mg, 0.0019 mmol, 4 mol %) and (S)—(CF$_3$)$_3$-tBu-PHOX (2.8 mg, 0.0047 mmol, 10 mol %) in hexanes/toluene (2:1, 0.5 mL). Purification by flash chromatography (EtOAc/hexanes 5%-10%-15%) gave propargyl tetrahydropyrimidinone 6i as a yellow oil (15 mg, 83% yield, 90% ee): $^1$H NMR (400 MHz, CDCl$_3$) δ 7.58 (s, 1H), 7.50 (t, J=7.4 Hz, 2H), 7.39 (t, J=7.5 Hz, 2H), 5.89-5.68 (m, 1H), 5.42 (s, 1H), 5.31-4.98 (m, 3H), 4.15-3.57 (m, 2H), 2.61 (dd, J=16.9, 2.7 Hz, 2H), 2.42 (dd, J=16.9, 2.7 Hz, 2H), 2.11 (t, J=2.6 Hz, 1H), 1.54 (s, 9H); $^{13}$C NMR (101 MHz, CDCl$_3$) δ (a mixture of two rotamers) 174.3, 173.7, 153.6, 135.4, 132.2, 131.8, 128.3, 128.2, 120.6, 82.0, 79.6, 72.4, 59.3, 58.9, 48.2, 47.8, 40.1, 39.6, 28.4, 25.1; IR (Neat Film, NaCl) 3271, 2978, 2930, 1698, 1478, 1450, 1425, 1368, 1284, 1247, 1139, 1028, 927, 854, 802, 764, 720, 695, 635 cm$^{-1}$; HRMS (MM: ESI-APCI): m/z calc'd for C$_{22}$H$_{27}$N$_2$O$_4$ [M+H]$^+$: 383.1965, found 383.1973; [α]D$^{23.0}$+22.1 (c 0.47, CHCl$_3$); SFC conditions: 10% IPA, 2.5 mL/min, Chiralpak AD-H column, λ=210 nm, t$_R$ (min): major=4.769, minor=4.399.

Example 33: Gram Scale Decarboxylative Asymmetric Allylic Alkylation of Benzyl Tetrahydropyrimidinone 5e

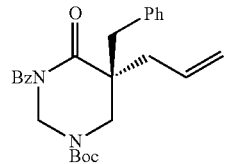

tert-butyl (S)-5-allyl-3-benzoyl-5-benzyl-4-oxotetrahydropyrimidine-1(2H)-carboxylate (6e). In a nitrogen-filled glovebox, a 250 mL schlenk flask was charged with Pd$_2$(pmdba)$_3$ (69 mg, 0.063 mmol, 4 mol %), (S)—(CF$_3$)$_3$-tBu-PHOX (99 mg, 0.17 mmol, 8 mol %), hexane/toluene (2:1, 50 mL), and a magnetic stir bar. The flask was stirred at ambient glovebox temperature (27° C.) for 30 min and then 5e (1g, 2.1 mmol, 1.0 equiv) was added as a solution in hexane/toluene (2:1, 100 mL, total concentration 0.014M). The flask was sealed with a Kontes valve, removed from the glovebox, and heated to 40° C. for 16 h. The solution was concentrated under reduced pressure and purified by silica gel flash chromatography (15% EtOAc/hexanes) to give benzyl tetrahydropyrimidinone 6e as a yellow oil (780 mg, 87% yield, 95% ee); spectroscopic data vide supra.

Example 34: Transformations of Decarboxylative Allylic Alkylation Products

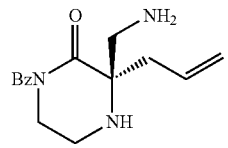

tert-butyl (R)-((2-allyl-4-benzoyl-3-oxopiperazin-2-yl)methyl)carbamate (8). Trifluoroacetic acid (114 µL, 1.5 mmol, 20 equiv) was added dropwise to a solution of methylcarbamate oxopiperazine 4m (35 mg, 0.07 mmol, 1.0 equiv) in CH$_2$Cl$_2$ (0.74 mL) at 0° C. The reaction mixture was allowed to warm up to room temperature, stirred for 3 h and concentrated under reduced pressure. The residue was repeatedly taken up in CH$_2$Cl$_2$ (1.0 mL) and concentrated, four times. The crude residue was then purified by silica gel flash chromatography (10% MeOH/CH$_2$Cl$_2$) to yield deprotected oxopiperazine 8 as a pale yellow foam (27 mg, 73% yield); $^1$H NMR (400 MHz, CDCl$_3$) δ 7.48 (t, J=8.0 Hz, 3H), 7.37 (t, J=7.4 Hz, 2H), 5.66 (dd, J=16.0, 8.8 Hz, 1H), 5.30 (d, J=9.8 Hz, 1H), 5.25 (d, J=16.8 Hz, 1H), 3.99-3.79 (m, 1H), 3.73-3.55 (m, 1H), 3.44-3.16 (m, 2H), 3.05 (d, J=13.2 Hz, 1H), 2.89 (d, J=11.6 Hz, 1H), 2.76 (dd, J=14.0, 7.0 Hz, 1H), 2.45 (dd, J=14.2, 7.1 Hz, 1H); $^{13}$C NMR (101 MHz, CDCl$_3$) δ 173.7, 172.4, 135.5, 132.2029.7, 128.4, 128.0, 122.5, 62.0, 47.0, 43.5, 39.7, 38.1; IR (Neat Film, NaCl) 2976, 1682, 1470, 1282, 1203, 1135, 926, 836, 799, 722, 696 cm$^{-1}$; HRMS (MM: ESI-APCI): m/z calc'd for C$_{15}$H$_{20}$N$_3$O$_4$ [M+H]$^+$: 274.1550, found 274.1555; [α]D$^{22.3}$+15.1 (c 1.0, CHCl$_3$).

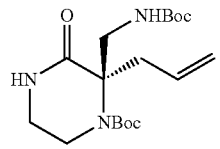 [SMILES: C=CC[C@@]1(CNC(=O)OC(C)(C)C)C(=O)NCCN1C(=O)OC(C)(C)C]

tert-butyl (R)-2-allyl-2-(((tert-butoxycarbonyl)amino)methyl)-3-oxopiperazine-1-carboxylate (9). LiOH monohydrate (2.5 mg, 0.06 mmol, 1.4 equiv) was added in one portion to a solution of methylcarbamate oxopiperazine 4m (20 mg, 0.04 mmol, 1.0 equiv) in methanol/water (1:1, 1.8 mL) at room temperature. The reaction mixture was stirred for 1 h, diluted with EtOAc (2 mL) and washed with saturated aqueous NaHCO$_3$(2 mL). The aqueous phase was extracted with EtOAc (3×3 mL) and the combined organic phases were washed with brine (3 mL), dried over anhydrous Na$_2$SO$_4$, decanted, and concentrated under reduced pressure onto silica gel. The silica-loaded residue was purified by silica gel flash chromatography (hexanes/EtOAc 1:1) to yield lactam 9 as a white foam (14 mg, 92% yield): $^1$H NMR (400 MHz, CDCl$_3$) δ 6.96 (s, 1H), 5.72 (ddt, J=17.2, 10.2, 7.4 Hz, 1H), 5.16-5.04 (m, 2H), 4.88 (t, J=6.9 Hz, 1H), 4.26-3.91 (m, 1H), 3.82 (s, 1H), 3.60 (dd, J=14.0, 5.9 Hz, 1H), 3.50 (s, 1H), 3.39-2.83 (m, 3H), 2.62 (s, 1H), 1.52 (s, 9H), 1.41 (s, 9H); $^{13}$C NMR (101 MHz, CDCl$_3$) δ 172.7, 155.7, 153.9, 132.7, 119.2, 81.2, 79.3, 69.1, 46.0, 43.1, 40.9, 38.9, 28.6, 28.5; IR (Neat Film, NaCl) 3337, 2977, 2360, 1698, 1520, 1367, 1243, 1168, 1085, 1058, 919, 866, 768, 733 cm$^{-1}$; HRMS (MM: ESI-APCI): m/z calc'd for C$_{18}$H$_{32}$N$_3$O$_5$ [M+H]$^+$: 370.2336, found 370.2337; [α]D$^{22.9}$−5.7 (c 1.0, CHCl$_3$).

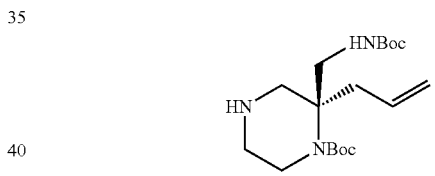

tert-butyl (S)-2-allyl-2-(((tert-butoxycarbonyl)amino)methyl)piperazine-1-carboxylate (10). To a solution of lactam 9 (50 mg, 0.14 mmol, 1 equiv) in THF (1.4 mL) at 0° C. was quickly added LAH (8 mg, 0.2 mmol, 1.5 equiv) in one portion. The mixture was stirred at room temperature and three portions of LAH (8 mg, 0.2 mmol, 1.5 equiv) were added over four hours until all starting material was consumed as determined by TLC analysis. The reaction mixture was then cooled to 0° C. and diluted with Et$_2$O. H$_2$O (40 µL), 15% aqueous NaOH (40 µL), and H$_2$O (120 µL) were added successively at 0° C. The mixture was stirred for 5 minutes at room temperature and then MgSO$_4$ was added. The mixture was stirred for another 5 minutes at room temperature and then filtered over a pad of celite, rinsing with EtOAc. The solvent was concentrated under reduced pressure and the crude residue was purified by silica gel flash chromatography (MeOH/CH$_2$Cl$_2$, 1-2-4%) to afford piperazine 10 as a colorless oil (30 mg, 63% yield); $^1$H NMR (400 MHz, CDCl$_3$) δ 5.84-5.66 (m, 1H), 5.28-5.01 (m, 3H), 3.75 (dd, J=14.1, 5.6 Hz, 1H), 3.62 (dt, J=13.6, 4.2 Hz, 1H), 3.35 (dd, J=14.1, 7.3 Hz, 1H), 3.24 (ddd, J=13.6, 9.8, 3.8 Hz, 1H), 3.02-2.91 (m, 1H), 2.85 (t, J=11.1 Hz, 2H), 2.79-2.63 (m, 2H), 2.57-2.26 (m, 2H), 1.46 (s, 9H), 1.44 (s, 9H); $^{13}$C NMR (101 MHz, CDCl$_3$) δ 156.8, 156.0, 133.1, 119.1, 80.6, 79.6, 59.9, 50.8, 46.2, 45.1, 42.3, 38.1, 28.6, 28.5; IR (Neat Film, NaCl) 3789, 3662, 3451, 3341, 3074, 2976, 2930, 2284, 1693, 1641, 1502, 1453, 1391, 1365, 1298, 1249, 1169, 1085, 996, 914, 859, 771 cm$^{-1}$; HRMS (MM: ESI-APCI): m/z calc'd for $C_{18}H_{34}N_3O_4$ [M+H]$^+$: 356.2544, found 356.2549; [α]D$^{22.8}$+5.3 (c 0.67, CHCl$_3$).

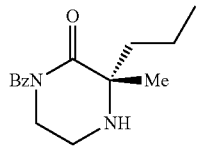

(S)-1-benzoyl-3-methyl-3-propylpiperazin-2-one (11). Piperazinone 4e (80 mg, 0.22 mmol, 1 equiv) was dissolved in MeOH (2.2 mL). The reaction flask was purged with Argon before adding Pd/C (10%, 24 mg, 0.022 mmol, 0.1 equiv). The flask was evacuated and filled with H$_2$ three times, and then sparged with H$_2$ for 5 minutes. The reaction was stirred at room temperature for 6 hours before being filtered through a pad of silica gel while rinsing with EtOAc. The crude hydrogenated product was then dissolved in CH$_2$Cl$_2$ (2.2 mL) and TFA (171 μL, 2.23 mmol, 10 equiv) was added. The reaction was stirred for 16 hours and then quenched with saturated aqueous NaHCO$_3$(5 mL). The solution was extracted with EtOAc (3×5 mL), dried over Na$_2$SO$_4$, decanted, and concentrated under reduced pressure. The crude piperazinone was purified by silica gel flash chromatography (2.5-5% MeOH/CH$_2$Cl$_2$) to afford the desired product 11 (55 mg, 94% yield over two steps): $^1$H NMR (400 MHz, CDCl$_3$) δ 7.58-7.50 (m, 2H), 7.54-7.46 (m, 1H), 7.46-7.36 (m, 2H), 3.92 (ddd, J=12.6, 5.4, 4.6 Hz, 1H), 3.81 (ddd, J=12.5, 6.7, 5.4 Hz, 1H), 3.32-3.18 (m, 2H), 1.92 (ddd, J=13.6, 12.1, 4.7 Hz, 1H), 1.62 (ddd, J=13.6, 12.2, 4.5 Hz, 1H), 1.42 (s, 3H), 1.54-1.23 (m, 2H), 0.96 (t, J=7.3 Hz, 3H); $^{13}$C NMR (101 MHz, CDCl$_3$) δ 176.7, 174.7, 136.4, 131.6, 128.3, 127.5, 61.2, 48.2, 41.2, 38.7, 25.0, 16.9, 14.5; IR (Neat Film, NaCl) 3331, 2960, 2872, 1681, 1600, 1448, 1378, 1284, 1202, 1176, 1152, 1112, 966, 794, 726, 694, 669 cm$^{-1}$; HRMS (MM: ESI-APCI): m/z calc'd for $C_{15}H_{21}N_2O_2$ [M+H]$^+$: 261.1598, found 261.1596; [α]D$^{22.6}$–59.6 (c 1.35, CHCl$_3$).

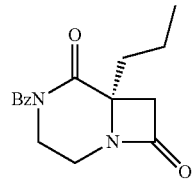

(R)-4-benzoyl-6-propyl-1,4-diazabicyclo[4.2.0]octane-5,8-dione (12). To a 10 mL round-bottom flask was added Pd(OPiv)$_2$ (3 mg, 0.0096 mmol, 0.1 equiv), AgOPiv$^7$ (60 mg, 0.29 mmol, 3 equiv), Xantphos (6 mg, 0.0096 mmol, 0.1 equiv), and 1,4-benzoquinone (21 mg, 0.19 mmol, 2 equiv). A solution of piperazine 11 (25 mg, 0.096 mmol, 1 equiv) in toluene (1 mL) was then added and the flask was evacuated and filled with carbon monoxide three times. The flask was then stirred at 80° C. for 16 hours. The reaction mixture was allowed to cool to room temperature, diluted with EtOAc, and filtered through celite while rinsing with additional EtOAc. The solvent was concentrated under reduced pressure onto silica gel and then purified by silica gel flash chromatography (2:1 hexanes/EtOAc) to provide the β-lactam 12 and as a light yellow oil (15 mg, 55% yield): $^1$H NMR (400 MHz, CDCl$_3$) δ (5:1 ratio of desired product and an inseparable isomer resulting from insertion into another β-CH) 7.56-7.51 (m, 3H), 7.46-7.40 (m, 2H), 4.51 (ddd, J=14.0, 6.1, 2.9 Hz, 1H), 3.94 (ddt, J=12.3, 10.8, 5.7 Hz, 1H), 3.78-3.67 (m, 1H), 3.40 (dddd, J=12.3, 4.8, 2.8, 1.5 Hz, 1H), 3.27-3.10 (m, 2H), 1.98 (ddd, J=14.2, 11.2, 5.5 Hz, 1H), 1.87 (ddd, J=14.2, 11.0, 5.7 Hz, 1H), 1.59-1.40 (m, 2H), 1.00 (t, J=7.3 Hz, 3H); $^{13}$C NMR (101 MHz, CDCl$_3$) δ 174.2, 173.2, 169.1, 135.1, 132.6, 128.6, 128.3, 59.7, 46.7, 41.5, 39.7, 37.8, 17.7, 14.3; IR (Neat Film, NaCl) 3374, 2961, 1760, 1688, 1600, 1505, 1449, 1350, 1318, 1279, 1228, 1183, 1151, 1110, 963, 936, 796, 726, 694, 662 cm$^{-1}$; HRMS (MM: ESI-APCI): m/z calc'd for $C_{16}H_{19}N_2O_3$ [M+H]$^+$: 287.1390, found 287.1385; [α]D$^{23.5}$–12.8 (c 0.47, CHCl$_3$).

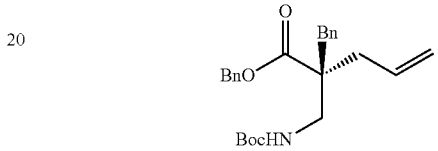

(S)-2-benzyl-2-(((tert-butoxycarbonyl)amino)methyl)pent-4-enoic acid (13). To a solution of benzyl tetrahydropyrimidinone 6d (200 mg, 0.46 mmol, 1 equiv) in methylene chloride (4.6 mL) was added TFA (352 μL, 4.6 mmol, 10 equiv) dropwise at room temperature. The solution was stirred for 24 hours at room temperature and then quenched with aqueous NaHCO$_3$ (10 mL). The layers were separated and the aqueous layer was extracted with CH$_2$Cl$_2$ (4×5 mL). The combined organic layers were dried over Na$_2$SO$_4$, filtered, and concentrated under reduced pressure. The crude residue was dissolved in MeOH/H2O (1:1, 5 mL) and LiOH monohydrate (290 mg, 6.9 mmol, 15 equiv) was added. The reaction mixture was heated to 80° C. for 60 hours and then allowed to cool to room temperature. Then, NEt$_3$ (77 μL, 0.55 mmol, 1.2 equiv) and Boc$_2$O (110 mg, 0.51 mmol, 1.1 equiv) were added successively at room temperature. The reaction was stirred for 1 hour at room temperature and then acidified with 1 M HCl (4 mL). The solution was extracted with EtOAc (3×5 mL). The combined organic layers were dried over Na$_2$SO$_4$. The crude Boc-protected fl-amino acid was taken up in DMF (2.3 mL). K$_2$CO$_3$ (95 mg, 0.69 mmol, 1.5 equiv) and BnBr (66 μL, 0.55 mmol, 1.2 equiv) were added at room temperature. The reaction was stirred at room temperature for 1 hour and then quenched with saturated aqueous NH$_4$Cl. The solution was extracted with EtOAc (3×5 mL) and the combined organic layers were concentrated under reduced pressure and placed under high vacuum until trace DMF had evaporated. The residue was taken up in CH$_2$Cl$_2$, concentrated under reduced pressure onto silica gel and purified by silica gel flash chromatography (5 10% EtOAc/hexanes) to afford protected β$^{2,2}$-amino acid 13 as a white solid (80 mg, 40% yield): $^1$H NMR (400 MHz, CDCl$_3$) δ 7.42-7.27 (m, 5H), 7.20 (dd, J=4.9, 1.9 Hz, 3H), 7.10-6.93 (m, 2H), 5.92-5.75 (m, 1H), 5.18-5.04 (m, 4H), 4.96-4.81 (m, 1H), 3.34 (qd, J=14.0, 6.5 Hz, 2H), 2.98 (d, J=13.8 Hz, 1H), 2.86 (d, J=13.8 Hz, 1H), 2.49 (ddt, J=14.2, 6.7, 1.4 Hz, 1H), 2.31 (ddt, J=14.2, 7.9, 1.1 Hz, 1H), 1.43 (s, 9H); $^{13}$C NMR (101 MHz, CDCl$_3$) δ 175.1, 156.1, 136.6, 135.6, 133.4, 130.2, 128.8, 128.6, 128.5, 128.4, 126.9, 119.2, 79.4, 66.8, 51.6, 44.1, 41.0, 38.8, 28.5; IR (Neat Film, NaCl) 3452, 3065, 3031, 2977, 2930, 1721, 1640, 1604, 1503, 1454, 1391, 1365, 1245, 1169, 1094, 1030z, 994, 917, 859, 776, 741, 700 cm$^{-1}$; HRMS (MM: ESI-APCI): m/z calc'd for $C_{25}H_{32}NO_4$ [M+H]$^+$: 410.2326, found 410.2324; [α]D$^{23.4}$+3.47 (c 1.0, CHCl$_3$).

Example 35: Determination of Enatiomeric Excess

Racemic products were synthesized according to the general procedure, using achiral GlyPHOX ligand instead of (S)—(CF$_3$)$_3$-tBu-PHOX. [(a) D. C. Behenna, B. M. Stoltz, J. Am. Chem. Soc. 2004, 126, 15044-15045. (b) K. Tani, D. C. Behenna, R. M. McFadden, B. M. Stoltz, Org. Lett. 2007, 9, 2529 2531. (c) M. R. Krout, J. T. Mohr, B. M. Stoltz, Org. Synth. 2009, 86, 181-193.]

| Entry | Product | Assay Conditions | Retention time of major isomer (min) | Retention time of minor isomer (min) | % ee |
|---|---|---|---|---|---|
| 1 | (structure: BzN piperidinone, NBoc, allyl) | SFC Chiralpak AD-H 15% iPrOH isocratic, 2.5 mL/min | 3.741 | 2.682 | 92% |
| 2 | (structure: AnN piperidinone, NBoc, allyl) | SFC Chiralpak AD-H 15% iPrOH isocratic, 2.5 mL/min | 4.708 | 3.998 | 96% |
| 3 | (structure: BzN piperidinone, NCbz, allyl) | SFC Chiralpak IC 30% iPrOH isocratic, 2.5 mL/min | 4.873 | 6.748 | 99% |
| 4 | (structure: BzN piperidinone, NBoc, 2-chloroallyl) | SFC Chiralpak AD-H 15% iPrOH isocratic, 2.5 mL/min | 4.462 | 3.224 | 98% |
| 5 | (structure: BzN piperidinone, NBoc, Me, allyl) | SFC Chiralpak AD-H 7% iPrOH isocratic, 2.5 mL/min | 7.208 | 4.714 | 96% |
| 6 | (structure: BzN piperidinone, NBz, Me, allyl) | SFC Chiralpak OJ-H 10% MeOH isocratic, 2.5 mL/min | 5.574 | 6.659 | 70% |
| 7 | (structure: AnN piperidinone, NBoc, Me, allyl) | SFC Chiralpak AD-H 10% iPrOH isocratic, 2.5 mL/min | 5.370 | 4.278 | 96% |
| 8 | (structure: AnN piperidinone, NBoc, CH$_2$Ph, allyl) | SFC Chiralpak AD-H 15% iPrOH isocratic, 2.5 mL/min | 7.471 | 5.802 | 96% |
| 9 | (structure: BzN piperidinone, NBoc, CH$_2$OBn, allyl) | SFC Chiralpak OJ-H 7% iPrOH isocratic, 2.5 mL/min | 3.737 | 4.398 | 92% |

-continued

| Entry | Product | Assay Conditions | Retention time of major isomer (min) | Retention time of minor isomer (min) | % ee |
|---|---|---|---|---|---|
| 10 | [structure with NHBoc, BzN, NBoc, allyl] | SFC Chiralpak OD-H 10% iPrOH isocratic, 2.5 mL/min | 4.429 | 3.910 | 93% |
| 11 | [structure with NHCbz, AnN, NBoc, allyl] | SFC Chiralpak OD-H 15% MeOH isocratic, 2.5 mL/min | 8.425 | 7.817 | 92% |
| 12 | [structure with CN, AnN, NBoc, allyl] | SFC Chiralpak OD-H 15% iPrOH isocratic, 2.5 mL/min | 6.049 | 5.143 | 97% |
| 13 | [structure with ketone, AnN, NBoc, allyl] | SFC Chiralpak OD-H 7% iPrOH isocratic, 2.5 mL/min | 9.712 | 10.434 | 97% |

VII. Palladium-Catalyzed Decarboxylative Asymmetric Allylic Alkylation of 1,4-diazepan-5-ones

Example 36: Optimizing Reaction Conditions for Decarboxylative Asymmetric Allylic Alkylation of 1,4-diazepan-5-ones We began by examining conditions for the asymmetric allylic alkylation of diazepanone 3a ($R^2$=Bn), utilizing $Pd_2$(pmdba)$_3$ as a palladium source and (S)—(CF$_3$)$_3$-t-BuPHOX as a chiral ligand (Table 27). Generally, polar solvents led to only modest ee of the enantioenriched product 4a (entries 1-3). An ee of 86% was obtained for compound 4a in 2:1 hexanes/toluene (entry 6). Finally, an even more nonpolar solvent, methylcyclohexane [*Can. J. Chem.* 1984, 62, 2560-2565], further enhanced enantioselectivity, yielding 4a in 89% ee (entry 9). In the course of examining reaction conditions, we also discovered that use of the highly electron-deficient ligand (S)-Ty-PHOX [*Chem. Sci.* 2019, 10, 5996-6000] resulted in a drop in ee (entry 8). This is in contrast with previous results indicating that more electron-deficient ligands often give higher enantioselectivity in related systems. [*Nature Chem.* 2012, 4, 130-133; *Chem. Eur. J.* 2013, 19, 4414-4418; *Angew. Chem. Int. Ed.* 2015, 54, 179-183; *Chem. Sci.* 2019, 10, 788-792] Using a more electron-rich ligand, (S)-t-BuPHOX, also decreased the ee of the product (entry 11).

TABLE 27

Optimization of reaction conditions[a]

[Scheme: 3a → 4a with $Pd_2$(pmdba)$_3$ (4 mol %), ligand (10 mol %), solvent, 40° C.]

| entry | solvent | ligand | 4a ee[b] (%) |
|---|---|---|---|
| 1 | THF | (S)-(CF$_3$)$_3$-t-BuPHOX | 20 |
| 2 | 1,4-dioxane | (S)-(CF$_3$)$_3$-t-BuPHOX | 38 |
| 3 | MTBE | (S)-(CF$_3$)$_3$-t-BuPHOX | 70 |
| 4 | toluene | (S)-(CF$_3$)$_3$-t-BuPHOX | 66 |
| 5 | 2:1 hexanes/benzene | (S)-(CF$_3$)$_3$-t-BuPHOX | 84 |
| 6 | 2:1 hexanes/toluene | (S)-(CF$_3$)$_3$-t-BuPHOX | 86 |
| 7 | cyclohexane | (S)-(CF$_3$)$_3$-t-BuPHOX | 88 |
| 8 | cyclohexane | (S)-Ty-PHOX | 80 |

TABLE 27-continued

Optimization of reaction conditions[a]

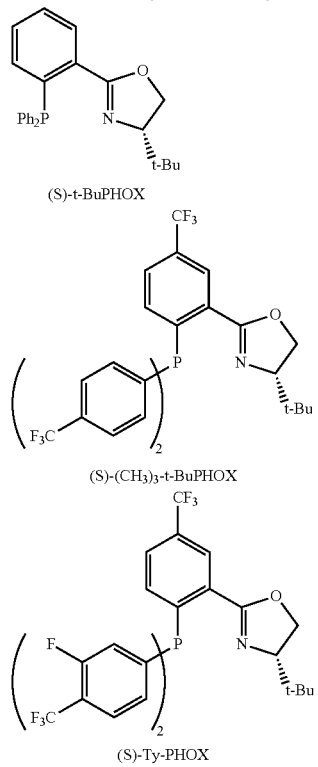

| entry | solvent | ligand | ee[b] (%) |
|---|---|---|---|
| 9 | MeCy | (S)-(CF$_3$)$_3$-t-BuPHOX | 89 |
| 10 | 2:1 MeCy/toluene | (S)-(CF$_3$)$_3$-t-BuPHOX | 86 |
| 11 | MeCy | (S)-t-BuPHOX | 50 |

[a]Screening was performed on a 0.02 mmol scale.
[b]Values determined by chiral SFC analysis.

Example 37: Substrate Scope

Firstly, the effect of the electronics of the lactam protecting group on the reaction outcome was investigated. Switching from a benzoyl group (4b) to a more electron-poor p-CF$_3$-benzoyl group (4c) resulted in a slight increase in enantioselectivity. The use of an electron-rich p-anisoyl group delivered product 4d in 94% ee. It is worth noting that use of the p-anisoyl protecting group was not beneficial to enantioselectivity in all cases (4a/4e, 4g/4h), and was often on par with the unsubstituted benzoyl group. A variety of functional groups at the quaternary carbon were tolerated, including groups bearing an alkenyl chloride (4f) and a ten-butyl carbamate (4l). This method also proved reliable for the formation of tertiary alkyl fluorides (4g, 4h). The propargyl lactam 4i was obtained in low yield. Additionally, this method allowed for the preparation of benzoyl lactam 4e on a 1 mmol scale, albeit in somewhat diminished yield and ee.

TABLE 28

Substrate Scope[a]

4b: R = Bz,
93% yield, 90% ee[b]
4c: R = p-CF$_3$-Bz,
90% yield, 90% ee
4d: R = An,
94% yield, 94% ee 4a: R = Bz,
93% yield, 90% ee[b]
4e: R = An,
>99% yield, 89% ee[c]

TABLE 28-continued
Substrate Scope[a]
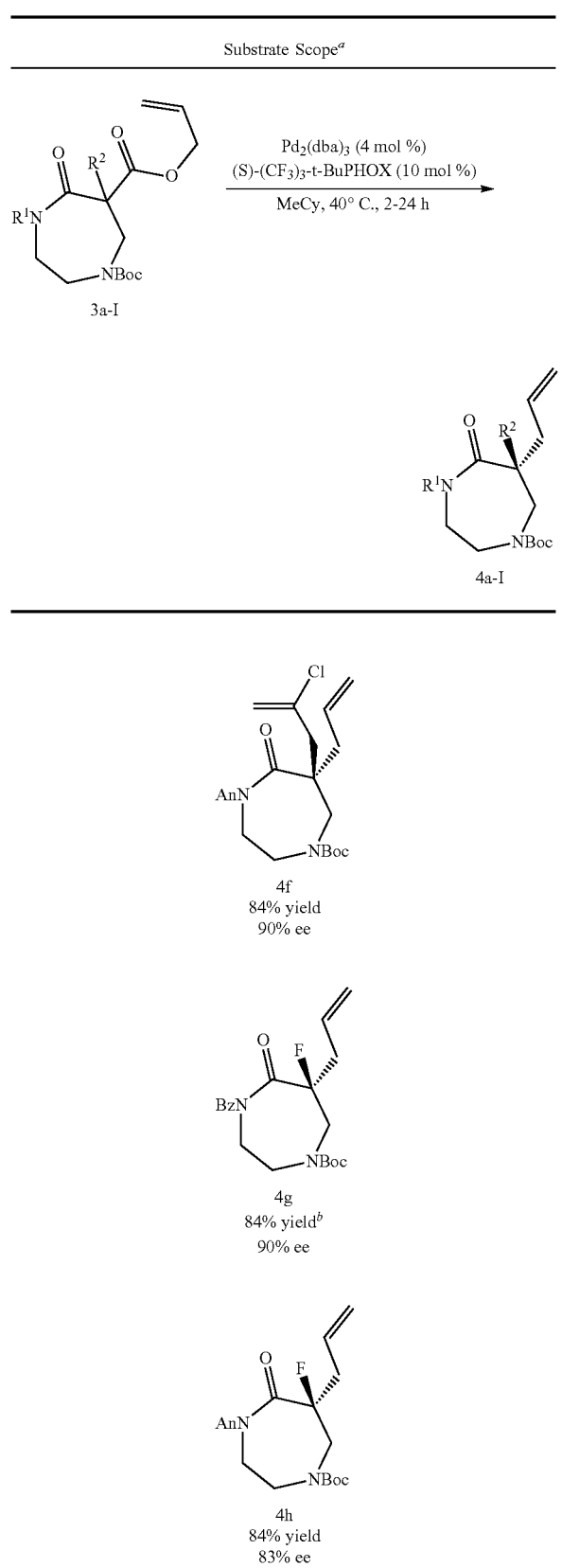
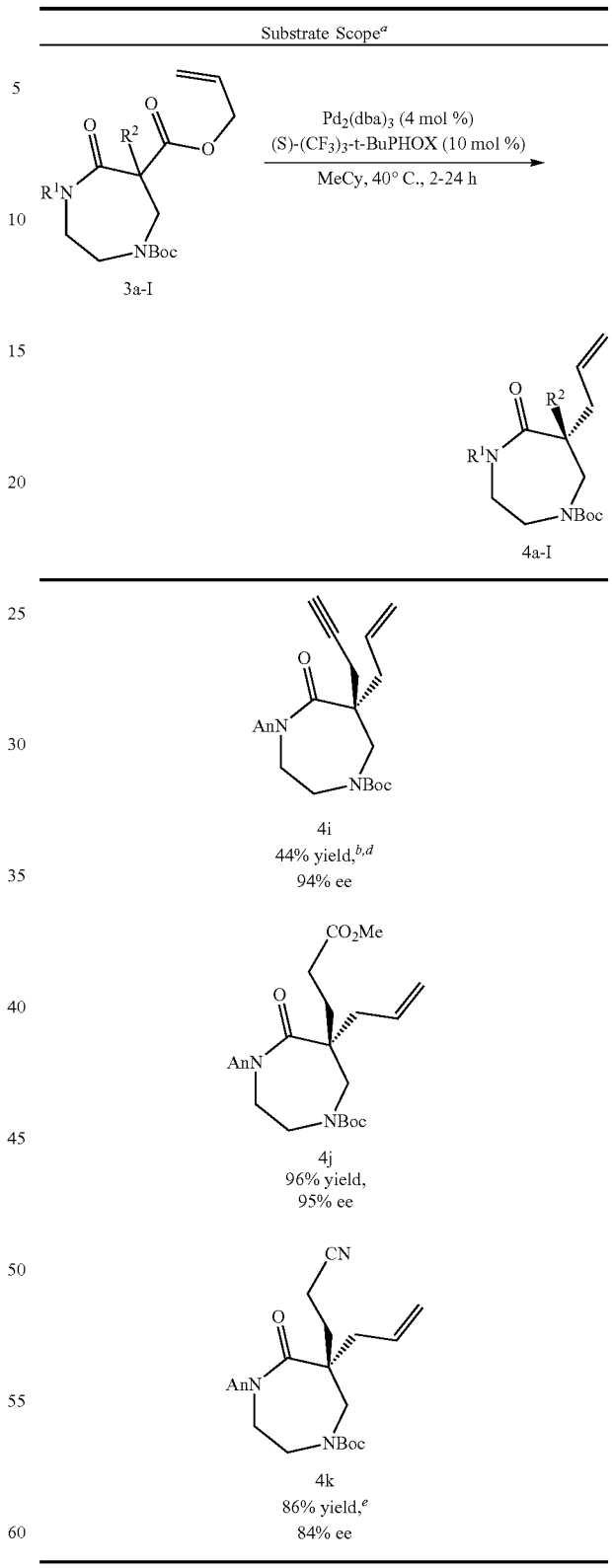
[a]Reactions were performed on a 0.1 mmol scale at a 0.014 M concentration. An = p-anisoyl.
[b]Pd$_2$(pmdba)$_3$ was used instead of Pd$_2$(dba)$_3$.
[c]On a 1 mmol scale: 82% yield, 83% ee.
[d]Conducted at 50° C. for 17 h.
[e]Performed in 9:1 MeCy/toluene to improve substrate solubility.

Example 38: Synthesis of a Suvorexant Analogue

Diazepanone 4a was subjected to selective debenzoylation under basic conditions, followed by reduction with LiAlH$_4$ to yield diazepane 5 bearing a free secondary amine. Then, nucleophilic aromatic substitution of aryl bromide 6 with 5 [Mangion, I. K.; Sherry, B. D.; Yin, J.; Fleitz, F. J. Enantioselective Synthesis of a Dual Orexin Receptor Antagonist. *Org. Lett.* 2012, 14, 3458-3461], followed by Boc deprotection, with in situ generated HCl, furnished secondary amine 7. A final coupling with the benzoyl chloride derived from carboxylic acid 8 [Mangion, I. K.; Sherry, B. D.; Yin, J.; Fleitz, F. J. Enantioselective Synthesis of a Dual Orexin Receptor Antagonist. *Org. Lett.* 2012, 14, 3458-3461] in the same pot provided target compound 9, an analogue of the drug suvorexant bearing an all-carbon quaternary stereocenter.

Scheme 5 Synthesis of a Suvorexant Analogue

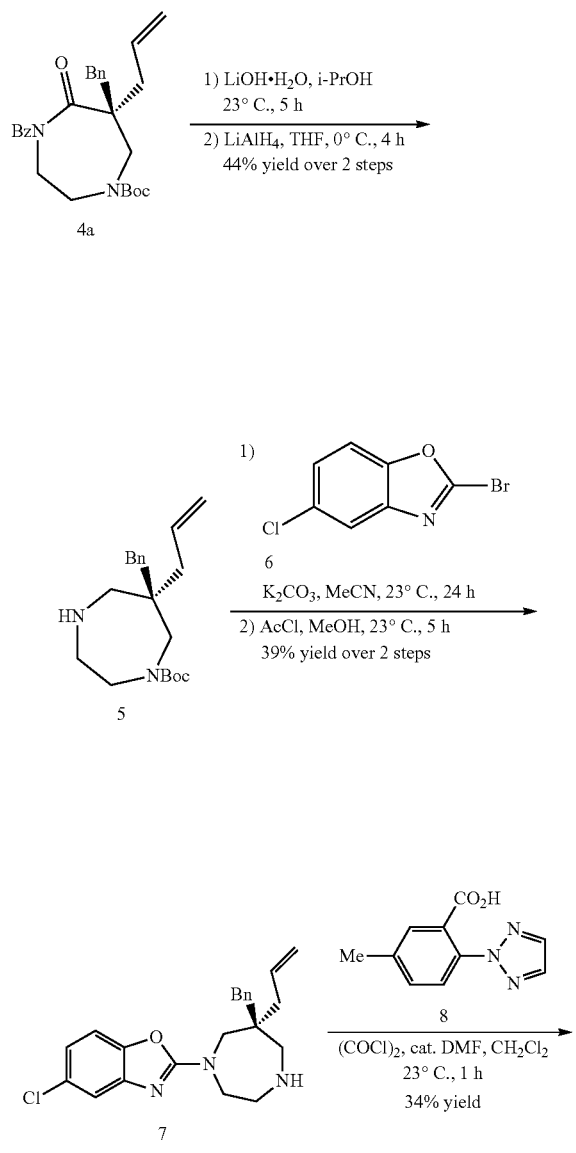

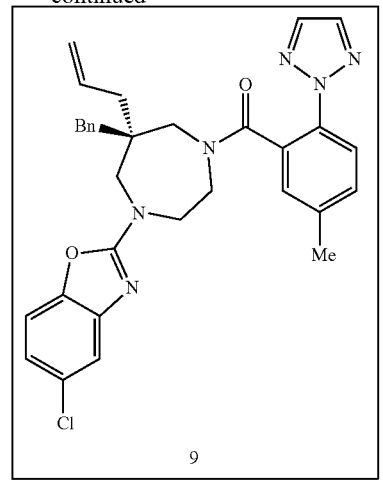

VIII. Experimental Procedures

General Information

Unless otherwise stated, reactions were performed in flame-dried glassware under an argon or nitrogen atmosphere using dry, deoxygenated solvents. Solvents were dried by passage through an activated alumina column under argon. Reaction progress was monitored by thin-layer chromatography (TLC) or Agilent 1290 UHPLC-MS. TLC was performed using E. Merck silica gel 60 F254 precoated glass plates (0.25 mm) and visualized by UV fluorescence quenching or KMnO$_4$ staining. Silicycle SiliaFlash® P60 Academic Silica gel (particle size 40-63 nm) was used for flash chromatography. $^1$H NMR spectra were recorded on Varian Inova 500 MHz, Varian 400 MHz, and Bruker 400 MHz spectrometers and are reported relative to residual CHCl$_3$ ($\delta$ 7.26 ppm). $^{13}$C NMR spectra were recorded on a Varian Inova 500 MHz spectrometer (125 MHz), a Varian 400 MHz spectrometer (100 MHz), and Bruker 400 MHz spectrometers (100 MHz) and are reported relative to CHCl$_3$ ($\delta$ 77.16 ppm). Data for $^1$H NMR are reported as follows: chemical shift ($\delta$ ppm) (multiplicity, coupling constant (Hz), integration). Multiplicities are reported as follows: s=singlet, d=doublet, t=triplet, q=quartet, p=pentet, sept=septuplet, m=multiplet, br s=broad singlet, br d=broad doublet. Data for $^{13}$C NMR are reported in terms of chemical shifts ($\delta$ ppm) Some reported spectra include minor solvent impurities of water ($\delta$ 1.56 ppm), ethyl acetate ($\delta$ 4.12, 2.05, 1.26 ppm), methylene chloride ($\delta$ 5.30 ppm), acetone ($\delta$ 2.17 ppm), grease ($\delta$ 1.26, 0.86 ppm), and/or silicon grease ($\delta$ 0.07 ppm), which do not impact product assignments. Most NMR spectra are complicated by rotational isomerism about amide bonds. This behavior is illustrated by variable-temperature NMR spectra of compound 4e in DMSO (p. S102). IR spectra were obtained by use of a Perkin Elmer Spectrum BXII spectrometer or Nicolet 6700 FTIR spectrometer using thin films deposited on NaCl plates and reported in frequency of absorption (cm$^{-1}$). Optical rotations were measured with a Jasco P-2000 polarimeter operating on the sodium D-line (589 nm), using a 100 mm path-length cell. Analytical SFC was performed with a Mettler SFC supercritical CO$_2$ analytical chromatography system utilizing Chiralpak (AD-H, AS-H or IC) or Chiralcel (OD-H, OJ-H, or OB-H) columns (4.6 mm×25 cm) obtained from Daicel Chemical Industries, Ltd. High resolution mass spectra (HRMS) were obtained from Agilent 6200 Series TOF with an Agilent G1978A Multimode source in electrospray ionization (ESI+), atmospheric pressure chemical ionization (APCI+), or mixed ionization mode (MM: ESI-APCI+). Absolute stereochemistry is assigned by analogy to previous results by our group. [*J. Am. Chem. Soc.* 2004, 126, 15044-15045; *Angew. Chem. Int. Ed.* 2005, 44, 6924-6927; *Angew. Chem. Int. Ed.* 2008, 47, 6873-6876; *Nat. Chem.* 2010, 2, 192-196; *Nat. Chem.* 2012, 4, 130-133; *Angew. Chem. Mt. Ed.* 2013, 52, 6718-6721.]

Reagents were purchased from commercial sources and used as received unless otherwise stated. Ligands (S)—($CF_3$)$_3$-t-BuPHOX and (S)-Ty-PHOX were prepared according to literature procedures. [*Tetrahedron Lett.* 2010, 51, 5550-5554; *Chem. Sci.* 2019, 10, 5996-6000]

List of Abbreviations: ee—enantiomeric excess, SFC—supercritical fluid chromatography, TLC—thin-layer chromatography, IPA—isopropanol, An=4-anisoyl, MeCy=methylcyclohexane Example 39: General Procedure for Pd-Catalyzed Allylic Alkylation Reactions

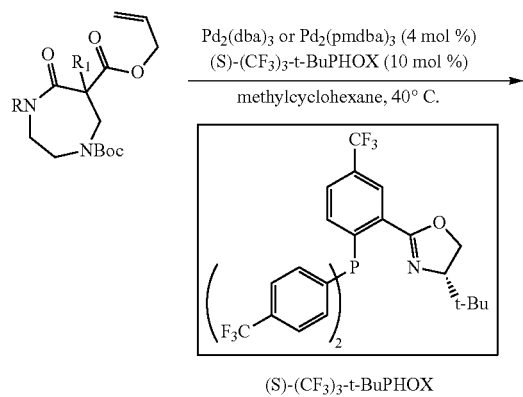

In a $N_2$ filled glovebox, $Pd_2$(dba)$_3$ (4 mol %) or $Pd_2$(pmdba)$_3$ (4 mol %) and (S)—($CF_3$)$_3$-t-BuPHOX (10 mol %) were suspended in methylcyclohexane (2 mL) in a 20 mL glass vial. After stirring for 20 minutes at 25° C., the appropriate diazepanone (1.0 equiv) and methylcyclohexane (5.2 mL, total substrate concentration 0.014 M) were added to the pre-stirred catalyst solution. The vial was then sealed and heated to 40° C. After full consumption of starting material, as monitored by TLC, the reaction mixture was exposed to air. The crude reaction mixture was loaded directly onto a flash column and the product was isolated by silica gel flash chromatography.

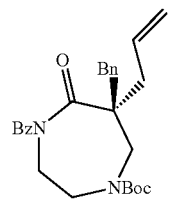

tert-butyl (S)-6-allyl-4-benzoyl-6-benzyl-5-oxo-1,4-diazepane-1-carboxylate (4a). Prepared according to the general procedure with allyl ester 3a (51.2 mg, 0.104 mmol, 1.0 equiv), $Pd_2$(pmdba)$_3$ (4.4 mg, 0.004 mmol, 4 mol %), and (S)—($CF_3$)$_3$-t-BuPHOX (5.9 mg, 0.01 mmol, 10 mol %). Purified by silica gel flash chromatography (15% EtOAc/hexanes) to provide benzyl diazepanone 4a as a colorless oil (43.4 mg, 0.0967 mmol, 93% yield, 90% ee); $^1$H NMR (400 MHz, CDCl$_3$) δ 7.56-7.40 (m, 3H), 7.40-7.32 (m, 2H), 7.32-7.19 (m, 3H), 7.19-7.00 (m, 2H), 5.88 (br s, 1H), 5.26-5.07 (m, 2H), 4.26-4.03 (m, 1H), 3.94 (d, J=15.4 Hz, 1H), 3.73 (d, J=42.2 Hz, 1H), 3.54 (d, J=15.3 Hz, 1H), 3.40 (s, 2H), 3.09 (dd, J=61.0, 13.7 Hz, 1H), 2.94-2.34 (m, 3H), 1.48 (s, 9H); $^{13}$C NMR (100 MHz, CDCl$_3$) δ 179.2, 174.8, 156.0, 155.4, 136.6, 136.4, 133.0, 131.5, 130.8, 128.6, 128.4, 127.8, 127.1, 120.0, 119.7, 80.8, 54.3, 53.9, 49.1, 47.4, 46.9, 42.5, 42.0, 41.5, 40.3, 28.5; IR (Neat Film, NaCl) 3062, 2975, 2928, 1693, 1682, 1601, 1452, 1415, 1392, 1365, 1322, 1283, 1246, 1156, 1044, 978, 917, 865, 728, 697 cm$^{-1}$; HRMS (MM: ESI-APCI): m/z calc'd for $C_{27}H_{33}N_2O_4$ [M+H]$^+$: 449.2435, found 449.2429; [α]$_D^{22.4}$+14.19 (c 0.66, CHCl$_3$); SFC conditions: 20% IPA, 2.5 mL/min, Chiralpak AD-H column, λ=210 nm, t$_R$ (min): major=3.51, minor=2.71.

tert-butyl (R)-6-allyl-4-benzoyl-6-methyl-5-oxo-1,4-diazepane-1-carboxylate (4b). Prepared according to the general procedure with allyl ester 3b (39.0 mg, 0.0937 mmol, 1.0 equiv), $Pd_2$(pmdba)$_3$ (4.4 mg, 0.004 mmol, 4 mol %), and (S)—($CF_3$)$_3$-t-BuPHOX (5.9 mg, 0.01 mmol, 10 mol %). Purified by silica gel flash chromatography (20% EtOAc/hexanes) to provide methyl diazepanone 4b as a colorless, waxy solid (32.3 mg, 0.868 mmol, 93% yield, 90% ee); $^1$H NMR (400 MHz, CDCl$_3$) δ 7.54-7.43 (m, 3H), 7.43-7.32 (m, 2H), 5.74 (ddt, J=17.1, 9.9, 7.4 Hz, 1H), 5.19-5.06 (m, 2H), 4.30-3.89 (m, 3H), 3.85-3.69 (m, 1H), 3.66-3.34 (m, 2H), 2.63-2.20 (m, 2H), 1.50 (s, 9H), 1.30 (s, 3H); $^{13}$C NMR (100 MHz, CDCl$_3$) δ 180.8, 174.5, 155.4, 155.0, 136.3, 132.9, 131.4, 128.3, 127.5, 119.5, 80.7, 50.9, 49.9, 47.2, 46.5, 42.5, 42.1, 41.8, 28.4, 23.5, 23.1; IR (Neat Film, NaCl) 2976, 2933, 1694, 1450, 1418, 1392, 1366, 1323, 1284, 1246, 1146, 1057, 983, 917, 868, 768, 729, 696 cm$^{-1}$; HRMS (MM: ESI-APCI): m/z calc'd for $C_{21}H_{29}N_2O_4$ [M+H]$^+$: 373.2122, found 373.2117; [α]$_D^{22.31}$-12.69 (c 1.0, CHCl$_3$); SFC Conditions: 20% IPA, 2.5 mL/min, Chiralpak IC column, λ=210 nm, t$_R$ (min): minor=4.31, major=5.68.

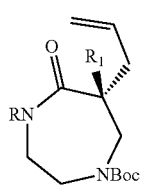

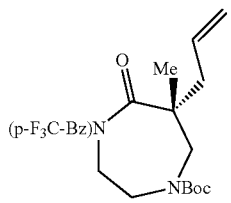

tert-butyl (R)-6-allyl-6-methyl-5-oxo-4-(4-(trifluoromethyl)benzoyl)-1,4-diazepane-1-carboxylate (4c). Prepared according to the general procedure with allyl ester 3c (55.3 mg, 0.114 mmol, 1.0 equiv), Pd$_2$(dba)$_3$ (4.2 mg, 4.57 μmol, 4 mol %), and (S)—(CF$_3$)$_3$-t-BuPHOX (6.7 mg, 0.011 mmol, 10 mol %). Purified by silica gel flash chromatography (20% EtOAc/hexanes) to provide methyl diazepanone 4c as a colorless oil (45.1 mg, 0.102 mmol, 90% yield, 92% ee); $^1$H NMR (400 MHz, CDCl$_3$) δ 7.64 (d, J=8.2 Hz, 2H), 7.55 (d, J=8.2 Hz, 2H), 5.71 (ddt, J=17.2, 10.1, 7.4 Hz, 1H), 5.23-5.07 (m, 2H), 4.21-4.03 (m, 2H), 4.02-3.64 (m, 2H), 3.58-3.38 (m, 2H), 2.59-2.21 (m, 2H), 1.49 (s, 9H), 1.29 (s, 3H); $^{13}$C NMR (100 MHz, CDCl$_3$) δ 181.0, 180.8, 173.1, 155.4, 155.1 140.0, 132.8 (q, J$_{C-F}$=32.9 Hz), 132.7, 127.6, 125.5 (q, J$_{C-F}$=3.7 Hz), 123.7 (q, J$_{C-F}$=272.5 Hz), 119.9, 81.0, 50.9, 50.0, 47.2, 46.4, 42.4, 42.0, 41.8, 28.5, 23.6, 23.3; IR (Neat Film, NaCl) 3366, 3077, 2978, 2934, 1694, 1452, 1410, 1394, 1367, 1326, 1248, 1167, 1147, 1066, 1014, 984, 925, 852, 764 cm$^{-1}$; HRMS (MM: ESI-APCI): m/z calc'd for C$_{22}$H$_{31}$F$_3$N$_3$O$_4$ [M+NH$_4$]$^+$: 458.2261, found 458.2250; [α]$_D^{22.6}$−12.32 (c 1.0, CHCl$_3$); SFC Conditions: 5% IPA, 2.5 mL/min, Chiralpak AD-H column, λ=210 nm, t$_R$ (min): minor=4.49, major=5.86.

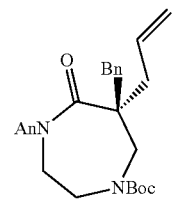

tert-butyl (S)-6-allyl-6-benzyl-4-(4-methoxybenzoyl)-5-oxo-1,4-diazepane-1-carboxylate (4e). Prepared according to the general procedure with allyl ester 3e (52.3 mg, 0.100 mmol, 1.0 equiv), Pd$_2$(dba)$_3$ (3.7 mg, 0.004 mmol, 4 mol %), and (S)—(CF$_3$)$_3$-t-BuPHOX (5.9 mg, 0.01 mmol, 10 mol %). Purified by silica gel flash chromatography (20% EtOAc/hexanes) to provide benzyl diazepanone 4e as a colorless oil (48.1 mg, 0.100 mmol, >99% yield, 89% ee); $^1$H NMR (400 MHz, CDCl$_3$) δ 7.51-7.44 (m, 2H), 7.32-7.20 (m, 3H), 7.18-7.09 (m, 2H), 6.87-6.81 (m, 2H), 5.93 (br s, 1H), 5.26-5.12 (m, 2H), 4.09-3.88 (m, 2H), 3.84 (s, 3H), 3.78-2.41 (m, 8H), 1.48 (s, 9H); $^{13}$C NMR (100 MHz, CDCl$_3$) δ 179.0, 174.6, 162.6, 156.0, 155.4, 136.7, 133.1, 130.8, 130.5, 128.5, 128.2, 127.0, 119.9, 119.6, 113.7, 80.9, 80.7, 55.5, 54.2, 53.8, 49.1, 47.5, 47.3, 42.4, 42.0, 41.2, 40.9, 40.0, 28.5; IR (Neat Film, NaCl) 3374, 2974, 2927, 1694, 1604, 1581, 1510, 1454, 1416, 1392, 1365, 1320, 1282, 1256, 1211, 1166, 1028, 979, 925, 838, 762, 742, 705, 678, 636, 610 cm$^{-1}$; HRMS (MM: ESI-APCI): m/z calc'd for C$_{28}$H$_{35}$N$_2$O$_5$ [M+H]$^+$: 479.2540, found 479.2533; [α]$_D^{22.81}$+19.02 (c 1.0, CHCl$_3$); SFC Conditions: 20% IPA, 2.5 mL/min, Chiralpak AD-H column, λ=210 nm, t$_R$ (min): minor=3.94, major=6.20.

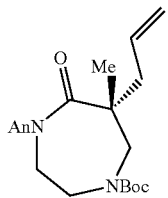

tert-butyl (R)-6-allyl-4-(4-methoxybenzoyl)-6-methyl-5-oxo-1,4-diazepane-1-carboxylate (4d). Prepared according to the general procedure with allyl ester 3d (45.8 mg, 0.103 mmol, 1.0 equiv), Pd$_2$(dba)$_3$ (3.7 mg, 0.004 mmol, 4 mol %), and (S)—(CF$_3$)$_3$-t-BuPHOX (5.9 mg, 0.01 mmol, 10 mol %). Purified by silica gel flash chromatography (20% EtOAc/hexanes) to provide methyl diazepanone 4d as a colorless oil (38.9 mg, 0.0966 mmol, 94% yield, 94% ee); $^1$H NMR (400 MHz, CDCl$_3$) δ 7.62-7.44 (m, 2H), 6.95-6.75 (m, 2H), 5.76 (m, 1H), 5.26-4.99 (m, 2H), 4.24-3.87 (m, 3H), 3.83 (s, 3H), 3.75 (m, 1H), 3.59-3.37 (m, 2H), 2.60-2.25 (m, 2H), 1.49 (s, 9H), 1.31 (s, 3H); $^{13}$C NMR (100 MHz, CDCl$_3$) δ 180.7, 180.6, 174.3, 162.5, 155.4, 155.0, 133.0, 130.1, 128.1, 119.4, 113.6, 80.7, 55.4, 50.8, 49.8, 47.4, 46.6, 42.7, 42.4, 28.4, 23.5, 23.1; IR (Neat Film, NaCl) 3352, 3076, 2975, 2932, 2841, 2568, 1690, 1605, 1579, 1542, 1511, 1458, 1420, 1392, 1366, 1322, 1284, 1256, 1214, 1168, 1146, 1056, 1032, 984, 924, 868, 842, 807, 762, 743, 736, 650, 633, 621, 608 cm$^{-1}$; HRMS (MM: ESI-APCI): m/z calc'd for C$_{22}$H$_{31}$N$_2$O$_5$ [M+H]$^+$: 403.2227, found 403.2225; [α]$_D^{22.45}$−40.51 (c 1.0, CHCl$_3$); SFC Conditions: 20% MeOH, 2.5 mL/min, Chiralpak IC column, λ=210 nm, t$_R$ (min): minor=5.11, major=5.66.

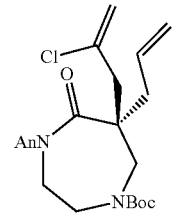

tert-butyl (S)-6-allyl-6-(2-chloroallyl)-4-(4-methoxybenzoyl)-5-oxo-1,4-diazepane-1-carboxylate (4f). Prepared according to the general procedure with allyl ester 3f (48.1 mg, 0.0949 mmol, 1.0 equiv), Pd$_2$(dba)$_3$ (3.7 mg, 0.004 mmol, 4 mol %), and (S)—(CF$_3$)$_3$-t-BuPHOX (5.9 mg, 0.01 mmol, 10 mol %). Purified by silica gel flash chromatography (20% EtOAc/hexanes) to provide alkenyl chloride 4f as a colorless oil (36.7 mg, 0.0793 mmol, 84% yield, 90% ee); $^1$H NMR (400 MHz, CDCl$_3$) δ 7.55 (d, J=8.8 Hz, 2H), 6.87 (d, J=8.8 Hz, 2H), 5.93-5.71 (m, 1H), 5.36-5.07 (m, 4H), 4.36-3.84 (m, 4H), 3.83 (s, 3H), 3.82-3.51 (m, 2H), 3.00-2.33 (m, 4H), 1.50 (s, 9H); $^{13}$C NMR (100 MHz, CDCl$_3$) δ 178.2, 174.6, 162.7, 155.8, 155.2, 137.5, 132.9, 130.5, 128.3, 120.1, 118.2, 113.7, 81.1, 80.9, 55.5, 52.6, 49.2, 47.7, 47.4, 47.0, 44.5, 43.8, 42.8, 42.0, 41.8, 40.3, 28.5; IR (Neat Film, NaCl) 2976, 2930, 1694, 1631, 1604, 1580, 1510, 1456, 1421, 1393, 1366, 1320, 1282, 1256, 1212, 1167, 1150, 1030, 980, 928, 840, 765, 682, 636, 610 cm$^{-1}$; HRMS (MM: ESI-APCI): m/z calc'd for C$_{24}$H$_{32}$ClN$_2$O$_5$ [M+H]$^+$: 463.1994, found 463.2005; [α]$_D^{22.68}$−24.10 (c 0.5, CHCl$_3$); SFC Conditions: 20% IPA, 2.5 ml/min, Chiralpak AD-H column, λ=210 nm, t$_R$ (min): minor=2.52, major=2.77.

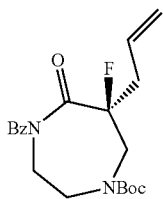

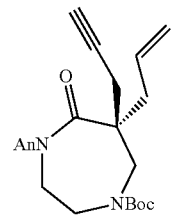

tert-butyl (S)-6-allyl-4-benzoyl-6-fluoro-5-oxo-1,4-diazepane-1-carboxylate (4g). Prepared according to the general procedure with allyl ester 3g (43.2 mg, 0.103 mmol, 1.0 equiv), Pd$_2$(pmdba)$_3$ (4.4 mg, 0.004 mmol, 4 mol %), and (S)—(CF$_3$)$_3$-t-BuPHOX (5.9 mg, 0.01 mmol, 10 mol %). Purified by silica gel flash chromatography (20% EtOAc/hexanes) to provide alkyl fluoride 4g as a white, amorphous solid (32.6 mg, 0.0866 mmol, 84% yield, 90% ee); $^1$H NMR (400 MHz, CDCl$_3$) δ 7.61-7.53 (m, 2H), 7.53-7.45 (m, 1H), 7.45-7.34 (m, 2H), 5.94-5.72 (m, 1H), 5.34-5.17 (m, 2H), 4.58-4.38 (m, 1H), 4.26-4.02 (m, 2H), 3.99-3.74 (m, 1H), 3.39-3.10 (m, 2H), 2.96-2.74 (m, 1H), 2.73-2.43 (m, 1H), 1.47 (s, 9H); $^{13}$C NMR (100 MHz, CDCl$_3$) δ 173.9, 173.9 (d, $J_{C-F}$=26.3 Hz), 155.1, 135.2, 132.1, 130.3, 128.4, 128.2, 121.0, 97.7 (dd, $J_{C-F}$=193.9, 47.2 Hz), 81.1, 49.8 (dd, $J_{C-F}$=35.3, 23.1 Hz), 47.2, 46.6, 42.6, 39.7 (dd, $J_{C-F}$=27.6, 21.9 Hz), 28.3; IR (Neat Film, NaCl) 2978, 2926, 1694, 1450, 1414, 1393, 1367, 1329, 1246, 1152, 1042, 999, 979, 926, 857, 766, 724, 694, 672, 648 cm$^{-1}$; HRMS (MM: ESI-APCI): m/z calc'd for C$_{20}$H$_{29}$FN$_3$O$_4$ [M+NH$_4$]$^+$: 438.2035, found 438.2040; [α]$_D^{22.5}$+28.89 (c 1.0, CHCl$_3$); SFC Conditions: 10% IPA, 2.5 mL/min, Chiralcel OD-H column, A, =210 nm, t$_R$ (min): minor=6.26, major=4.99.

tert-butyl (S)-6-allyl-4-(4-methoxybenzoyl)-5-oxo-6-(prop-2-yn-1-yl)-1,4-diazepane-1-carboxylate (4i). Prepared according to the general procedure with allyl ester 3i (70.0 mg, 0.149 mmol, 1.0 equiv), Pd$_2$(pmdba)$_3$ (5.4 mg, 4.9 μmol, 4 mol %), and (S)—(CF$_3$)$_3$-t-BuPHOX (8.8 mg, 0.015 mmol, 10 mol %) at 50° C. Purification by automated silica gel flash chromatography (Teledyne ISCO, 0→40% acetone/hexanes) provided alkyne 4i as a colorless oil (28.0 mg, 0.0656 mmol, 44% yield, 94% ee); $^1$H NMR (400 MHz, CDCl$_3$) δ 7.59 (d, J=8.2 Hz, 2H), 6.89-6.82 (m, 2H), 5.93-5.63 (m, 1H), 5.30-5.10 (m, 2H), 4.36-4.15 (m, 1H), 4.09-3.68 (m, 4H), 3.83 (s, 3H), 3.62-3.37 (m, 1H), 2.83-2.43 (m, 4H), 2.20-1.99 (m, 1H), 1.51 (s, 9H); $^{13}$C NMR (100 MHz, CDCl$_3$) δ 177.5, 174.6, 162.9, 155.6, 155.2, 132.1, 130.7, 127.9, 120.0, 113.7, 81.1, 80.9, 80.5, 72.1, 55.6, 52.7, 49.1, 46.9, 47.7, 43.0, 42.3, 39.1, 37.5, 28.5, 26.5, 25.9; IR (Neat Film, NaCl) 3283, 2972, 2922, 1692, 1603, 1511, 1454, 1418, 1365, 1322, 1255, 1169, 1031, 980, 926, 839, 766, 670 cm$^{-1}$; HRMS (MM: ESI-APCI): m/z calc'd for C$_{24}$H$_{31}$N$_2$O$_5$ [M+H]$^+$: 427.2227, found 427.2238; [α]$_D^{22.1}$−7.69 (c 1.0, CHCl$_3$); SFC conditions: 10% IPA, 2.5 ml/min, Chiralpak AD-H column, λ=210 nm, t$_R$ (min): major=10.85, minor=10.29.

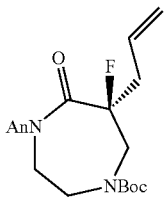

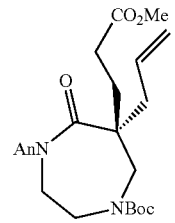

tert-butyl (S)-6-allyl-6-fluoro-4-(4-methoxybenzoyl)-5-oxo-1,4-diazepane-1-carboxylate (4h). Prepared according to the general procedure with allyl ester 3h (60 mg, 0.133 mmol, 1.0 equiv), Pd$_2$(dba)$_3$ (4.9 mg, 0.0053 mmol, 4 mol %), and (S)—(CF$_3$)$_3$-t-BuPHOX (7.9 mg, 0.013 mmol, 10 mol %). Purified by automated silica gel flash chromatography (0→50% acetone/hexanes) to provide alkyl fluoride 4h as a colorless oil (45 mg, 0.111 mmol, 84% yield, 83% ee); $^1$H NMR (400 MHz, CDCl$_3$) δ 7.61-7.53 (m, 2H), 6.92-6.84 (m, 2H), 5.93-5.78 (m, 1H), 5.30-5.21 (m, 2H), 4.35 (t, J=16.0 Hz, 1H), 4.22-4.02 (m, 2H), 3.96-3.85 (m, 1H), 3.84 (s, 3H), 3.40-3.19 (m, 2H), 2.94-2.78 (m, 1H), 2.71-2.48 (m, 1H), 1.47 (s, 9H); $^{13}$C NMR (100 MHz, CDCl$_3$) δ 173.9, 173.7, 163.1, 155.3, 131.0, 130.6, 127.1, 121.0, 113.8, 97.8 (dd, $J_{C-F}$=193.7, 52.5 Hz), 81.2, 55.5, 49.8 (dd, $J_{C-F}$=33.5, 23.3 Hz), 47.5, 46.9, 43.2, 39.8 (dd, $J_{C-F}$=32.1, 21.8 Hz), 28.3; IR (Neat Film, NaCl) 2977, 2932, 1696, 1603, 1578, 1511, 1448, 1413, 1366, 1327, 1256, 1169, 1152, 1029, 1000, 977, 923, 835, 766 cm$^{-1}$; HRMS (MM: ESI-APCI): m/z calc'd for C$_{21}$H$_{28}$FN$_2$O$_5$ [M+H]$^+$: 407.1977, found 407.1973; [α]$_D^{22.5}$+46.99 (c 1.7, CHCl$_3$); SFC conditions: 20% IPA, 2.5 mL/min, Chiralcel OD-H column, λ=210 nm, t$_R$ (min): major=2.69, minor=3.25.

tert-butyl (R)-6-allyl-6-(3-methoxy-3-oxopropyl)-4-(4-methoxybenzoyl)-5-oxo-1,4-diazepane-1-carboxylate (4j). Prepared according to the general procedure with allyl ester 3j (51.9 mg, 0.100 mmol, 1.0 equiv), Pd$_2$(dba)$_3$ (3.7 mg, 0.004 mmol, 4 mol %), and (S)—(CF$_3$)$_3$-t-BuPHOX (5.9 mg, 0.01 mmol, 10 mol %). Purified by silica gel flash chromatography (33% EtOAc/hexanes) to provide methyl ester 4j as a white, amorphous solid (45.8 mg, 0.0965 mmol, 96% yield, 95% ee); $^1$H NMR (400 MHz, CDCl$_3$) δ 7.57-7.48 (m, 2H), 6.92-6.83 (m, 2H), 5.80-5.64 (m, 1H), 5.22-5.09 (m, 2H), 4.21 (ddd, J=15.7, 6.6, 2.1 Hz, 1H), 4.13-3.85 (m, 3H), 3.83 (s, 3H), 3.62 (s, 3H), 3.51 (d, J=15.2 Hz, 1H), 3.42-3.29 (m. 1H), 2.64-2.20 (m, 4H), 2.20-1.86 (m, 2H), 1.49 (s, 9H); $^{13}$C NMR (100 MHz, CDCl$_3$) δ 179.2, 174.7, 173.6, 173.4, 162.7, 155.4, 155.0, 132.7, 132.5, 130.3, 128.3, 120.0, 113.8, 81.1, 80.9, 55.5, 51.8, 50.1, 48.9, 47.6, 46.8, 43.2, 42.9, 40.3, 39.7, 29.3, 28.8, 28.5; IR (Neat Film, NaCl) 2975, 2360, 1736, 1694, 1605, 1580, 1510, 1426, 1393, 1366, 1321, 1283, 1254, 1167, 1031, 980, 927, 842, 811, 762, 647, 610 cm$^{-1}$; HRMS (MM: ESI-APCI): m/z calc'd for C$_{25}$H$_{35}$N$_2$O$_7$ [M+H]$^+$: 475.2439, found 475.2438;

[α]$_D^{22.52}$+7.73 (c 1.0, CHCl$_3$); SFC conditions: 15% IPA, 2.5 mL/min, Chiralcel OD-H column, λ=210 nm, t$_R$ (min): major=5.27, minor=4.84.

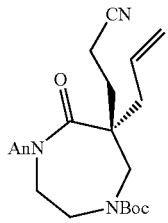

tert-butyl (R)-6-allyl-6-(2-cyanoethyl)-4-(4-methoxybenzoyl)-5-oxo-1,4-diazepane-1-carboxylate (4k). Prepared according to the general procedure with allyl ester 3k (62.2 mg, 0.128 mmol, 1.0 equiv), Pd$_2$(dba)$_3$ (4.7 mg, 0.00512 mmol, 4 mol %), and (S)—(CF$_3$)$_3$-t-BuPHOX (7.6 mg, 0.0128 mmol, 10 mol %), using 9:1 methylcyclohexane-toluene as the reaction solvent. Purified by silica gel flash chromatography (33% EtOAc/hexanes) to provide nitrile 4j as a white, amorphous solid (48.6 mg, 0.110 mmol, 86% yield, 84% ee); $^1$H NMR (400 MHz, CDCl$_3$) δ 7.59-7.47 (m, 2H), 6.96-6.85 (m, 2H), 5.82-5.64 (m, 1H), 5.30-5.11 (m, 2H), 4.09-3.93 (m, 2H), 3.93-3.72 (m, 2H), 3.85 (s, 3H), 3.70-3.38 (m, 2H), 2.60-2.25 (m, 4H), 2.22-1.93 (m, 2H), 1.50 (s, 9H); $^{13}$C NMR (100 MHz, CDCl$_3$) δ 178.0, 174.5, 163.0, 155.6, 154.9, 131.7, 130.3, 127.9, 120.7, 119.7, 113.9, 81.4, 55.6, 52.2, 49.6, 48.0, 47.4, 46.8, 43.0, 42.6, 39.9, 39.0, 32.1, 31.5, 28.4, 12.4; IR (Neat Film, NaCl) 2975, 2931, 2361, 2246, 1690, 1604, 1579, 1510, 1456, 1419, 1366, 1321, 1256, 1168, 1148, 1031, 980, 926, 840, 811, 766, 607 cm$^{-1}$; HRMS (MM: ESI-APCI): m/z calc'd for C$_{24}$H$_{35}$N$_4$O$_5$ [M+NH$_4$]$^+$: 459.2602, found 459.2602; [α]$_D^{22.4}$+9.31 (c 0.5, CHCl$_3$); SFC conditions: 20% IPA, 2.5 mL/min, Chiralcel OD-H column, λ=310 nm, t$_R$ (min): major=8.33, minor=6.18.

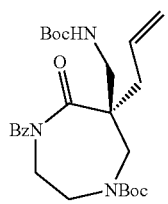

tert-butyl (S)-6-allyl-4-benzoyl-6-(((tert-butoxycarbonyl)amino)methyl)-5-oxo-1,4-diazepane-1-carboxylate (4l). Prepared according to the general procedure with allyl ester 3l (53 mg, 0.0997 mmol, 1.0 equiv) and Pd$_2$(dba)$_3$. Purification by automated silica gel flash chromatography (0→50% EtOAc/hexanes) provided carbamate 4l as a white foam (37 mg, 0.0759 mmol, 76% yield, 93% ee). $^1$H NMR (400 MHz, CDCl$_3$) δ 7.55-7.44 (m, 3H), 7.44-7.35 (m, 2H), 5.74 (ddt, J=15.7, 10.5, 7.4 Hz, 1H), 5.35 (br s, 0.5H), 5.21-5.06 (m, 2H), 4.79 (br s, 0.5H), 4.48-4.28 (m, 1H), 4.14-3.09 (m, 7H), 2.69-2.18 (m, 2H), 1.50 (s, 9H), 1.44 (s, 9H); $^{13}$C NMR (100 MHz, CDCl$_3$) δ 179.3, 178.8, 174.5, 156.3, 155.9, 155.1, 136.3, 132.5, 132.1, 131.7, 128.5, 127.7, 120.1, 81.3, 81.1, 79.5, 54.8, 48.9, 47.3, 46.8, 46.3, 42.6, 41.1, 38.7, 37.1, 28.5, 28.5; IR (Neat Film, NaCl) 2977, 1687, 1502, 1422, 1391, 1365, 1322, 1282, 1245, 1168, 978, 916, 753 cm$^{-1}$; HRMS (MM: ESI-APCI): calc'd for C$_{26}$H$_{37}$N$_3$O$_6$ [M+H]$^+$: 488.2755, found 488.2747; [α]$_D^{23.2}$–3.70 (c 1.85, CHCl$_3$); SFC conditions: 20% IPA, 2.5 mL/min, Chiralpak IC column, =254 nm, t$_R$ (min): major=5.85, minor=4.65.

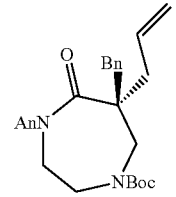

Example 40: Procedure for the Large Scale Preparation of Diazepanone 4e

To a 500 mL Schlenk flask was added Pd$_2$(dba)$_3$ (37 mg, 0.04 mmol, 4 mol %), (S)—(CF$_3$)$_3$-t-BuPHOX (59 mg, 0.1 mmol, 10 mol %), and MeCy (20 mL). After stirring for 20 minutes at 25° C., allyl ester 3e (523 mg, 1.0 mmol, 1.0 equiv) and methylcyclohexane (52 mL, total substrate concentration 0.014 M) were added to the pre-stirred catalyst solution. After stirring for 23 h at 40° C., the reaction mixture was directly loaded onto a flash column and purified by silica gel flash chromatography (20% EtOAc/hexanes) to provide benzyl diazepanone 4e as a colorless oil (393 mg, 0.82 mmol, 82% yield, 83% ee); All characterization data matched those reported above for compound 4e; [α]$_D^{21.96}$+ 14.757 (c 1.0, CHCl$_3$); SFC Conditions: 20% IPA, 2.5 ml/min, Chiralpak AD-H column, λ=210 nm, t$_R$ (min): minor=3.76, major=5.90.

Example 41: Synthesis of Allylic Alkylation Substrates

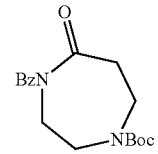

tert-butyl 4-benzoyl-5-oxo-1,4-diazepane-1-carboxylate (SI1). To a solution of tert-butyl 5-oxo-1,4-diazepane-1-carboxylate (5.00 g, 23.3 mmol, 1.0 equiv) in THF (230 mL, 0.1 M) at –78° C. was slowly added n-BuLi (2.18 M in hexanes, 12.8 mL, 27.9 mmol, 1.2 equiv). The opaque mixture was allowed to warm to ambient temperature until the solution became homogeneous, at which point it was again cooled to 78° C. Then, benzoyl chloride (3.52 mL, 30.3 mmol, 1.3 equiv) was added dropwise and the reaction turned light orange over several minutes. The reaction was stirred for 1 h at –78° C., then poured into saturated aqueous NH$_4$Cl (200 mL) and extracted with EtOAc (3×100 mL). The combined organic extracts were dried over Na$_2$SO$_4$ and concentrated. The crude product was purified by silica gel flash chromatography (20% acetone/hexanes) to afford benzoyl-protected lactam SI1 as a white solid (7.43 g, 23.3 mmol, >99% yield); $^1$H NMR (400 MHz, CDCl$_3$) δ 7.57-7.49 (m, 2H), 7.49-7.41 (m, 1H), 7.41-7.32 (m, 2H), 4.03-3.96 (m, 2H), 3.71 (m, 4H), 2.82-2.75 (m, 2H), 1.47 (s, 9H); $^{13}$C NMR (100 MHz, CDCl$_3$) δ 175.6, 173.7, 154.5, 135.9, 131.7, 128.2, 127.9, 80.7, 47.8, 47.10, 45.4, 41.6, 41.0, 40.6, 28.3; IR (Neat Film, NaCl) 2976, 2932, 2251, 1682, 1599, 1582, 1450, 1422, 1392, 1366, 1327, 1285, 1247, 1229, 1157, 1115, 1032, 1018, 976, 954, 915, 862, 793, 769, 729, 696, 647 cm$^{-1}$; HRMS (MM: ESI-APCI): nz/z calc'd for $C_{17}H_{26}N_3O_4$ [M+NH$_4$]$^+$: 336.1918, found 336.1912.

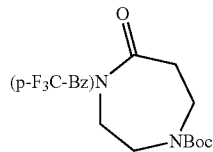

tert-butyl 5-oxo-4-(4-(trifluoromethyl)benzoyl)-1,4-diazepane-1-earboxylate (SI2). To a solution of tert-butyl 5-oxo-1,4-diazepane-1-carboxylate (500 mg, 2.33 mmol, 1 equiv) in THF (25 mL, 0.1 M) at −78° C. was slowly added n-BuLi (2.5 M in hexanes, 1.02 mL, 2.56 mmol, 1.1 equiv), and the reaction mixture was stirred at −78° C. for 15 min. Then, 4-trifluoromethylbenzoyl chloride (450 µL, 3.03 mmol, 1.3 equiv) was added dropwise, and the reaction was stirred for 30 min at −78° C. The reaction mixture was then poured into saturated aqueous NH$_4$Cl (20 mL), the layers were separated, and the aqueous layer was extracted with EtOAc (3×10 mL). The combined organic extracts were dried over Na$_2$SO$_4$ and concentrated under reduced pressure. The crude product was purified by silica gel flash chromatography (25% EtOAc/hexanes) to afford the title compound as a white solid (698 mg, 1.81 mmol, 77% yield); $^1$H NMR (400 MHz, CDCl$_3$) δ 7.66 (d, J=8.2 Hz, 2H), 7.60 (d, J=8.1 Hz, 2H), 4.14-4.02 (m, 2H), 3.84-3.66 (m, 4H), 2.91-2.77 (m, 2H), 1.50 (s, 9H); $^{13}$C NMR (100 MHz, CDCl$_3$) δ 175.7, 172.5, 154.6, 139.6, 133.0 (q, $J_{C-F}$=32.8 Hz), 130.6, 128.0, 125.5 (q, $J_{C-F}$=3.8 Hz), 123.7 (q, $J_{C-F}$=272.6 Hz), 81.2, 47.7 (br), 45.3, 41.4 (br), 40.8, 28.5; IR (Neat Film, NaCl) 2981, 1689, 1455, 1422, 1367, 1326, 1301, 1249, 1230, 1159, 1127, 1066, 1028, 1015, 977, 955, 852, 832, 769 cm$^{-1}$; HRMS (MM: ESI-APCI): m/z calc'd for $C_{18}H_{25}F_3N_3O_4$ [M+NH$_4$]$^+$: 404.1742, found 404.1797.

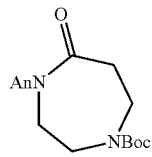

tert-butyl 4-(4-methoxybenzoyl)-5-oxo-1,4-diazepane-1-carboxylate (SI3). To a solution of tert-butyl 5-oxo-1,4-diazepane-1-carboxylate (800 mg, 3.73 mmol, 1 equiv) in THF (37 mL, 0.1 M) at −78° C. was slowly added n-BuLi (2.5 M in hexanes, 1.64 mL, 4.1 mmol, 1.1 equiv). The opaque mixture was allowed to warm to ambient temperature until the solution became homogeneous, at which point it was again cooled to −78° C. Then, 4-methoxybenzoyl chloride (657 µL, 4.85 mmol, 1.3 equiv) was added dropwise and the reaction was stirred for 30 min at −78° C. The reaction mixture was then poured into saturated aqueous NH$_4$Cl (30 mL), the layers were separated, and the aqueous layer was extracted with EtOAc (3×10 mL). The combined organic extracts were dried over Na$_2$SO$_4$ and concentrated under reduced pressure. The crude product was purified by automated silica gel flash chromatography (Teledyne ISCO, 0→100% EtOAc/hexanes) to afford the title compound as a white solid (1.2 g, 3.44 mmol, 92% yield); $^1$H NMR (400 MHz, CDCl$_3$) δ 7.62-7.54 (m, 2H), 6.93-6.84 (m, 2H), 4.00-3.93 (m, 2H), 3.83 (s, 3H), 3.78-3.69 (m, 4H), 2.85-2.78 (m, 2H), 1.48 (s, 9H); $^{13}$C NMR (100 MHz, CDCl$_3$) δ 175.7, 173.4, 162.9, 154.6, 130.9, 130.6, 127.7, 113.7, 80.8, 55.5, 48.0, 47.4, 46.1, 41.9, 41.3, 40.8, 28.5; IR (Neat Film, NaCl) 2974, 2936, 1774, 1687, 1604, 1578, 1510, 1458, 1420, 1391, 1366, 1327, 1284, 1249, 1166, 1114, 1023, 977, 956, 916, 860, 842, 809, 767, 632 cm$^{-1}$; HRMS (MM: ESI-APCI): m/z calc'd for $C_{18}H_{25}N_2O_5$ [M+H]$^+$: 349.1758, found 349.1760.

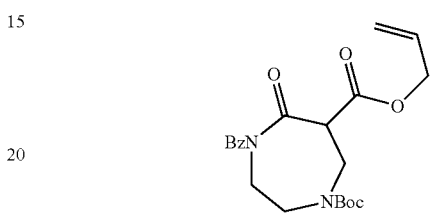

6-allyl 1-(tert-butyl) 4-benzoyl-5-oxo-1,4-diazepane-1,6-dicarboxylate (2a). To a solution of diisopropylamine (266 µL, 1.88 mmol, 1.2 equiv) in THF (10 mL) at −78° C. in a flame-dried round-bottom flask was added n-BuLi (2.5 M in hexanes, 792 µL, 1.73 mmol, 1.1 equiv), the resulting solution was stirred at −78° C. for 45 min. To this solution was then added lactam SI1 (500 mg, 1.57 mmol, 1.0 equiv) in THF (6 mL, 0.1 M total concentration) dropwise while stirring at −78° C. The reaction mixture was stirred for 75 min at −78° C. Allyl cyanoformate (201 µL, 1.88 mmol, 1.2 equiv) was then added dropwise at −78° C. After stirring for 3 h at −78° C., the reaction mixture was poured into saturated aqueous NH$_4$Cl (10 mL) and extracted with ethyl acetate (3×20 mL). The combined organic extracts were concentrated under reduced pressure onto silica (4 g). The silica-adsorbed crude mixture was purified by silica gel flash chromatography (20→30% EtOAc/hexanes) to provide allyl ester 2a as an off-white solid (550 mg, 1.37 mmol, 87% yield); $^1$H NMR (500 MHz, CDCl$_3$) δ 7.65-7.57 (m, 2H), 7.53-7.45 (m, 1H), 7.42-7.34 (m, 2H), 5.92 (ddt, J=17.2, 10.4, 5.9 Hz, 1H), 5.40-5.22 (m, 2H), 4.79-4.59 (m, 2H), 4.33-4.03 (m, 2H), 4.02-3.88 (m, 3H), 3.87-3.66 (m, 1H), 3.55-3.40 (m, 1H), 1.48 (s, 9H); $^{13}$C NMR (125 MHz, CDCl$_3$) δ 173.7, 171.4, 167.5, 154.7, 135.3, 132.2, 131.4, 128.4, 128.4, 119.5, 81.3, 66.6, 56.0, 46.7 (br), 44.5, 43.3 (br), 28.4; IR (Neat Film, NaCl) 3374, 3062, 2977, 2934, 1746, 1694, 1600, 1582, 1450, 1419, 1393, 1367, 1327, 1246, 1156, 1037, 1020, 995, 968, 939, 857, 792, 769, 727, 695, 616 cm$^{-1}$; HRMS (MM: ESI-APCI): m/z calc'd for $C_{21}H_{30}N_3O_6$ [M+NH$_4$]+: 420.2129, found 420.2109.

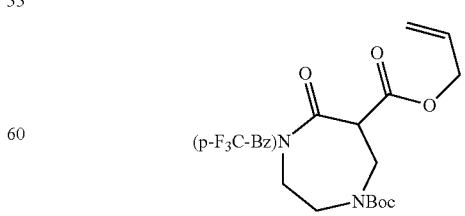

6-allyl 1-(tert-butyl) 5-oxo-4-(4-(trifluoromethyl)benzoyl)-1,4-diazepane-1,6-dicarboxylate (2b). To a solution of lactam SI2 (500 mg, 1.29 mmol, 1.0 equiv) in THF (8 mL, 0.1 M total concentration) at −78° C. was added LiHMDS (303 mg, 1.81 mmol, 1.4 equiv) in THF (5 mL) dropwise. The resulting yellow reaction mixture was stirred for 15 min at −78° C. Then, allyl cyanoformate (166 μL, 1.55 mmol, 1.2 equiv) was added dropwise at −78° C., after which the solution slowly became colorless. After stirring for 1 h at −78° C., the reaction was poured into 2 M HCl (20 mL) and extracted with ethyl acetate (4×20 mL). The combined organic extracts were dried over anhydrous $Na_2SO_4$ and $NaHCO_3$, passed through filter paper, and concentrated under reduced pressure. The crude product was purified by silica gel flash chromatography (20→33% EtOAc/hexanes) to provide allyl ester 2b as a white solid (266 mg, 0.565 mmol, 44% yield); $^1$H NMR (400 MHz, $CDCl_3$) δ 7.69 (d, J=8.3 Hz, 2H), 7.64 (d, J=8.4 Hz, 2H), 5.92 (ddt, J=17.2, 10.4, 5.9 Hz, 1H), 5.42-5.23 (m, 2H), 4.79-4.59 (m, 2H), 4.46-3.63 (m, 6H), 3.52 (m, 1H), 1.47 (s, 9H); $^{13}$C NMR (100 MHz, $CDCl_3$) δ 172.4, 171.4, 167.4, 154.6, 138.9, 133.3 (q, $J_{C-F}$=32.6 Hz), 131.2, 128.3, 125.4 (q, $J_{C-F}$=3.8 Hz), 123.7 (q, $J_{C-F}$=272.5 Hz), 119.8, 81.5, 66.8, 56.0, 47.4, 46.3, 44.2, 43.0, 28.4; IR (Neat Film, NaCl) 3377, 3083, 2980, 2935, 2463, 2358, 1928, 1798, 1747, 1694, 1652, 1619, 1584, 1513, 1455, 1414, 1394, 1368, 1327, 1246, 1156, 1131, 1067, 1034, 1016, 994, 970, 940, 879, 853, 824, 770, 723, 679, 639, 630, 612 cre; HRMS (MM: ESI-APCI): m/z calc'd for $C_{22}H_{29}F_3N_3O_6$ $[M+NH_4]^+$: 488.2003, found 488.2022.

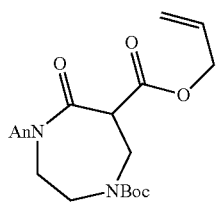

6-allyl 1-(tert-butyl) 4-(4-methoxybenzoyl)-5-oxo-1,4-diazepane-1,6-dicarboxylate (2c). To a solution of lactam SI3 (1.00 g, 2.87 mmol, 1.0 equiv) in THF (20 mL, 0.1 M total concentration) at −78° C. was added LiHMDS (528 mg, 3.16 mmol, 1.1 equiv) in THF (9 mL) dropwise. The resulting pale yellow reaction mixture was stirred for 15 min at −78° C. Allyl cyanoformate (368 3.44 mmol, 1.2 equiv) was then added dropwise at −78° C., resulting in a clear solution. After stirring for 1.5 h at −78° C., the reaction was poured into 1 M HCl (10 mL) and diluted with ethyl acetate (20 mL). The layers were separated and the aqueous phase was extracted with ethyl acetate (3×30 mL). The combined organic extracts were dried over anhydrous $Na_2SO_4$ and $NaHCO_3$, filtered, and concentrated under reduced pressure onto silica. The silica-adsorbed crude mixture was purified by silica gel flash chromatography (10→20% EtOAc/hexanes) to provide allyl ester 2c as a colorless oil (600 mg, 1.39 mmol, 48% yield); $^1$H NMR (400 MHz, $CDCl_3$) δ 7.72-7.60 (m, 2H), 6.91-6.79 (m, 2H), 5.92 (ddt, J=17.3, 10.4, 5.9 Hz, 1H), 5.42-5.20 (m, 2H), 4.77-4.56 (m, 2H), 4.40-3.92 (m, 4H), 3.92-3.62 (m, 2H), 3.82 (s, 3H), 3.58-3.24 (m, 1H), 1.46 (s, 9H); $^{13}$C NMR (100 MHz, $CDCl_3$) δ 173.1, 171.3, 167.6, 163.2, 154.6, 131.4, 131.2, 127.0, 119.4, 113.7, 81.1, 66.5, 55.9, 55.4, 47.7 and 46.7, 45.1, 43.3, 42.8, 28.3; IR (Neat Film, NaCl) 2977, 1746, 1693, 1603, 1578, 1511, 1454, 1419, 1392, 1366, 1324, 1255, 1168, 1025, 995, 965, 842, 766 cm$^{-1}$; HRMS (MM: ESI-APCI): m/z calc'd for $C_{22}H_{28}N_2O_7$ $[M+H]^+$: 433.1969, found 433.1966.

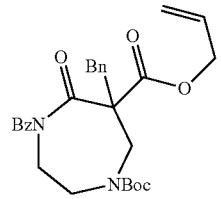

6-allyl 1-(tert-butyl) 4-benzoyl-6-benzyl-5-oxo-1,4-diazepane-1,6-dicarboxylate (3a). To a flame-dried round bottom flask containing a solution of allyl ester 2a (1.00 g, 2.49 mmol, 1.0 equiv) in THF (25 mL, 0.1 M) at 0° C. was added NaH (60% dispersion in mineral oil, 107 mg, 2.74 mmol, 1.1 equiv) and the mixture was stirred at 0° C. for 30 min. BnBr (1.50 mL, 12.45 mmol, 5.0 equiv) was then added dropwise and the reaction mixture was warmed to 45° C. After 16 h, the temperature was further increased to 53° C. due to sluggish reactivity. After another 45 min of stirring at 53° C., the reaction mixture was cooled to 23° C. and poured into saturated aqueous $NH_4Cl$ (25 mL), the layers were separated, and the aqueous layer was extracted with ethyl acetate (3×10 mL). The combined organic extracts were dried over anhydrous $Na_2SO_4$, filtered, and concentrated under reduced pressure. The crude product was purified by silica gel flash chromatography (20% EtOAc/hexanes) to provide the title compound as a colorless foam (922 mg, 1.87 mmol, 75% yield); $^1$H NMR (400 MHz, $CDCl_3$) δ 7.68 (d, J=7.6 Hz, 2H), 7.55-7.46 (m, 1H), 7.37 (t, J=7.7 Hz, 2H), 7.31-7.25 (m, 3H), 7.24-7.12 (m, 2H), 5.86 (tq, J=22.8, 6.5 Hz, 1H), 5.42-5.26 (m, 2H), 4.71-4.55 (m, 2H), 4.22 (dd, J=75.3, 15.5 Hz, 1H), 4.05-3.57 (m, 4H), 3.57-3.36 (m, 2H), 3.22 (dd, J=68.5, 13.7 Hz, 1H), 1.45 (s, 9H); $^{13}$C NMR (100 MHz, $CDCl_3$) δ (174.4, 174.0, 172.2, 172.0, 170.8, 170.2, 155.5, 155.0, 135.7, 135.6, 135.5, 132.0, 131.1, 130.9, 130.8, 130.6, 128.5, 128.5, 128.3, 127.5, 127.4, 120.6, 120.2, 81.2, 81.0, 67.0, 66.9, 62.6, 62.2, 47.3, 46.7, 46.2, 45.8, 42.4, 42.1, 42.0, 28.5; IR (Neat Film, NaCl) 3063, 3030, 2977, 2933, 1694, 1601, 1583, 1495, 1450, 1416, 1393, 1366, 1325, 1280, 1247, 1154, 1132, 1092, 1041, 1023, 980, 939, 868, 796, 768, 728, 703, 662 cm$^{-1}$; HRMS (MM: ESI-APCI): m/z calc'd for $C_{24}H_{25}N_2O_6$ $[MSu+2H]^+$: 437.1707, found 437.1697.

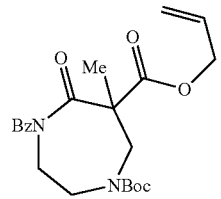

6-allyl 1-(cert-butyl) 4-benzoyl-6-methyl-5-oxo-1,4-diazepane-1,6-dicarboxylate (3b). To a solution of allyl ester 2a (240 mg, 0.596 mmol, 1.0 equiv) in THF (6 mL, 0.1 M) at 0° C. was added 60% NaH (26 mg, 0.657 mmol, 1.1 equiv). The solution was stirred at 0° C. for 40 min, after which MeI (186 μL, 2.98 mmol, 5.0 equiv) was added rapidly. The reaction was heated to 45° C. and stirred for 16 h, cooled to 23° C., poured into saturated aqueous $NH_4Cl$ (5 mL), and extracted with EtOAc (3×3 mL). The combined organic extracts were dried over $Na_2SO_4$ and concentrated onto silica gel. The silica-adsorbed crude product was purified by silica gel flash chromatography (20% EtOAc/hexanes) to afford the title compound as a light yellow oil (200 mg, 0.480 mmol, 81% yield). $^1$H NMR (400 MHz, CDCl$_3$) δ 7.78-7.63 (m, 2H), 7.58-7.43 (m, 1H), 7.38 (t, J=7.6 Hz, 2H), 5.96 (ddt, J=16.6, 10.4, 6.0 Hz, 1H), 5.49-5.26 (m, 2H), 4.85-4.64 (m, 2H), 4.46-4.22 (m, 1H), 4.10 (br d, J=14.8 Hz, 1H), 3.86-3.42 (m, 4H), 1.57 (s, 3H), 1.45 (s, 9H); $^{13}$C NMR (100 MHz, CDCl$_3$) δ 174.5 174.1, 173.0, 171.7, 155.1, 154.9, 135.7, 132.0, 131.2, 128.3, 128.2, 120.2, 81.1, 66.9, 57.7, 49.8, 49.0, 47.1, 46.0, 43.2, 28.4, 23.6; IR (Neat Film, NaCl) 2977, 1693, 1449, 1416, 1366, 1325, 1281, 1249, 1139, 1104, 1047, 983, 938, 768, 727, 694 cm$^{-1}$; HRMS (MM: ESI-APCI): m/z calc'd for C$_{22}$H$_{29}$N$_2$O$_6$ [M+H]$^+$: 417.2020, found 417.2010.

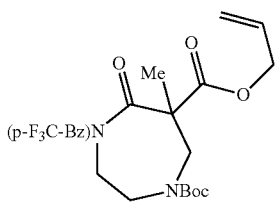

6-allyl 1-(tert-butyl) 6-methyl-5-oxo-4-(4-(trifluoromethyl)benzoyl)-1,4-diazepane-1,6-dicarboxylate (3c). To a suspension of allyl ester 2b (150 mg, 0.319 mmol, 1.0 equiv) and Cs$_2$CO$_3$ (208 mg, 0.638 mmol, 2.0 equiv) in acetonitrile (3.2 mL, 0.1 M) was added MeI (99 μL 1.59 mmol, 5.0 equiv) at 23° C. The reaction was heated to 45° C. and stirred for 5 h, then cooled to 23° C., poured into saturated aqueous NH$_4$Cl (6 mL), and extracted with EtOAc (3×3 mL). The combined organic extracts were dried over anhydrous Na$_2$SO$_4$, filtered, and concentrated under reduced pressure. The crude product was purified by silica gel flash chromatography (15% EtOAc/petroleum ether) to provide the title compound as a colorless oil (146 mg, 0.301 mmol, 95% yield); $^1$H NMR (400 MHz, CDCl$_3$) δ 7.75 (d, J=8.1 Hz, 2H), 7.63 (d, J=8.1 Hz, 2H), 5.97 (ddt, J=17.3, 10.3, 6.1 Hz, 1H), 5.48-5.29 (m, 2H), 4.84-4.68 (m, 2H), 4.49-4.30 (m, 1H), 4.18-3.98 (m, 1H), 3.90-3.39 (m, 4H), 1.57 (s, 3H), 1.45 (s, 9H); $^{13}$C NMR (100 MHz, CDCl$_3$) δ 173.2, 172.7, 171.7, 154.9, 139.2, 133.1 (q, J$_{C-F}$=32.5 Hz), 131.1, 128.2, 125.4, 123.8 (q, J$_{C-F}$=272.7 Hz), 120.5, 81.3, 67.0, 57.7, 49.7, 49.0, 46.9, 45.8, 43.1, 42.9, 28.4, 23.7; IR (Neat Film, NaCl) 3384, 3083, 2979, 2937, 1698, 1619, 1584, 1514, 1478, 1453, 1416, 1394, 1367, 1326, 1285, 1250, 1207, 1166, 1136, 1110, 1066, 1022, 1012, 985, 938, 855, 832, 817, 790, 769, 740, 722, 680 cm$^{-1}$; HRMS (MM: ESI-APCI): m/z calc'd for C$_{23}$H$_{28}$F$_3$N$_2$O$_6$ [M+H]$^+$: 485.1894, found 485.1907.

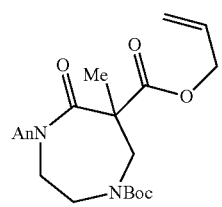

6-allyl 1-(tert-butyl) 4-(4-methoxybenzoyl)-6-methyl-5-oxo-1,4-diazepane-1,6-dicarboxylate (3d). To a suspension of allyl ester 2c (200 mg, 0.462 mmol, 1.0 equiv), Cs$_2$CO$_3$ (301 mg, 0.925 mmol, 2.0 equiv) in acetonitrile (4.6 mL, 0.1 M) was added MeI (143 μL, 2.31 mmol, 5.0 equiv) at 23° C.

The reaction was heated to 45° C. and stirred for 40 min, then cooled to 23° C., poured into saturated aqueous NH$_4$Cl (10 mL), and extracted with EtOAc (3×5 mL). The combined organic extracts were dried over anhydrous Na$_2$SO$_4$, filtered, and concentrated under reduced pressure. The crude product was purified by automated silica gel flash chromatography (Teledyne ISCO, 0→90% EtOAc/hexanes) to provide the title compound as a colorless oil (70 mg, 0.157 mmol, 34% yield). $^1$H NMR (400 MHz, CDCl$_3$) δ 7.75-7.65 (m, 2H), 6.90-6.82 (m, 2H), 5.96 (ddt, J=17.3, 10.4, 6.0 Hz, 1H), 5.44-5.29 (m, 2H), 4.77-4.66 (m, 2H), 4.27-4.15 (m, 1H), 4.14-4.04 (m, 1H), 3.83 (s, 3H), 3.80-3.70 (m, 1H), 3.67-3.58 (m, 2H), 3.56-3.46 (m, 1H), 1.57 (s, 3H), 1.44 (s, 9H); $^{13}$C NMR (100 MHz, CDCl$_3$) δ 174.0, 173.6, 172.9, 172.0, 171.8, 162.9, 155.2, 154.9, 131.2, 131.2, 131.0, 127.6, 120.1, 120.0, 113.6, 81.0, 66.8, 57.5, 55.5, 49.6, 48.9, 47.2, 46.1, 43.7, 28.4, 23.7; IR (Neat Film, NaCl) 2974, 2937, 1698, 1604, 1578, 1511, 1453, 1416, 1392, 1366, 1324, 1280, 1256, 1169, 1139, 1103, 1031, 1001, 983, 929, 840, 768, 733 cm$^{-1}$; HRMS (MM: ESI-APCI): m/z calc'd for C$_{23}$H$_{31}$N$_2$O$_7$ [M+H]$^+$: 447.2126, found 447.2128.

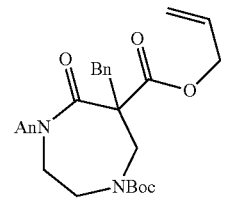

6-allyl 1-(tert-butyl) 6-benzyl-4-(4-methoxybenzoyl)-5-oxo-1,4-diazepane-1,6-dicarboxylate (3e). To a flame-dried round bottom flask containing a solution of allyl ester 2c (300 mg, 0.694 mmol, 1.0 equiv) in THF (7 mL, 0.1 M) at 0° C. was added NaH (60% dispersion in mineral oil, 38 mg, 0.972 mmol, 1.4 equiv) and the mixture was stirred at 0° C. for 15 min and then allowed to warm to 23° C. over 15 min. BnBr (412 μL, 3.47 mmol, 5.0 equiv) was then added dropwise and the reaction mixture was heated to 50° C. After stirring for 8 h, the reaction mixture was allowed to cool to 23° C. and poured into saturated aqueous NH$_4$Cl (5 mL), the layers were separated, and the aqueous phase was extracted with ethyl acetate (3×2 mL). The combined organic extracts were dried over anhydrous Na$_2$SO$_4$, filtered, and concentrated under reduced pressure. The crude product was purified by silica gel flash chromatography (20% EtOAc/hexanes) to provide the title compound as a colorless foam (303 mg, 0.580 mmol, 84% yield); $^1$H NMR (500 MHz, CDCl$_3$) δ 7.72 (d, J=8.5 Hz, 2H), 7.31-7.12 (m, 5H), 6.90-6.80 (m, 2H), 5.95-5.75 (m, 1H), 5.41-5.26 (m, 2H), 4.69-4.54 (m, 2H), 4.21-4.05 (m, 1H), 4.02-3.86 (m, 2H), 3.83 (s, 3H), 3.78-3.62 (m, 2H), 3.56-3.49 (m, 1H), 3.43-3.10 (m, 2H), 1.45 (s, 9H); $^{13}$C NMR (125 MHz, CDCl$_3$) δ 173.7, 173.4, 172.0, 171.7, 170.8, 170.2, 162.9, 155.4, 154.8, 135.7, 135.6, 131.1, 130.9, 130.7, 130.5, 128.5, 128.3, 128.2, 127.5, 127.3, 127.0, 120.2, 119.9, 113.5, 80.9, 80.7, 66.6, 62.4, 62.0, 55.3, 47.1, 46.8, 46.0, 45.8, 42.8, 42.5, 41.9, 28.3; IR (Neat Film, NaCl) 2976, 2359, 1698, 1604, 1512, 1455, 1416, 1366, 1324, 1258, 1155, 1028, 979, 840, 741, 703, 671, 634 cm$^{-1}$; HRMS (MM: ESI-APCI): m/z calc'd for C$_{29}$H$_{35}$N$_2$O$_7$ [M+H]$^+$: 523.2439, found 523.2446.

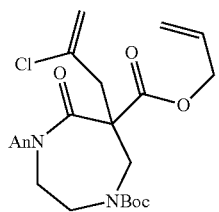

6-allyl 1-(tert-butyl) 6-(2-chloroallyl)-4-(4-methoxybenzoyl)-5-oxo-1,4-diazepane-1,6-dicarboxylate (3f). To a suspension of allyl ester 2c (300 mg, 0.694 mmol, 1.0 equiv) and Cs$_2$CO$_3$ (453 mg, 1.39 mmol, 2.0 equiv) in acetonitrile (7 mL, 0.1 M) was added 2,3-dichloropropene (320 μL, 3.47 mmol, 5.0 equiv) at 23° C. The reaction mixture was heated to 50° C. and stirred for 19 h, after which starting material remained as judged by TLC. Tetrabutylammonium iodide (25.6 mg, 0.0694 mmol, 0.1 equiv) was added and the reaction mixture was stirred at 50° C. for an additional 9 h, then allowed to cool to 23° C. The mixture was filtered through a cotton plug and concentrated under reduced pressure. The crude product was purified by silica gel flash chromatography (20% EtOAc/petroleum ether) to provide the title compound as a colorless oil (196 mg, 0.387 mmol, 56% yield); $^1$H NMR (400 MHz, CDCl$_3$) δ 7.71 (d, J=8.8 Hz, 2H), 6.85 (d, J=8.9 Hz, 2H), 6.12-5.94 (m, 1H), 5.60-5.25 (m, 4H), 4.78 (qdt, J=12.8, 6.0, 1.2 Hz, 2H), 4.25 (br t, J=13.9 Hz, 1H), 4.17-3.87 (m, 3H), 3.84 (s, 3H), 3.76-3.51 (m, 1H), 3.48-3.30 (m, 1H), 3.29-2.99 (m, 2H), 1.43 (d, J=16.9 Hz, 9H); $^{13}$C NMR (100 MHz, CDCl$_3$) δ 173.9, 173.3, 170.3, 163.1, 155.9, 155.1, 137.0, 136.7, 131.1, 127.2, 120.6, 120.3, 119.4, 118.4, 113.6, 81.4, 81.0, 67.5, 60.0, 55.5, 47.1, 45.9, 46.0, 45.2, 45.6, 44.7, 43.1, 42.8, 28.4; IR (Neat Film, NaCl) 3356, 3080, 2977, 2933, 2841, 2568, 2254, 1700, 1629, 1605, 1579, 1512, 1456, 1417, 1393, 1367, 1326, 1281, 1257, 1217, 1196, 1153, 1029, 988, 910, 842, 811, 780, 757, 732, 668, 634, 621 cm$^{-1}$; HRMS (MM: ESI-APCI): m/z calc'd for C$_{25}$H$_{32}$ClN$_2$O$_7$ [M+H]$^+$: 507.1893, found 507.1902.

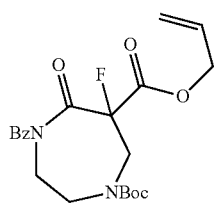

6-allyl 1-(tert-butyl) 4-benzoyl-6-fluoro-5-oxo-1,4-diazepane-1,6-dicarboxylate (3g). To a 20 mL vial containing allyl ester 2a (250 mg, 0.621 mmol, 1.0 equiv) in THF (7.4 mL, 0.1 M) at 23° C. was added NaH (60% dispersion in mineral oil, 27.3 mg, 0.683 mmol, 1.1 equiv). After stirring for 12 min, Selectfluor™ (264 mg, 0.745 mmol, 1.2 equiv) was added in a single portion, and the reaction mixture was warmed to 50° C. and stirred for 24 h, after which starting material remained as judged by TLC. Additional Selectfluor™ (264 mg, 0.745 mmol, 1.2 equiv) was then added, and the reaction mixture was stirred for an additional 8 h at 50° C. The reaction mixture was allowed to cool to 23° C. and water (5 mL) was added. The layers were separated and the aqueous layer was extracted with EtOAc (3×5 mL). The combined organic extracts were dried over anhydrous Na$_2$SO$_4$, concentrated under reduced pressure, and purified by silica gel flash chromatography (25% EtOAc/hexanes) to provide the title compound (167 mg, 0.397 mmol, 64% yield); $^1$H NMR (500 MHz, CDCl$_3$) δ 7.64-7.56 (m, 2H), 7.52-7.43 (m, 1H), 7.36 (t, J=7.7 Hz, 2H), 5.99-5.80 (m, 1H), 5.43-5.19 (m, 2H), 4.83-4.56 (m, 2H), 4.52-4.17 (m, 3H), 4.03-3.56 (m, 2H), 3.27-3.08 (m, 1H), 1.47 (s, 9H); $^{13}$C NMR (125 MHz, CDCl$_3$) δ 173.1, 169.6, 169.4, 164.8, 164.6, 154.9, 134.3, 132.5, 130.7, 128.5, 128.4, 119.7, 95.7 (d, J=204.8 Hz), 81.5, 67.2, 47.6 (dd, J$_{C-F}$=137.5, 24.1 Hz), 47.3, 46.4, 42.8, 28.3; IR (Neat Film, NaCl) 2978, 2926, 1694, 1450, 1414, 1393, 1367, 1329, 1246, 1152, 1042, 999, 979, 926, 857, 766, 724, 694, 672, 648 cm$^{-1}$; HRMS (MM: ESI-APCI): m/z calc'd for C$_{21}$H$_{29}$FN$_3$O$_6$ [M+NH$_4$]$^+$: 438.2035, found 438.2040.

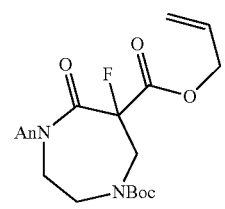

6-allyl 1-(tert-butyl) 6-fluoro-4-(4-methoxybenzoyl)-5-oxo-1,4-diazepane-1,6-dicarboxylate (3h). To a 20 mL vial containing allyl ester 2c (320 mg, 0.740 mmol, 1.0 equiv) and NaH (60% dispersion in mineral oil, 32.5 mg, 0.814 mmol, 1.1 equiv) was added THF (7.4 mL, 0.1 M) at 23° C. After stirring for 30 min, Selectfluor™ (315 mg, 0.889 mmol, 1.2 equiv) was added in a single portion, and the reaction mixture was warmed to 50° C. and stirred for 5 h. The crude reaction mixture was then concentrated under reduced pressure and purified by silica gel flash chromatography (30% acetone/hexanes) to provide the title compound (290 mg, 0.644 mmol, 87% yield); $^1$H NMR (400 MHz, CDCl$_3$) δ 7.66-7.58 (m, 2H), 6.90-6.82 (m, 2H), 5.91 (ddt, J=16.3, 10.9, 5.7 Hz, 1H), 5.43-5.21 (m, 2H), 4.84-4.40 (m, 3H), 4.40-4.16 (m, 2H), 4.00-3.86 (m, 1H), 3.82 (s, 3H), 3.77-3.56 (m, 1H), 3.22-3.09 (m, 1H), 1.47 (s, 9H); $^{13}$C NMR (100 MHz, CDCl$_3$) δ 172.6, 169.6 (dd, J$_{C-F}$=48.2, 25.4 Hz), 164.9 (d, J$_{C-F}$=25.8 Hz), 163.4, 155.0, 131.3, 130.8, 126.1, 119.8, 113.9, 95.7 (dd, J$_{C-F}$=205.6, 14.6 Hz), 81.5, 67.3, 55.5, 47.5 (dd, J$_{C-F}$=109.0, 23.7 Hz), 47.2 (d, J$_{C-F}$=92.2 Hz), 43.4, 28.3; IR (Neat Film, NaCl) 2976, 2936, 2844, 1759, 1698, 1603, 1578, 1512, 1449, 1414, 1367, 1327, 1258, 1168, 1151, 1076, 1030, 997, 977, 942, 929, 841, 817, 770, 760, 730, 698 cm$^{-1}$; HRMS (MM: ESI-APCI): m/z calc'd for C$_{22}$H$_{28}$FN$_2$O$_7$ [M+H]$^+$: 451.1875, found 451.1877.

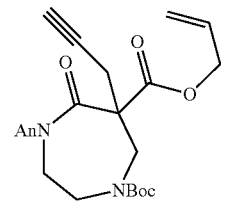

6-allyl 1-(tert-butyl) 4-(4-methoxybenzoyl)-5-oxo-6-(prop-2-yn-1-yl)-1,4-diazepane-1,6-dicarboxylate (3i). To a solution of allyl ester 2c (250 mg, 0.578 mmol, 1.0 equiv) in THF (5.8 mL, 0.1 M) was added NaH (60% dispersion in mineral oil, 25 mg, 0.636 mmol, 1.1 equiv) at 0° C. After stirring for 30 min at 0° C., propargyl bromide (80% wt/wt in toluene, 125 µL, 1.16 mmol, 2.0 equiv) was added at 0° C. The reaction mixture was heated to 50° C. and stirred for 16 h. The mixture was allowed to cool to 23° C., quenched with aqueous NaHCO$_3$ (10 mL) and extracted with EtOAc (3×5 mL). The combined organic extracts were dried over anhydrous Na$_2$SO$_4$, filtered, and concentrated under reduced pressure. The crude product was purified by automated silica gel flash chromatography (Teledyne ISCO, acetone/hexanes) to provide propargyl allyl ester 3i as a colorless oil (220 mg, 0.468 mmol, 81% yield). $^1$H NMR (500 MHz, CDCl$_3$) δ 7.73-7.59 (m, 2H), 6.84 (d, J=8.6 Hz, 2H), 5.99 (ddt, J=17.3, 10.4, 6.0 Hz, 1H), 5.54-5.27 (m, 2H), 4.85-4.69 (m, 2H), 4.33-3.85 (m, 4H), 3.82 (s, 3H), 3.76-3.56 (m, 1H), 3.56-3.39 (m, 1H), 3.14-2.90 (m, 2H), 2.08 (s, 1H), 1.42 (d, J=14.3 Hz, 9H); $^{13}$C NMR (125 MHz, CDCl$_3$) δ 173.7, 173.2, 170.5, 170.3, 169.7, 169.3, 163.0, 155.6, 154.9, 131.2, 131.0, 127.1, 120.3, 120.0, 113.6, 81.1, 81.0, 78.9, 78.6, 72.3, 67.3, 60.7, 60.4, 55.5, 47.1, 46.5, 46.2, 46.0, 43.0, 28.3, 27.0, 26.9; IR (Neat Film, NaCl) 3280, 2975, 2936, 1737, 1694, 1604, 1579, 1547, 1512, 1454, 1416, 1393, 1366, 1326, 1280, 1258, 1156, 1134, 1030, 994, 980, 841, 778, 770, 737, 706, 677, 634, 622 cm$^{-1}$; HRMS (MM: ESI-APCI): m/z calc'd for C$_{25}$H$_{31}$N$_2$O$_7$ [M+H]$^+$: 471.2126, found 471.2130.

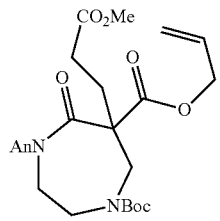

6-allyl 1-(tert-butyl) 6-(3-methoxy-3-oxopropyl)-4-(4-methoxybenzoyl)-5-oxo-1,4-diazepane-1,6-dicarboxylate (3j). To a 20 mL vial containing allyl ester 2c (300 mg, 0.694 mmol, 1.0 equiv) and K$_2$CO$_3$ (480 mg, 3.47 mmol, 5.0 equiv) was added acetone (2.8 mL, 0.25 M) and methyl acrylate (126 µL, 1.39 mmol, 2.0 equiv) at 23° C. The vessel was sealed and heated to 50° C. After stirring for 5 h, additional methyl acrylate (126 µL, 1.39 mmol, 2.0 equiv) was added and the reaction was stirred for an additional 14 h. The reaction mixture was then filtered through a plug of cotton, concentrated under reduced pressure, and purified by silica gel flash chromatography (33% EtOAc/petroleum ether) to provide diester 3j as a colorless, waxy solid (185 mg, 0.357 mmol, 51% yield); $^1$H NMR (500 MHz, CDCl$_3$) δ 7.77-7.65 (m, 2H), 6.92-6.79 (m, 2H), 5.96 (ddt, J=17.2, 10.3, 6.1 Hz, 1H), 5.48-5.27 (m, 2H), 4.82-4.63 (m, 2H), 4.32-3.84 (m, 3H), 3.83 (s, 3H), 3.81-3.66 (m, 1H), 3.62 (s, 3H), 3.58-3.40 (m, 2H), 2.56-2.13 (m, 4H), 1.44 (s, 9H); $^{13}$C NMR (125 MHz, CDCl$_3$) δ 173.8, 173.5, 173.0, 171.9, 170.9, 170.6, 163.0, 155.1, 154.8, 131.1, 131.0, 127.5, 120.6, 113.6, 81.2, 67.0, 60.4, 55.5, 51.7, 48.7, 47.8, 47.0, 46.0, 43.4, 31.4, 29.8, 28.3; IR (Neat Film, NaCl) 3354, 2976, 2843, 2568, 2255, 2044, 1694, 1605, 1579, 1556, 1513, 1416, 1393, 1367, 1260, 1168, 1030, 982, 916, 843, 811, 782, 766, 732, 648, 634 cm$^{-1}$; HRMS (MM: ESI-APCI): m/z calc'd for C$_{26}$H$_{38}$N$_3$O$_9$ [M+NH$_4$]$^+$: 536.2603, found 536.2603.

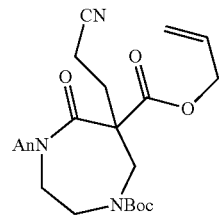

6-allyl 1-(tert-butyl) 6-(2-cyanoethyl)-4-(4-methoxybenzoyl)-5-oxo-1,4-diazepane-1,6-dicarboxylate (3k). To a 20 mL vial containing allyl ester 2c (300 mg, 0.694 mmol, 1.0 equiv) and K$_2$CO$_3$ (480 mg, 3.47 mmol, 5.0 equiv) was added acetone (2.8 mL, 0.25 M) and acrylonitrile (182 µL, 2.78 mmol, 4.0 equiv) at 23° C. The vessel was sealed and heated to 50° C. After 17 h of stirring, the reaction mixture was filtered through a plug of cotton, concentrated under reduced pressure, and purified by silica gel flash chromatography (33% EtOAc/petroleum ether) to provide 3k as a colorless foam (176 mg, 0.362 mmol, 52% yield); $^1$H NMR (400 MHz, CDCl$_3$) δ 7.74 (d, J=8.8 Hz, 2H), 6.89 (d, J=8.9 Hz, 2H), 6.01 (ddt, J=16.7, 10.3, 6.3 Hz, 1H), 5.51-5.36 (m, 2H), 4.89-4.75 (m, 2H), 4.32-3.88 (m, 3H), 3.86 (s, 3H), 3.84-3.34 (m, 3H), 2.71-2.09 (m, 4H), 1.53-1.34 (m, 9H); $^{13}$C NMR (100 MHz, CDCl$_3$) 170.8, 170.3, 163.2, 155.3, 131.0, 130.6, 127.1, 121.4, 121.1, 119.1, 113.7, 81.4, 67.5, 60.2, 55.5, 47.5, 46.8, 43.6, 32.9, 28.3, 13.6; IR (Neat Film, NaCl) 2975, 2934, 2250, 1694, 1605, 1579, 1512, 1455, 1419, 1393, 1367, 1326, 1255, 1164, 1031, 1000, 979, 941, 916, 842, 813, 781, 762, 733, 648, 634 ere; HRMS (MM: ESI-APCI): m/z calc'd for C$_{25}$H$_{35}$N$_4$O$_7$ [M+NH$_4$]$^+$: 503.2500, found 503.2505.

6-allyl 1-(tert-butyl) 4-benzoyl-6-(((tert-butoxycarbonyl)amino)methyl)-5-oxo-1,4-diazepane-1,6-dicarboxylate (3l). A solution of allyl ester 2a (200 mg, 0.497 mmol, 1.0 equiv) and tert-butyl ((phenylsulfonyl)methyl)carbamate (162 mg, 0.597 mmol, 1.2 equiv) in CH$_2$Cl$_2$ (2.5 mL, 0.2 M) at 23° C. was stirred for 5 min, after which time Cs$_2$CO$_3$ (405 mg, 1.24 mmol, 2.5 equiv) was added at the same temperature. [Klepacz, A.; Zwierzak, A. Tetrahedron Lett. 2002, 43, 1079-1080; Sikriwal, D.; Kant, R.; Maulik, P. R.; Dikshit, D. K. Tetrahedron 2010, 66, 6167-6173.] After an additional 30 min of stirring, saturated aqueous NH$_4$Cl (1 mL) was added and the biphasic mixture was vigorously stirred for 20 min. The layers were separated and the aqueous phase was extracted with CH$_2$Cl$_2$ (3×3 mL). The combined organic extracts were dried over anhydrous Na$_2$SO$_4$, filtered, and concentrated under reduced pressure onto silica gel (2 g). The silica-adsorbed crude reaction mixture was purified by automated silica gel flash chromatography (Teledyne ISCO, 10-40% acetone/hexanes) to provide carbamate 3l as a white foam (200 mg, 0.376 mmol, 76% yield): $^1$H NMR (400 MHz, CDCl$_3$) δ 7.83-7.71 (m, 2H), 7.59-7.46 (m, 1H), 7.46-7.36 (m, 2H), 6.00 (ddt, J=16.6, 10.3, 6.1 Hz, 1H), 5.51-5.25 (m, 2H), 5.17 (br s, 1H), 4.79-4.64 (m, 2H), 4.48-4.23 (m, 1H), 4.14-3.20 (m, 7H), 1.44 (s, 9H), 1.42 (s, 9H); $^{13}$C NMR (100 MHz, CDCl$_3$) δ 174.1, 173.8, 172.7, 170.1, 169.6, 156.0, 155.2, 154.7, 135.5, 132.2, 131.4, 128.5, 128.4, 120.2, 81.4, 79.6, 67.4, 62.7, 47.1, 46.8, 45.9, 43.2, 28.5, 28.4; IR (Neat Film, NaCl) 3457, 2977, 2934, 2253, 1704, 1600, 1503, 1450, 1417, 1392, 1367, 1325, 1283, 1248, 1158, 1042, 980, 913, 77 860, 767, 729, 693, 663 cm$^{-1}$; HRMS (MM: ESI-APCI): m/z calc'd for C$_{27}$H$_{38}$N$_3$O$_8$ [M+H]$^+$: 532.2653, found 532.2664.

Example 41: Derivatization of Allylic Alkylation Products

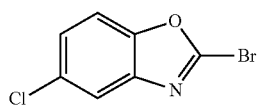 [SMILES: Clc1ccc2oc(Br)nc2c1]

2-bromo-5-chlorobenzo[d]oxazole (6)

Prepared according to the literature procedure by Mangion and coworkers and used directly in the synthesis of 7. [*Org. Lett.* 2012, 14, 3458-3461].

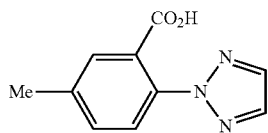 [SMILES: Cc1ccc(-n2nccn2)c(C(=O)O)c1]

5-methyl-2-(2H-1,2,3-triazol-2-yl)benzoic acid (8). Prepared according to the literature procedure by Mangion and coworkers. [*Org. Lett.* 2012, 14, 3458-3461]. All characterization data matched those reported in the literature.

was removed under reduced pressure and the resulting aqueous mixture extracted with EtOAc (4×50 mL). The combined organic extracts were dried with sodium sulfate, filtered, and concentrated under reduced pressure to yield a crude oil (400 mg) that was used without further purification.

tert-butyl (R)-6-allyl-6-benzyl-1,4-diazepane-1-carboxylate (5). Crude lactam SI4 (350 mg [theoretical maximum 310 mg lactam], 0.903 mmol, 1 equiv) was dissolved in THF (10.2 mL, 0.1 M) and cooled to 0° C. LiAlH$_4$ (77 mg, 2.03 mmol, 2.25 equiv) was then added, and the reaction mixture was stirred at 0° C. for 4 h, over the course of which an additional 3.37 equiv (116 mg, 3.05 mmol) of LiAlH$_4$ were added in total (77 mg, followed by 39 mg, at equal intervals). The reaction mixture was then diluted with diethyl ether (10 mL) and water (300 μL) was added. After gas generation subsided, 15% aqueous NaOH (300 μL) was added, followed by additional water (900 μL). After stiffing at 0° C. for 15 min, anhydrous MgSO$_4$ was added, and the mixture was stirred for an additional 10 min, whereafter it was filtered through celite and concentrated under reduced pressure. Purification by automated silica gel flash chromatography (Teledyne ISCO, 0→20% MeOH/CH$_2$Cl$_2$) provided the product as a light yellow oil (130 mg, 0.393 mmol, 44% yield); $^1$H NMR (400 MHz, CDCl$_3$) δ 7.40-7.14 (m, 5H), 6.01 (dq, J=17.1, 7.8 Hz, 1H), 5.18 (d, J=15.9 Hz, 2H), 3.67-3.30 (m, 4H), 2.97 (m, 2H), 2.88-2.48 (m, 4H), 2.30-2.06 (m, 3H), 1.50 (s, 9H); $^{13}$C NMR (100 MHz, CDCl$_3$) δ 155.8, 138.1, 134.6, 130.7, 128.0, 126.2, 118.2, 79.8, 79.5, 57.9, 57.2, 55.3, 54.2, 50.9, 49.8, 49.3, 43.5, 41.3, 39.8, 39.4, 28.5; IR (Neat Film, NaCl) 3357, 3066, 3028, 2976, 2928, 1694, 1602, 1464, 1455, 1416, 1391, 1365, 1334, 1302, 1248, 1166, 1031, 996, 952, 912, 866, 771, 733, 703, 685, 672, 659, 644, 612 cm$^{-1}$; HRMS (MM: ESI-APCI): m/z calc'd for C$_{20}$H$_{31}$N$_2$O$_2$ [M+H]$^+$: 331.2380, found 331.2399; [α]$_D^{22.24}$ –6.496 (c 2.0, CHCl$_3$).

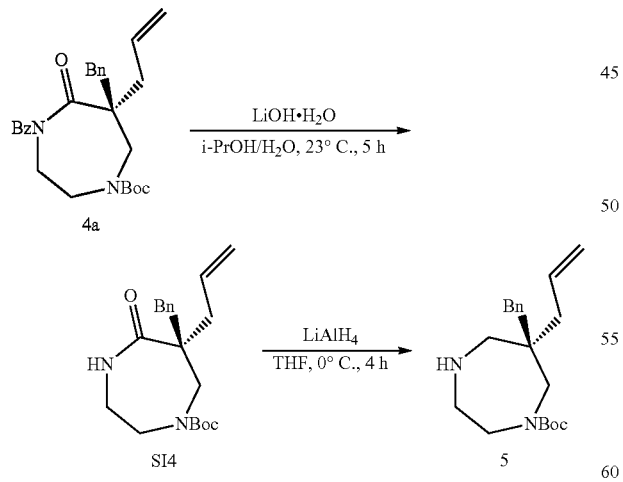

tert-butyl (S)-6-allyl-6-benzyl-5-oxo-1,4-diazepane-1-carboxylate (SI4). To a flask containing benzoyl-protected diazepanone 4a (460 mg, 1.03 mmol, 1.0 equiv) was added isopropyl alcohol (100 mL, 0.01 M) and water (10 mL), followed by LiOH.H$_2$O (61 mg, 1.45 mmol, 1.5 equiv) at 23° C. After stiffing for 4 h at 23° C., the isopropyl alcohol

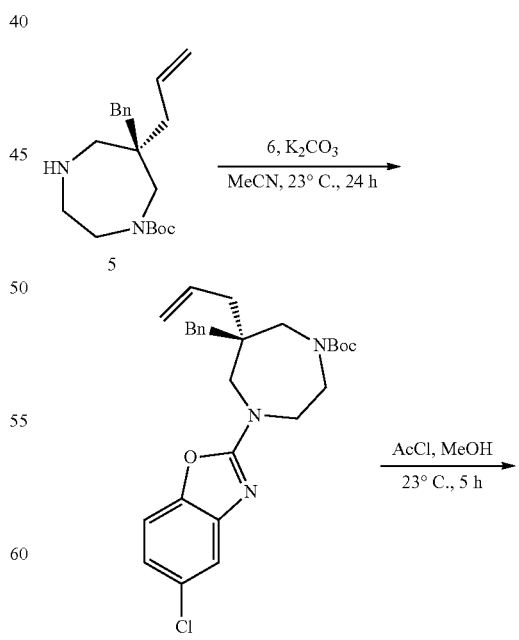

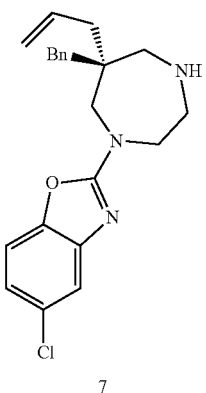

tert-butyl (R)-6-allyl-6-benzyl-4-(5-chlorobenzo[d]oxazol-2-yl)-1,4-diazepane-1-carboxylate (SI5). To a 1 dram vial containing diazepane 5 (9.5 mg, 0.0287 mmol, 1.0 equiv), aryl bromide 6 (10.0 mg, 0.0431 mmol, 1.5 equiv), and K$_2$CO$_3$ (7.9 mg, 0.0574 mmol, 2 equiv) was added MeCN (0.3 mL, 0.1 M) at 23° C. After stirring for 24 h at 23° C., saturated aqueous NH$_4$Cl (1 mL) was added, and the mixture was extracted with EtOAc (3×1 mL). The combined organic extracts were dried over anhydrous Na$_2$SO$_4$ and concentrated under reduced pressure. The crude material (15.4 mg) thus obtained was carried forward without further purification.

(S)-2-(6-allyl-6-benzyl-1,4-diazepan-1-yl)-5-chlorobenzo[d]oxazole (7). Crude carbamate SI5 was dissolved in MeOH (0.3 mL, 0.1 M) and AcCl (20.5 µL, 0.288 mmol, 10 equiv) was added at 23° C. After stirring for 5 h at 23° C., the reaction mixture was concentrated under reduced pressure and purified by silica gel flash chromatography (66% EtOAc/benzene+1% Et$_3$N) to provide 7 as a beige, amorphous solid (4.3 mg, 0.0113 mmol, 39% yield from 5) of sufficient purity for use in the next reaction, however, further purification was possible by silica gel flash chromatography with 2% Et$_3$N in Et$_2$O; $^1$H NMR (400 MHz, CDCl$_3$) δ 7.34-7.27 (m, 3H), 7.25-7.17 (m, 3H), 7.12 (d, J=8.4 Hz, 1H), 6.94 (dd, J=8.4, 2.3 Hz, 1H), 5.99 (ddt, J=14.5, 10.4, 7.2 Hz, 1H), 5.30 (d, J=3.1 Hz, 1H), 5.20-5.10 (m, 1H), 3.87-3.61 (m, 3H), 3.15-3.00 (m, 2H), 2.90-2.66 (m, 3H), 2.57 (d, J=13.9 Hz, 1H), 2.22-2.10 (m, 3H); $^{13}$C NMR (100 MHz, CDCl$_3$) δ 147.5, 137.8, 134.1, 130.8, 129.4, 128.2, 126.4, 120.1, 118.8, 116.2, 109.2, 57.8, 56.5, 53.3, 49.2, 43.8, 41.3, 39.8; IR (Neat Film, NaCl) 2922, 1638, 1570, 1458, 1249, 1167, 921, 792, 710 cm$^{-1}$; HRMS (MM: ESI-APCI): m/z calc'd for C$_{22}$H$_{25}$ClN$_3$O [M+H]$^+$: 382.1681, found 382.1695; [α]$_D^{21.89}$+7.524 (c 0.07, CHCl$_3$).

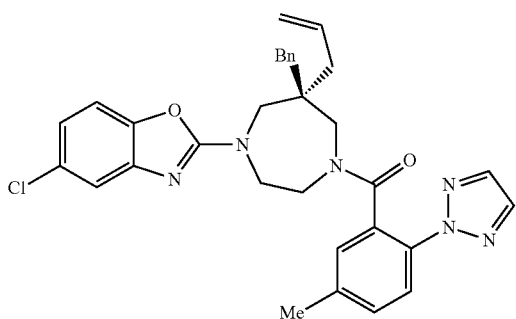 [SMILES: C=CC[C@]1(Cc2ccccc2)CN(C(=O)c2cc(C)ccc2-n2nccn2)CCN(c2nc3cc(Cl)ccc3o2)C1]

(R)-(6-allyl-6-benzyl-4-(5-chlorobenzo[d]oxazol-2-yl)-1,4-diazepan-1-yl)(5-methyl-2-(2H-1,2,3-triazol-2-yl)phenyl)methanone (9). To a vial containing carboxylic acid 8 (35 mg, 0.172 mmol, 1.0 equiv) in CH$_2$Cl$_2$ (1.8 mL) at 23° C. was added DMF (4 µL, 0.0517 mmol, 0.3 equiv) and oxalyl chloride (18 µL, 0.207 mmol, 1.2 equiv). After stirring for 1 h, Et$_3$N (48 µL, 0.344 mmol, 2.0 equiv) was added, followed by amine 7 (60 mg, 0.155 mmol, 0.9 equiv) in CH$_2$Cl$_2$ (1.8 mL, 0.05 M total concentration). After stirring for an additional 1 h at 23° C., the reaction mixture was quenched with saturated aqueous NaHCO$_3$ (3 mL), the layers were separated, and the aqueous layer was extracted with CH$_2$Cl$_2$ (3×2 mL). The combined organic extracts were dried over anhydrous Na$_2$SO$_4$, concentrated under reduced pressure, and purified by automated silica gel flash chromatography (Teledyne ISCO, 0→40% Et$_2$O/hexanes) to provide amide 9 as a beige oil (29.6 mg, 0.0522 mmol, 34% yield); $^1$H NMR (400 MHz, CDCl$_3$) δ 7.73 (s, 1H), 7.55 (s, 1H), 7.34-7.27 (m, 6H), 7.20-7.09 (m, 3H), 7.04-6.92 (m, 2H), 6.11 (ddt, J=17.6, 10.4, 7.3 Hz, 1H), 5.26-5.12 (m, 2H), 4.24-4.07 (m, 1H), 3.96 (dd, J=17.1, 14.4 Hz, 1H), 3.90-3.75 (m, 1H), 3.70-3.40 (m, 4H), 3.38-3.12 (m, 2H), 2.99-2.80 (m, 2H), 2.43-2.38 (m, 2H), 2.38-2.33 (m, 2H); $^{13}$C NMR (100 MHz, CDCl$_3$) δ 170.7, 170.5, 170.0, 163.0, 147.2, 144.4, 138.7, 138.6, 138.5, 136.9, 135.9, 135.8, 135.8, 135.7, 135.7, 135.6, 135.6, 134.2, 133.9, 133.8, 133.6, 133.5, 133.2, 132.9, 130.9, 130.8, 130.6, 130.6, 130.4, 130.4, 129.9, 129.5, 129.5, 129.0, 129.0, 128.3, 128.3, 128.2, 128.2, 128.2, 128.1, 128.1, 126.6, 126.6, 122.2, 122.0, 121.9, 120.5, 120.5, 119.2, 119.1, 119.0, 116.3, 116.3, 109.3, 109.2, 56.2, 56.1, 55.5, 54.3, 52.9, 52.2, 49.5, 49.3, 49.2, 48.9, 47.6, 45.0, 43.5, 43.1, 42.4, 42.2, 42.0, 41.8, 39.5, 39.5, 37.6, 21.0, 21.0, 20.9; IR (Neat Film, NaCl) 3431, 2923, 2854, 2356, 1644, 1634, 1574, 1568, 1538, 1505, 1462, 1454, 1428, 1372, 1308, 1251, 1216, 1172, 1054, 952, 921, 852, 822, 794, 737, 704 cm$^{-1}$; HRMS (MM: ESI-APCI): m/z calc'd for C$_{32}$H$_{32}$ClN$_6$O$_2$ [M+H]$^+$: 567.2270, found 567.2294; [α]$_D^{22.24}$+41.90 (c 1.0, CHCl$_3$).

INCORPORATION BY REFERENCE

All publications and patents mentioned herein are hereby incorporated by reference in their entirety as if each individual publication or patent was specifically and individually indicated to be incorporated by reference. In case of conflict, the present application, including any definitions herein, will control.

EQUIVALENTS

While specific embodiments of the subject disclosure have been discussed, the above specification is illustrative and not restrictive. Many variations of the disclosure will become apparent to those skilled in the art upon review of this specification and the claims below. The full scope of the disclosure should be determined by reference to the claims, along with their full scope of equivalents, and the specification, along with such variations.

The invention claimed is:

1. A compound of formula (III) or formula (IV):

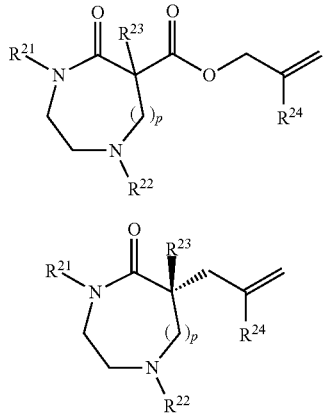

wherein, as valence and stability permit,
$R^{21}$ is —C(O)aryl or —C(O)heteroaryl, each optionally substituted with alkoxy, alkyl, or haloalkyl;
$R^{22}$ is —C(O)OR$^{22a}$, —C(O)aryl, or —C(O)heteroaryl, wherein each of aryl and heteroaryl are optionally substituted with alkoxy, alkyl, or haloalkyl;
$R^{22a}$ is $C_{1-6}$ alkyl, $C_{6-10}$ aryl, or $C_{5-9}$ heteroaryl, wherein each of aryl and heteroaryl are optionally substituted with alkoxy, alkyl, or haloalkyl;
$R^{23}$ is H, halogen, alkynyl, alkenyl, or $C_{1-6}$ alkyl, each optionally substituted with OH, cyano, alkoxy, aryloxy, acyl, alkoxycarbonyl, halogen, aryl, or —NHC(O)OR$^{23a}$;
$R^{23a}$ is $C_{1-6}$ alkyl, ($C_{6-10}$ aryl)alkyl, or ($C_{5-9}$ heteroaryl)alkyl;
$R^{24}$ is H or halogen; and
p is 1,
or
a compound of formula (E):

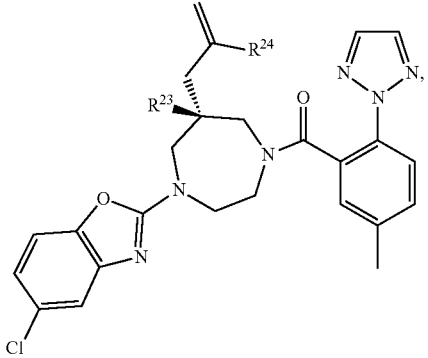

or a salt thereof,
wherein, as valence and stability permit,
$R^{23}$ is halogen, alkynyl, alkenyl, or $C_{1-6}$ alkyl, each optionally substituted with halogen, OH, cyano, alkoxy, aryloxy, alkoxycarbonyl, or —NHC(O)OR$^{23a}$;
$R^{23a}$ is $C_{1-6}$ alkyl; and
$R^{24}$ is H.

2. A compound selected from:

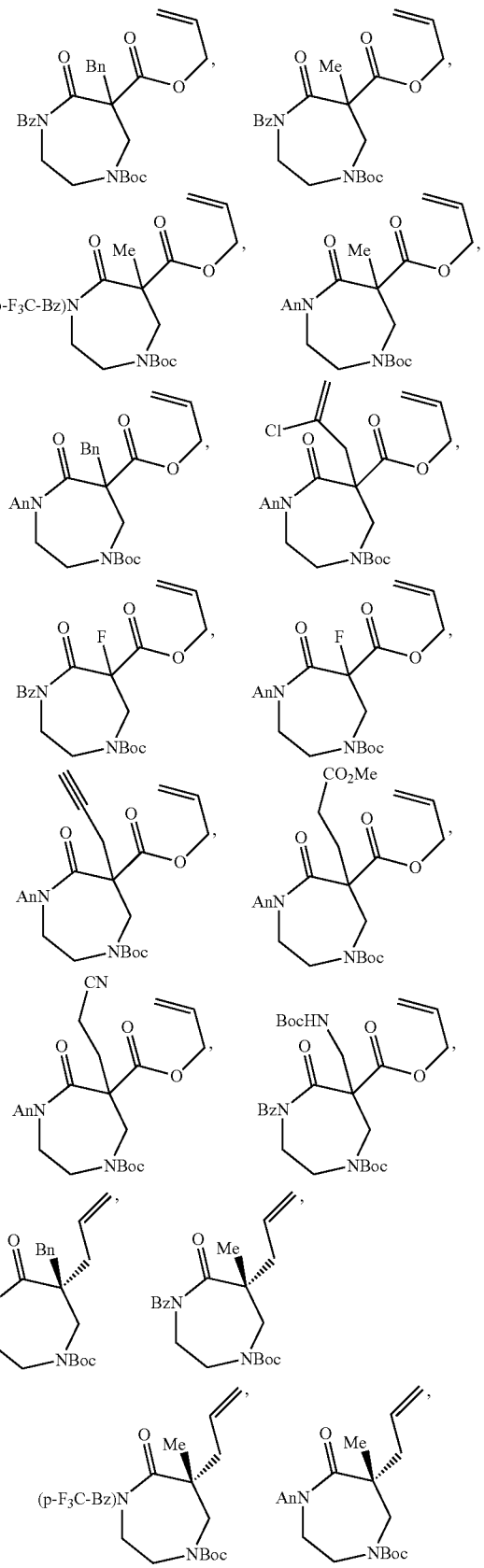

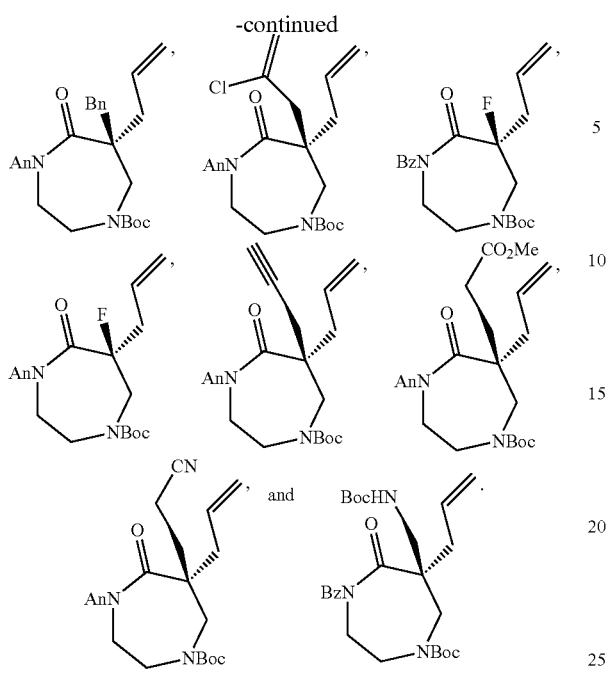

3. A method comprising preparing a compound of formula (IV):

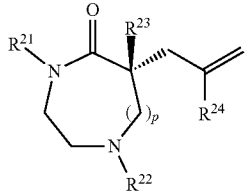
(IV)

by treating a compound of formula (III)

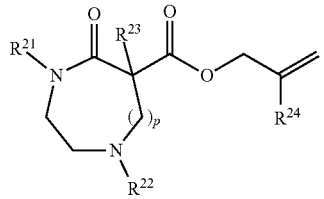
(III)

or a salt thereof,
with a Pd(0) catalyst and a ligand L under alkylation conditions,
wherein, as valence and stability permit,
$R^{21}$ is —C(O)aryl or —C(O)heteroaryl, optionally substituted with alkoxy, alkyl, or haloalkyl;
$R^{22}$ is —C(O)OR$^{22a}$, —C(O)aryl, or —C(O)heteroaryl, wherein each of aryl and heteroaryl is optionally substituted with alkoxy, alkyl, or haloalkyl;
$R^{22a}$ is $C_{1-6}$ alkyl, $C_{6-10}$ aryl, or $C_{5-9}$ heteroaryl;
$R^{23}$ is H, halogen, alkynyl, alkenyl, or $C_{1-6}$ alkyl, each optionally substituted with cyano, OH, alkoxy, aryloxy, acyl, alkoxycarbonyl, halogen, aryl, or —NHC(O)OR$^{23a}$;

$R^{23a}$ is $C_{1-6}$ alkyl, $(C_{6-10}$ aryl)alkyl, or $(C_{5-9}$ heteroaryl)alkyl;
$R^{24}$ is H or halogen; and
p is 1.

4. The method of claim 3, wherein:
the compound of formula (IV) is a compound of formula (IVb)

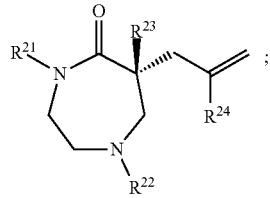
(IVb)

and
the compound of formula (III) is a compound of formula (IIIb)

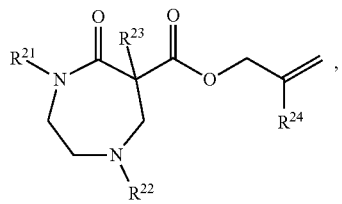
(IIIb)

or a salt thereof,
wherein, as valence and stability permit,
$R^{22}$ is —C(O)OR$^{22a}$;
$R^{22a}$ is $C_{1-6}$ alkyl;
$R^{23}$ is halogen, alkynyl, alkenyl, or $C_{1-6}$ alkyl, each optionally substituted with halogen, OH, cyano, alkoxy, aryloxy, alkoxycarbonyl, or —NHC(O)OR$^{23a}$;
$R^{23a}$ is $C_{1-6}$ alkyl; and
$R^{24}$ is H.

5. The method of claim 3, wherein the Pd(0) catalyst is Pd(dmdba)$_2$ or Pd$_2$(dmdba)$_3$.

6. The method of claim 3, wherein:
ligand L is an enantioenriched ferrocelane ligand, wherein the enantioenriched ferrocelane ligand is 1,1'-bis[(2S,5S)-2,5-diethyl-1-phospholanyl]ferrocene, 1,1'-bis[(2S,5S)-2,5-dimethyl-1-phospholanyl]ferrocene, or 1,1'-bis[(2S,5S)-2,5-diisopropyl-1-phospholanyl]ferrocene.

7. The method of claim 3, wherein the ligand L is

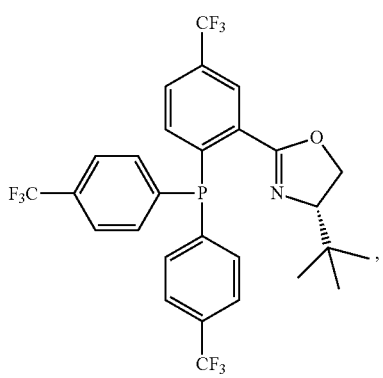
((S)-L1)

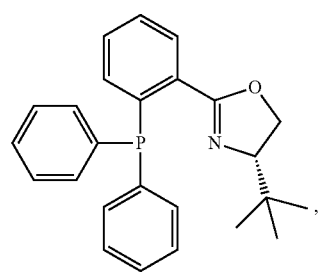
((S)-L2)

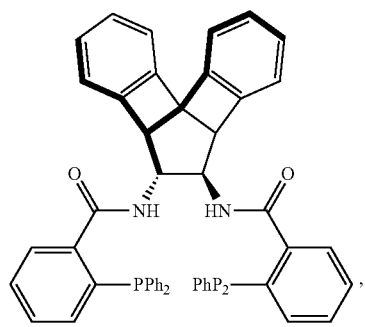
((S,S)-L3)

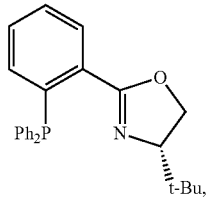
(S)-tBuPHOX

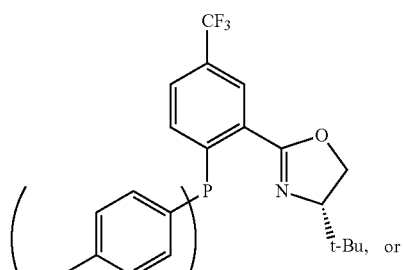
(S)-(CF₃)₃-tBuPHOX or

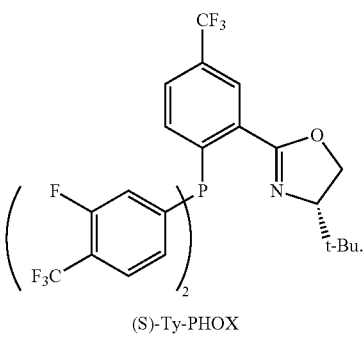
(S)-Ty-PHOX

8. The method of claim 4, whereby the compound of formula (IVb) is enantioenriched.

9. The method of claim 4, wherein a medicinal product is prepared.

10. The method of claim 9, wherein preparing the medicinal product comprises:

treating the compound of formula (IVb)

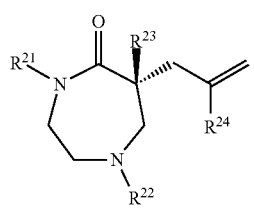
(IVb)

with lithium hydroxide and subsequently with lithium aluminum hydride, to form a product of formula (A)

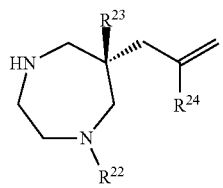
(A)

treating the compound of formula (A) with a compound of formula (B)

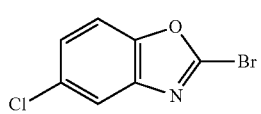
(B)

and subsequently with acetyl chloride in methanol, to form a product of formula (C)

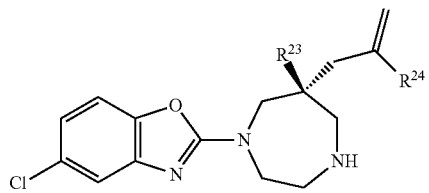

treating the compound of formula (C) with a compound of formula (D)

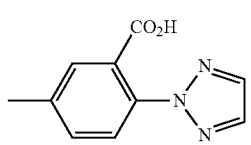

to form a medicinal product of formula (E)

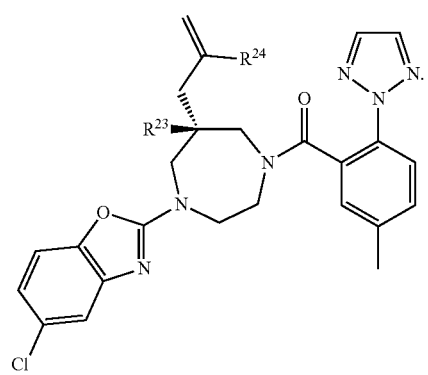

11. The method of claim 4, wherein:
$R^{21}$ is Bz, An, or pCF$_3$Bz;
$R^{22}$ is Boc; and
$R^{23}$ is CH$_3$, CH$_2$Ph, CH$_2$CCl=CH$_2$, F, CH$_2$CCH, CH$_2$CH$_2$CO$_2$CH$_3$, CH$_2$CH$_2$CN, or CH$_2$NHBoc.

12. The method of claim 4, wherein the compound of formula (IIIb) is:

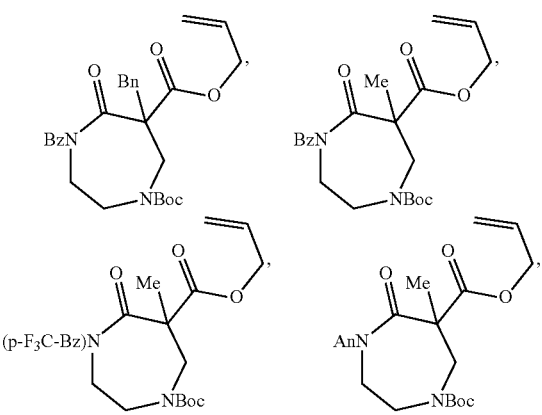

-continued

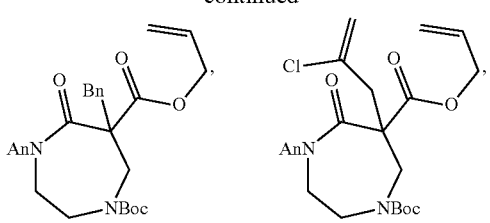

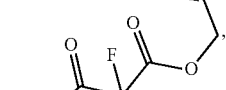 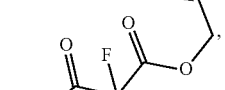

 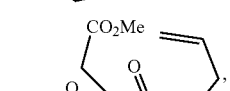

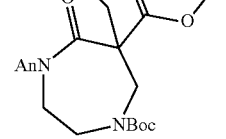 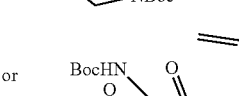

13. The method of claim 4, wherein the compound of formula (IVb) is:

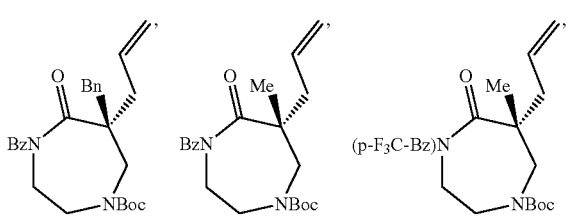

-continued
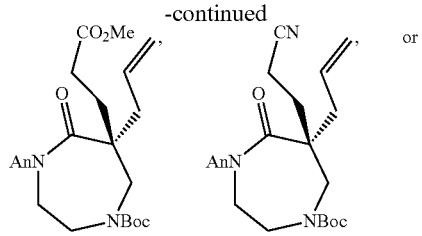
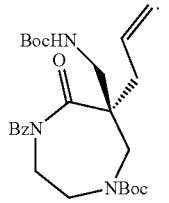
14. The method of claim 4, wherein the compound of formula (IVb) is
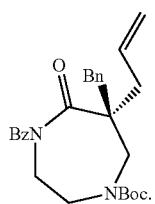
* * * * *